US009926307B2

(12) United States Patent
Jones et al.

(10) Patent No.: US 9,926,307 B2
(45) Date of Patent: Mar. 27, 2018

(54) COMPOUNDS

(71) Applicant: MISSION THERAPEUTICS LTD, Cambridge, Cambridgeshire (GB)

(72) Inventors: Alison Jones, Cambridge (GB); Mark Ian Kemp, Cambridge (GB); Martin Lee Stockley, Cambridge (GB); Karl Richard Gibson, Deal (GB); Gavin Alistair Whitlock, Deal (GB); Andrew Madin, Bishop's Stortford (GB)

(73) Assignee: MISSION THERAPEUTICS LTD, Cambridge (GB)

( * ) Notice: Subject to any disclaimer, the term of this patent is extended or adjusted under 35 U.S.C. 154(b) by 0 days.

(21) Appl. No.: 15/513,125

(22) PCT Filed: Sep. 22, 2015

(86) PCT No.: PCT/GB2015/052729
§ 371 (c)(1),
(2) Date: Mar. 21, 2017

(87) PCT Pub. No.: WO2016/046530
PCT Pub. Date: Mar. 31, 2016

(65) Prior Publication Data
US 2017/0247365 A1 Aug. 31, 2017

(30) Foreign Application Priority Data

Sep. 23, 2014 (GB) .................... 1416754.8

(51) Int. Cl.
C07D 401/12 (2006.01)
C07D 403/12 (2006.01)
C07D 405/12 (2006.01)
C07D 417/12 (2006.01)
C07D 413/12 (2006.01)
C07D 417/14 (2006.01)
C07D 401/14 (2006.01)
C07D 405/14 (2006.01)
C07D 413/14 (2006.01)
C07D 471/04 (2006.01)
C07D 487/04 (2006.01)
C07D 513/04 (2006.01)

(52) U.S. Cl.
CPC ......... *C07D 417/12* (2013.01); *C07D 401/12* (2013.01); *C07D 401/14* (2013.01); *C07D 403/12* (2013.01); *C07D 405/14* (2013.01); *C07D 413/12* (2013.01); *C07D 413/14* (2013.01); *C07D 417/14* (2013.01); *C07D 471/04* (2013.01); *C07D 487/04* (2013.01); *C07D 513/04* (2013.01)

(58) Field of Classification Search
CPC .. C07D 401/12; C07D 417/12; C07D 403/12; C07D 405/12
See application file for complete search history.

(56) References Cited

U.S. PATENT DOCUMENTS

2004/0138465 A1 7/2004 Spurr
2012/0077806 A1 3/2012 Donato et al.

FOREIGN PATENT DOCUMENTS

| EP | 1072263 A1 | 1/2001 |
| EP | 1970373 A1 | 9/2008 |
| WO | 95/08534 A1 | 3/1995 |
| WO | 01/77073 A1 | 10/2001 |
| WO | 2005089763 A1 | 9/2005 |
| WO | 2010052222 A1 | 5/2010 |
| WO | 2012174312 A2 | 12/2012 |
| WO | 2014015157 A2 | 1/2014 |
| WO | 2014179755 A2 | 11/2014 |

OTHER PUBLICATIONS

Targeted Cancer Therapies Fact Sheet, retrieved from http://www.cancer.gov/about-cancer/treatment/types/targeted-therapies/targeted-therapies-fact-sheet on Dec. 8, 2015.*
Cancer Prevention Overview, retrieved from http://www.cancer.gov/cancertopics/pdq/prevention/overview/patient on Nov. 14, 2012.*
Ashida et al. "Exploitation of the host ubiquitin system by human bacterial pathogens" Nature Rev. Microbiology 12(6):399-413, 2014.
Bedford et al., "Ubiquitin-like protein conjugation and the ubiquitin-proteasome system as drug targets" Nature Rev. Drug Discovery 10:29-46, 2011.
Clague et al., "Deubiquitylases From Genes to Organism" Physiol. Rev. 93:1289-1315, 2013.
Hurst-Kennedy et al., "Ubiquitin C-Terminal Hydrolast L1 in Tumorigenesis" Hindawi Publishing Corporation, Biochem. Res. Int'l. 2012:1-10, 2012.
Hussain et al., "The de-ubiquitinase UCH-L1 is an oncogene that drives the development of lymphoma in vivo by deregulating PHLPP1 and Akt signalling" Leukemia 34:1641-1655, 2010.

(Continued)

*Primary Examiner* — Rebecca L Anderson
*Assistant Examiner* — Karen Cheng

(57) ABSTRACT

The present invention relates to novel compounds and methods for the manufacture of inhibitors of deubiquitylating enzymes (DUBs). In particular, the invention relates to the inhibition of ubiquitin C-terminal hydrolase L1 (UCHL1). The invention further relates to the use of DUB inhibitors in the treatment of cancer and other indications. Compounds of the invention include compounds having the formula (I) or a pharmaceutically acceptable salt thereof, wherein R1 to R8 are as defined herein.

16 Claims, 2 Drawing Sheets

(56) References Cited

OTHER PUBLICATIONS

Lill et al., "Toward understanding ubiquitin-modifying enzymes: from pharmacological targeting to proteomics" Trends in Pharm. Sci. 35(4):187-207, 2014.

Lim et al., "Deubiquitinating Enzymes as Therapeutic Targets in Cancer" Curr. Pharm. Design 19:4039-4052, 2013.

Nicholson et al., "Discovery of Therapeutic Deubiquitylase Effector Molecules: Current Perspectives" J. Biomol. Screening 19(7):989-999, 2014.

Ristic et al., "An optimal ubiquitin-proteasome pathway in the nervous system: the role of deubiquitinating enzymes" Front. Mol. Neurosc. 7(72):1-15, 2014.

* cited by examiner

Figure 1 Expression and purification of FLAG-UCHL1 from mammalian cells
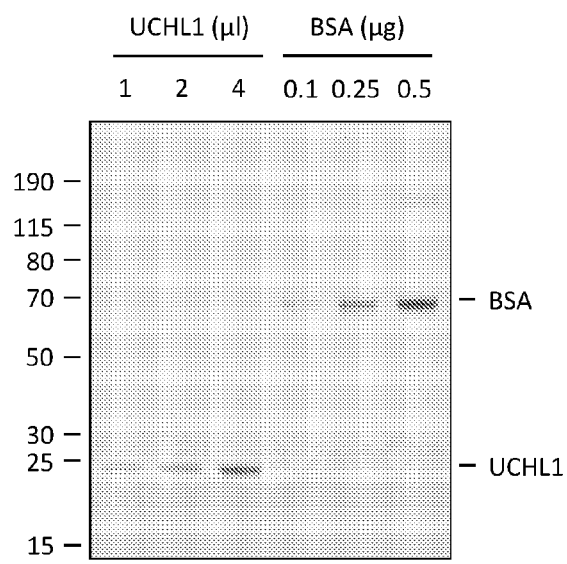
FLAG-purified protein or the indicated concentrations of BSA were separated by SDS-PAGE and stained with Imperial Protein Stain (Pierce Biotechnology).

Figure 2 UCHL1 kinetic assay for high throughput screening of compounds using an isopeptide linked substrate
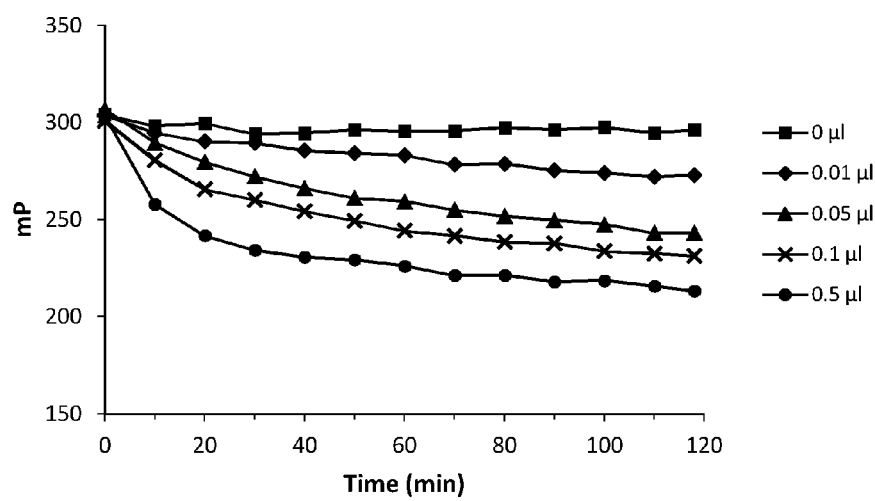
Proteolytic activity of purified FLAG-UCHL1 measured using a fluorescence polarisation assay. Various volumes of purified UCHL1 as indicated were incubated with a TAMRA labelled peptide linked to ubiquitin via an isopeptide bond.

COMPOUNDS

RELATED APPLICATION INFORMATION

This application is a 35 U.S.C. §371 national stage filing of International Application No. PCT/GB2015/052729, filed on Sep. 22, 2015, which claims the benefit of United Kingdom Patent Application No. 1416754.8, filed on Sep. 23, 2014.

The present invention relates to novel compounds and methods for the manufacture of inhibitors of deubiquitylating enzymes (DUBs). In particular, the invention relates to the inhibition of ubiquitin C-terminal hydrolase L1 (UCHL1). The invention further relates to the use of DUB inhibitors in the treatment of cancer and methods of screening.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein. These processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis (Clague et al., Physiol Rev 93:1289-1315, 2013). A number of ubiquitin-like (Ubls) molecules have been identified that regulate protein functions in cells in a similar manner to ubiquitin.

Ubiquitin and Ubls molecules are cleaved from proteins by enzymes called isopeptidases or deubiquitinating enzymes (DUBs), of which there are approximately 95 DUBs in human cells, divided into sub-families based on sequence homology: ubiquitin C-terminal hydrolases (UCHs), ubiquitin-specific proteases (USPs), ovarian tumour proteases (OTUs), Machado-Josephin domain proteases (MJDs), JAB1/MPN/MOV34 metalloproteases (JAMMs) or Sentrin-specific proteases (SENPs). DUBs can process ubiquitin or ubiquitin-like adducts. A number of DUBs have been linked to various diseases including cancer, inflammation, neurodegenerative diseases and anti-infectives (Kim K H et al., Cliff Pharm Des. 2013; 19 (22):4039-52; Nicholson B et al., J Biomol Screen. 2014 Mar. 14:19 (7); 989-999; Ristic G et al., Front Mol Neurosci. 2014 Aug. 19; 7:72; Ashida H et al., Nat Rev Microbiol. 2014 June; 12 (6):399-413. The ubiquitin C-terminal hydrolase (UCH) family, consisting of UCHL1, UCHL3, UCHL5, and BAP1, are cysteine proteases that operate through an active site thiol. UCHs are thought to be involved in the processing and recycling of ubiquitin and to preferentially cleave small protein substrates. UCHL1 is a 223 amino acid protein whose expression is normally limited to the brain, peripheral nervous system, ovaries and testis in mammals. However, UCHL1 has been reported to be up-regulated in several pathological conditions, including tumour tissues, COPD, stroke, Parkinson's disease, Alzheimer's disease, neuropathic pain or lysosomal storage disorders. Furthermore, UCHL1 functions as an oncogene in the progression of many cancers including breast, lymphoma, colorectal cancer, osteosarcoma, pancreatic and non small cell lung carcinoma and is inversely correlated with patient survival (Hurst-Kennedy et al., Biochem Res Int, 2012; Hussain et al., Leukemia 24:1641-1655, 2010). Pharmacological inhibition of UCHL1 would thus serve as novel treatment for pathologies such as cancers.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated (Bedford et al., Nature Rev 10:29-46, 2011). To date, although there have been a handful of inhibitors published in the literature (for a review see: Lill and Wertz, Trends in Pharmaceutical Sciences, 35 (4), 2014), there have been no reports of DUB inhibitors that have successfully entered the clinic. Thus, there is a need for compounds and pharmaceutical compositions to inhibit DUBs such as UCHL1, USP6 or USP30 for the treatment of cancer or other indications where DUB activity is observed. Alternative DUBs that have also been suggested to be potential therapeutic targets for the treatment of cancer include USP1, USP2, USP4, USP6, USP7, USP8, USP9x, USP10, USP11, USP13, USP14, USP17, USP28. Additional indications where DUB inhibition may prove beneficial include CNS disorders (e.g. USP30, USP14) or inflammation (e.g. A20, CYLD).

SUMMARY OF THE INVENTION

In accordance with a first aspect of the invention there is provided a compound of formula (I) A compound having the formula (I)

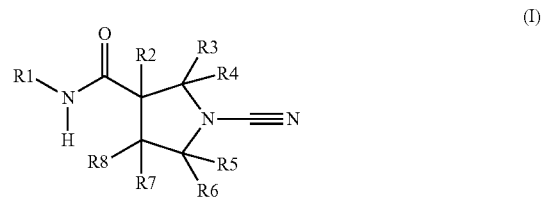

or a pharmaceutically acceptable salt thereof, wherein:

$R_1$ represents a 5 to 10 membered heteroaryl ring which may be optionally substituted; and $R_2$, $R_3$, $R_4$, $R_5$, $R_6$ and $R_8$ each independently represent a hydrogen atom, cyano, an optionally substituted $C_1$-$C_6$ alkyl, an optionally substituted $C_1$-$C_6$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, or $R_6$ is linked to $R_7$ to form an optionally substituted $C_3$-$C_4$ cycloalkyl ring; and $R_7$ represents a hydrogen atom, a fluorine atom, cyano, an optionally substituted $C_1$-$C_3$ alkyl, an optionally substituted $C_1$-$C_3$ alkoxy group or an optionally substituted aryl or 5 to 6 membered heteroaryl ring, or is linked to $R_8$ to form a spirocyclic group, or is linked to $R_6$ to form an optionally substituted $C_3$-$C_4$ cycloalkyl ring.

$R_1$ may represent a 5 to 10 membered heteroaryl ring substituted with one or more of $Q_1$-$(R_9)_n$, wherein:

n is 0 or 1

$Q_1$ represents a hydrogen atom, a halogen atom, cyano, a covalent bond, $—NR_{10}—$, $—CONR_{10}—$, $—NR_{10}CO—$, an oxygen atom, oxo, nitro, $—S(O)_m—$, $C_1$-$C_6$ alkoxy, $C_1$-$C_6$ haloalkoxy, $C_1$-$C_6$ hydroxyalkyl, $—CO—$, $—SO_2R_{11}$, $—NR_{11}R_{12}$, $—NR_{11}COR_{12}$, $—NR_{10}CONR_{11}R_{12}$, $—CONR_{11}R_{12}$, $—CO_2R_{11}$, $—NR_{11}CO_2R_{12}$, $—SO_2NR_{11}R_{12}$, $—CONR_{11}$, $—C(O)R_{11}$, $—NR_{11}SO_2R_{12}NR_{11}SO_2NR_{13}R_{14}$ and $SO_2NR_{11}$ or an optionally substituted $C_1$-$C_6$ alkylene, $—C_2$-$C_6$ alkenylene or $—C_1$-$C_6$ alkyl group;

m is 0, 1 or 2;

$R_{10}$, $R_{11}$ and $R_{12}$ each independently represent a hydrogen atom or an optionally substituted $C_1$-$C_6$ alkyl, or an optionally substituted $C_1$-$C_6$ alkylene group.

When n is 1, $R_9$ represents an optionally substituted 3 to 10 membered heterocyclyl, heteroaryl, aryl or cycloalkyl ring. (When n is 0, Q is present and $R_9$ is absent).

$R_9$ may be optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, nitro, optionally substituted heterocyclyl, optionally substituted cycloalkyl, optionally substituted heteroaryl, optionally substituted aryl, -$Q_2$-$NR_{13}CONR_{14}R_{15}$, -$Q_2$-$NR_{13}R_{14}$, -$Q_2$-$NR_{13}COR_{14}$, -$Q_2$-$COR_{13}$, -$Q_2$-$SO_2R_{13}$, -$Q_2$-$CONR_{13}$, $Q_2$-$CONR_{13}R_{14}$, -$Q_2$-$CO_2R_{13}$, -$Q_2$-$SO_2NR_{13}R_{14}$, -$Q_2$-$NR_{13}SO_2R_{14}$ and -$Q_2$-$NR_{13}SO_2NR_{14}R_{15}$, wherein $Q_2$ represents a covalent bond or a $C_1$-$C_6$ alkylene or $C_2$-$C_6$ alkenylene group; and $R_{13}$, $R_{14}$ and $R_{15}$ each independently represent hydrogen or an optionally substituted $C_1$-$C_6$ alkyl, or an optionally substituted heterocyclyl, or an optionally substituted heteroaryl, or an optionally substituted aryl, or an optionally substituted cycloalkyl.

BRIEF DESCRIPTION OF THE FIGURES

FIG. 1 provides an image of FLAG-UCHL1 purified from mammalian cells. FLAG-purified protein or the indicated concentrations of BSA were separated by SDS-PAGE and stained with Imperial (Pierce Biotechnology).

FIG. 2 is a graph showing proteolytic activity of purified FLAG-UCHL1 using a fluorescence polarisation assay. Various volumes of purified UCHL1 as indicated were incubated with a TAMIRA labelled peptide linked to ubiquitin via an isopeptide bond.

DETAILED DESCRIPTION OF THE INVENTION

Where any group of the compounds of Formula (I) have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkenyl, or alkynyl substituent group or an alkyl, alkenyl moiety in a substituent group may be linear or branched. Alkyl and alkenyl chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2, 2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl.

A $C_x$-$C_y$ alkylene group or moiety may be linear or branched and refers to a divalent hydrocarbon group having one less hydrogen atom from $C_x$-$C_y$ alkyl as defined above. Examples of $C_1$-$C_6$ alkylene groups include methylene, ethylene, n-propylene, n-butylene, methylmethylene and dimethylmethylene.

$C_2$-$C_6$ alkenyl refers to a linear or branched hydrocarbon chain radical containing at least two carbon atoms and at least one double bond. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl.

$C_2$-$C_6$ alkynyl refers to a linear or branched hydrocarbon chain radical containing at least two carbon atoms and at least one triple bond. Examples of alkynyl groups include ethynyl, propynyl, 2-propynyl, 1-butynyl, 2-butynyl and 1-hexynyl.

$C_1$-$C_6$ alkoxy refers to a group or part of a group having an $—O—C_x$-$C_y$ alkyl group according to the definition of $C_x$-$C_y$ alkyl above. Examples of $C_1$-$C_6$ alkoxy include methoxy, ethoxy, propoxy, isopropoxy, butoxy, pentoxy and hexoxy.

$C_1$-$C_6$ haloalkyl and $C_1$-$C_6$ haloalkoxy refers to a $C_x$-$C_y$ alkyl group as defined above wherein at least one hydrogen atom is replaced with a halogen atom. Examples of $C_1$-$C_6$ haloalkyl groups include fluoromethyl, difluoromethyl, trifluoromethyl, trifluoroethyl, pentafluoroethyl, fluoromethoxy, difluoromethoxy and trifluoromethoxy.

$C_1$-$C_6$ hydroxyalkyl refers to $C_x$-$C_y$ alkyl group as defined above wherein at least one hydrogen atom is replaced with a hydroxy ($—OH$) group. Examples of hydroxy $C_{1-6}$ alkyl groups include hydroxymethyl, hydroxyethyl, dihydroxyethyl, hydroxypropyl and hydroxyisopropyl.

The term "halogen" or "halo" refers to chlorine, bromine, fluorine or iodine atoms.

For the avoidance of doubt it will be understood that a 3 to 10 membered heteroaryl, aryl, cycloalkyl or heterocyclic ring as defined according to $R_1$ or $R_9$ does not include any unstable ring structures or any O—O, O—S or S—S bonds and that a substituent if present may be attached to any suitable ring atom which may be a carbon atom or a heteroatom. Substitution on a ring may also include a change in the ring atom at the position of the substitution. For example, substitution on a phenyl ring may include a change in the ring atom at the position of substitution from carbon to nitrogen, resulting in a pyridine ring. The 3 to 10 membered heteroaryl, aryl, cycloalkyl or heterocyclic ring may be monocyclic or bicyclic.

"$C_x$-$C_y$ cycloalkyl" refers to a cyclic non-aromatic hydrocarbon group of x-y carbon atoms. For example $C_3$-$C_8$ cycloalkyl refers to a hydrocarbon ring containing 3-8 carbon atoms. Examples of $C_3$-$C_8$ cycloalkyl are cyclopropyl, cyclobutyl, cyclopentyl, cyclohexyl, cyclopentyl, cyclohexyl cycloheptyl and cyclooctyl.

An "aryl" group/moiety refers to any monocyclic or bicyclic hydrocarbon group comprising at least one aromatic group, for example having up to 12 carbon atom ring members. Examples of aryl groups include phenyl, naphthyl, tetrahydronaphthyl and biphenyl.

"Heteroaryl" groups may be monocyclic or bicyclic. Bicyclic rings may be fused aromatic rings where both rings are aromatic or may be fused rings where one of the rings is non aromatic. In the case of R1, the ring attached to the amide nitrogen is an aromatic ring, which can be fused to a further aromatic or non-aromatic ring. Heteroaryl rings comprise 1, 2 or 3 heteroatoms selected from oxygen, sulphur and nitrogen. When the heteroatom is nitrogen it may be oxidised. Examples of heteroaryl groups include pyridinyl, pyrazinyl, pyrimidinyl, pyridazinyl, furyl, thiophenyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, oxazinanyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, indolinyl, isoindolinyl, triazinyl, pyridazinyl, and quinoxalinyl.

"Heterocyclyl" groups may also be moncyclic or comprise 2 or more fused rings which may be saturated or partially unsaturated comprising 1, 2 or 3 heteroatoms selected from oxygen, sulphur and nitrogen. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), 4,5-dihydro-1H-maleimido, dioxolanyl, morpholinyl, oxazolidinyl, piperazinyl, tetrahydrofuranyl, thiomorpholinyl, dihydropyranyl (e.g. 3,4-dihydropyranyl, 3,6-dihydropyranyl), dioxanyl, hexahydropyrimidinyl, pyrazolinyl, pyrazolidinyl, pyridazinyl, 4H-quinolizinyl, quinuclinyl, tetrahydropyranyl, tetrahydropyridinyl, tetrahydropyrimidinyl, tetrahydrothiophenyl, tetramethylenesulfoxide, thiazolidinyl, hydantoinyl, benzopyranyl, tetrahydrothiazolopyridinyl, tetrahydroquinolinyl, tetrahydroisoquinolinyl, tetrahydropyrazolopyrazinyl and tetrahydrothiazoloazepinyl.

"Optionally substituted" as applied to any group means that the said group may if desired be substituted with one or more substituents, which may be the same or different. The optional substituents within the definitions of $R_2$, $R_3$, $R_4$, $R_5$, $R_6$ and $R_8$ may include halo, deutero, $C_{1-3}$ alkyl, $C_{1-3}$ alkoxy, cyano, amino, nitro or $SF_5$ (a known mimetic of $NO_2$). Examples of suitable substituents for all remaining "substituted" and "optionally substituted" moieties, including rings $R_1$ and $R_9$ may include halo, deutero, $C_{1-3}$ alkyl, hydroxy, $C_{1-3}$ alkoxy, cyano, amino, nitro, oxo, aryl, heteroaryl, heterocyclyl, $C_3$-$C_6$ cycloalkyl, $C_{1-3}$ alkylamino, $C_{2-6}$ alkenylamino, di-$C_{1-3}$ alkylamino, $C_{1-3}$ acylamino, di-$C_{1-3}$ acylamino, carboxy, $C_{1-3}$ alkoxycarbonyl, carbamoyl, mono-$C_{1-3}$ carbamoyl, di-$C_{1-3}$ carbamoyl or any of the above in which a hydrocarbyl moiety is itself substituted by halo. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substituted groups thus include for example CN, CFH$_2$, CF$_2$H, CF$_3$, OCF$_3$, CH$_2$NH$_2$, CH$_2$OH, CH$_2$CN, CH$_2$SCH$_3$, CH$_2$OCH$_3$, OMe, OEt, OPr, Me, Et, t-Bu, —OCH$_2$O—, CO$_2$Me, C(O)Me, i-Pr, SCF$_3$, SO$_2$Me, NMe$_2$ etc. In the case of aryl groups, the substitutions may be in the form of rings from adjacent carbon atoms in the aryl ring, for example cyclic acetals such as O—CH$_2$—O.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reoccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from inorganic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of formula (I).

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an enantiomeric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Included herein is the compound according to formula (II)

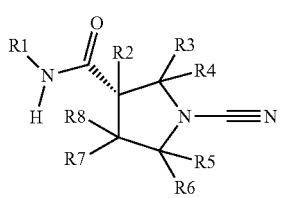

(II)

or a pharmaceutically acceptable salt thereof, wherein:

$R_1$ represents a 5 to 10 membered heteroaryl ring which may be optionally substituted; and $R_2$, $R_3$, $R_4$, $R_5$, $R_6$ and $R_8$ each independently represent a hydrogen atom, cyano, an optionally substituted $C_1$-$C_6$ alkyl, an optionally substituted $C_1$-$C_6$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, or $R_6$ is linked to $R_7$ to form an optionally substituted $C_3$-$C_4$ cycloalkyl ring; and $R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group, or is linked to $R_6$ to form an optionally substituted $C_3$-$C_4$ cycloalkyl ring.

In one embodiment, $R_1$ represents a 5 to 10 membered heteroaryl ring which may be optionally substituted; and $R_2$, $R_3$, $R_4$, $R_5$, $R_6$ and $R_8$ each independently represent a hydrogen atom, cyano, an optionally substituted $C_1$-$C_3$ alkyl, an optionally substituted $C_1$-$C_3$ alkoxy group, one or more spirocyclic groups where $R_3$ is linked to $R_4$, $R_5$ is linked to $R_6$ or $R_8$ is linked to $R_7$, or $R_2$ is linked to $R_8$ to form a $C_3$-$C_4$ cycloalkyl ring; and $R_7$ represents a hydrogen atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group.

Where $R_3$ and $R_4$ are different, the $R_3$ group can be cis or trans in relation to the amide. Compounds are preferably cis when $R_4$ is H. When $R_3$=Me and $R_2$=$R_4$=H the compound may be represented according to formula (III)

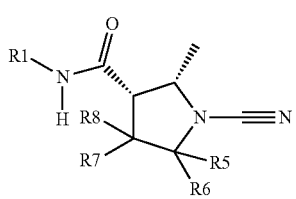

(III)

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$, $^{36}Cl$, $^{18}F$, $^{123}I$, $^{125}I$ $^{13}N$, $^{15}N$, $^{15}O$, $^{17}O$, $^{18}O$ $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of cancer, including small molecule therapeutics or antibody based therapeutics.

The disclosure includes compound having the formula (I)

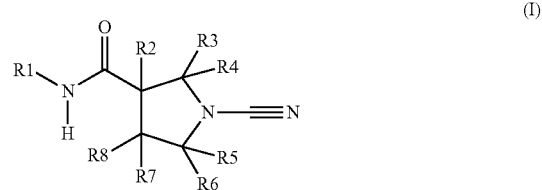

or a pharmaceutically acceptable salt thereof, wherein:
$R_1$ represents a 5 to 10 membered heteroaryl ring which may be optionally substituted;
$R_2$, $R_3$, $R_4$, $R_5$, $R_6$ and $R_8$ each independently represent a hydrogen atom, cyano, an optionally substituted $C_1$-$C_6$ alkyl, an optionally substituted $C_1$-$C_6$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, $R_6$ is linked to $R_7$ to form an optionally substituted $C_3$-$C_4$ cycloalkyl ring; and
$R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring, or is linked to $R_8$ to form a spirocyclic group, or is linked to $R_6$ to form an optionally substituted $C_3$-$C_4$ cycloalkyl ring.

In one embodiment, $R_1$ represents a 5 to 10 membered heteroaryl ring which may be optionally substituted;
$R_2$, $R_3$, $R_4$, $R_5$, $R_6$ and $R_8$ each independently represent a hydrogen atom, cyano, an optionally substituted $C_1$-$C_3$ alkyl, an optionally substituted $C_1$-$C_3$ alkoxy group, one or more spirocyclic groups where $R_3$ is linked to $R_4$, $R_5$ is linked to $R_6$ or $R_8$ is linked to $R_7$, or $R_2$ is linked to $R_8$ to form a $C_3$-$C_4$ cycloalkyl ring; and
$R_7$ represents a hydrogen atom, cyano, an optionally substituted $C_1$-$C_3$ alkyl, an optionally substituted $C_1$-$C_3$ alkoxy group or an optionally substituted aryl or heteroaryl ring, or is linked to $R_8$ to form a spirocyclic group.

In formula (I) defined herein, the $R_1$ heteroaryl ring may be attached directly to the amide nitrogen atom to form an N-aryl bond. The aryl ring may be monocyclic or bicyclic. Where the ring is bicyclic, the second ring may be aromatic, or may be partly saturated, and thus not every atom in the 5-10 membered heteroaryl ring need be in an aryl system, there must be at least one heteroaryl ring within the 5-10 atoms.

In one embodiment $R_1$ represents a 5 to 10 membered (e.g. 5, 6, 7, 8, 9 or 10 membered) heteroaryl ring which may be optionally substituted with one or more (e.g. one, two, three or four) of $-Q_1-(R_9)_n$.

In a another embodiment $R_1$ represents a 5 or 6 membered heteroaryl ring which may be optionally substituted with one or more (e.g. one, two, three or four) of $-Q_1-(R_9)_n$.

In a further embodiment $R_1$ represents 9 membered bicyclic heteroaryl ring which may be optionally substituted with one or more (e.g. one, two, three or four) of $-Q_1-(R_9)_n$.

The heteroaryl ring of $R_1$ may be monocyclic or bicyclic and comprise one or more (e.g. 1, 2 or 3) heteroatoms independently selected from nitrogen, oxygen and sulphur.

In one embodiment the optionally substituted 5 to 10 membered heteroaryl ring of $R_1$ is selected from thiazolyl, pyridinyl, isoxazolyl, thiadiazolyl, indazolyl, imidazolyl, benzimidazolyl, benzothiazolyl, pyrazolyl, pyridazinyl, pyrimidinyl, naphthyridinyl, isoquinolinyl, pyrazinyl, tetrahydrothiazolopyridinyl, imidazopyridinyl, triazolyl, pyrazolopyridinyl, tetrahydropyrazolopyrazinyl, tetrahydrothiazoloazepinyl, thiazolopyridinyl The 5 to 10 membered heteroaryl ring of $R_1$ may be selected from thiazolyl, pyridinyl, isoxazolyl, thiadiazolyl, indazolyl, imidazolyl, benzimidazolyl, benzothiazolyl, pyrazolyl, pyridazinyl, pyrimidinyl, naphthyridinyl, isoquinolinyl, pyrazinyl, tetrahydrothiazolopyridinyl, imidazopyridinyl, triazolyl, and pyrazolopyridinyl.

In a further embodiment the 5 to 10 membered heteroaryl ring of $R_1$ is selected from thiazolyl, imidazolyl, benzothiazolyl, pyrazolyl, imidazopyridinyl and tetrahydrothiazolopyridinyl, pyridinyl, tetrahydropyrazolopyrazinyl, pyrimidinyl, isoquinolinyl, pyrazolopyridinyl, pyridazinyl, tetrahydrothiazoloazeptine, phenyl, thiazolopyridinyl, and indazolyl.

The 5 to 10 membered heteroaryl ring of $R_1$ may be selected from thiazolyl, imidazolyl, benzothiazolyl, pyrazolyl, imidazopyridinyl and tetrahydrothiazolopyridinyl.

In a further embodiment the 5 to 10 membered heteroaryl ring of $R_1$ is selected from thiazolyl and imidazolyl.

Typical examples of the 5 to 10 membered heteroaryl ring of $R_1$ include thiazol-2-yl, thiazol-5-yl, pyridin-2-yl, pyridin-3-yl, thiadiazol-2-yl, isoxazol-5-yl, indazol-5-yl, benzoimidazol-5-yl, benzonthiazol-2-yl, pyrazol-5-yl, pyrazol-3-yl, pyrimidin-5-yl, pyrimidin-4-yl pyridazin-3-yl, imidazol-4-yl, 1,8-napthylridin-2-yl, imidazo[1,2-a]pyridin-2-yl, imidazo[1,2-a]pyridin-6-yl, imidazo[1,2-a]pyridin-5-yl, pyrazin-2-yl, thiazolo[5,4-c]pyridine-2-yl, imidazo-4-yl, 1,2,3-triazol-4-yl, 4,5,6,7-tetrahydrothiazolo[5,4-c]pyridine-2-yl, 5,6,7,8-tetrahydro-4H-thiazolo[4,5-d]azepine-2-yl, thiazolo[4,5-b]pyridine-2-yl, thiazolo[4,5-c]pyridine-2-yl, tetrahydropyrazolo[1,5-a]pyrazin-2-yl, pyrazolo[1,5-a]pyridine-2-yl, quinolin-3-yl, isoquinolin-3-yl, benzo[d]thiazol-2-yl.

The group $R_1$ may be further substituted. $R_1$ may represent a 5 to 10 membered heteroaryl ring substituted with one or more of $Q_1$-$(R_9)_n$, wherein n is 0 or 1;

$Q_1$ represents a hydrogen atom, a halogen atom, cyano, a covalent bond, —$NR_{10}$—, —$CONR_{10}$—, —$NR_{10}CO$—, an oxygen atom, oxo, nitro, —$S(O)_m$—, $C_1$-$C_6$ alkoxy, $C_1$-$C_6$ haloalkoxy, $C_1$-$C_6$ hydroxyalkyl, —CO—, —$SO_2R_{11}$, —$NR_{11}R_{12}$, —$NR_{11}COR_{12}$, —$NR_{10}CONR_{11}R_{12}$, —$CONR_{11}R_{12}$, —$CO_2R_{11}$, —$NR_{11}CO_2R_{12}$, —$SO_2NR_{11}R_{12}$, —$CONR_{11}$, —$C(O)R_{11}$, —$NR_{11}SO_2R_{12}$, $NR_{11}SO_2NR_{13}R_{14}$ and $SO_2NR_{11}$ or an optionally substituted $C_1$-$C_6$ alkylene, —$C_2$-$C_6$ alkenylene or —$C_1$-$C_6$ alkyl group;

m is 0, 1 or 2;

$R_{10}$, $R_{11}$ and $R_{12}$ each independently represent a hydrogen atom or an optionally substituted $C_1$-$C_6$ alkyl or optionally substituted $C_1$-$C_6$ alkylene group.

When n is 1, $R_9$ represents an optionally substituted 3 to 10 membered heterocyclyl, heteroaryl, aryl or cycloalkyl ring. (When n is 0, Q is present and $R_9$ is absent).

$R_9$ may be optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, nitro, optionally substituted heterocyclyl, optionally substituted cycloalkyl, optionally substituted heteroaryl, optionally substituted aryl, -$Q_2$-$NR_{13}CONR_{14}R_{15}$, -$Q_2$-$NR_{13}R_{14}$, -$Q_2$-$NR_{13}COR_{14}$, -$Q_2$-$COR_{13}$, -$Q_2$-$SO_2R_{13}$, -$Q_2$-$CONR_{13}$, $Q_2$-$CONR_{13}R_{14}$, -$Q_2$-$CO_2R_{13}$, -$Q_2$-$SO_2NR_{13}R_{14}$, -$Q_2$-$NR_{13}SO_2R_{14}$ and -Q-$NR_{13}SO_2NR_{14}R_{15}$, wherein $Q_2$ represents a covalent bond or a $C_1$-$C_6$ alkylene or $C_2$-$C_6$ alkenylene group; and $R_{13}$, $R_{14}$ and $R_{15}$ each independently represent hydrogen or an optionally substituted $C_1$-$C_6$ alkyl, or an optionally substituted heterocyclyl, or an optionally substituted heteroaryl, or an optionally substituted aryl, or an optionally substituted cycloalkyl.

Alternatively $R_9$ may be substituted with further optionally substituted 3 to 10 membered heterocyclyl, heteroaryl, aryl or cycloalkyl rings, either directly attached or via linking group. The linking group may be an oxygen, a carbonyl, an optionally substituted $C_1$-$C_6$ alkylene or an optionally substituted $C_1$-$C_6$ alkyleneoxy chain. The linking group may be oxygen, —CO—, a $C_1$-$C_6$ alkylene group or a $C_1$-$C_6$ alkyleneoxy group. In one embodiment the linking group may be a carbonyl, or an alkylene chain, for example, —CO— or a $C_1$-$C_6$ alkylene group.

In one embodiment $R_2$ represents $C_1$-$C_6$ alkyl. In one embodiment $R_2$ represents $C_1$-$C_4$ alkyl. In one embodiment $R_2$ represents $C_1$-$C_3$ alkyl. In one embodiment $R_2$ represents $C_1$-$C_2$ alkyl. In one embodiment $R_2$ represents $C_1$-$C_3$ alkoxy. In one embodiment $R_2$ represents $C_1$-$C_2$ alkoxy. In one embodiment $R_2$ represents cyano. In one embodiment $R_2$ represents methyl. In one embodiment $R_2$ represents substituted methyl. In one embodiment $R_2$ represents $CH_2X$ where X is OMe, F or Cl. In one embodiment $R_2$ represents methoxy. In one embodiment $R_2$ represents $C_1$-$C_6$ alkyl, $C_1$-$C_4$ alkyl, $C_1$-$C_3$ alkyl or $C_1$-$C_2$ alkyl, $C_1$-$C_3$ alkoxy, $C_1$-$C_2$ alkoxy, cyano, methyl or substituted methyl and $R_3$, $R_4$, $R_5$, $R_6$, $R_7$ and $R_8$ each independently represent a hydrogen atom.

In another embodiment $R_3$ represents $C_1$-$C_6$ alkyl. In another embodiment $R_3$ represents $C_1$-$C_4$ alkyl. In another embodiment $R_3$ represents $C_1$-$C_3$ alkyl. In another embodiment $R_3$ represents $C_1$-$C_2$ alkyl (e.g. methyl or ethyl). In another embodiment $R_3$ represents $C_1$-$C_6$ alkyl, $C_1$-$C_4$ alkyl, $C_1$-$C_3$ alkyl or $C_1$-$C_2$ alkyl (e.g. methyl or ethyl) and $R_1$, $R_2$, $R_4$, $R_5$, $R_6$, $R_7$ and $R_8$ each independently represent a hydrogen atom.

In an alternative embodiment $R_3$ is linked to $R_4$ to form a spirocyclic group. The spirocyclic group may be made of carbon atoms, or may contain one or more heteroatoms. The spirocyclic group can contain 3, 4, 5 or 6 atoms, i.e. a $C_3$-$C_6$ spirocyclic group. The spirocyclic groups can be optionally further substituted.

In an alternative embodiment $R_5$ is linked to $R_6$ to form a spirocyclic group. The spirocyclic group may be made of carbon atoms, or may contain one or more heteroatoms. The spirocyclic group can contain 3, 4, 5 or 6 atoms, i.e. a $C_3$-$C_6$ spirocyclic group. The spirocyclic groups can be optionally further substituted.

In a further embodiment $R_2$ represents methyl or methoxy. In one embodiment $R_2$ represents methyl or methoxy and $R_3$, $R_4$, $R_5$, $R_6$, $R_7$ and $R_8$ each independently represent a hydrogen atom. In a further embodiment $R_2$ represents methyl. In one embodiment $R_2$ represents methyl and $R_3$, $R_4$, $R_5$, $R_6$, $R_7$ and $R_8$ each independently represent a hydrogen atom.

In a further embodiment when $R_2$ is other than hydrogen, $R_3$ is hydrogen. When $R_3$ is other than hydrogen, $R_2$ is hydrogen such that either $R_2$ or $R_3$ must be H.

In a further embodiment $R_2$ is linked to $R_8$ to form a $C_3$-$C_4$ cycloalkyl ring. The cycloalkyl ring may be cyclopropyl or cyclobutyl.

In a further embodiment $R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring. In a still further embodiment $R_7$ represents a hydrogen atom, cyano, an optionally substituted $C_1$-$C_3$ alkyl, an optionally substituted $C_1$-$C_3$ alkoxy group or an optionally substituted aryl or heteroaryl ring. $R_7$ can represent H, methyl or substituted methyl. $R_7$ may be methyl. $R_7$ may be $CF_3$. $R_7$ can represent an optionally substituted aryl or heteroaryl ring. $R_7$ can represent an optionally substituted phenyl, pyridyl or pyrimidyl ring. $R_7$ can represent an optionally substituted phenyl or pyridyl ring.

In an alternative embodiment $R_7$ is linked to $R_8$ to form a spirocyclic group. The spirocyclic group may be made of carbon atoms, or may contain one or more heteroatoms. The spirocyclic group can contain 3, 4, 5 or 6 atoms. The spirocyclic groups can be optionally further substituted.

In an alternative embodiment, $R_7$ is linked to $R_6$ to form a $C_3$-$C_4$ cycloalkyl ring, i.e. cyclopropyl or cyclobutyl. In one embodiment, $R_7$ and $R_6$ together form a cyclopropyl ring.

The $C_3$-$C_4$ cycloalkyl rings disclosed herein with respect to $R_2$, $R_6$, $R_7$ and $R_8$ may be optionally substituted with halo, deutero, $C_{1-3}$ alkyl, $C_{1-3}$ alkoxy, cyano, amino, nitro or $SF_5$.

$Q_1$ represents a hydrogen atom, a halogen atom, cyano, a covalent bond, $-NR_{10}-$, $-CONR_{10}-$, $-NR_{10}CO-$, an oxygen atom, oxo, nitro, $-S(O)_m-$, $C_1$-$C_6$ alkoxy, $C_1$-$C_6$ haloalkoxy, $C_1$-$C_6$ hydroxyalkyl, $-CO-$, $-SO_2R_{11}$, $-NR_{11}R_{12}$, $-NR_{11}COR_{12}$, $-NR_{10}CONR_{11}R_{12}$, $-CONR_{11}R_{12}$, $-CO_2R_{11}$, $-NR_{11}CO_2R_{12}$, $-SO_2NR_{11}R_{12}$, $-CONR_{11}$, $-C(O)R_{11}$, $-NR_{11}SO_2R_{12}$, $NR_{11}SO_2NR_{13}R_{14}$ and $SO_2NR_{11}$ or an optionally substituted $C_1$-$C_6$ alkylene, $-C_2$-$C_6$ alkenylene or $-C_1$-$C_6$ alkyl group;

In one embodiment $Q_1$ represents a hydrogen atom, a halogen atom, cyano, a covalent bond, $-NR_{10}-$, $-CONR_{10}-$, $-NR_{10}CO-$, an oxygen atom, $-S(O)_m-$, $C_1$-$C_6$ alkoxy, $C_1$-$C_6$ haloalkoxy, $C_1$-$C_6$ hydroxyalkyl, $-CO-$, $-SO_2R_{11}$, $-NR_{11}R_{12}$, $-NR_{11}COR_{12}$, $-NR_{10}CONR_{11}R_{12}$, $-CONR_{11}R_{12}$, $-CO_2R_{11}$, $-NR_{11}CO_2R_{12}$, $-SO_2NR_{11}R_{12}$, $-CONR_{11}$, $-C(O)R_{11}$ and $-NR_{11}SO_2R_{12}$ or an optionally substituted $C_1$-$C_6$ alkylene, $-C_2$-$C_6$ alkenylene or $-C_1$-$C_6$ alkyl group. For example, $Q_1$ may be selected from a halogen atom, hydrogen atom, a covalent bond, $NR_{10}$ a $C_1$-$C_6$ alkylene or $C_2$-$C_6$ alkenylene group which may be optionally substituted with hydroxy, a halogen atom, $C_1$-$C_6$ alkyl, $C_1$-$C_6$ haloalkyl, $C_1$-$C_6$ alkoxy, $C_1$-$C_6$ haloalkoxy, $C_1$-$C_6$ hydroxyalkyl, $-COR_{11}$, $-SO_2R_{11}$, $-NR_{11}R_{12}$, $-NR_{11}COR_{12}$, $-CONR_{11}R_{12}$, $-CO_2R_{11}$, $-NR_{11}CO_2R_{12}$, $-SO_2NR_{11}R_{12}-C(O)N$, $-C(O)$ and $-NR_{11}SO_2R_{12}$.

In another embodiment $Q_1$ may be selected from a hydrogen atom, a covalent bond, $NR_{10}$ or a $C_1$-$C_6$ alkylene, $-C_1$-$C_4$ alkylene, $C_1$-$C_2$ alkylene, $C_2$-$C_6$ alkenylene or $C_2$-$C_4$ alkenylene group which may be optionally substituted with hydroxy, a halogen atom (e.g. fluorine, chlorine or bromine), $C_1$-$C_6$ alkyl, $C_1$-$C_4$ alkyl, $C_1$-$C_2$ alkyl, $C_1$-$C_6$ haloalkyl, $C_1$-$C_4$ haloalkyl, $C_1$-$C_2$ haloalkyl, $C_1$-$C_6$ alkoxy, $C_1$-$C_4$ alkoxy, $C_1$-$C_2$ alkoxy, $C_1$-$C_6$ haloalkoxy, $C_1$-$C_4$ haloalkoxy, $C_1$-$C_2$ haloalkoxy, $-C_1$-$C_6$ hydroxyalkyl, $C_1$-$C_4$ hydroxyalkyl, $C_1$-$C_2$ hydroxyalkyl, $-COR_{11}$, $-SO_2R_{11}$, $-NR_{11}R_{12}$, $-NR_{11}COR_{12}$, $-CONR_{11}R_{12}$, $-CO_2R_{11}$, $-NR_{11}CO_2R_{12}$, $-SO_2NR_{11}R_{12}$ and $-NR_{11}SO_2R_{12}$.

In a further embodiment $Q_1$ may be selected from a covalent bond, $NR_{10}$ (e.g. methyamino), $-C_1$-$C_4$ alkylene (e.g. methylene or ethylene) or a $C_2$-$C_4$ alkenylene (e.g. vinyl) group which may be optionally substituted with hydroxy, a halogen atom (e.g. fluorine, bromine or chlorine), $C_1$-$C_4$ alkyl (e.g. propyl, isobutyl or tert butyl), $C_1$-$C_2$ alkyl (e.g. methyl or ethyl), $C_1$-$C_2$ haloalkyl (e.g. trifluoromethyl), $C_1$-$C_2$ alkoxy (e.g. methoxy or methoxymethyl), $C_1$-$C_2$ haloalkoxy (e.g. trifluoromethoxy), $C_1$-$C_2$ hydroxyalkyl (e.g. hydroxymethyl or hydroxyethyl), $-COR_{11}$ (e.g. acetyl), $-SO_2R_{11}$ (e.g. methylsulphonyl) $-NR_{11}R_{12}$ (e.g. amino or N,N-dimethylamino), $-NR_{11}COR_{12}$ (e.g. N-acetyl), $-CONR_{11}R_{12}$ (e.g. amido), $-CO_2R_{11}$ (e.g. methoxycarbonyl or ethoxycarbonyl), $-NR_{11}CO_2R_{12}$, $-SO_2NR_{11}R_{12}$ (e.g. dimethylaminosulphonyl) and $-NR_{11}SO_2R_{12}$.

In a further embodiment $Q_1$ may be selected from a halogen atom (e.g. bromine, chlorine or fluorine), $C_1$-$C_4$ alkyl (e.g. propyl or tert butyl), $C_1$-$C_2$ alkyl (e.g. methyl or ethyl), $C_1$-$C_2$ haloalkyl (e.g. trifluoromethyl), $C_1$-$C_2$ alkoxy (e.g. methoxy), $-COR_{11}$ (e.g. acetyl), $-SO_2R_{11}$ (e.g. methylsulphonyl), cyano, $CONR_{11}R_{12}$ and $C_1$-$C_2$ haloalkoxy (e.g. trifluoromethoxy).

In a further embodiment $Q_1$ may be selected from a halogen atom (e.g. bromine or chlorine), $C_1$-$C_4$ alkyl (e.g. propyl or tert butyl), $C_1$-$C_2$ alkyl (e.g. methyl or ethyl), $C_1$-$C_2$ haloalkyl (e.g. trifluoromethyl), $C_1$-$C_2$ alkoxy (e.g. methoxy), $-COR_{11}$ (e.g. acetyl) and $-SO_2R_{11}$ (e.g. methylsulphonyl).

In one embodiment $Q_2$ may be selected from a hydrogen atom, a covalent bond or an optionally substituted $C_1$-$C_6$ alkylene (e.g. $C_1$-$C_3$ alkylene, $C_1$-$C_4$ alkylene, $C_1$-$C_2$ alkylene, $C_2$-$C_6$ alkenylene, $C_2$-$C_4$ alkenylene.

In another embodiment $Q_2$ may be selected from a hydrogen atom, a covalent bond, $C_1$-$C_2$ alkylene (e.g. methylene, ethylene), $C_2$-$C_4$ alkenylene (e.g. ethenylene).

In a further embodiment $Q_2$ is selected from H, a covalent bond, methylene and ethylene.

When n is 0, $Q_1$ may be selected from a hydrogen atom, a halogen atom, optionally substituted $C_1$-$C_6$ alkyl, $COR_{11}$, $-SO_2R_{11}$, $-C(O)NR_{11}R_{12}$, optionally substituted $C_1$-$C_6$ alkoxy, $C_1$-$C_6$ haloalkyl and $C_1$-$C_6$ haloalkoxy, wherein $R_{11}$ and $R_{12}$ are as defined above.

Optionally, when n is 0, $Q_1$ may be selected from a hydrogen atom, a halogen atom, $C_1$-$C_6$ alkyl, $COR_{11}$ or $-SO_2R_{11}$, wherein $R_{11}$ is as defined above.

Alternatively, when n is 1 $Q_1$ may be selected from a covalent bond, $-CO-$, a $C_1$-$C_6$ alkylene or $C_2$-$C_6$ alkenylene group which may be optionally substituted with hydroxy and $-NR_{10}$.

In one embodiment n is 1

In one embodiment $R_9$ represents a 3 to 10 membered (e.g. 3, 4, 5, 6, 7, 8, 9 or 10 membered) heterocyclyl, heteroaryl or cycloalkyl ring which may be optionally substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, $C_2$-$C_6$ alkynyl, $C_1$-$C_6$ hydroxyalkyl, oxo, cyano, nitro, heterocyclyl, -$Q_2$-$NR_{13}CONR_{14}R_{15}$, -$Q_2$-$NR_{13}R_{14}$, -$Q_2$-$NR_{13}COR_{14}$, -$Q_2$-$COR_{13}$, -$Q_2$-$SO_2R_{13}$, -$Q_2$-$CONR_{13}R_{14}$, -$Q_2$-$CO_2R_{13}$, -$Q_2$-$SO_2NR_{13}R_{14}$, -$Q_2$-$NR_{13}SO_2R_{14}$ and -$Q_2$-$NR_{13}SO_2R_{14}R_{15}$.

In one embodiment $R_9$ represents a 3 to 10 membered (e.g. 3, 4, 5, 6, 7, 8, 9 or 10 membered) heterocyclyl, heteroaryl or cycloalkyl ring which may be optionally substituted with one or more (e.g. one, two or three) substituents selected from a halogen atom (e.g. fluorine, bromine or chlorine), $C_1$-$C_6$ haloalkyl, $C_1$-$C_4$ haloalkyl, $C_1$-$C_2$ haloalkyl, $C_1$-$C_6$ alkoxy, $C_1$-$C_4$ alkoxy, $C_1$-$C_2$ alkoxy, $C_1$-$C_6$ haloalkoxy, $C_1$-$C_4$ haloalkoxy, $C_1$-$C_2$ haloalkoxy, $C_1$-$C_6$ alkyl, $C_1$-$C_4$ alkyl, $C_1$-$C_2$ alkyl, $C_2$-$C_6$ alkenyl, $C_2$-$C_4$ alkenyl, $C_1$-$C_6$ hydroxyalkyl, oxo, cyano, -$Q_2$-$NR_{13}CONR_{14}$, -$Q_2$-$NR_{13}R_{14}$, -$Q_2$-$NR_{13}SO_2R_{14}$, -$Q_2$-$NR_{13}COR_{14}$, -$Q_2$-$COR_{13}$, -$Q_2$-$SO_2R_{13}$, -$Q_2$-$CONR_{13}$, -$Q_2$-$CO_2R_{13}$, -$Q_2$-$SO_2NR_{13}R_{14}$ and -$Q_2$-$NR_{13}SO_2R_{14}$.

In another embodiment $R_9$ represents a 3 to 10 membered (e.g. 3, 4, 5, 6, 7, 8, 9 or 10 membered) heterocyclyl, heteroaryl, aryl or cycloalkyl ring which may be optionally substituted with one or more (e.g. one, two or three) substituents selected from a halogen atom (e.g. fluorine, bromine or chlorine), $C_1$-$C_2$ alkoxy (e.g. methoxy, methoxymethyl), $C_1$-$C_4$ alkyl (e.g. methyl, ethyl, propyl, tert butyl), oxo, cyano, -$Q_2$-$NR_{13}CONR_{14}$ (e.g. acetamido, acetamidomethyl), -$Q_2$-$NR_{13}R_{14}$ (e.g. amino), -$Q_2$-$NR_{13}SO_2R_{14}$ (e.g. methylsulphonylamino), -$Q_2$-$SO_2R_{13}$ (e.g. methylsulphonyl) or a further optionally substituted 3 to 10 membered heterocyclyl, heteroaryl, aryl or cycloalkyl ring.

In another embodiment $R_9$ represents a 3 to 10 membered (e.g. 3, 4, 5, 6, 7, 8, 9 or 10 membered) heterocyclyl, aryl, heteroaryl or cycloalkyl ring such as morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl, triazolyl, isoquinolinyl, indazolyl, pyrazolopyridinyl, pyrazolopyrimidinyl, imidazolpyridinyl, imidazopyrimidinyl, imidazopyrazinyl, oxazolyl and quinolinyl, which may be optionally substituted. $R_9$ may be optionally substituted with one or more (e.g. one, two or three) substituents selected from a halogen atom (e.g. fluorine, bromine or chlorine), optionally substituted $C_1$-$C_3$alkoxy (e.g. methoxy, methoxymethyl), optionally substituted $C_1$-$C_4$alkyl (e.g. methyl, ethyl, propyl, tert butyl), oxo, cyano, -$Q_2$-$NR_{13}CONR_{14}$ (e.g. acetamido, acetamidomethyl), -$Q_2$-$NR_{13}R_{14}$ (e.g. amino), -$Q_2$-$NR_{13}SO_2R_{14}$ (e.g. methylsulphonylamino), -$Q_2$-$SO_2R_{13}$ (e.g. methylsulphonyl), -$Q_2$-$SO_2NR_{13}R_{14}$, and -$Q_2$-$CONR_{13}R_{14}$.

In yet another embodiment $R_9$ represents a 3 to 10 membered (e.g. 3, 4, 5, 6, 7, 8, 9 or 10 membered) heterocyclyl, aryl, heteroaryl or cycloalkyl ring such as morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl and triazolyl, which may be optionally substituted. $R_9$ may be optionally substituted with one or more (e.g. one, two or three) substituents selected from a halogen atom (e.g. fluorine, bromine or chlorine), $C_1$-$C_2$alkoxy (e.g. methoxy, methoxymethyl), $C_1$-$C_4$alkyl (e.g. methyl, ethyl, propyl, tert butyl), oxo, cyano, -$Q_2$-$NR_{13}CONR_{14}$ (e.g. acetamido, acetamidomethyl), -$Q_2$-$NR_{13}R_{14}$ (e.g. amino), -$Q_2$-$NR_{13}SO_2R_{14}$ (e.g. methylsulphonylamino), -$Q_2$-$SO_2R_{13}$ (e.g. methylsulphonyl).

In another embodiment $R_9$ represents a 3 to 10 membered (e.g. 3, 4, 5, 6, 7, 8, 9 or 10 membered) heterocyclyl, aryl, heteroaryl or cycloalkyl ring such as phenyl, morpholinyl, piperidinyl, pyrrolidinyl, diazepanyl, piperazinyl, cyclopropyl, cyclohexyl, cyclopentyl, pyridinyl, imidazolyl, indolinyl, pyrimidinyl, isoxazolyl, quinolinyl, triazolyl, isoquinolinyl, indazolyl, pyrazolopyridinyl, pyrazolopyrimidinyl, imidazolpyridinyl, imidazopyrimidinyl, imidazopyrazinyl, oxazolyl and quinolinyl, which may be optionally substituted with one or more (e.g. one, two or three) substituents selected from a halogen atom, $C_1$-$C_6$alkoxy, $C_1$-$C_6$alkyl, oxo, cyano, -$Q_2$-$NR_{13}CONR_{14}$, -$Q_2$-$NR_{13}R_{14}$, -$Q_2$-$NR_{13}SO_2R_{14}$, -$Q_2$-$SO_2NR_{13}R_{14}$, and -$Q_2$-$CONR_{13}R_{14}$.

In another embodiment $R_9$ represents a 3 to 10 membered (e.g. 3, 4, 5, 6, 7, 8, 9 or 10 membered) heterocyclyl, aryl, heteroaryl or cycloalkyl ring such as phenyl, morpholinyl, piperidinyl, pyrrolidinyl, diazepanyl, piperazinyl, cyclopropyl, cyclohexyl, cyclopentyl, pyridinyl, imidazolyl, indolinyl, pyrimidinyl, isoxazolyl, quinolinyl, triazolyl, which may be optionally substituted with one or more (e.g. one, two or three) substituents selected from a halogen atom, $C_1$-$C_6$alkoxy, $C_1$-$C_6$alkyl, oxo, cyano, -$Q_2$-$NR_{13}CONR_{14}$, -$Q_2$-$NR_{13}R_{14}$ and -$Q_2$-$NR_{13}SO_2R_{14}$.

In a further embodiment, $R_9$ represents an optionally substituted 5 or 6 membered monocyclic heterocyclyl, aryl, heteroaryl or cycloalkyl ring. In another embodiment, $R_9$ represents an optionally substituted 9 or 10 membered bicyclic heterocyclyl, aryl, heteroaryl or cycloalkyl ring.

In an even further embodiment $R_9$ represents an optionally substituted 6 membered heterocyclyl, aryl, heteroaryl or cycloalkyl ring.

Typical examples of the 3 to 10 membered heterocyclyl, aryl, heteroaryl or cycloalkyl ring of $R_9$ include piperidin-1-yl, indolin-1-yl, indolin-2-yl, piperazin-1-yl, pyrrolidin-1-yl, 3,4-dihydroisoquinolin-2 (1H)-yl, phenyl, pyridin-2,3,4-yl, imidazol-1-yl, isoxazol-4-yl, pyrimidin-4-yl, 1H-1,2,3-triazol-2-yl, thiazol-2-yl, thiazolyl, cyclohexyl cyclopropyl, indazol-5-yl, indozol-4-yl, pyrazolo[1,5-a]pyrimidin-7-yl, imidazo[1,2-a]pyrazine-6-yl, oxazol-5-yl, pyrazol-4-yl, isoxazol-4-yl, imidazole-4-yl and quinolin-4-yl.

In certain embodiments $R_9$ is selected from substituted or unsubstituted phenyl, morpholinyl, isoxazolyl, pyridinyl, piperazinyl, cyclopropyl, indolinyl, pyrrolidinyl, isoquinolinyl, indazolyl, pyrazolopyridinyl, pyrazolopyrimidinyl, imidazolpyridinyl, imidazopyrimidinyl, imidazopyrazinyl, oxazolyl and quinolinyl.

In certain embodiments $R_9$ is selected from substituted or unsubstituted phenyl, morpholinyl, isoxazolyl, pyridinyl, piperazinyl, cyclopropyl, indolinyl and pyrrolidinyl.

In certain embodiments $R_9$ is substituted or unsubstituted phenyl.

In one embodiment m is 1 or 2, preferably 2.

In another embodiment $R_{10}$, $R_{11}$ and $R_{12}$ each independently represent hydrogen or optionally substituted $C_1$-$C_6$ alkyl. $C_1$-$C_6$ alkyl may be substituted with one or more halogen, e.g. fluorine.

In another embodiment $R_{10}$, $R_{11}$ and $R_{12}$ each independently represent hydrogen, $C_1$-$C_6$ alkyl, $C_1$-$C_4$ alkyl or $C_1$-$C_2$ alkyl.

In another embodiment $R_{10}$, $R_{11}$ and $R_{12}$ each independently represent hydrogen or $C_1$-$C_2$ alkyl (e.g. methyl or ethyl).

$R_{10}$, $R_{11}$ and $R_{12}$ can each independently represent an optionally substituted $C_1$-$C_6$ alkylene group which acts a linking moiety to a further ring.

$R_{13}$, $R_{14}$ and $R_{15}$ each independently represent hydrogen or an optionally substituted $C_1$-$C_6$ alkyl, or an optionally substituted heterocyclyl, or an optionally substituted heteroaryl, or an optionally substituted aryl, or an optionally substituted cycloalkyl. $R_{13}$, $R_{14}$ and $R_{15}$ may each independently represent hydrogen or $C_1$-$C_3$ alkyl.

In a further embodiment n is 0 and $R_1$ may be optionally substituted by one or more (e.g. one, two, three or four) $Q_1$ substituents independently selected from a halogen atom (e.g. bromine, chlorine or fluorine), $C_1$-$C_4$ alkyl (e.g. propyl or tert butyl), $C_1$-$C_2$ alkyl (e.g. methyl or ethyl), $C_1$-$C_2$ haloalkyl (e.g. trifluoromethyl), $C_1$-$C_2$ alkoxy (e.g. methoxy), —$COR_{11}$ (e.g. acetyl), —$SO_2R_{11}$ (e.g. methylsulphonyl), cyano, $CONR_{11}R_{12}$ and $C_1$-$C_2$ haloalkoxy.

In a further embodiment n is 0 and $R_1$ may be optionally substituted by one or more (e.g. one, two, three or four) $Q_1$ substituents independently selected from a halogen atom (e.g. bromine or chlorine), $C_1$-$C_4$ alkyl (e.g. propyl or tert butyl), $C_1$-$C_2$ alkyl (e.g. methyl or ethyl), $C_1$-$C_2$ haloalkyl (e.g. trifluoromethyl), $C_1$-$C_2$ alkoxy (e.g. methoxy), —$COR_{11}$ (e.g. acetyl) and —$SO_2R_{11}$ (e.g. methylsulphonyl).

In one embodiment n is 0 and $R_1$ represents a 5 or 6 membered heteroaryl ring which may be optionally substituted with one or more (e.g. one, two, three or four) $Q_1$ substituents independently selected from a halogen atom (e.g. fluorine, bromine or chlorine), $C_1$-$C_4$ alkyl (e.g. propyl, isobutyl or tert butyl), $C_1$-$C_2$ alkyl (e.g. methy or ethyl), $C_1$-$C_2$ haloalkyl (e.g. trifluoromethyl), $C_1$-$C_2$ alkoxy (e.g. methoxy or methoxymethy), $C_1$-$C_2$ haloalkoxy (e.g. trifluoromethoxy), $C_1$-$C_2$ hydroxyalkyl (e.g. hydroxymethyl or hydroxyethyl), —$COR_{11}$ (e.g. acetyl), —$SO_2R_{11}$ (e.g. methylsulphonyl), —$NR_{11}R_{12}$ (e.g. amino or N,N-dimethylamino), —$NR_{11}COR_{12}$ (e.g. N-acetyl), —$CONR_{11}R_{12}$ (e.g. amido), —$CO_2R_{11}$ (e.g. methoxycarbonyl or ethoxycarbonyl), —$NR_{11}CO_2R_{12}$, —$SO_2NR_{11}R_{12}$ (e.g. dimethylaminosulphonyl) and —$NR_{11}SO_2R_{12}$;

In another embodiment n is 0 and $R_1$ represents 9 membered heteroaryl ring which may be optionally substituted with one or more (e.g. one, two, three or four) $Q_1$ substituents independently selected from a halogen atom (e.g. fluorine, bromine or chlorine), $C_1$-$C_4$ alkyl (e.g. propyl, isobutyl or tert butyl), $C_1$-$C_2$ alkyl (e.g. methy or ethyl), $C_1$-$C_2$ haloalkyl (e.g. trifluoromethyl), $C_1$-$C_2$ alkoxy (e.g. methoxy or methoxymethy), $C_1$-$C_2$ haloalkoxy (e.g. trifluoromethoxy), $C_1$-$C_2$ hydroxyalkyl (e.g. hydroxymethyl or hydroxyethyl), —$COR_{11}$ (e.g. acetyl), —$SO_2R_{11}$ (e.g. methylsulphonyl) —$NR_{11}R_{12}$ (e.g. amino or N,N-dimethylamino), —$NR_{11}COR_{12}$ (e.g. N-acetyl), —$CONR_{11}R_{12}$ (e.g. amido) —$CO_2R_{11}$ (e.g. methoxycarbonyl or ethoxycarbonyl), —$NR_{11}CO_2R_{12}$, —$SO_2NR_{11}R_{12}$ (e.g. dimethylaminosulphonyl) and —$NR_{11}SO_2R_{12}$;

In another embodiment n is 0 and $R_1$ represents 9 membered heteroaryl ring which may be optionally substituted with one or more (e.g. one, two, three or four) $Q_1$ substituents independently selected from a halogen atom (e.g. fluorine, bromine or chlorine), cyano, $C_1$-$C_4$ alkyl (e.g. propyl, isobutyl or tert butyl), $C_1$-$C_2$ alkyl (e.g. methy or ethyl), $C_1$-$C_2$ haloalkyl (e.g. trifluoromethyl), $C_1$-$C_2$ alkoxy (e.g. methoxy or methoxymethy), $C_1$-$C_2$ haloalkoxy (e.g. trifluoromethoxy), $C_1$-$C_2$ hydroxyalkyl (e.g. hydroxymethyl or hydroxyethyl), —$COR_{11}$ (e.g. acetyl), —$SO_2R_{11}$ (e.g. methylsulphonyl) —$NR_{11}R_{12}$ (e.g. amino or N,N-dimethylamino), —$NR_{11}COR_{12}$ (e.g. N-acetyl), —$CONR_{11}R_{12}$ (e.g. amido) —$CO_2R_{11}$ (e.g. methoxycarbonyl or ethoxycarbonyl), —$NR_{11}CO_2R_{12}$, —$SO_2NR_{11}R_{12}$ (e.g. dimethylaminosulphonyl) and —$NR_{11}SO_2R_{12}$;

Compounds of the disclosure may have a nitrogen atom in the ortho position with respect to the carbon atom attached to the amide nitrogen. In such instances $R_1$ has an ortho nitrogen atom to form compounds including the moiety N—C—NH—CO; as represented by the Formula (IV):

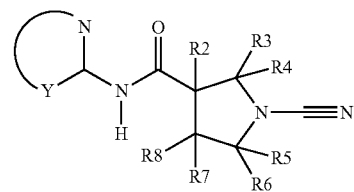

(IV)

or a pharmaceutically acceptable salt thereof, wherein:

Y represents the remaining atoms of a 5 or 6 membered heteroaryl ring which may optionally substituted or fused with further ring which may be further optionally substituted;

$R_2$, $R_3$, $R_4$, $R_5$, $R_6$ and $R_8$ each independently represent a hydrogen atom, cyano, an optionally substituted $C_1$-$C_6$ alkyl, an optionally substituted $C_1$-$C_6$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, or $R_6$ is linked to $R_7$ to form an optionally substituted $C_3$-$C_4$ cycloalkyl ring; and $R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group, or is linked to $R_6$ to form an optionally substituted $C_3$-$C_4$ cycloalkyl ring.

In one embodiment, Y represents the remaining atoms of a 5 or 6 membered heteroaryl ring which may optionally substituted or fused with further ring which may be further optionally substituted;

$R_2$, $R_3$, $R_4$, $R_5$, $R_6$ and $R_8$ each independently represent a hydrogen atom, cyano, an optionally substituted $C_1$-$C_6$ alkyl, an optionally substituted $C_1$-$C_6$ alkoxy group, one or more spirocyclic groups where $R_3$ is linked to $R_4$, $R_5$ is linked to $R_6$ or $R_8$ is linked to $R_7$, or $R_2$ is linked to $R_8$ to form a $C_3$-$C_4$ cycloalkyl ring; and $R_7$ represents a hydrogen atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group.

The moiety symbolised by Y may be substituted according to $Q_1$-$(R_9)_n$ as defined herein.

Examples of $R_1$ include those shown below:

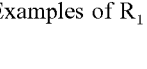

A

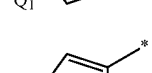

B

C

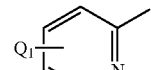

D

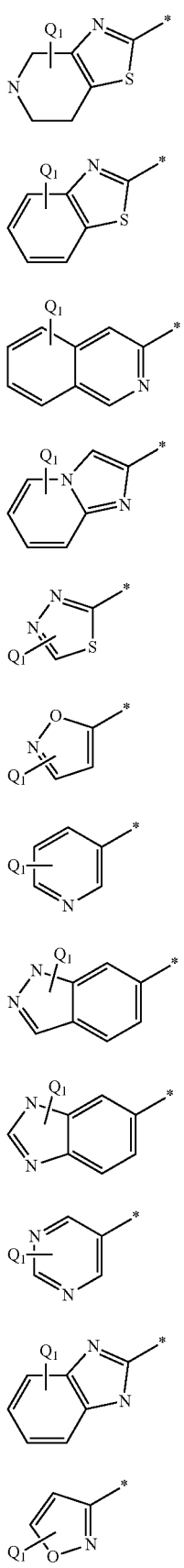

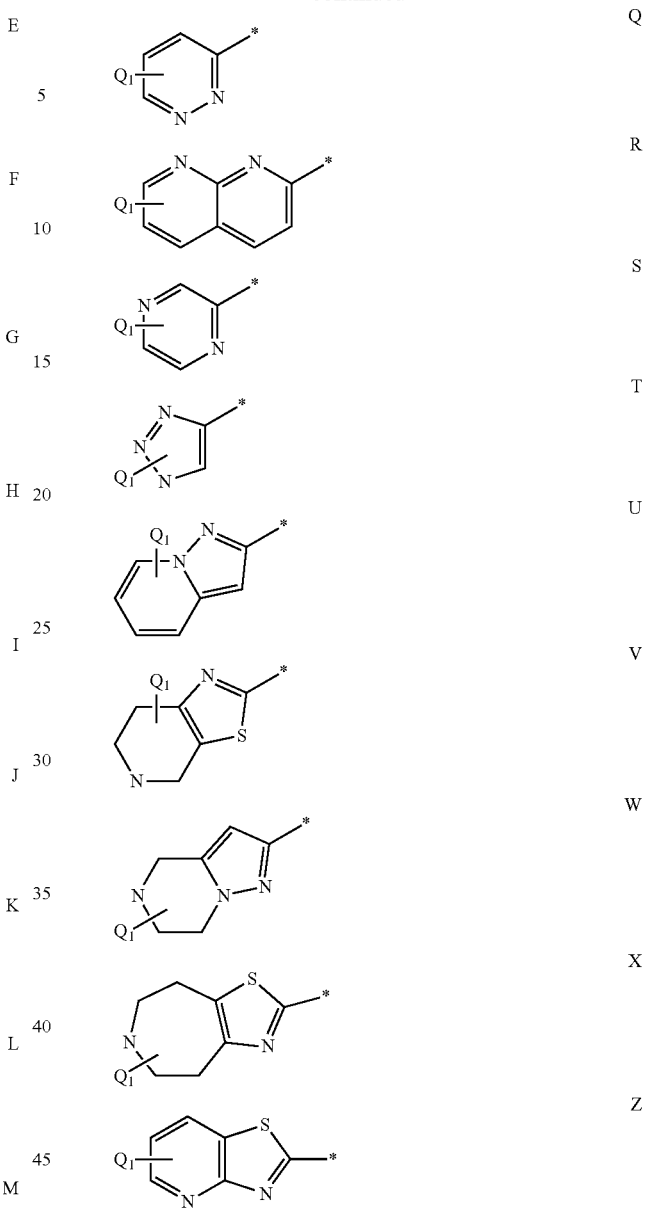

Examples of compounds of the invention include:
(S)-1-cyano-N-(5-phenylthiazol-2-yl)pyrrolidine-3-carboxamide
1-cyano-N-(5-(3-fluorophenyl)thiazol-2-yl)pyrrolidine-3-carboxamide
1-cyano-N-(5-(2-fluorophenyl)thiazol-2-yl)pyrrolidine-3-carboxamide
N-(5-(4-chlorophenyl)thiazol-2-yl)-1-cyanopyrrolidine-3-carboxamide
N-(5-(3-chlorophenyl)thiazol-2-yl)-1-cyanopyrrolidine-3-carboxamide
N-(5-(2-chlorophenyl)thiazol-2-yl)-1-cyanopyrrolidine-3-carboxamide
1-cyano-N-(5-methylthiazol-2-yl)pyrrolidine-3-carboxamide
N-(5-(tert-butyl)thiazol-2-yl)-1-cyanopyrrolidine-3-carboxamide
1-cyano-N-(4-phenylthiazol-2-yl)pyrrolidine-3-carboxamide 1-cyano-N-(2-phenylthiazol-5-yl)pyrrolidine-3-carboxamide
1-cyano-N-(5-phenyl-1,3,4-thiadiazol-2-yl)pyrrolidine-3-carboxamide
1-cyano-N-(5-ethyl-1,3,4-thiadiazol-2-yl)pyrrolidine-3-carboxamide
1-cyano-N-(3-phenylisoxazol-5-yl)pyrrolidine-3-carboxamide
1-cyano-N-(3-(4-methoxyphenyl)isoxazol-5-yl)pyrrolidine-3-carboxamide
1-cyano-N-(5-phenylisoxazol-3-yl)pyrrolidine-3-carboxamide
N-(5-(tert-butyl)isoxazol-3-yl)-1-cyanopyrrolidine-3-carboxamide
N-(3-(tert-butyl)-1H-pyrazol-5-yl)-1-cyanopyrrolidine-3-carboxamide
N-(benzo[d]thiazol-2-yl)-1-cyanopyrrolidine-3-carboxamide
1-cyano-N-(6-methylbenzo[d]thiazol-2-yl)pyrrolidine-3-carboxamide
1-cyano-N-(6-(trifluoromethyl)benzo[d]thiazol-2-yl)pyrrolidine-3-carboxamide
1-cyano-N-(6-methoxybenzo[d]thiazol-2-yl)pyrrolidine-3-carboxamide
N-(6-bromobenzo[d]thiazol-2-yl)-1-cyanopyrrolidine-3-carboxamide
N-(1H-benzo[d]imidazol-2-yl)-1-cyanopyrrolidine-3-carboxamide
1-cyano-N-(pyridin-2-yl)pyrrolidine-3-carboxamide
N-(5-chloropyridin-2-yl)-1-cyanopyrrolidine-3-carboxamide
1-cyano-N-(5-methylpyridin-2-yl)pyrrolidine-3-carboxamide
1-cyano-N-(5-methoxypyridin-2-yl)pyrrolidine-3-carboxamide
1-cyano-N-(5-morpholinopyridin-2-yl)pyrrolidine-3-carboxamide
1-cyano-N-(5-(piperidin-1-yl)pyridin-2-yl)pyrrolidine-3-carboxamide
N-(5-(1H-imidazol-1-yl)pyridin-2-yl)-1-cyanopyrrolidine-3-carboxamide
1-cyano-N-(4-phenylpyridin-2-yl)pyrrolidine-3-carboxamide
N-([2,3'-bipyridin]-6'-yl)-1-cyanopyrrolidine-3-carboxamide
N-([3,3'-bipyridin]-6-yl)-1-cyanopyrrolidine-3-carboxamide
N-([3,4'-bipyridin]-6-yl)-1-cyanopyrrolidine-3-carboxamide
1-cyano-N-(6-phenylpyridin-3-yl)pyrrolidine-3-carboxamide
1-cyano-N-(6-phenylpyridazin-3-yl)pyrrolidine-3-carboxamide
1-cyano-N-(2-phenylpyrimidin-5-yl)pyrrolidine-3-carboxamide
1-cyano-N-(5-cyclohexylpyridin-2-yl)pyrrolidine-3-carboxamide
N-(1-benzyl-1H-indazol-5-yl)-1-cyanopyrrolidine-3-carboxamide
1-cyano-N-(1-propyl-1H-benzo[d]imidazol-5-yl)pyrrolidine-3-carboxamide
(S)-1-cyano-N-(1-phenyl-1H-imidazol-4-yl)pyrrolidine-3-carboxamide
(S)-1-cyano-N-(5-phenyl-1H-pyrazol-3-yl)pyrrolidine-3-carboxamide
(S)-1-cyano-N-(5-(tetrahydro-2H-pyran-4-yl)-1H-pyrazol-3-yl)pyrrolidine-3-carboxamide
(S)-1-cyano-N-(1-phenyl-1H-1,2,3-triazol-4-yl)pyrrolidine-3-carboxamide
(S)-1-cyano-N-(1-phenyl-1H-pyrazol-3-yl)pyrrolidine-3-carboxamide
(S)-1-cyano-N-(4-methylbenzo[d]thiazol-2-yl)pyrrolidine-3-carboxamide
(S)-1-cyano-N-(7-methylbenzo[d]thiazol-2-yl)pyrrolidine-3-carboxamide
(S)—N-(4-bromobenzo[d]thiazol-2-yl)-1-cyanopyrrolidine-3-carboxamide
(S)-1-cyano-N-(imidazo[1,2-a]pyridin-2-yl)pyrrolidine-3-carboxamide
(S)—N-(7-bromoimidazo[1,2-a]pyridin-2-yl)-1-cyanopyrrolidine-3-carboxamide
(S)—N-(6-bromoimidazo[1,2-a]pyridin-2-yl)-1-cyanopyrrolidine-3-carboxamide
(S)-1-cyano-N-(pyrazolo[1,5-a]pyridin-2-yl)pyrrolidine-3-carboxamide
(S)-1-cyano-N-(4-methoxypyridin-2-yl)pyrrolidine-3-carboxamide
(S)-1-cyano-N-(5-phenylpyridin-2-yl)pyrrolidine-3-carboxamide
(S)-1-cyano-N-(6-phenylpyridin-2-yl)pyrrolidine-3-carboxamide
(S)-1-cyano-N-(1,8-naphthyridin-2-yl)pyrrolidine-3-carboxamide
(S)—N-(5-benzylthiazol-2-yl)-1-cyanopyrrolidine-3-carboxamide
(S)-1-cyano-N-(isoquinolin-3-yl)pyrrolidine-3-carboxamide
(S)-1-cyano-N-(5-(tetrahydro-2H-pyran-4-yl)thiazol-2-yl)pyrrolidine-3-carboxamide
(S)-1-cyano-N-(1-methyl-5-phenyl-1H-pyrazol-3-yl)pyrrolidine-3-carboxamide
1-cyano-N-(5-(4-methoxypiperidin-1-yl)pyridin-2-yl)pyrrolidine-3-carboxamide
(S)—N-(6-(1H-1,2,3-triazol-1-yl)benzo[d]thiazol-2-yl)-1-cyanopyrrolidine-3-carboxamide
(S)—N-(6-(2H-1,2,3-triazol-2-yl)benzo[d]thiazol-2-yl)-1-cyanopyrrolidine-3-carboxamide
(S)-1-cyano-N-(5-(4-(methylcarbamoyl)phenyl)thiazol-2-yl)pyrrolidine-3-carboxamide
(S)-1-cyano-N-(4-methyl-5-(morpholinomethyl)thiazol-2-yl)pyrrolidine-3-carboxamide
(S)-1-cyano-N-(5-(4-fluorophenyl)thiazol-2-yl)pyrrolidine-3-carboxamide
(S)-1-cyano-N-(5-(3,4-difluorophenyl)thiazol-2-yl)pyrrolidine-3-carboxamide
(S)-1-cyano-N-(5-(4-(trifluoromethyl)phenyl)thiazol-2-yl)pyrrolidine-3-carboxamide
(S)-1-cyano-N-(5-(pyridin-4-yl)thiazol-2-yl)pyrrolidine-3-carboxamide
(S)-1-cyano-N-(5-(pyridin-2-yl)thiazol-2-yl)pyrrolidine-3-carboxamide
(R)-1-cyano-N-(5-phenylpyridin-2-yl)pyrrolidine-3-carboxamide
(2S,3S)-1-cyano-2-methyl-N-(5-phenylthiazol-2-yl)pyrrolidine-3-carboxamide
(2S,3S)-1-cyano-N-(5-(4-fluorophenyl)thiazol-2-yl)-2-methylpyrrolidine-3-carboxamide
(2S,3S)-1-cyano-2-methyl-N-(1-phenyl-1H-imidazol-4-yl)pyrrolidine-3-carboxamide
(2S,3S)-1-cyano-2-methyl-N-(5-phenyl-1H-pyrazol-3-yl)pyrrolidine-3-carboxamide
(2S,3S)-1-cyano-2-methyl-N-(5-(tetrahydro-2H-pyran-4-yl)thiazol-2-yl)pyrrolidine-3-carboxamide (2S,3S)—N-(5-(2-chlorophenyl)thiazol-2-yl)-1-cyano-2-methylpyrrolidine-3-carboxamide
1-cyano-3-methyl-N-(5-phenylthiazol-2-yl)pyrrolidine-3-carboxamide
1-cyano-3-methyl-N-(1-phenyl-1H-imidazol-4-yl)pyrrolidine-3-carboxamide
1-cyano-3-(methoxymethyl)-N-(5-phenylthiazol-2-yl)pyrrolidine-3-carboxamide
1,3-dicyano-N-(5-phenylthiazol-2-yl)pyrrolidine-3-carboxamide
(3S,4S)-1-cyano-4-methyl-N-(5-phenylthiazol-2-yl)pyrrolidine-3-carboxamide
(3S,4S)-1-cyano-4-methyl-N-(5-methylthiazol-2-yl)pyrrolidine-3-carboxamide
(3S,4S)—N-(5-(2-chlorophenyl)thiazol-2-yl)-1-cyano-4-methylpyrrolidine-3-carboxamide
(3S,4S)-1-cyano-4-methyl-N-(1-phenyl-1H-imidazol-4-yl)pyrrolidine-3-carboxamide
(3S,4S)-1-cyano-4-ethyl-N-(5-phenylthiazol-2-yl)pyrrolidine-3-carboxamide
(3S,4S)-1-cyano-4-ethyl-N-(1-phenyl-1H-imidazol-4-yl)pyrrolidine-3-carboxamide
1-cyano-5-methyl-N-(5-phenylthiazol-2-yl)pyrrolidine-3-carboxamide
1-cyano-5-methyl-N-(1-phenyl-1H-imidazol-4-yl)pyrrolidine-3-carboxamide
1-cyano-5-methyl-N-(5-phenyl-1H-pyrazol-3-yl)pyrrolidine-3-carboxamide
(S)-1-cyano-N-(5-morpholinothiazol-2-yl)pyrrolidine-3-carboxamide
1-cyano-N-(5-(4-methylpiperazin-1-yl)thiazol-2-yl)pyrrolidine-3-carboxamide
N-(5-(2-(acetamidomethyl)piperidin-1-yl)thiazol-2-yl)-1-cyanopyrrolidine-3-carboxamide
1-cyano-N-(5-(methyl(phenyl)amino)thiazol-2-yl)pyrrolidine-3-carboxamide
1-cyano-N-(5-(indolin-1-yl)thiazol-2-yl)pyrrolidine-3-carboxamide
(S)-1-cyano-N-(5-(piperidin-1-yl)thiazol-2-yl)pyrrolidine-3-carboxamide
(S)-1-cyano-N-(5-(isoindolin-2-yl)thiazol-2-yl)pyrrolidine-3-carboxamide
(S)-1-cyano-N-(5-(3,4-dihydroisoquinolin-2 (1H)-yl)thiazol-2-yl)pyrrolidine-3-carboxamide
(S)-1-cyano-N-(5-((R)-2-(methoxymethyl)pyrrolidin-1-yl)thiazol-2-yl)pyrrolidine-3-carboxamide
(S)-1-cyano-N-(5-((S)-2-(methoxymethyl)pyrrolidin-1-yl)thiazol-2-yl)pyrrolidine-3-carboxamide
(S)-1-cyano-N-(5-(5-oxo-1,4-diazepan-1-yl)thiazol-2-yl)pyrrolidine-3-carboxamide
(R)-1-cyano-N-(5-morpholinothiazol-2-yl)pyrrolidine-3-carboxamide
(R)-1-cyano-N-(5-(piperidin-1-yl)thiazol-2-yl)pyrrolidine-3-carboxamide
(3S,4S)-1-cyano-4-methyl-N-(5-(piperidin-1-yl)thiazol-2-yl)pyrrolidine-3-carboxamide
1-cyano-5-methyl-N-(5-(piperidin-1-yl)thiazol-2-yl)pyrrolidine-3-carboxamide
(S)-1-cyano-N-(6-(pyrrolidin-1-yl)pyridin-2-yl)pyrrolidine-3-carboxamide
(S)-1-cyano-N-(4-(pyrrolidin-1-yl)pyridin-2-yl)pyrrolidine-3-carboxamide
(S)-1-cyano-N-(5-(pyrrolidin-1-yl)pyrazin-2-yl)pyrrolidine-3-carboxamide
N-(5-(2-aminophenyl)thiazol-2-yl)-1-cyanopyrrolidine-3-carboxamide
N-(5-(3-aminophenyl)thiazol-2-yl)-1-cyanopyrrolidine-3-carboxamide
N-(5-(4-aminophenyl)thiazol-2-yl)-1-cyanopyrrolidine-3-carboxamide
1-cyano-N-(5-(pyridin-3-yl)thiazol-2-yl)pyrrolidine-3-carboxamide
(E)-1-cyano-N-(5-(2-cyclopropylvinyl)thiazol-2-yl)pyrrolidine-3-carboxamide
N-(5-(4-acetamidophenyl)thiazol-2-yl)-1-cyanopyrrolidine-3-carboxamide
N-(5-(2-acetamidophenyl)thiazol-2-yl)-1-cyanopyrrolidine-3-carboxamide
1-cyano-N-(5-(3-(methylsulfonamido)phenyl)thiazol-2-yl)pyrrolidine-3-carboxamide
(S)-1-cyano-N-(5-(3-cyanophenyl)thiazol-2-yl)pyrrolidine-3-carboxamide
(S)-1-cyano-N-(5-(4-cyanophenyl)thiazol-2-yl)pyrrolidine-3-carboxamide
1-cyano-N-(5-(3,5-dimethylisoxazol-4-yl)benzo[d]thiazol-2-yl)pyrrolidine-3-carboxamide
(S)-1-cyano-N-(6-(3,5-dimethylisoxazol-4-yl)benzo[d]thiazol-2-yl)pyrrolidine-3-carboxamide
(S)-1-cyano-N-(6-(4-methoxyphenyl)benzo[d]thiazol-2-yl)pyrrolidine-3-carboxamide
(S)-1-cyano-N-(6-phenylbenzo[d]thiazol-2-yl)pyrrolidine-3-carboxamide
(S)-1-cyano-N-(6-(1-methyl-1H-pyrazol-5-yl)benzo[d]thiazol-2-yl)pyrrolidine-3-carboxamide
(S)-1-cyano-N-(6-(1-methyl-1H-pyrazol-4-yl)benzo[d]thiazol-2-yl)pyrrolidine-3-carboxamide
(S)-1-cyano-N-(6-(3,5-dimethyl-1H-pyrazol-4-yl)benzo[d]thiazol-2-yl)pyrrolidine-3-carboxamide
(S)-1-cyano-N-(6-(5-methylisoxazol-4-yl)benzo[d]thiazol-2-yl)pyrrolidine-3-carboxamide
(S)-1-cyano-N-(7-(3,5-dimethylisoxazol-4-yl)imidazo[1,2-a]pyridin-2-yl)pyrrolidine-3-carboxamide
(S)-1-cyano-N-(6-(3,5-dimethylisoxazol-4-yl)imidazo[1,2-a]pyridin-2-yl)pyrrolidine-3-carboxamide
(S)-1-cyano-N-(6-cyclopropylimidazo[1,2-a]pyridin-2-yl)pyrrolidine-3-carboxamide
1-cyano-N-(6-cyclopropylbenzo[d]thiazol-2-yl)pyrrolidine-3-carboxamide
(S)-1-cyano-N-(6-(3,6-dimethoxypyridazin-4-yl)imidazo[1,2-a]pyridin-2-yl)pyrrolidine-3-carboxamide
(S)-1-cyano-N-(6-(3,6-dimethoxypyridazin-4-yl)benzo[d]thiazol-2-yl)pyrrolidine-3-carboxamide
(2S,3S)-1-cyano-N-(6-(3, 5-dimethylisoxazol-4-yl)benzo[d]thiazol-2-yl)-2-methylpyrrolidine-3-carboxamide
1-cyano-N-(5-(p-tolyl)pyridin-2-yl)pyrrolidine-3-carboxamide
1-cyano-N-(5-(m-tolyl)pyridin-2-yl)pyrrolidine-3-carboxamide
1-cyano-N-(5-(o-tolyl)pyridin-2-yl)pyrrolidine-3-carboxamide
(S)-1-cyano-N-(6-(3,5-dimethylisoxazol-4-yl)-5-methylimidazo[1,2-a]pyridin-2-yl)pyrrolidine-3-carboxamide
(S)-1-cyano-N-(6-(3,5-dimethylisoxazol-4-yl)-7-methylbenzo[d]thiazol-2-yl)pyrrolidine-3-carboxamide
(S)-1-cyano-N-(7-methyl-6-(1-methyl-1H-pyrazol-4-yl)benzo[d]thiazol-2-yl)pyrrolidine-3-carboxamide
1-cyano-N-(5-(morpholinomethyl)thiazol-2-yl)pyrrolidine-3-carboxamide
1-cyano-N-(5-(pyrrolidin-1-ylmethyl)thiazol-2-yl)pyrrolidine-3-carboxamide
(3S)-1-cyano-N-(5-((2,6-dimethylmorpholino)methyl)thiazol-2-yl)pyrrolidine-3-carboxamide (S)-1-cyano-N-(5-(((R)-2-(methoxymethyl)pyrrolidin-1-yl)methyl)thiazol-2-yl)pyrrolidine-3-carboxamide
(S)-1-cyano-N-(5-(((S)-2-(methoxymethyl)pyrrolidin-1-yl)methyl)thiazol-2-yl)pyrrolidine-3-carboxamide
(2S,3S)-1-cyano-N-(5-(4R)-2-(methoxymethyl)pyrrolidin-1-yl)methyl)thiazol-2-yl)-2-methylpyrrolidine-3-carboxamide
(S)—N-(1-benzyl-1H-imidazol-4-yl)-1-cyanopyrrolidine-3-carboxamide
(S)-1-cyano-N-(1-phenethyl-1H-imidazol-4-yl)pyrrolidine-3-carboxamide
(S)-1-cyano-N-(1-isobutyl-1H-imidazol-4-yl)pyrrolidine-3-carboxamide
(2S,3S)—N-(1-benzyl-1H-imidazol-4-yl)-1-cyano-2-methylpyrrolidine-3-carboxamide
(S)-1-cyano-N-(1-(4-fluorophenyl)-1H-imidazol-4-yl)pyrrolidine-3-carboxamide
(S)-1-cyano-N-(1-(3-fluorophenyl)-1H-imidazol-4-yl)pyrrolidine-3-carboxamide
(S)-1-cyano-N-(1-(2-fluorophenyl)-1H-imidazol-4-yl)pyrrolidine-3-carboxamide
(S)-1-cyano-N-(1-(4-(trifluoromethyl)phenyl)-1H-imidazol-4-yl)pyrrolidine-3-carboxamide
(S)-1-cyano-N-(1-(3-(trifluoromethyl)phenyl)-1H-imidazol-4-yl)pyrrolidine-3-carboxamide
(S)-1-cyano-N-(1-(4-(methylcarbamoyl)phenyl)-1H-imidazol-4-yl)pyrrolidine-3-carboxamide
(S)-1-cyano-N-(1-(3-(methylcarbamoyl)phenyl)-1H-imidazol-4-yl)pyrrolidine-3-carboxamide
(S)-1-cyano-N-(1-(2-(methylcarbamoyl)phenyl)-1H-imidazol-4-yl)pyrrolidine-3-carboxamide
(S)-1-cyano-N-(1-(4-((2-methoxyethyl)carbamoyl)phenyl)-1H-imidazol-4-yl)pyrrolidine-3-carboxamide
(S)-1-cyano-N-(1-(4-methoxyphenyl)-1H-imidazol-4-yl)pyrrolidine-3-carboxamide
(S)-1-cyano-N-(1-(2-methoxyphenyl)-1H-imidazol-4-yl)pyrrolidine-3-carboxamide
(S)-1-cyano-N-(1-(tetrahydro-2H-pyran-4-yl)-1H-imidazol-4-yl)pyrrolidine-3-carboxamide
(S)-1-cyano-N-(1-cyclohexyl-1H-imidazol-4-yl)pyrrolidine-3-carboxamide
(3S)-1-cyano-N-(1-(2,3-dihydro-1H-inden-1-yl)-1H-imidazol-4-yl)pyrrolidine-3-carboxamide
(S)-1-cyano-N-(1-(2,3-dihydro-1H-inden-2-yl)-1H-imidazol-4-yl)pyrrolidine-3-carboxamide
(S)-1-cyano-N-(1-(((tetrahydro-2H-pyran-4-yl)methyl)-1H-imidazol-4-yl)pyrrolidine-3-carboxamide
(S)-1-cyano-N-(1((S)-1-phenylethyl)-1H-imidazol-4-yl)pyrrolidine-3-carboxamide
(S)-1-cyano-N-(1-((R)-1-phenylethyl)-1H-imidazol-4-yl)pyrrolidine-3-carboxamide
(S)-1-cyano-N-(1-(pyridin-2-ylmethyl)-1H-imidazol-4-yl)pyrrolidine-3-carboxamide
(S)-1-cyano-N-(1-(pyridin-3-ylmethyl)-1H-imidazol-4-yl)pyrrolidine-3-carboxamide
(S)-1-cyano-N-(1-(pyridin-4-ylmethyl)-1H-imidazol-4-yl)pyrrolidine-3-carboxamide
(S)-1-cyano-N-(1-((3,5-dimethylisoxazol-4-yl)methyl)-1H-imidazol-4-yl)pyrrolidine-3-carboxamide
(2S,3S)-1-cyano-2-methyl-N-(1-((S)-1-phenylethyl)-1H-imidazol-4-yl)pyrrolidine-3-carboxamide
(3S,4S)-1-cyano-4-methyl-N-(1((S)-1-phenylethyl)-1H-imidazol-4-yl)pyrrolidine-3-carboxamide
(S)-1-cyano-N-(1-(4-methylpyridin-2-yl)-1H-imidazol-4-yl)pyrrolidine-3-carboxamide
(S)-1-cyano-N-(1-(6-methylpyridin-2-yl)-1H-imidazol-4-yl)pyrrolidine-3-carboxamide
(R)-1-cyano-N-(1-(2-methylpyrimidin-4-yl)-1H-imidazol-4-yl)pyrrolidine-3-carboxamide
(S)-1-cyano-N-(1-(4-cyanophenyl)-1H-imidazol-4-yl)pyrrolidine-3-carboxamide
(S)—N-(1-benzyl-2-methyl-1H-imidazol-4-yl)-1-cyanopyrrolidine-3-carboxamide
(S)-1-cyano-N-(1-(2-(3,5-dimethylisoxazol-4-yl)ethyl)-1H-imidazol-4-yl)pyrrolidine-3-carboxamide
(S)-1-cyano-N-(1-(3-cyanophenyl)-1H-imidazol-4-yl)pyrrolidine-3-carboxamide
(S)-1-cyano-N-(1-(pyridin-3-yl)-1H-imidazol-4-yl)pyrrolidine-3-carboxamide
(S)-1-cyano-N-(1-(pyridin-4-yl)-1H-imidazol-4-yl)pyrrolidine-3-carboxamide
(S)-1-cyano-N-(1-(3-methoxyphenyl)-1H-imidazol-4-yl)pyrrolidine-3-carboxamide
(3S)—N-(1-(1-benzoylpiperidin-3-yl)-1H-imidazol-4-yl)-1-cyanopyrrolidine-3-carboxamide
(3S)—N-(1-(1-benzoylpyrrolidin-3-yl)-1H-imidazol-4-yl)-1-cyanopyrrolidine-3-carboxamide
(3S)—N-(1-(1-benzylpiperidin-3-yl)-1H-imidazol-4-yl)-1-cyanopyrrolidine-3-carboxamide
(3S)-1-cyano-N-(1-(1-methylpiperidin-3-yl)-1H-imidazol-4-yl)pyrrolidine-3-carboxamide
(3S)-1-cyano-N-(1-(1-methylpyrrolidin-3-yl)-1H-imidazol-4-yl)pyrrolidine-3-carboxamide
(S)—N-(5-acetyl-4,5,6,7-tetrahydrothiazolo[5,4-c]pyridin-2-yl)-1-cyanopyrrolidine-3-carboxamide
(S)-1-cyano-N-(5-isobutyryl-4,5,6,7-tetrahydrothiazolo[5,4-c]pyridin-2-yl)pyrrolidine-3-carboxamide
(S)—N-(5-benzoyl-4,5,6,7-tetrahydrothiazolo[5,4-c]pyridin-2-yl)-1-cyanopyrrolidine-3-carboxamide
(S)-1-cyano-N-(5-(2-methoxybenzoyl)-4,5,6,7-tetrahydrothiazolo[5,4-c]pyridin-2-yl)pyrrolidine-3-carboxamide
(S)-1-cyano-N-(5-picolinoyl-4,5,6,7-tetrahydrothiazolo[5,4-c]pyridin-2-yl)pyrrolidine-3-carboxamide
(S)-1-cyano-N-(5-(1-methyl-1H-pyrazole-3-carbonyl)-4,5,6,7-tetrahydrothiazolo[5,4-c]pyridin-2-yl)pyrrolidine-3-carboxamide
(S)-1-cyano-N-(5-(1-methyl-2-oxo-1,2-dihydropyridine-3-carbonyl)-4,5,6,7-tetrahydrothiazolo[5,4-c]pyridin-2-yl)pyrrolidine-3-carboxamide
(S)-1-cyano-N-(5-nicotinoyl-4,5,6,7-tetrahydrothiazolo[5,4-c]pyridin-2-yl)pyrrolidine-3-carboxamide
(S)-1-cyano-N-(5-(dimethylglycyl)-4,5,6,7-tetrahydrothiazolo[5,4-c]pyridin-2-yl)pyrrolidine-3-carboxamide
methyl (S)-2-(1-cyanopyrrolidine-3-carboxamido)-6,7-dihydrothiazolo[5,4-c]pyridine-5(4H)-carboxylate
2-methoxyethyl (S)-2-(1-cyanopyrrolidine-3-carboxamido)-6,7-dihydrothiazolo[5,4-c]pyridine-5(4H)-carboxylate
(S)-1-cyano-N-(5-methyl-4,5,6,7-tetrahydrothiazolo[5,4-c]pyridin-2-yl)pyrrolidine-3-carboxamide
(S)—N-(5-benzyl-4,5,6,7-tetrahydrothiazolo[5,4-c]pyridin-2-yl)-1-cyanopyrrolidine-3-carboxamide
(S)-1-cyano-N-(5-(methylsulfonyl)-4,5,6,7-tetrahydrothiazolo[5,4-c]pyridin-2-yl)pyrrolidine-3-carboxamide
(S)-1-cyano-N-(5-(isopropylsulfonyl)-4,5,6,7-tetrahydrothiazolo[5,4-c]pyridin-2-yl)pyrrolidine-3-carboxamide
(S)-1-cyano-N-(5-(phenylsulfonyl)-4,5,6,7-tetrahydrothiazolo[5,4-c]pyridin-2-yl)pyrrolidine-3-carboxamide
(S)-1-cyano-N-(5-(4-ethynylphenyl)thiazol-2-yl)pyrrolidine-3-carboxamide
(S)-1-cyano-N-(5-(3-ethynylphenyl)thiazol-2-yl)pyrrolidine-3-carboxamide
(3S)-1-cyano-N-(5-(N-(1-phenylethyl)sulfamoyl)pyridin-2-yl)pyrrolidine-3-carboxamide (3S)-1-cyano-N-(5-(N-methyl-N-(1-phenylethyl)sulfamoyl)pyridin-2-yl)pyrrolidine-3-carboxamide
(S)-1-cyano-N-(6-(5-methyl-1,2,4-oxadiazol-3-yl)imidazo[1,2-a]pyridin-2-yl)pyrrolidine-3-carboxamide
(3S,4S)-1-cyano-N-(6-(3,5-dimethylisoxazol-4-yl)imidazo[1,2-a]pyridin-2-yl)-4-(trifluoromethyl)pyrrolidine-3-carboxamide
(S)-1-cyano-N-(4-(1-methyl-1H-pyrazol-4-yl)pyridin-2-yl)pyrrolidine-3-carboxamide
(S)-1-cyano-N-(5-(N,N-dimethylsulfamoyl)-4,5,6,7-tetrahydrothiazolo[5,4-c]pyridin-2-yl)pyrrolidine-3-carboxamide
(S)-1-cyano-N-(5-(pyridazin-4-yl)thiazol-2-yl)pyrrolidine-3-carboxamide
(S)-1-cyano-N-(5-(4-cyano-3-fluorophenyl)thiazol-2-yl)pyrrolidine-3-carboxamide
(S)—N-(5-(1H-indazol-7-yl)thiazol-2-yl)-1-cyanopyrrolidine-3-carboxamide
(S)—N-(5-(3-(1H-imidazol-1-yl)phenyl)thiazol-2-yl)-1-cyanopyrrolidine-3-carboxamide
(S)-1-cyano-N-(5-(4-(methylsulfonamido)phenyl)thiazol-2-yl)pyrrolidine-3-carboxamide
(S)—N-(5-(3-(1H-pyrazol-1-yl)phenyl)thiazol-2-yl)-1-cyanopyrrolidine-3-carboxamide
(S)-1-cyano-N-(5-(4-cyano-3-(trifluoromethoxy)phenyl)thiazol-2-yl)pyrrolidine-3-carboxamide
(S)-1-cyano-N-(5-(4-cyano-3-methoxyphenyl)thiazol-2-yl)pyrrolidine-3-carboxamide
(S)-1-cyano-N-(5-(4-sulfamoylphenyl)thiazol-2-yl)pyrrolidine-3-carboxamide
(S)—N-(5-(1H-indazol-6-yl)thiazol-2-yl)-1-cyanopyrrolidine-3-carboxamide
(S)—N-(5-(1H-indazol-5-yl)thiazol-2-yl)-1-cyanopyrrolidine-3-carboxamide
(S)-6-(2-(1-cyanopyrrolidine-3-carboxamido)thiazol-5-yl)-N-methylpicolinamide
(S)-6-(2-(1-cyanopyrrolidine-3-carboxamido)thiazol-5-yl)-N-ethylpicolinamide
(S)-1-cyano-N-(5-(1-methyl-1H-indazol-5-yl)thiazol-2-yl)pyrrolidine-3-carboxamide
(S)-1-cyano-N-(5-(1-(2-methoxyethyl)-1H-indazol-5-yl)thiazol-2-yl)pyrrolidine-3-carboxamide
(S)-1-cyano-N-(5-(2-oxoindolin-7-yl)thiazol-2-yl)pyrrolidine-3-carboxamide
(S)-1-cyano-N-(5-(3-methyl-1H-indazol-5-yl)thiazol-2-yl)pyrrolidine-3-carboxamide
(S)—N-(5-(1H-indazol-4-yl)thiazol-2-yl)-1-cyanopyrrolidine-3-carboxamide
(S)-1-cyano-N-(5-(4-fluoro-3-(methylcarbamoyl)phenyl)thiazol-2-yl)pyrrolidine-3-carboxamide
(S)—N-(5-(3-carbamoylphenyl)thiazol-2-yl)-1-cyanopyrrolidine-3-carboxamide
(S)-1-cyano-N-(5-(3-(methylcarbamoyl)phenyl)thiazol-2-yl)pyrrolidine-3-carboxamide
(S)-1-cyano-N-(5-(3-(ethylcarbamoyl)phenyl)thiazol-2-yl)pyrrolidine-3-carboxamide
(S)-1-cyano-N-(5-(3-(dimethylcarbamoyl)phenyl)thiazol-2-yl)pyrrolidine-3-carboxamide
(S)—N-(5-(3-carbamoyl-4-fluorophenyl)thiazol-2-yl)-1-cyanopyrrolidine-3-carboxamide
(S)—N-(5-(3-carbamoyl-4-chlorophenyl)thiazol-2-yl)-1-cyanopyrrolidine-3-carboxamide
(S)—N-(5-(4-chloro-3-(methylcarbamoyl)phenyl)thiazol-2-yl)-1-cyanopyrrolidine-3-carboxamide
(S)—N-(5-(4-chloro-3-(prop-2-yn-1-ylcarbamoyl)phenyl)thiazol-2-yl)-1-cyanopyrrolidine-3-carboxamide
(S)-1-cyano-N-(5-(isopropylsulfonyl)-4,5,6,7-tetrahydropyrazolo[1,5-a]pyrazin-2-yl)pyrrolidine-3-carboxamide
(S)-1-cyano-N-(5-phenyl-4,5,6,7-tetrahydropyrazolo[1,5-a]pyrazin-2-yl)pyrrolidine-3-carboxamide
(S)—N-(5-benzyl-4,5,6,7-tetrahydropyrazolo[1,5-a]pyrazin-2-yl)-1-cyanopyrrolidine-3-carboxamide
(S)-1-cyano-N-(1-(4-cyano-3-(2-methoxyethoxy)phenyl)-1H-imidazol-4-yl)pyrrolidine-3-carboxamide
(S)-1-cyano-N-(1-(2-cyano-5-(2-methoxyethoxy)phenyl)-1H-imidazol-4-yl)pyrrolidine-3-carboxamide
(S)-1-cyano-N-(1-(4-cyano-3-(3-morpholinopropoxy)phenyl)-1H-imidazol-4-yl)pyrrolidine-3-carboxamide
(S)-1-cyano-N-(1-(2-cyano-5-(3-morpholinopropoxy)phenyl)-1H-imidazol-4-yl)pyrrolidine-3-carboxamide
(S)-1-cyano-N-(1-(4-cyano-3-(((S)-tetrahydrofuran-3-yl)oxy)phenyl)-1H-imidazol-4-yl)pyrrolidine-3-carboxamide
(S)-1-cyano-N-(1-(2-cyano-5-(((S)-tetrahydrofuran-3-yl)oxy)phenyl)-1H-imidazol-4-yl)pyrrolidine-3-carboxamide
(S)-1-cyano-N-(1-(4-cyano-3-(oxetan-3-yloxy)phenyl)-1H-imidazol-4-yl)pyrrolidine-3-carboxamide
(S)-1-cyano-N-(1-(2-cyano-5-(oxetan-3-yloxy)phenyl)-1H-imidazol-4-yl)pyrrolidine-3-carboxamide
(S)-1-cyano-N-(4-(pyrazolo[1,5-a]pyrimidin-7-yl)pyridin-2-yl)pyrrolidine-3-carboxamide
(S)-1-cyano-N-(4-(imidazo[1,2-a]pyrimidin-5-yl)pyridin-2-yl)pyrrolidine-3-carboxamide
(S)-1-cyano-N-(4-(imidazo[1,2-a]pyridin-5-yl)pyridin-2-yl)pyrrolidine-3-carboxamide
(S)-1-cyano-N-(4-(imidazo[1,2-a]pyrazin-6-yl)pyridin-2-yl)pyrrolidine-3-carboxamide
(S)-1-cyano-N-(4-(imidazo[1,2-a]pyrimidin-6-yl)pyridin-2-yl)pyrrolidine-3-carboxamide
(S)-1-cyano-N-(1,7-naphthyridin-6-yl)pyrrolidine-3-carboxamide
(S)—N-(6-(3-chlorophenyl)pyrimidin-4-yl)-1-cyanopyrrolidine-3-carboxamide
(S)—N-(2'-amino-[4,4'-bipyridin]-2-yl)-1-cyanopyrrolidine-3-carboxamide
(S)-1-cyano-N-(2'-(methylamino)-[4,4'-bipyridin]-2-yl)pyrrolidine-3-carboxamide
(S)-3-(1-cyanopyrrolidine-3-carboxamido)-N-methylisoquinoline-6-carboxamide
(S)-1-cyano-N-(6-(3,5-dimethylisoxazol-4-yl)isoquinolin-3-yl)pyrrolidine-3-carboxamide
(S)—N-(4-(1H-indazol-4-yl)pyridin-2-yl)-1-cyanopyrrolidine-3-carboxamide
(S)-1-cyano-N-(6-ethynylisoquinolin-3-yl)pyrrolidine-3-carboxamide
(2S,3S)-1-cyano-N-(6-ethynylisoquinolin-3-yl)-2-methylpyrrolidine-3-carboxamide
(S)-3-(1-cyanopyrrolidine-3-carboxamido)isoquinoline-6-carboxamide
(2S,3S)—N-(6-(1H-pyrazol-4-yl)isoquinolin-3-yl)-1-cyano-2-methylpyrrolidine-3-carboxamide
(S)-1-cyano-N-(pyrazolo[1,5-a]pyridin-2-yl)pyrrolidine-3-carboxamide
(S)-1-cyano-N-(4-phenylpyridin-2-yl)pyrrolidine-3-carboxamide
(S)-1-cyano-N-(5-(pyridin-3-yl)thiazol-2-yl)pyrrolidine-3-carboxamide
(S)-1-cyano-N-(5-(pyridin-3-yl)thiazol-2-yl)pyrrolidine-3-carboxamide
(S)-1-cyano-N-(6-(trifluoromethyl)imidazo[1,2-a]pyridin-2-yl)pyrrolidine-3-carboxamide (S)-1-cyano-N-(1-methyl-5-(m-tolyl)-1H-pyrazol-3-yl)pyrrolidine-3-carboxamide
(S)-1-cyano-N-(quinolin-3-yl)pyrrolidine-3-carboxamide
(S)—N-(4-(tert-butyl)pyridin-2-yl)-1-cyanopyrrolidine-3-carboxamide
(S)-1-cyano-N-(6-(pyridin-4-yl)pyrimidin-4-yl)pyrrolidine-3-carboxamide
(S)-1-cyano-N-(5-phenylpyridazin-3-yl)pyrrolidine-3-carboxamide
(S)-1-cyano-N-(6-(oxazol-5-yl)imidazo[1,2-a]pyridin-2-yl)pyrrolidine-3-carboxamide
(S)-1-cyano-N-(6-(isopropylsulfonyl)-5,6,7,8-tetrahydro-4H-thiazolo[4,5-d]azepin-2-yl)pyrrolidine-3-carboxamide
(S)-1-cyano-N-(1-(4-(1-(2-methoxyethyl)-1H-pyrazol-4-yl)phenyl)-1H-imidazol-4-yl)pyrrolidine-3-carboxamide
3-cyano-N-(5-phenylthiazol-2-yl)-3-azabicyclo[3.1.0]hexane-1-carboxamide
2-cyano-N-(5-phenylthiazol-2-yl)-2-azabicyclo[3.1.0]hexane-4-carboxamide
(3S,4S)-1-cyano-N-(5-phenylthiazol-2-yl)-4-(trifluoromethyl)pyrrolidine-3-carboxamide
(3 S,4R)-1-cyano-N-(5-phenylthiazol-2-yl)-4-(pyridin-3-yl)pyrrolidine-3-carboxamide
(3 S,4R)-1-cyano-N-(5-phenylthiazol-2-yl)-4-(pyrimidin-5-yl)pyrrolidine-3-carboxamide
1-cyano-3-methoxy-N-(5-phenylthiazol-2-yl)pyrrolidine-3-carboxamide
(S)-1-cyano-N-(6-(3,5-dimethylisoxazol-4-yl)thiazolo[4,5-b]pyridin-2-yl)pyrrolidine-3-carboxamide
(S)-1-cyano-N-(5-(3,5-dimethylisoxazol-4-yl)thiazolo[5,4-b]pyridin-2-yl)pyrrolidine-3-carboxamide
(S)-1-cyano-N-(6-(2,6-dimethylphenyl)benzo[d]thiazol-2-yl)pyrrolidine-3-carboxamide
(S)-1-cyano-N-(6-(1,3-dimethyl-1H-pyrazol-4-yl)benzo[d]thiazol-2-yl)pyrrolidine-3-carboxamide
(S)-1-cyano-N-(6-(5-(trifluoromethyl)-1H-pyrazol-4-yl)isoquinolin-3-yl)pyrrolidine-3-carboxamide
(S)-1-cyano-N-(4-(3-(5-methylisoxazol-4-yl)phenyl)pyridin-2-yl)pyrrolidine-3-carboxamide
(S)—N-(4-(1H-pyrazol-4-yl)pyridin-2-yl)-1-cyanopyrrolidine-3-carboxamide
(S)—N-(6-(1H-pyrazol-4-yl)benzo[d]thiazol-2-yl)-1-cyanopyrrolidine-3-carboxamide
(S)—N-(1-(4-(1H-pyrazol-4-yl)phenyl)-1H-imidazol-4-yl)-1-cyanopyrrolidine-3-carboxamide
(S)-1-cyano-N-(4-(5-methyl-1H-pyrazol-4-yl)pyridin-2-yl)pyrrolidine-3-carboxamide
(S)-1-cyano-N-(6-(3,5-dimethylisoxazol-4-yl)thiazolo[4,5-c]pyridin-2-yl)pyrrolidine-3-carboxamide
(S)-1-cyano-N-(2'-(5-methylisoxazol-4-yl)-[4,4'-bipyridin]-2-yl)pyrrolidine-3-carboxamide
(S)-1-cyano-N-(1-(1,3-dimethyl-1H-indazol-5-yl)-1H-imidazol-4-yl)pyrrolidine-3-carboxamide
(S)-1-cyano-N-(1-(3-methyl-1H-indazol-6-yl)-1H-imidazol-4-yl)pyrrolidine-3-carboxamide
(S)—N-(1-(1H-indazol-5-yl)-1H-imidazol-4-yl)-1-cyanopyrrolidine-3-carboxamide
(S)—N-(1-(1H-indazol-6-yl)-1H-imidazol-4-yl)-1-cyanopyrrolidine-3-carboxamide
(S)-1-cyano-N-(1-(4-fluoro-3-methoxyphenyl)-1H-imidazol-4-yl)pyrrolidine-3-carboxamide
(S)—N-(1-(1H-indazol-4-yl)-1H-imidazol-4-yl)-1-cyanopyrrolidine-3-carboxamide
(S)-1-cyano-N-(1-(4-cyano-3-cyclopropylphenyl)-1H-imidazol-4-yl)pyrrolidine-3-carboxamide
(S)-1-cyano-N-(1-(quinolin-4-yl)-1H-imidazol-4-yl)pyrrolidine-3-carboxamide
(S)-1-cyano-N-methyl-N-(4-(4-(methylcarbamoyl)phenyl)thiazol-2-yl)pyrrolidine-2-carboxamide
(S)-1-cyano-N-(1-(4-cyano-3-methoxyphenyl)-1H-imidazol-4-yl)pyrrolidine-3-carboxamide
(S)-1-cyano-N-(1-(4-cyano-3-methylphenyl)-1H-imidazol-4-yl)pyrrolidine-3-carboxamide
(S)-1-cyano-N-(1-(4-cyano-3-(trifluoromethyl)phenyl)-1H-imidazol-4-yl)pyrrolidine-3-carboxamide
(S)-1-cyano-N-(1-(4-cyano-3-(trifluoromethoxy)phenyl)-1H-imidazol-4-yl)pyrrolidine-3-carboxamide It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an acid of formula (V) with a compound $R_1$—$NH_2$ to form an amide:

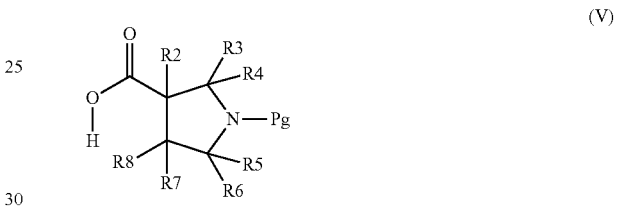

(V)

Where $R_2$-$R_8$ are as defined elsewhere and Pg is an amine protecting group. The protecting group may be but is not limited to BOC. It is clear to a person skill in the art to combine or adjust such a protecting chemical group. After coupling of $R_1$—$NH_2$ to form an amide, the protecting group may be removed to leave the free amine according to formula (VI) which can then be treated with cyanogen bromide to form cpds according to formula (I).

According to a further aspect of the invention there is provided a process for the preparation of a compound of formula (I) or a pharmaceutically acceptable salt thereof comprising the steps of reacting an amine of formula (VI) with cyanogen bromide to form N—CN compounds:

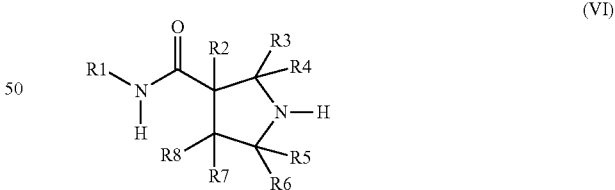

(VI)

According to a further aspect of the invention there is provided a pharmaceutical composition comprising a compound of formula (I).

Pharmaceutical compositions of this invention comprise any of the compounds of formula (I) of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

According to a further aspect of the invention there is provided a compound of formula (I) or pharmaceutical composition thereof for use in therapy. In particular compounds of the invention according to formula (I) have use in the treatment of cancer and more particularly in the treatment of cancers linked to DUB activity. Compounds of the invention may be useful against any DUB enzyme, including by not limited to UCHL1, USP6 or USP30.

The compounds of formula (I) as described herein may be used in the manufacture of a medicament for the treatment of a cancer linked to DUB activity.

UCHL1 is overexpressed in many turnout types. In a further aspect of the invention there is provided a method of treatment or prevention of a cancer linked to UCHL1 activity, the method comprising administering a pharmaceutically effective amount of a compound of formula (I) of a pharmaceutical composition thereof to an individual suffering from a cancer linked to UCHL1 activity.

The compounds or compositions according to formula (I) may be used to treat cancer. References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include breast, lymphoma, multiple myeloma, colorectal cancer, osteosarcoma, pancreatic and non small cell lung carcinoma.

The compounds or compositions according to formula (I) may be used to treat additional disease linked to UCHL1 activity. For example a disease linked to UCHL1 activity may be selected from neurodegenerative disorders (such as Alzheimer's disease, Parkinson's disease), COPD, inflammation, viral infections, including MERS or SARS, bacterial infections, including tuberculosis or metabolic disorders.

The compounds of formula (I) or pharmaceutical compositions thereof as described herein may be combined with one or more additional agents. The compounds may be combined with an additional anti-tumour therapeutic agent, for example chemotherapeutic drugs or inhibitors of other regulatory proteins. In one embodiment the additional anti-tumour therapeutic agent is selected from a PARP (poly ADP ribose polymerase) inhibitor, a BRCA2 inhibitor and an ATM inhibitor. In another embodiments the PARP inhibitor is an inhibitory RNA (RNAi) molecule (PARPi). In a further embodiment PARP inhibitors may be selected from one or more of Iniparib (BSI 201), Olaparib (AZD-2281), Rucaparib (AG014699, PF-01367338) and Veliparib (ABT-888), MK-4827, CEP-9722, E716 (GPI-221016), LT-673, MP-124, NMS-P118. In a further embodiment the additional anti-tumour agent is a chemotherapeutic agent. Chemotherapeutic agents may be selected from olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

The pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations.

The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 µg to about 100 mg per kg body weight of a human and non-human animal and in general may be around 10 µg to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art. Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by liquid chromatography-mass spectroscopy (LCMS) and $^1$H NMR.

Abbreviations
aq Aqueous
Ar Aryl
BOC Tert-butoxycarbonyl
br Broad (NMR signal)
d Doublet (NMR signal)
dba dibenzylideneacetone
DCE 1,2-Dichloroethane
DCM Dichloromethane
DIAD Diisopropyl azodicarboxylate
DIPEA Diisopropylethylamine
DMA Dimethylacetamide
DMAP Dimethylaminopyridine
DMF Dimethylformamide
DMSO Dimethylsulphoxide
dppf 1,1'-bis(diphenylphosphino)ferrocene
EDC 1-Ethyl-3-(3-dimethylaminopropyl)carbodiimide
ES Electrospray
EtOAc Ethyl acetate
EtOH Ethanol
FA Formic Acid
Fmoc Fluorenylmethyloxycarbonyl
h Hour(s)
HATU (1-[Bis(dimethylamino)methylene]-1H-1,2,3-triazolo[4,5-b]pyridinium 3-oxidhexafluorophosphate)
HBTU O-Benzotriazole-N,N,N',N'-tetramethyl-uronium-hexafluoro-phosphate
HPLC High performance liquid chromatography
HOAt 1-Hydroxy-7-azabenzotriazole
IPA Isopropyl alcohol
LDA Lithium diisopropylamide
LiHMDS Lithium Hexamethyldisilazide
m Multiplet (NMR signal)
MeCN Acetonitrile
MeOH Methanol
n-BuLi n-Butyllithium
rt Room temperature
s Singlet (NMR signal)
t Triplet (NMR signal)
T3P 2,4,6-Tripropyl-1,3,5,2,4,6-trioxatriphosphorinane-2,4,6-trioxide
TBAI Tetrabutylammonium Iodide
TEA Triethylamine
TFA Trifluoroacetic acid
TFAA Trifluoroacetic anhydride
THF Tetrahydrofuran
X-phos 2-Dicyclohexylphosphino-2',4',6'-triisopropylbiphenyl Analytical Methods:

| Method A | | |
|---|---|---|
| Column | BEH C18, 50 × 2.1 mm, 1.7 μm or equivalent | |
| Mobile Phase | (A) 5 mM Ammonium Acetate + 0.1% Formic Acid in Water | |
| | (B) 0.1% Formic Acid in Acetonitrile | |
| Flow Rate | 0.55 mL/min | |
| Gradient | Time | % B |
| | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

| Method B | | |
|---|---|---|
| Column | BEH C18, 50 × 2.1 mm, 1.7 μm or equivalent | |
| Mobile Phase | (A) 5 mM Ammonium Acetate + 0.1% Formic Acid in Water | |
| | (B) 0.1% Formic Acid in Acetonitrile | |
| Flow Rate | 0.45 mL/min | |
| Gradient | Time | % B |
| | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

| Method C | | |
|---|---|---|
| Column | X-bridge C18, 50 × 4.6 mm, 3.5 μm or equivalent | |
| Mobile Phase | (A) 0.1% Ammonia in Water | |
| | (B) 0.1% Ammonia in Acetonitrile | |
| Flow Rate | 1.0 mL/min | |
| Gradient | Time | % B |
| | 0.01 | 5 |
| | 5.00 | 90 |
| | 5.80 | 95 |
| | 7.20 | 95 |
| | 7.21 | 5 |
| | 10.00 | 5 |

Synthetic Schemes

Scheme 1

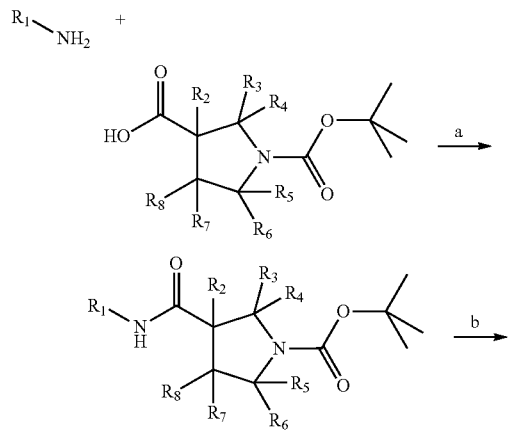

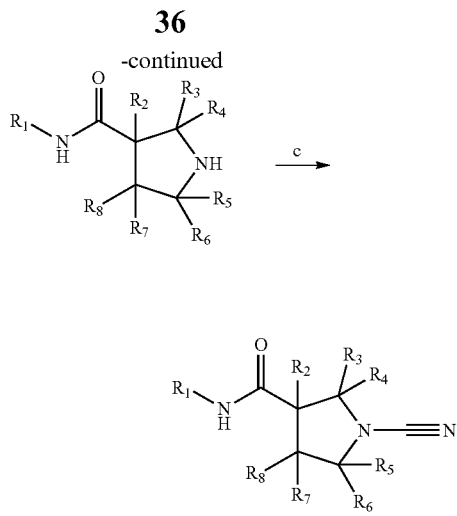

Reagents and conditions: a) T3P (50% in EtOAc), DIPEA, THF, 0° C., 1 h OR POCl$_3$, pyridine, DCM, 0° C. to rt 1 h b) 4M HCl in EtOAc, 0° C. to rt 4 h OR TFA, DCM, 0° C. to rt 1 h c) cyanogen bromide, K$_2$CO$_3$, DCM, 0° C. to rt 16 h

Scheme 2

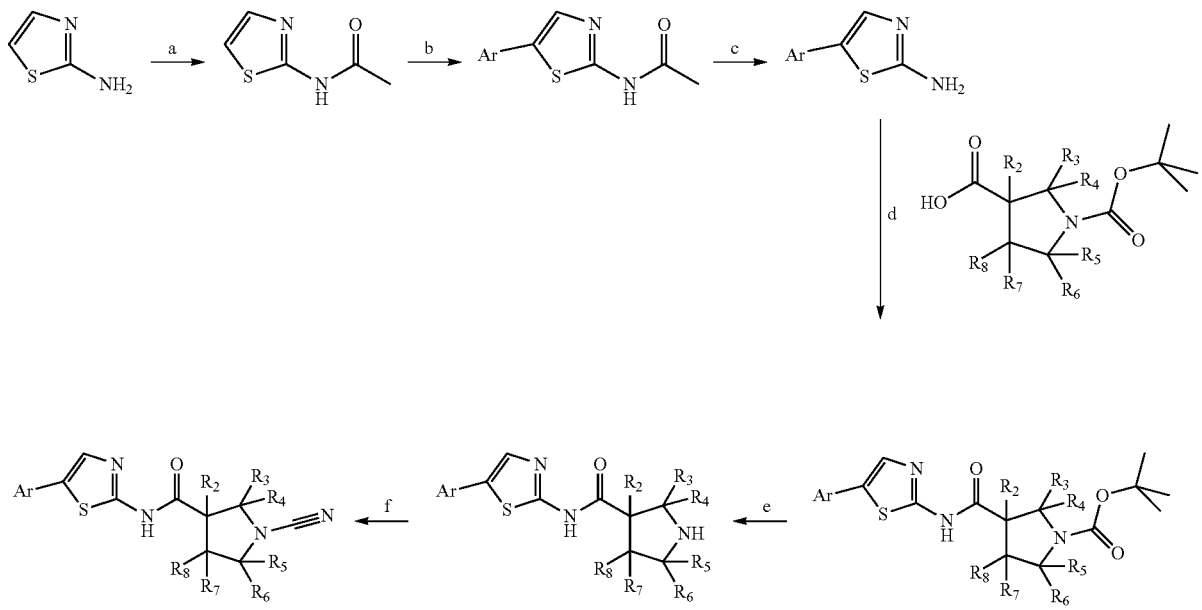

Reagents and conditions:
a) Ac$_2$O, TEA, THF, 0° C., rt 2 h
b) ArBr, K$_3$PO$_4$, Pd(OAc)$_2$, tricyclohexylphosphine, DMF, rt, 140° C. microwave 1.5 h
c) 1,4-dioxane, conc HCl, 100° C. 4 h
d) T3P (50% in EtOAc), DIPEA, THF, 0° C., rt 1 h
e) 4M HCl in EtOAc, 0° C., rt 4 h OR TFA, DCM, 0° C., rt 1 h
f) cyanogen bromide, K$_2$CO$_3$, DCM, 0° C., rt 16 h

Scheme 3

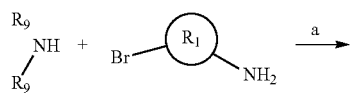

-continued
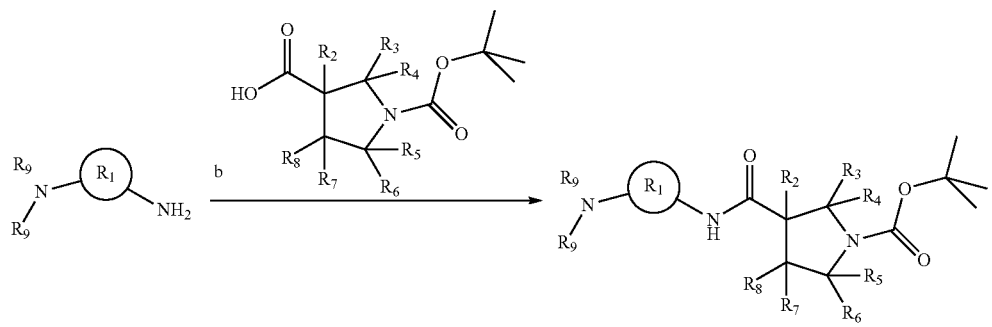
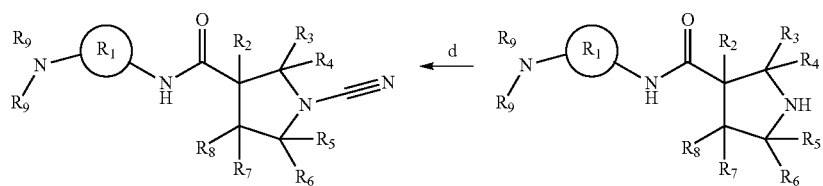
Reagents and conditions:
a) Cs$_2$CO$_3$, MeCN, rt 2 h
b) T3P (50% in EtOAc), DIPEA, THF, 0° C. 1 h, then at rt 1 h
b) 4M HCl in EtOAc, 0° C., rt 4 h OR TFA, DCM, 0° C., rt 1 h
c) cyanogen bromide K$_2$CO$_3$, DCM, 0° C., rt 16 h
Scheme 4
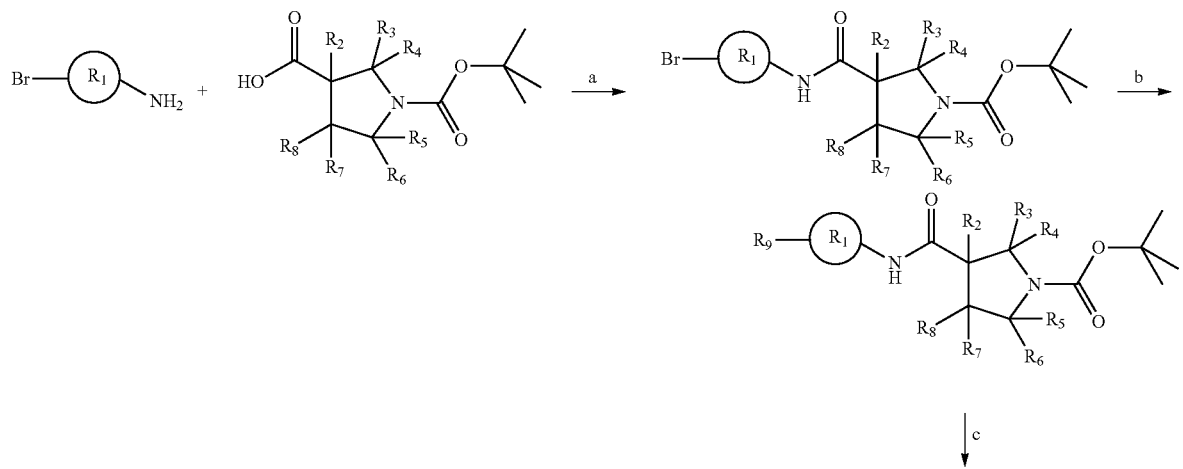

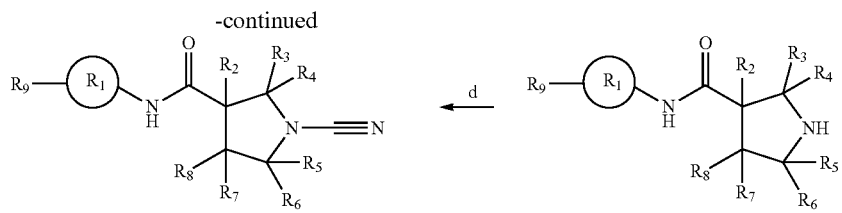

Reagents and conditions: a) T3P (50% in EtOAc), TEA, THF, rt 24 h b) R9B(OH)2 or boronate ester, Na2CO3, Pd(PPh3)4, 1,4-dioxane, water, 110° C., 24 h OR potassium trifluoroborate salt, K3PO4, Pd(dppf)Cl2·DCM, toluene, water, 100° C., sealed tube, 18 h c) 4M HCl in 1,4-dioxane, 0° C., rt 24 h OR TFA, DCM, 0° C., rt 1 h d) cyanogen bromide, TEA, DCM, 0° C., rt 30 min Scheme 5

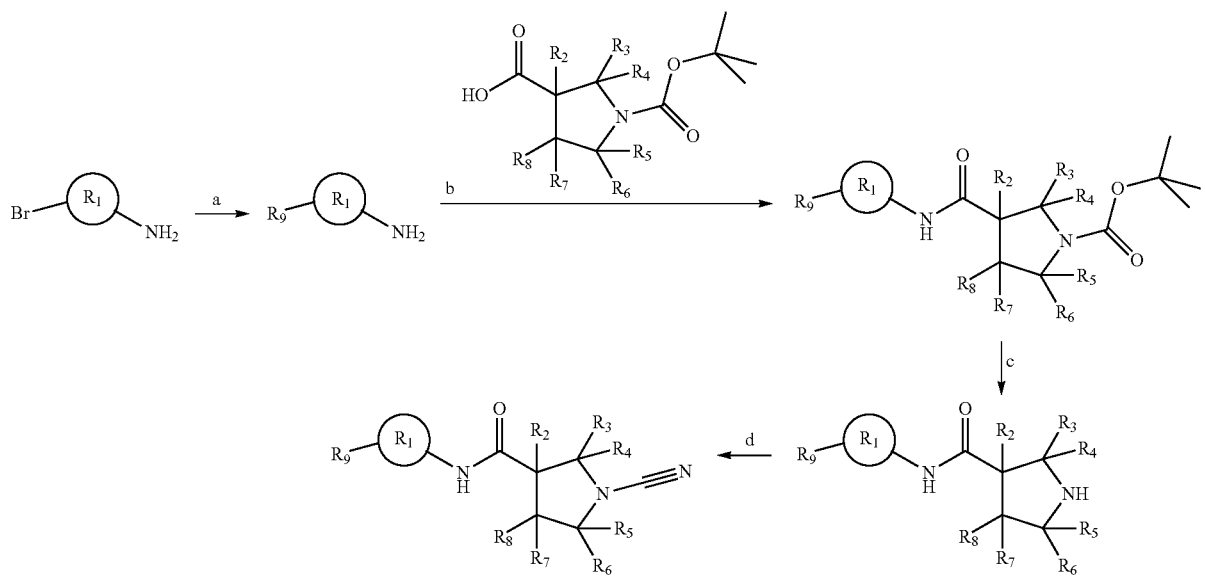

Reagents and conditions:
a) R9B(OH)2 or boronate ester, Na2CO3, Pd(PPh3)4, ethanol, toluence, water, microwave irradiation, 100° C., 3 h
b) HBTU, DIPEA, DCM, rt, 2.5 h OR POCl3, pyridine, DCM, 0° C. to rt 2 h
c) TFA, DCM, 0° C., rt 1 h
d) cyanogen bromide, K2CO3, THF, 0° C. 10 min Scheme 6

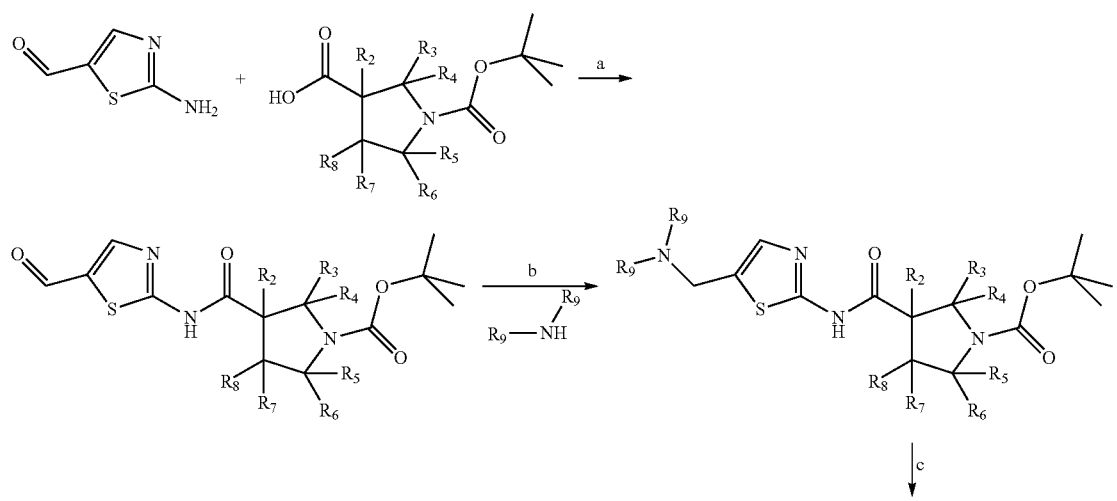

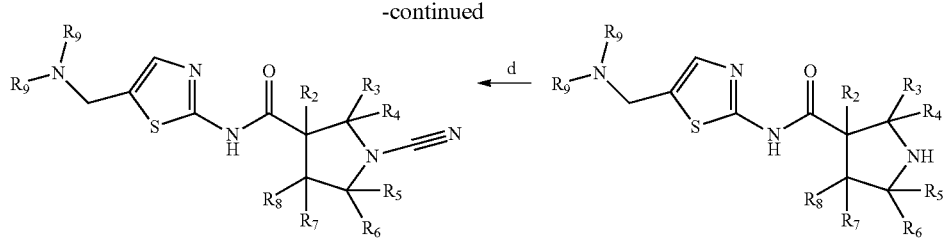
Reagents and conditions:
a) HOAt, DIPEA, EDC•HCl, DMF, rt 3 h
b) NaBH(OAc)₃, DCE, rt 3 h
c) TFA, 0° C., rt 40 min
d) cyanogen bromide, K₂CO₃, THF, 0° C., rt 2 h
Scheme 7
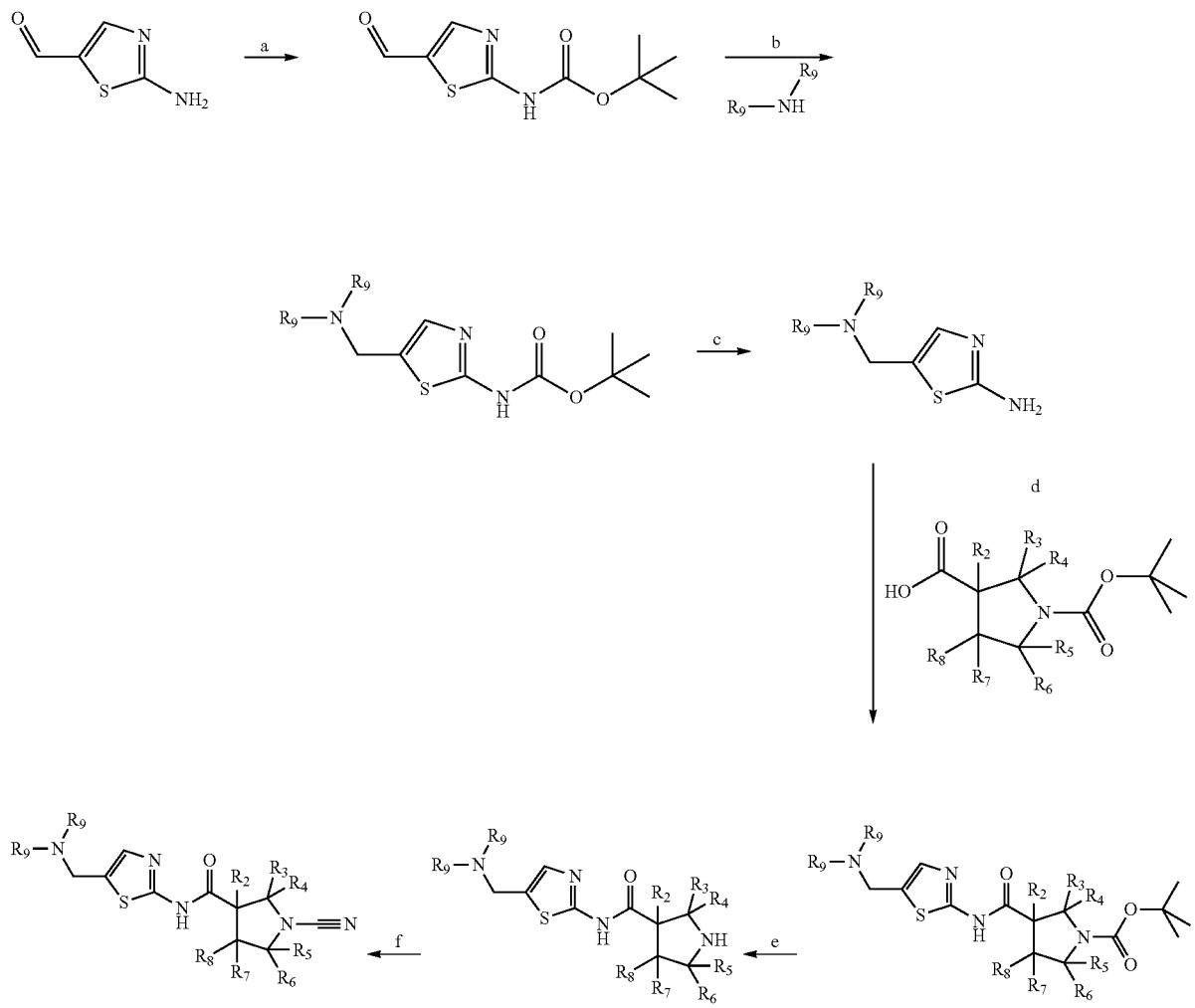
Reagents and conditions: a) (BOC)₂O, DMAP, THF, 0° C., rt 1 h b) NaBH(OAc)₃, MeOH, rt, 80° C. 2 h c) TFA, DCM, rt 1 h d) T3P (50% in EtOAc), DIPEA, THF, rt 1 h e) TFA, DCM, rt 1 h f) cyanogen bromide, K₂CO₃, THF, 0° C., rt 1 h Scheme 8
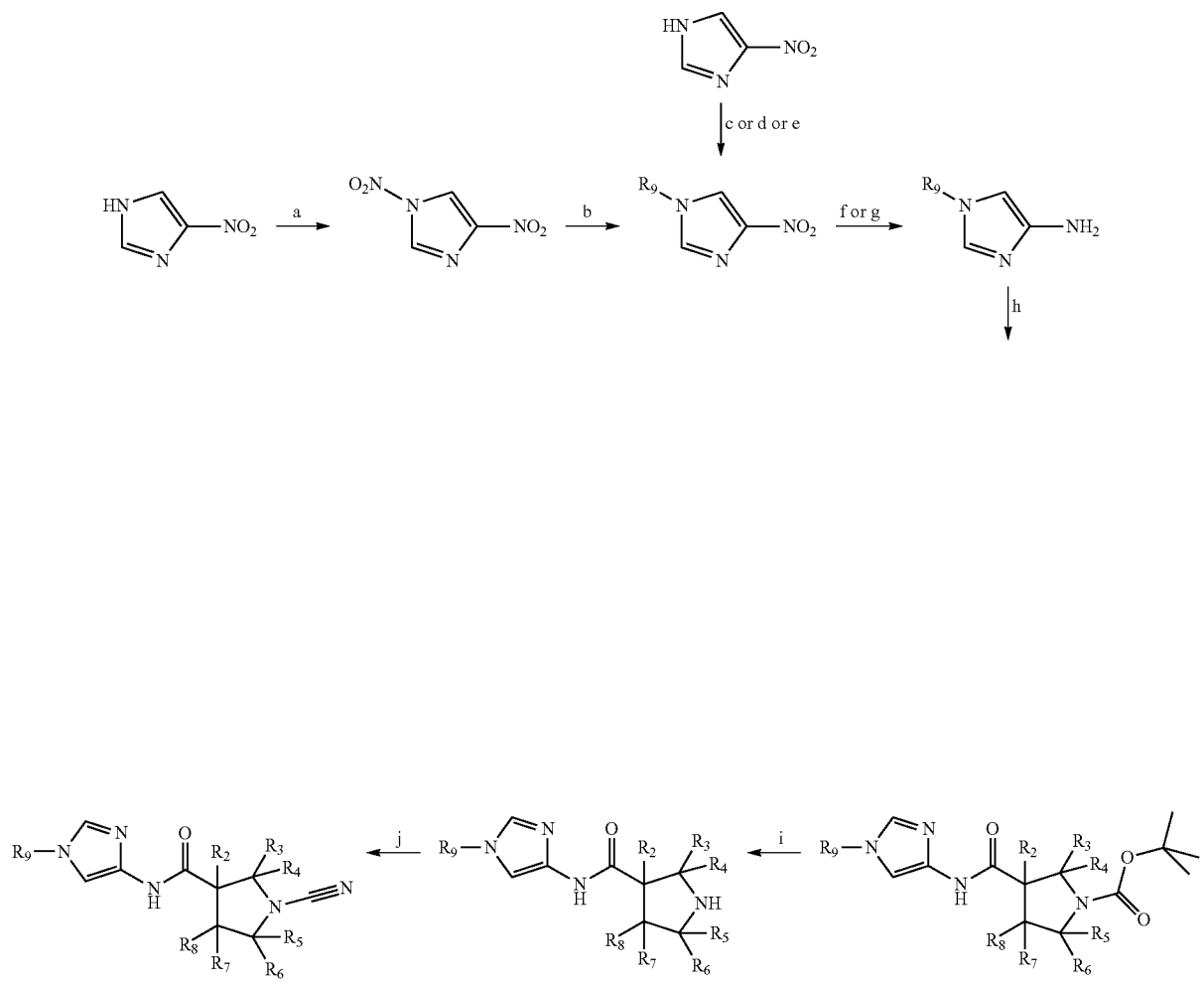
Reagents and conditions:
a) Fuming HNO$_3$, acetic acid, acetic anhydride, 0° C., rt 2 h
b) R$_9$NH$_2$, MeOH: water (1:1), rt 2 h
c) ArX or R$_9$Br, KOH, DMSO, rt 3 h
d) ArX, KI, K$_2$CO$_3$, DMF, 100° C. 18 h
e) R$_9$B(OH)$_2$, CuCl$_2$, NaOH, MeOH, O$_2$, 80° C., 18 h
f) Fe (or Zn) powder, NH$_4$Cl, MeOH : water (1:1), 60-80° C. 2 h
g) 10% Pd/C, H$_2$, MeOH, rt 2 h
h) T3P (50% in EtOAc), TEA, THF, 0° C., rt 2 h
i) 4M HCl in 1,4-dioxane, DCM, 0° C. 1 h
j) cyanogen bromide, K$_2$CO$_3$, DMF, 0° C., rt 30 min

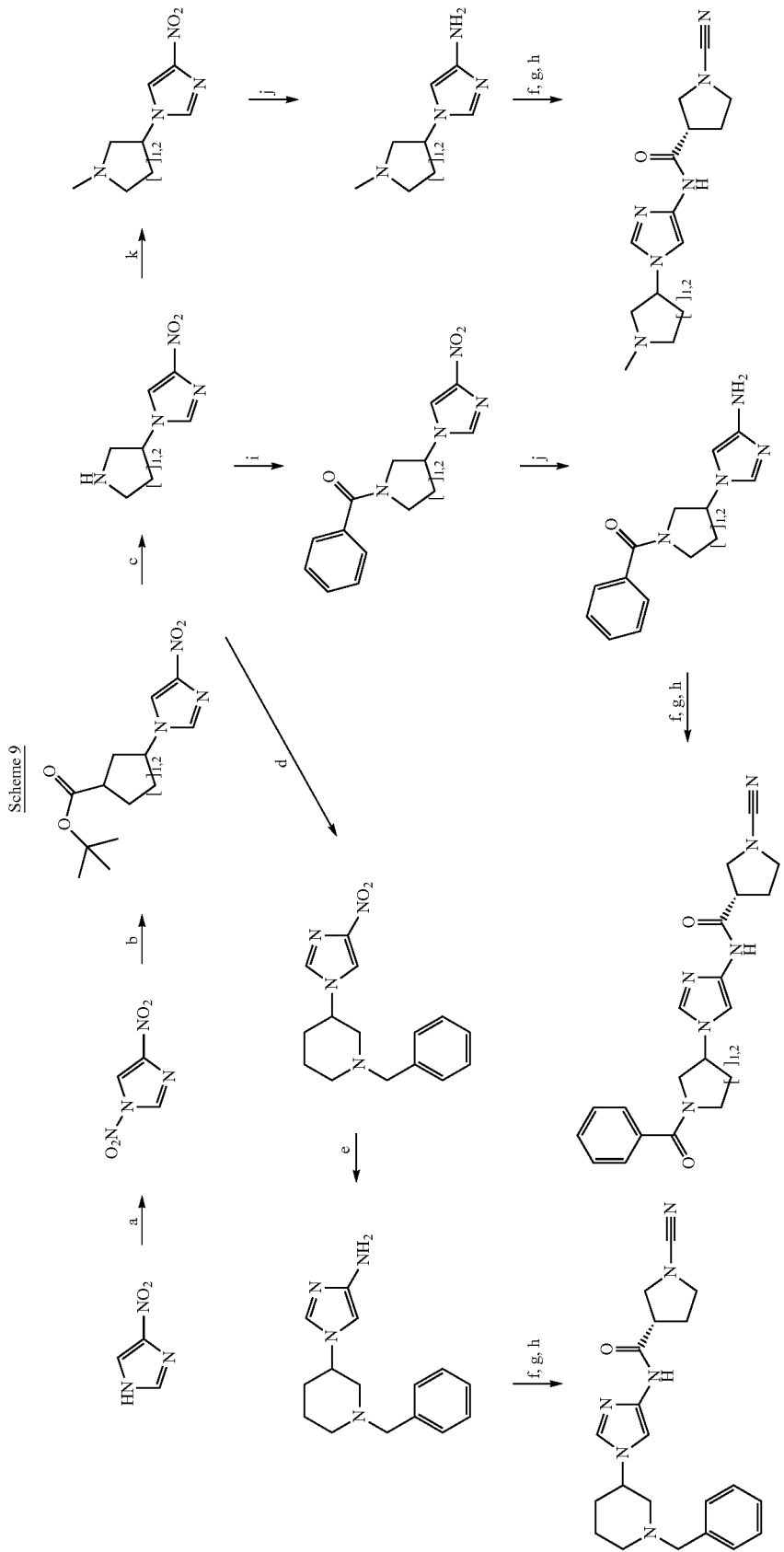

Scheme 10
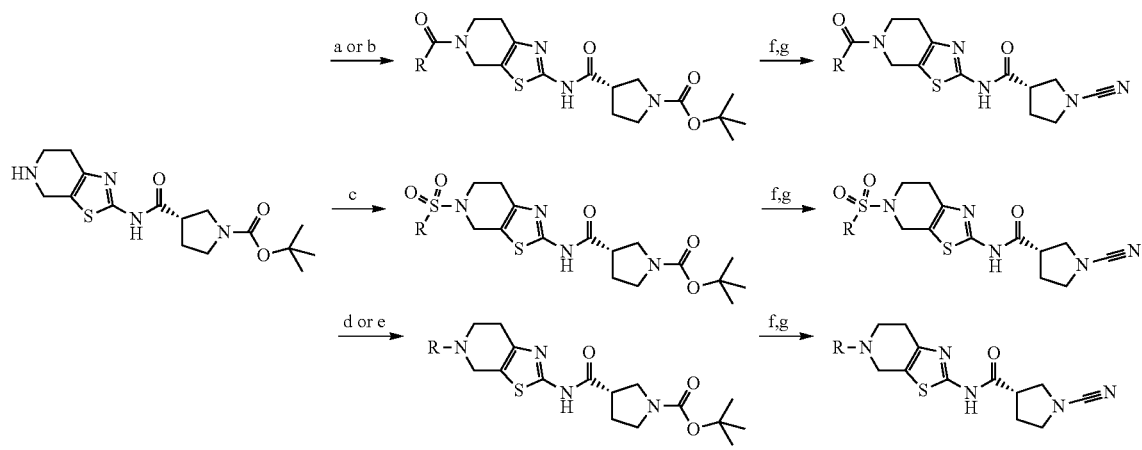
Reagents and conditions:
a) RCOCl, TEA, DCM, 0° C., rt 1 h
b) RCO₂H, T3P (50% in EtOAc), DIPEA, THF, 0° C., rt
c) sulphonyl chloride, TEA, DCM, 0° C., rt 1 h
d) 37% aq formaldehyde, acetic acid, NaCNBH₃, MeOH, 0° C., 0.5 h, then at rt 3 h
e) benzaldehyde, acetic acid, NaCNBH₃, MeOH, 0° C. 0.5 h, then at rt 3 h
f) TFA, DCM, rt 3 h
g) cyanogen bromide, TEA, DCM, 0° C. 30 min
Scheme 11
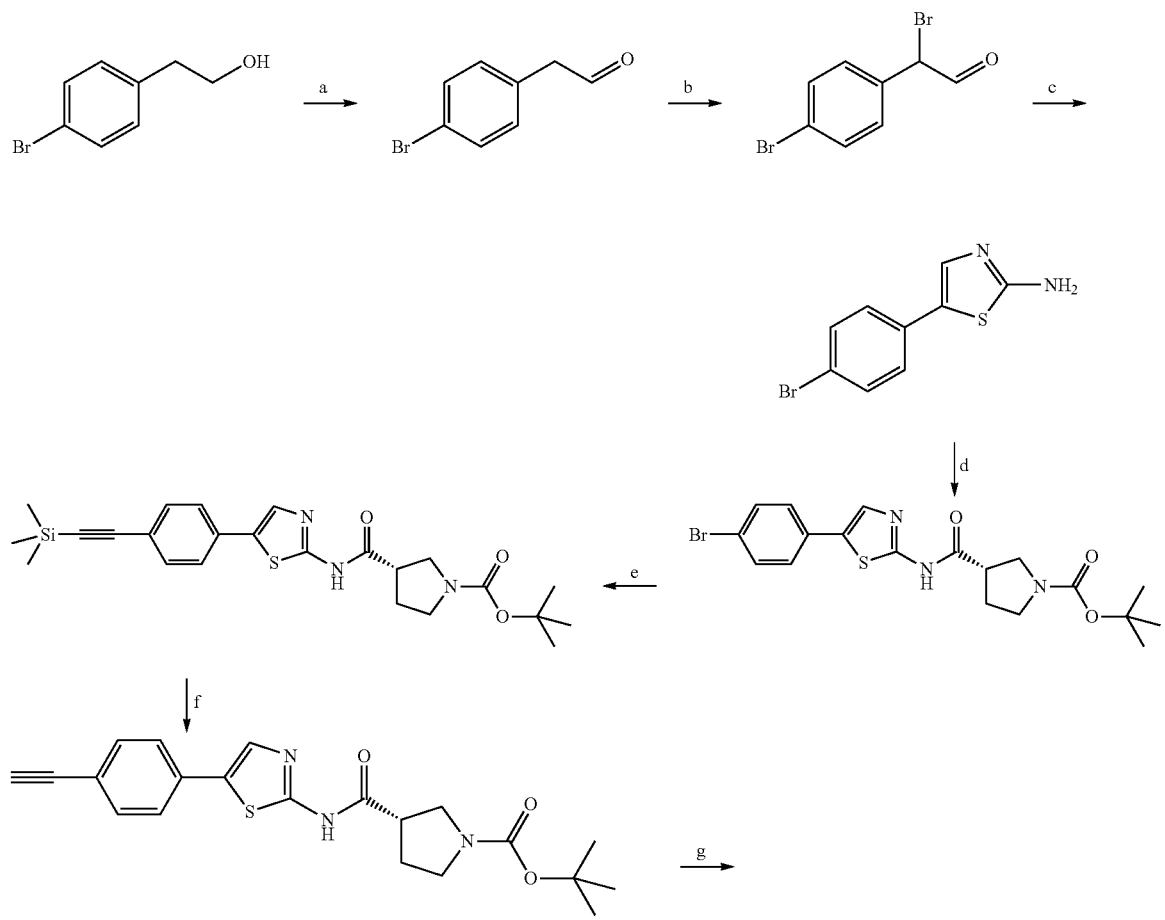

49 50

-continued

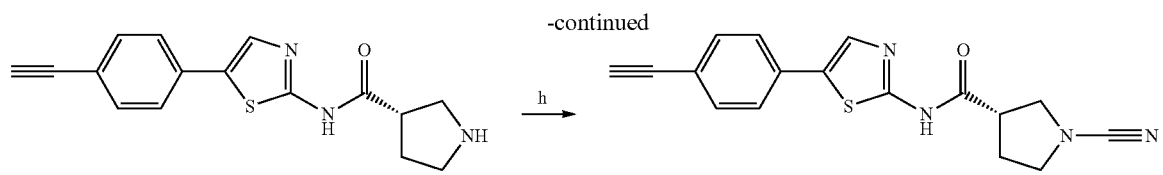

Reagents and conditions: a) Dess-Martin periodinane, DCM, rt 16 h b) bromine, DCM, 0° C., rt 2 h c) thiourea, ethanol, 90° C. 6 h d) T3P (50% in EtOAc), TEA, THF, 0° C., rt 1 h e) thimethylsilylacetylene, CuI, Pd(PPh₃)₂Cl₂, DIPEA, 110° C., 16 h f) 5M aqueous KOH, MeOH, 0° C., rt 30 min g) TFA, DCM, 0° C., rt 2 h h) cyanogen bromide, K₂CO₃, DMF, 0° C., rt 1 h Scheme 12

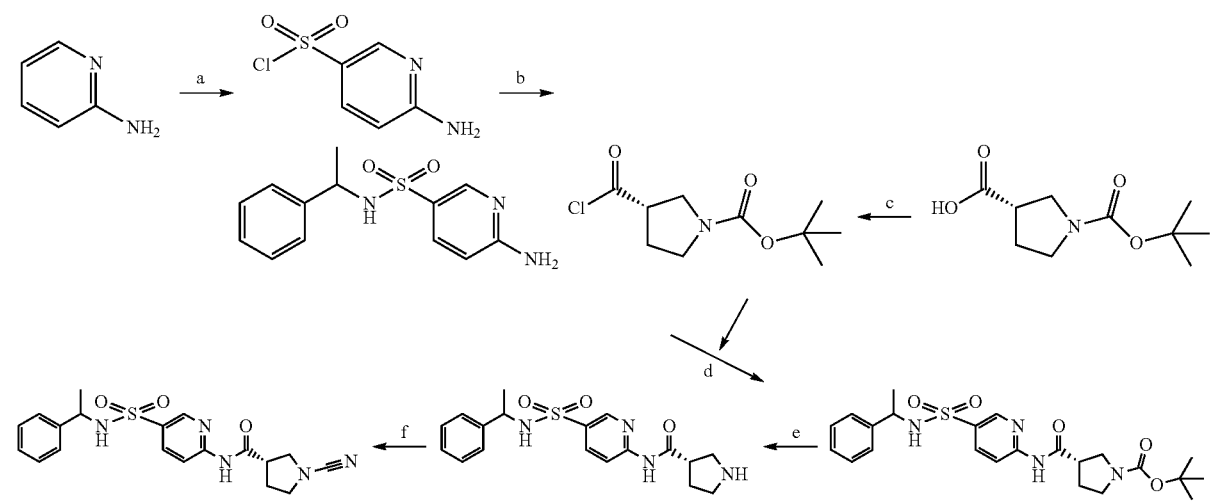

Reagents and conditions:
a) chlorosulfonic acid, 150° C., 2 h
b) 1-phenylethan-1-amine, TEA, THF, 0° C. to rt, 30 min
c) DCM, (COCl)₂, DMF, pyridine, 0° C. to rt, 1 h
d) TEA, DMF, 0° C. to rt, 16 h
e) DCM, TFA, rt, 15 min
f) cyanogen bromide, TEA, THF, 0° C., rt 30 min Scheme 13

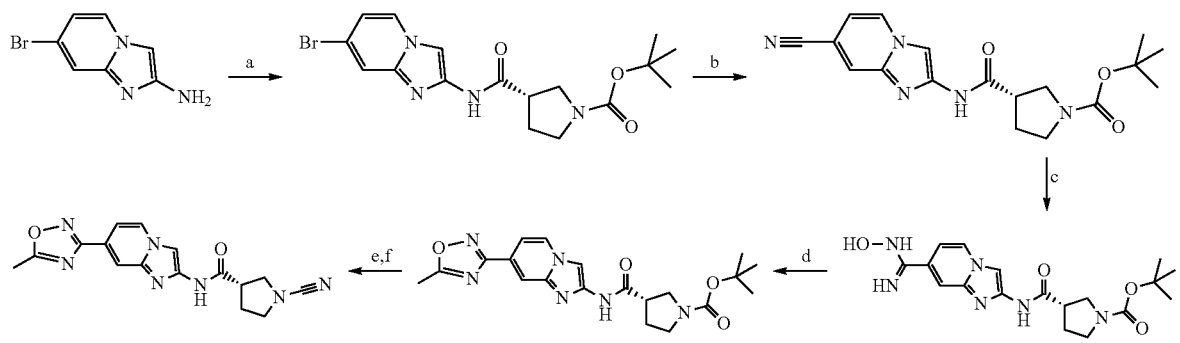

Reagents and conditions:
a) T3P (50% in EtOAc), DIPEA, THF, 0° C., 1 h
b) Zn(CN)₂, Pd(dba)₂, 1,1'bis(diphenylphosphino)ferrocene, TEA, DMF, 100° C. 24 h
c) hydroxylamine hydrochloride, TEA, IPA, 70° C. 3 h
d) N,N-dimethylacetamide dimethyl acetal, 70° C. 1 h
e) DCM, TFA, rt 1 h
f) cyanogen bromide, K₂CO₃, THF, 0° C. 30 min, then at rt 1 h Scheme 14

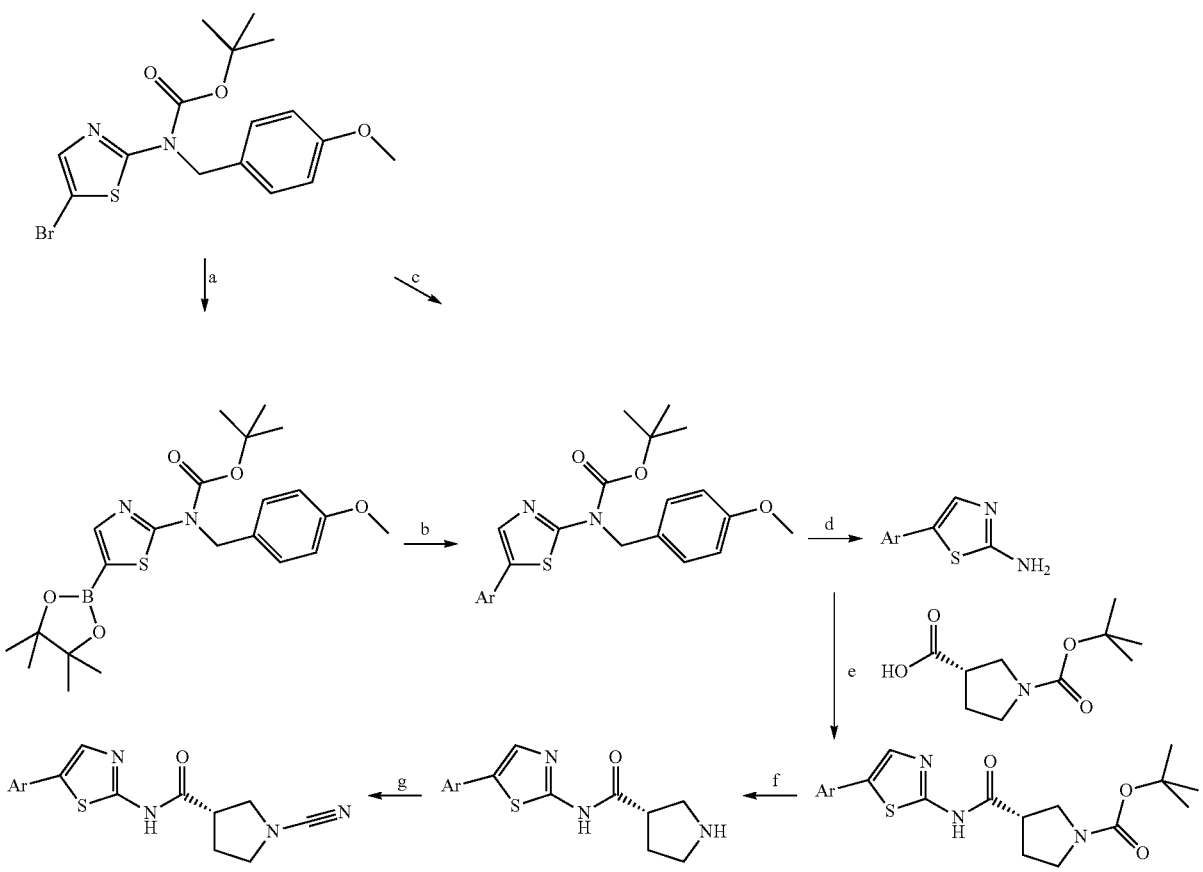

Reagents and conditions:
a) n-BuLi, 4,4,5,5-tetramethyl-1,3,2-dioxaborolane, THF, -78° C. to 0° C., 30 min
b) Aryl halide, PdCl₂(dppf), Na₂CO₃, toluene : water (5:1), rt then 100° C., 1 h
c) Arylboronic acid / boronate, PdCl₂(dppf), Cs₂CO₃, 1,4-dioxane : water (9:1), rt then 80° C., 2 h
d) TFA, 80° C., 8 h
e) HATU, DIPEA, THF, rt, 2 h
f) TFA, DCM, 0° C., then rt, 4 h
g) cyanogen bromide, K₂CO₃, THF : DMF (1:1), 0° C. then rt, 30 min Scheme 15

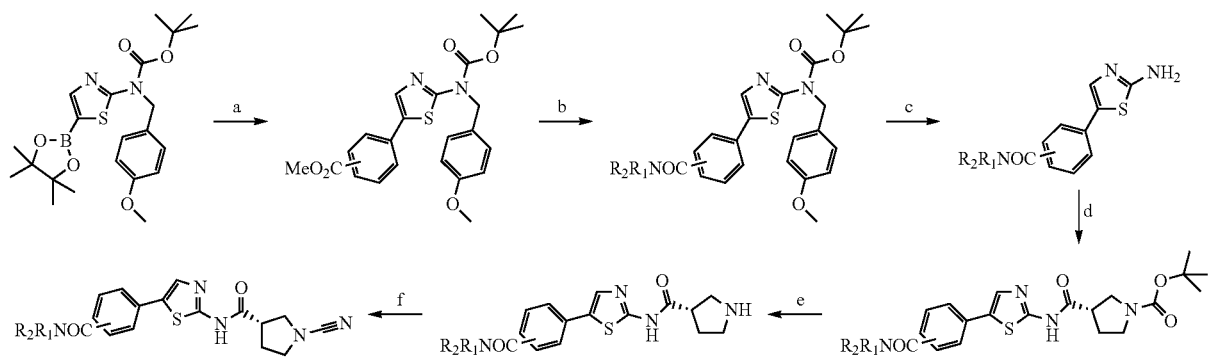

Reagents and conditions:
a) Aryl PdCl₂(dppf), Na₂CO₃, toluene : water (5:1), rt then 100° C., 1 h
b) R₁R₂NH, triazabicyclodecene, THF, 0° C. to rt, 4 h
c) TFA, 80° C., 8 h
d) (3S)-BOC-1-pyrrolidine-3-carboxylic acid, HATU, DIPEA, THF, rt 2 h
e) TFA, DCM, 0° C. to rt, 4 h
f) cyanogen bromide, K₂CO₃, THF : DMF (1:1), 0° C. then rt, 30 min

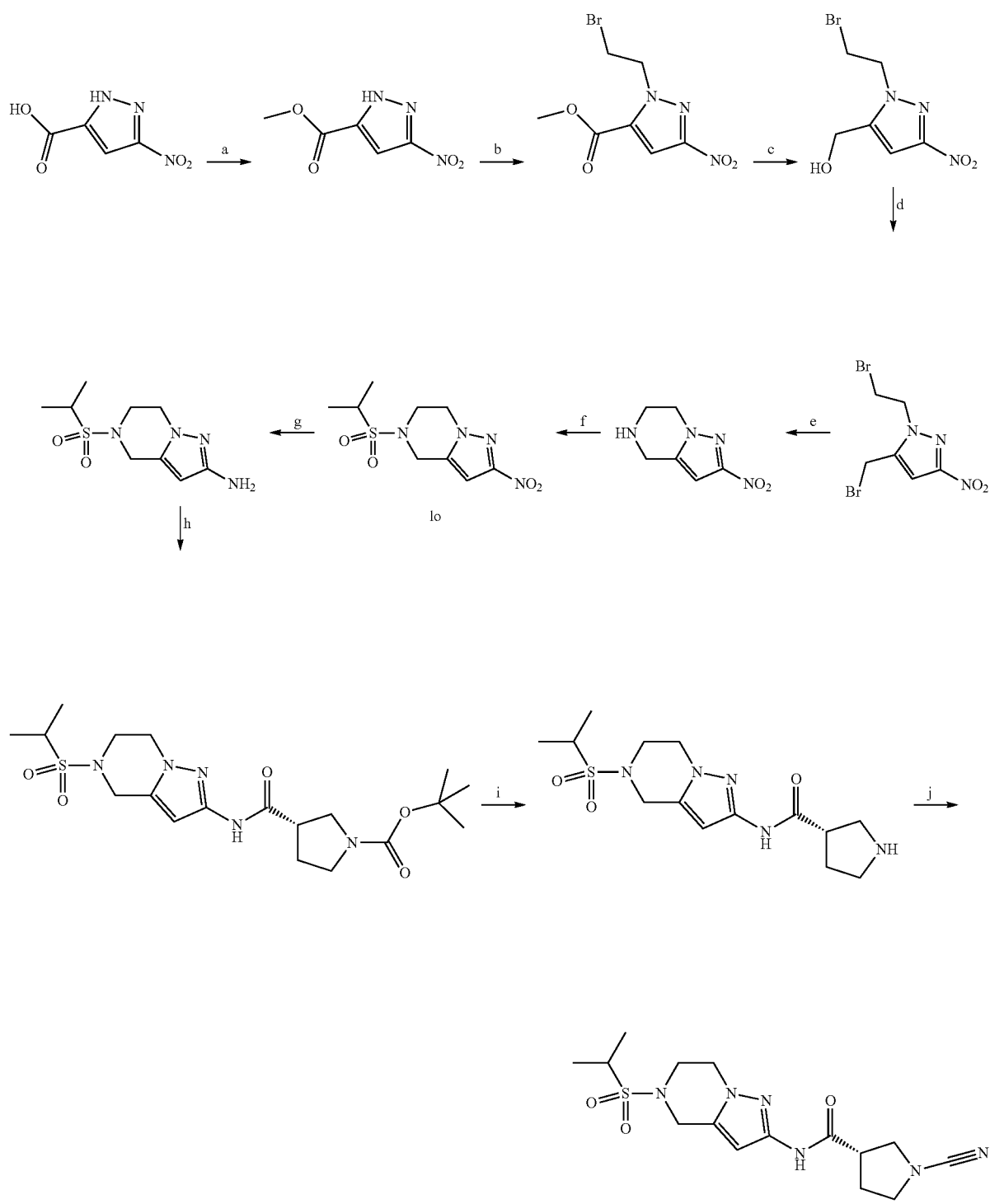
Scheme 16
Reagents and conditions:
a) SOCl$_2$, MeOH, DMF, 70° C., 4 h
b) 1,2-dibromoethane, K$_2$CO$_3$, acetone, 60° C., 4 h
c) LiBH$_4$ (3M in THF), THF, 0° C. then rt 2 h
d) PBr$_3$, chloroform, 0° C. then rt, 2 h
e) aqueous ammonia, THF, rt, 72 h
f) Isopropyl sulfonyl chloride, TEA, DCM, rt, 4 h
g) H$_2$, Pd/C (10% Dry), MeOH, rt, 3 h
h) T3P (50% in EtOAc), DIPEA, THF, rt 1 h
i) TFA, DCM, rt, 30 min
j) cyanogen bromide, K$_2$CO$_3$ THF, rt, 30 min Scheme 17
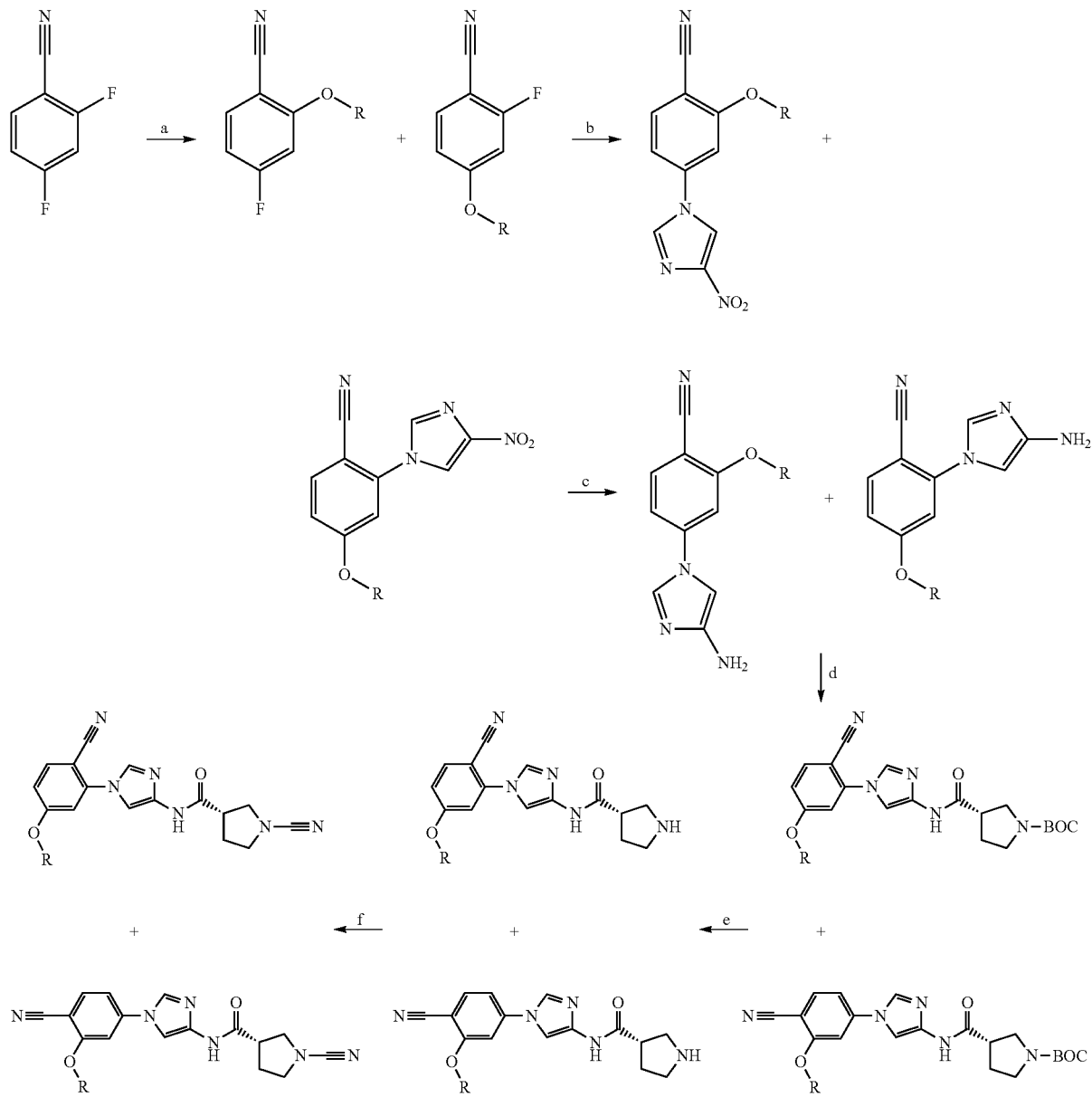
Reagents and conditions: a) ROH, NaH, THF, 1,4-dioxane, rt to 70° C., 16 h b) 4-nitro-1H-imidazole, K$_2$CO$_3$, KI, DMF, 130° C., 16 h c) H$_2$, 10% Pd/C (50% moisture), THF, rt, 2 h d) T3P (50% in EtOAc), DIPEA, THF, rt, 1 h e) TFA, DCM, rt, 30 min f) cyanogen bromide, K$_2$CO$_3$, THF, rt, 30 min
Scheme 18
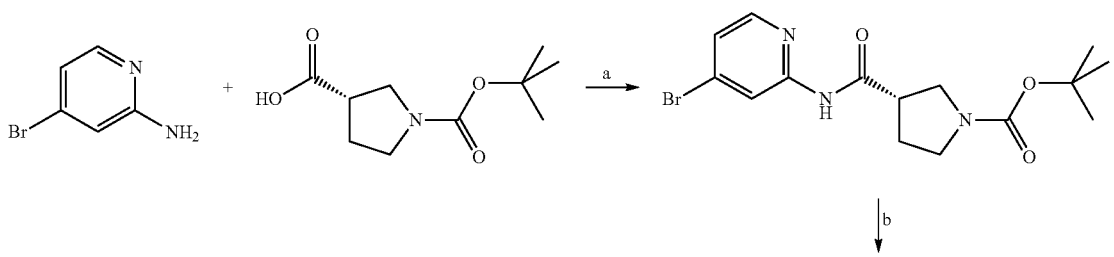

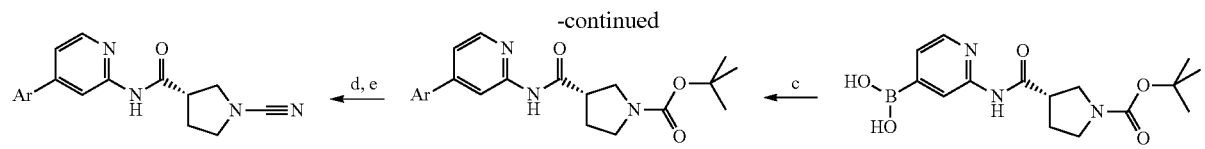

Reagents and conditions: a) POCl₃, pyridine, 0° C. to rt, 1 h b) bispinacolato diborane, Pd₂(dba)₃, X-Phos, CH₃CO₂K, 1,4-dioxane, 110° C., 2 h c) Ar-Hal, Pd(dppf)Cl₂, K₂CO₃, DMF, 80° C., 2 h d) DCM, TFA, rt, 1 h e) cyanogen bromide, K₂CO₃, THF, rt 1 h Scheme 19

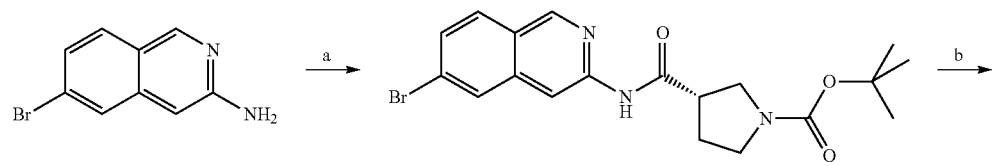

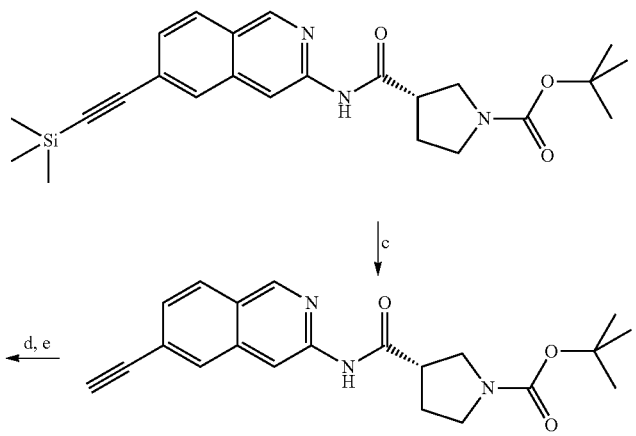

Reagents and conditions: a) (3S)-BOC-1-pyrrolidine-3-carboxylic acid, POCl₃, pyridine, DCM, 0° C., 30 min b) trimethylsilylacetylene, CuI, PdCl₂(PPh₃)₂, diisopropylamine, 120° C. 30 min c) K₂CO₃, MeOH, 0° C. to rt, 1 h d) TFA, DCM, 0° C. to rt, 1 h e) cyanogen bromide, K₂CO₃, THF, 0° C. to rt, 1 h Scheme 20

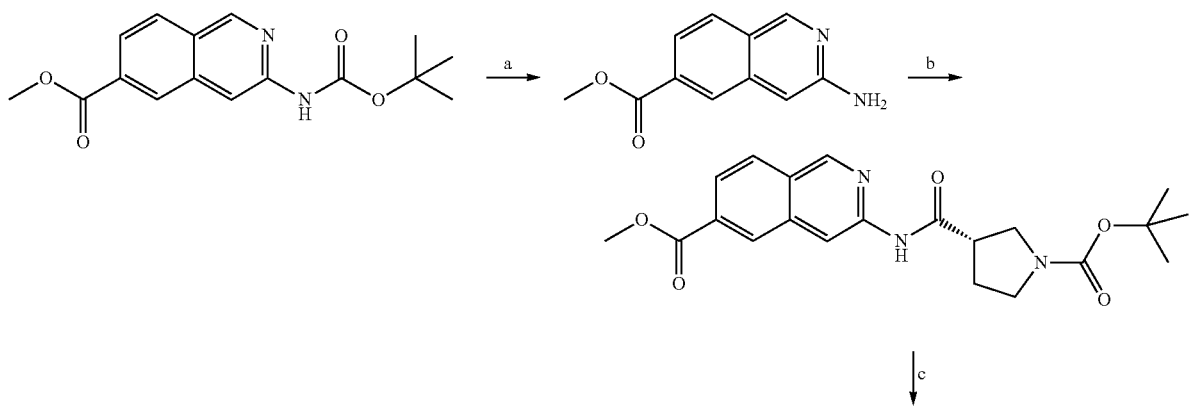

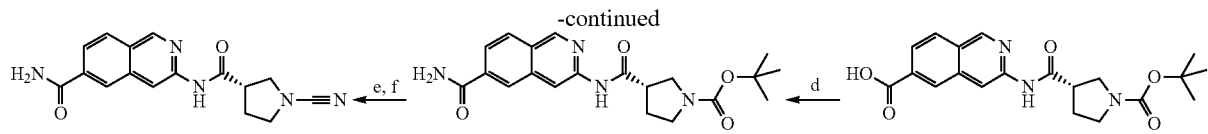

Reagents and conditions: a) TFA, DCM, 0° C. to rt, 3 h b) (3S)-BOC-1-pyrrolidine-3-carboxylic acid, POCl₃, pyridine, DCM, 0° C., 30 min c) LiOH, MeOH, water, 60° C., 3 h d) NH₄HCO₃, HATU, DIPEA, THF, rt 42 h e) TFA, DCM, 0° C. to rt, 2 h f) cyanogen bromide, K₂CO₃, THF, 0° C. to rt, 30 min Intermediate 1 ((2S,3S)-1-[(tert-butoxy)carbonyl]-2-methylpyrrolidine-3-carboxylic Acid)

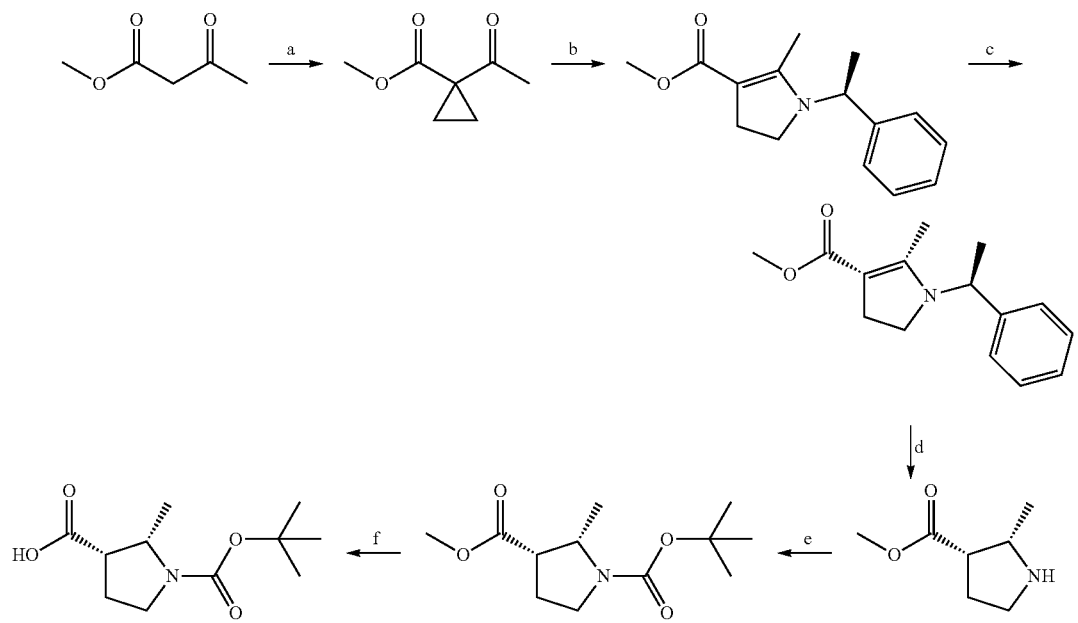

Reagents and conditions: a) K₂CO₃, acetone, 1,2-dibromoethane, 70° C. 24 h
b) (S)-1-phenylethan-1-amine, toluene, 110° C. 22 h c) NaBH(OAc)₃, acetic acid, MeCN, 0° C. 3 h d) 10% Pd/C, H₂ 425 psi, MeOH, autoclave, rt 16 h e) BOC anhydride, DMAP, THF, 0° C., rt 16 h f) LiOH, water:MeOH (1:1), 0° C. to 20° C. 6 h Step a.

To a solution of methyl acetoacetate (1.72 mol) and 1,2-dibromoethane (1.90 mol) in acetone (2000 ml) was added K₂CO₃ (2.59 mol) at rt. The reaction mixture was heated at 70° C. for 24 h. The resulting reaction mixture was allowed to cool to rt and filtered through celite hyflow. The celite cake was washed with acetone (2×100 ml). The filtrate was concentrated under reduced pressure and the resulting residue was purified by column chromatography (4% EtOAc in hexane) yielding methyl 1-acetylcyclopropane-1-carboxylate (0.70 mol). MS: ES+ 143.14.

Step b.

A solution of methyl 1-acetylcyclopropane-1-carboxylate (0.70 mol) and (S)-1-phenylethan-1-amine (0.84 mol) in toluene (1000 ml) was charged in a clean stark glass assembly. The reaction mixture was heated at a temperature (130-140° C.) to remove the water by azeotropic distillation. The process was continued for 22 h. The reaction mixture was allowed to cool to rt and concentrated under reduced pressure. The resulting residue was purified by column chromatography (2% EtOAc in hexane) yielding methyl (S)-2-methyl-1-(1-phenyl ethyl)-4,5-dihydro-1H-pyrrole-3-carboxylate (0.37 mol). MS: ES+ 246.33; $^1$H NMR (400 MHz, DMSO-d₆) δ ppm 7.36-7.39 (m, 2H), 7.26-7.29 (m, 3H), 4.95 (q, J=7.01 Hz, 1H), 3.50 (s, 3H), 3.41-3.49 (m, 1H), 3.03-3.10 (m, 1H), 2.55-2.57 (m, 2H), 2.25 (s, 3H), 1.48 (d, J=7.01 Hz, 3H).

Step c.

To a solution of (S)-2-methyl-1-(1-phenylethyl)-4,5-dihydro-1H-pyrrole-3-carboxylate (375 mmol) in MeCN (1000 ml) was added acetic acid (300 ml) at 0° C. Sodium triacetoxyborohydride (751 mmol) was added at 0° C. in equal portions. The reaction mixture was stirred at 0° C. for 3 h and the resulting reaction mixture was distilled under reduced pressure to remove majority of MeCN. The resulting mixture was poured into ice water (500 ml) and was neutralized by solid Na₂CO₃. The resulting mixture was extracted with EtOAc (3×200 ml). The combined organic phase was collected, dried over Na₂SO₄, filtered and concentrated under reduced pressure. The resulting residue was purified by column chromatography (2 to 10% EtOAc in hexane) yielding (210 mmol) of the title compound as a mixture of diastereomers. The diastereomeric mixture was further crystallized from hexane (350 ml) at −70° C. yielding methyl (2S,3S)-2-methyl-1-((S)-1-phenylethyl)pyrrolidine-3-carboxylate (137 mmol). MS: ES+ 248.15; $^1$H NMR (400

MHz, DMSO-d$_6$) δ ppm 7.28-7.36 (m, 4H), 7.19-7.24 (m, 1H), 3.59 (s, 3H), 3.55-3.58 (m, 1H), 3.31-3.39 (m, 1H), 3.03-3.10 (m, 1H), 2.56-2.62 (m, 1H), 2.40-2.46 (m, 1H), 1.93-2.04 (m, 1H), 1.76-1.84 (m, 1H), 1.25 (d, J=6.71 Hz, 3H), 0.71 (d, J=6.40 Hz, 3H).

Step d.

A solution of methyl (2S,3S)-2-methyl-1-((S)-1-phenylethyl)pyrrolidine-3-carboxylate (137 mmol) in MeOH (700 ml) was charged in an autoclave vessel at rt under nitrogen atmosphere. 10% Pd/C (0.3% w/w) was added to the reaction mixture at rt under nitrogen atmosphere. The resulting reaction mixture was stirred in the autoclave at rt under 425 psi H$_2$ pressure for 16 h. The resulting reaction mixture was carefully filtered through celite hyflow and concentrated under reduced pressure to yield methyl (2S,3S)-2-methylpyrrolidine-3-carboxylate (quantitative). The material was immediately used for the next step. MS: ES+ 144.05; $^1$H NMR (400 MHz, DMSO-d$_6$) δ ppm 3.59 (s, 3H), 3.18-3.25 (m, 1H), 2.96-3.02 (m, 1H), 2.82-2.88 (m, 1H), 2.61-2.66 (m, 1H), 1.80-1.97 (m, 2H), 0.94 (d, J=6.714 Hz, 3H).

Step e.

To stirred a solution of methyl (2S,3S)-2-methylpyrrolidine-3-carboxylate (139 mmol) in THF (200 ml) were added DMAP (8.1 mmol) and BOC anhydride (751 mmol) at 0° C. The reaction mixture stirred at 0° C. for 16 h. The resulting reaction mixture was poured into water (100 ml) and extracted with DCM (2×200 ml). The combined organic phase was collected, dried over Na$_2$SO$_4$, filtered and concentrated under reduced pressure. The resulting residue was purified by column chromatography (10% EtOAc in hexane) yielding 1-(tert-butyl) 3-methyl (2S,3S)-2-methylpyrrolidine-1,3-dicarboxylate (111 mmol). MS: ES+ 188 (M−56) 144 (M−100); $^1$H NMR (400 MHz, DMSO-d$_6$) δ ppm 3.98-4.03 (m, 1H), 3.64 (s, 3H), 3.30-3.41 (m, 1H), 3.12-3.29 (m, 2H), 2.06-2.14 (m, 1H), 1.91-1.99 (m, 1H), 1.40 (s, 9H), 0.95 (d, J=6.40 Hz, 3H).

Step f.

A solution of 1-(tert-butyl) 3-methyl (2S,3S)-2-methylpyrrolidine-1,3-dicarboxylate (111 mmol) in mixture of MeOH:water (1:1, 400 ml) was stirred at 0° C. for 10 min. Solid LiOH (166 mmol) was added portion wise to the reaction mixture at 0° C. The reaction mixture was stirred at 20° C. for 6 h. The resulting reaction mixture was extracted with EtOAc (2×100 ml). The aqueous layer was cooled to 0° C. and was neutralised by slow addition of 1N HCl. The resulting mixture was extracted with EtOAc (3×200 ml). The combined organic phase was dried over Na$_2$SO$_4$, filtered and concentrated under reduced pressure yielding title compound (87.33 mmol). MS: ES− 228; $^1$H NMR (400 MHz, DMSO-d$_6$) δ ppm 12.43 (br s, 1H), 3.97-4.02 (m, 1H), 3.30-3.35 (m, 1H) 3.06-3.18 (m, 2H), 2.01-2.10 (m, 1H), 1.85-1.93 (m, 1H), 1.40 (s, 9H), 1.00 (d, J=5.79 Hz, 3H).

Intermediate 2 (1-[(tert-butoxy)carbonyl]-(±)-trans-4-methylpyrrolidine-3-carboxylic Acid)

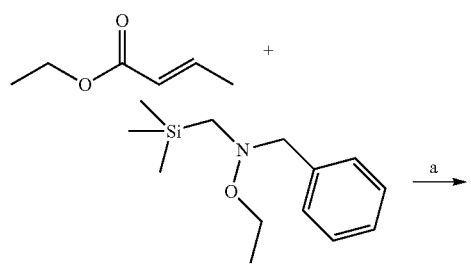

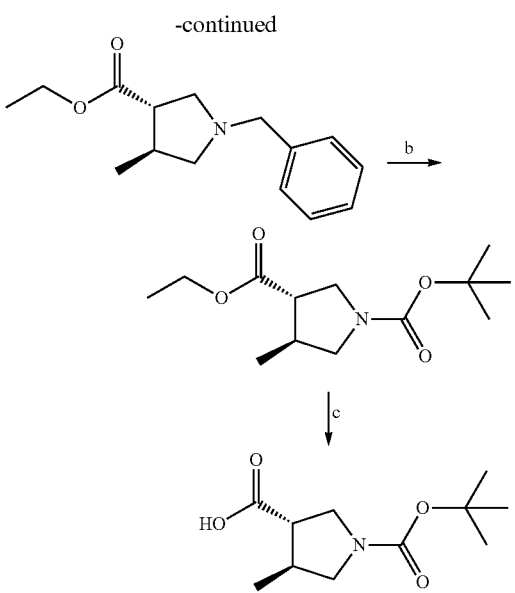

Reagents and conditions: a) TFA, toluene, 50° C., 16 h b) 20% Pd(OH)$_2$ on carbon, polymethyl hydrosiloxane, BOC anhydride, ethanol, 0° C., rt 1.5 h c) aqueous NaOH, water:THF (1:1), 0° C., rt 16 h Step a.

A solution of ethyl crotonate (17.5 mmol) and N-benzyl-O-ethyl-N-((trimethylsilyl)methyl) hydroxyl amine (19.2 mmol) in toluene (40 ml) was stirred at rt for 5 min. TFA (17.5 mmol) was added dropwise to the reaction mixture at rt. The reaction mixture was then heated at 50° C. for 16 h. The resulting reaction mixture was poured into water (100 ml) and basified with solid NaHCO$_3$. The resulting mixture was extracted with EtOAc (2×180 ml). The combined organic phase was collected, dried over Na$_2$SO$_4$, filtered and concentrated under reduced pressure. The resulting residue was purified by column chromatography (0-9% EtOAc in hexane) yielding ethyl-(±)-trans-1-benzyl-4-methylpyrrolidine-3-carboxylate (9.0 mmol). MS: ES+ 248.33; $^1$H NMR (400 MHz, CDCl$_3$) δ ppm 7.24-7.36 (m, 5H), 4.13 (q, J=8.0, 5.2 Hz, 2H), 3.67 (d, J=13 Hz, 1H), 3.58 (d, J=13 Hz, 1H), 2.77-2.91 (m, 3H), 2.47-2.59 (m, 2H), 2.21-2.26 (m, 1H), 1.27 (t, J=7.2 Hz, 3H), 1.16 (d, J=6.71 Hz, 3H).

Step b.

To a solution of ethyl-(±)-trans-1-benzyl-4-methylpyrrolidine-3-carboxylate (10 mmol) in ethanol (30 ml) were added polymethyl hydrosiloxane (1.0 w/w), 20% Pd(OH)$_2$ on carbon (0.5 w/w) and BOC anhydride (20 mmol) at 0° C. The reaction mixture was stirred at rt for 1.5 h. The resulting reaction mixture was carefully filtered through celite hyflow and the filtrate was concentrated under reduced pressure. The resulting residue was purified by column chromatography (0-10% EtOAc in hexane) yielding 1-tert-butyl 3-ethyl (±)-4-methylpyrrolidine-1,3-dicarboxylate (8.5 mmol). MS: ES+ 202.2 (M−56)

Step c.

A solution of 1-tert-butyl 3-ethyl (±)-4-methylpyrrolidine-1,3-dicarboxylate (8.5 mmol) in THF (15 ml) was stirred at 0° C. for 5 min. A solution of NaOH (34.0 mmol) in water (15 ml) was added dropwise to the reaction mixture at 0° C. The reaction mixture was stirred at rt for 16 h. The resulting reaction mixture was poured into water (200 ml) and acidified to pH 4.0 with dilute HCl. The obtained mixture was extracted with EtOAc (2×150 ml). The combined organic phase was collected, dried over Na$_2$SO$_4$, filtered and concentrated under reduced pressure yielding 1-[(tert-butoxy)carbonyl]-(±)-trans-4-methylpyrrolidine-3-carboxylic acid (7.1 mmol). This material was used directly for the next step without further purification. MS: ES– 228.28; ¹H NMR (400 MHz, DMSO-d₆) δ ppm 12.51 (br s, 1H), 3.47-3.56 (m, 2H), 3.28-3.34 (m, 1H), 2.78-2.86 (m, 1H), 2.58-2.64 (m, 1H), 2.27-2.34 (m, 1H), 1.38 (s, 9H), 1.04 (d, J=4.8 Hz, 3H).

Intermediate 3
5-(tetrahydro-2H-pyran-4-yl)thiazol-2-amine

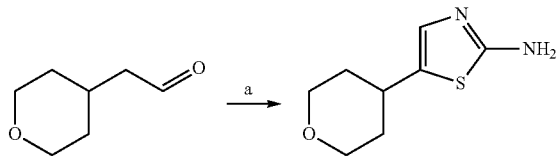

Reagents and conditions: a) p-toluenesulfonic acid monohydrate, pyrrolidine, cyclohexane 80° C., 3 h, followed by S-powder, cyanamide, MeOH, 0° C., rt 16 h.

Step a.
To a stirred solution of 2-(tetrahydro-2H-pyran-4-yl) acetaldehyde (4.7 mmol), pyrrolidine (5.6 mmol) and p-toluenesulfonic acid monohydrate (0.5 mmol) in cyclohexane (20 ml) was added oven dried molecular sieves. The reaction mixture was heated at 80° C. for 3 h. The resulting reaction mixture was concentrated under reduced pressure. The obtained residue was re-dissolved in MeOH (3 ml) and cooled to 0° C. To this solution were added sulphur powder (4.7 mmol) and a solution of cyanamide (4.7 mmol) in MeOH (0.5 ml) at 0° C. The reaction mixture was stirred at rt for 16 h. The resulting reaction mixture was concentrated under reduce pressure, poured into water (50 ml) and extracted with EtOAc (3×50 ml). The combined organic phase was collected, dried over Na₂SO₄, filtered and concentrated under reduced pressure. The resulting residue was purified by column chromatography (2-3% MeOH in DCM) yielding 5-(tetrahydro-2H-pyran-4-yl)thiazol-2-amine (1.6 mmol). MS: ES+ 185.14

Intermediate 4
1-methyl-5-phenyl-1H-pyrazol-3-amine

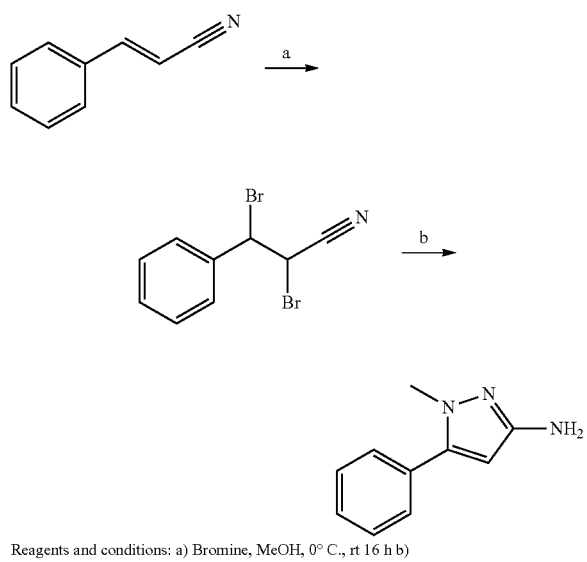

Reagents and conditions: a) Bromine, MeOH, 0° C., rt 16 h b) methylhydrazine, MeOH, 75° C., 16 h Step a.
A solution of cinnamonitrile (7.7 mmol) in MeOH (10 ml) was stirred at 0° C. for 5 min. Bromine (15.5 mmol) was added to the reaction mixture at 0° C. The reaction mixture was stirred at rt for 16 h. The resulting reaction mixture was poured into water (50 ml) and basified with solid NaHCO₃. The resulting mixture was extracted with EtOAc (3×50 ml). The combined organic phase was collected, dried over Na₂SO₄, filtered and concentrated under reduced pressure. The resulting residue was purified by column chromatography (0-4% EtOAc in hexane) yielding 2,3-dibromo-3-phenylpropanenitrile (1.66 mmol). This material was used immediately for the next step without further purification.

Step b.
To a solution of 2,3-dibromo-3-phenylpropanenitrile (1.6 mmol) in MeOH (10 ml) was added methylhydrazine (1.6 mmol) at rt. The reaction mixture was heated at 75° C. for 16 h. The resulting reaction mixture was concentrated under reduced pressure. The resulting residue was purified by flash chromatography (2-3% MeOH in DCM) yielding 1-methyl-5-phenyl-1H-pyrazol-3-amine (quantitative). This material was used directly for the next step without further purification. MS: ES+ 174.24

Intermediate 5
5-(4-methoxypiperidin-1-yl)pyridin-2-amine

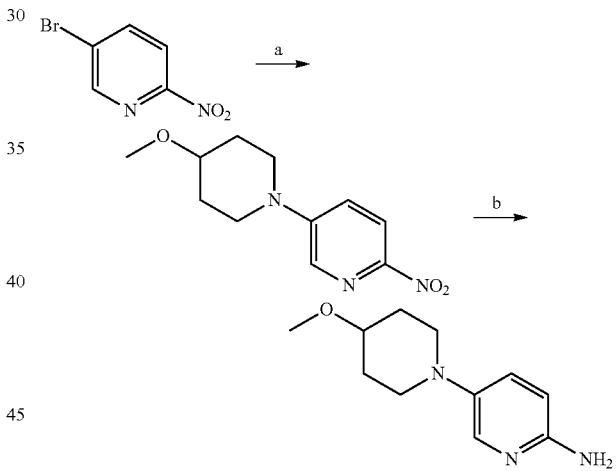

Reagents and conditions: a) 4-methoxy piperidine HCl, K₂CO₃, TBAI, DMSO, 80° C. 15 h b) 10% Pd/C, H₂, MeOH, rt 1 h Step a.
A solution of 5-bromo-2-nitro-pyridine (2.0 mmol) and 4-methoxypiperidine HCl (4.0 mmol) in DMSO (10 ml) was stirred at rt for 5 min. K₂CO₃ (4.0 mmol) and TBAI (0.2 mmol) were then added to the reaction mixture at rt. The reaction mixture was stirred at 80° C. for 15 h. The resulting reaction mixture was poured into water (200 ml) and extracted with EtOAc (2×150 ml). The combined organic phase was collected, dried over Na₂SO₄, filtered and concentrated under reduced pressure. The resulting residue was purified by flash chromatography (15% EtOAc in hexane) yielding 5-(4-methoxypiperidin-1-yl)-2-nitropyridine (1.6 mmol). MS: ES+ 238.35; ¹H NMR (400 MHz, DMSO-d₆) δ ppm 8.27 (d, J=3.05 Hz, 1H), 8.14 (d, J=9.16 Hz, 1H), 7.49 (dd, J=9.16, 3.05 Hz, 1H), 3.75-3.84 (m, 2H), 3.46-3.48 (m, 1H), 3.30-3.35 (m, 2H), 3.28 (s, 3H), 1.90-1.95 (m, 2H), 1.48-1.53 (m, 2H).

Step b.

To a solution of 5-(4-methoxypiperidin-1-yl)-2-nitropyridine (1.6 mmol) in MeOH (20 ml) was added 10% Pd/C (0.25% w/w) at rt. The reaction mixture was purged with $H_2$ gas at rt for 1 h. The resulting reaction mixture was carefully filtered through celite hyflow and concentrated under reduced pressure to yield 5-(4-methoxypiperidin-1-yl)pyridin-2-amine (1.55 mmol). MS: ES+ 208.08; $^1$H NMR (400 MHz, DMSO-$d_6$) δ ppm 7.61 (d, J=3.05 Hz, 1H), 7.16 (dd, J=8.85, 2.75 Hz, 1H), 6.38 (d, J=8.85 Hz, 1H), 5.40 (br s, 2H), 3.22-3.31 (m, 4H), 3.15-3.22 (m, 2H), 2.61-2.71 (m, 2H), 1.88-1.97 (m, 2H), 1.46-1.58 (m, 2H).

Intermediate 6 5-cyclohexylpyridin-2-amine

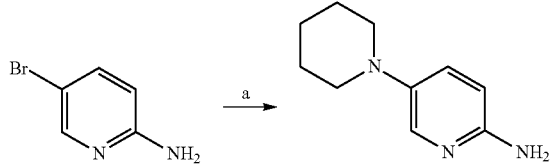

Reagents and conditions: a) ZnCl$_2$ (0.7M in THF), cyclohexylmagnesium bromide (1M in THF), 2-amino-5-bromopyridine, Pd(dppf)Cl$_2$·CH$_2$Cl$_2$, 1,4-dioxane, 0° C., then at rt to reflux for 20 h Step a.

Pd(dppf)Cl$_2$.CH$_2$Cl$_2$ (0.06 mmol) was added to a solution of 2-amino-5-bromopyridine (2.8 mmol) in 1,4-dioxane (5 ml) at 0° C. The resulting reaction mixture was allowed to stir at 0° C. Meanwhile a fresh Grignard solution was prepared by adding cyclohexylmagnesium bromide (1M in THF) (11.5 mmol) to ZnCl$_2$ (0.7M in THF) (5.8 mmol) at 0° C. The Grignard solution was diluted by dropwise addition of 1,4-dioxane (10 ml) at 0° C. The freshly prepared Grignard solution was added dropwise to the reaction mixture maintaining the temperature at 0° C. The resulting reaction mixture was then allowed to reach at rt and then refluxed for 20 h. The resulting reaction mixture was cooled and then poured into saturated NaHCO$_3$ solution (25 ml) and extracted with EtOAc (3×50 ml). The combined organic phase was dried over Na$_2$SO$_4$, filtered and concentrated under reduced pressure. The resulting residue was purified by flash chromatography (40-50% EtOAc in hexane) yielding 5-cyclohexylpyridin-2-amine (2.3 mmol). MS: ES+ 177.19.

Intermediates 7 and 8 6-(1H-1,2,3-triazol-1-yl) benzo[d]thiazol-2-amine and 6-(2H-1,2,3-triazol-2-yl)benzo[d]thiazol-2-amine

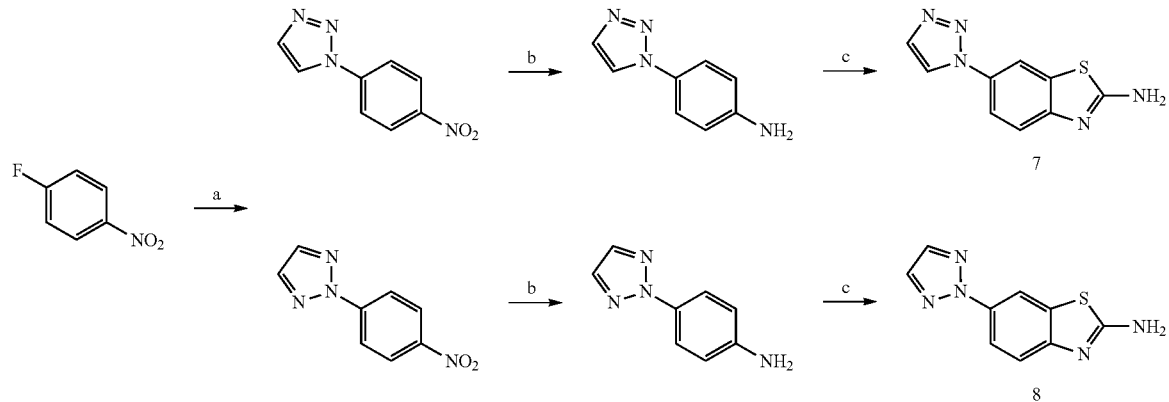

Reagents and conditions: a) 1,2,3-triazole, Cs$_2$CO$_3$, DMF, 70° C. 3 h b) Fe, acetic acid, water, ethanol, 80° C. 1 h c) ammonium thiocyanate, bromine, acetic acid, 0° C., rt 3 h Step a.

A solution of 1,2,3-triazole (14.17 mmol) and Cs$_2$CO$_3$ (35.5 mmol) in DMF (20 ml) was stirred at rt for 30 min. 1-Fluoro-4-nitrobenzene (14.17 mmol) was added to the reaction mixture at rt and then stirred at 70° C. for 3 h. The resulting reaction mixture was poured into a chilled brine solution (50 ml). The obtained white precipitates were collected by filtration under reduced pressure and washed with chilled water (2×10 ml). The obtained solid was a mixture of regio-isomers which were further separated by column chromatography (0-9% EtOAc in hexane) yielding 1-(4-nitrophenyl)-1H-1,2,3-triazole (4.3 mmol) MS: ES+ 191.34; $^1$H NMR (400 MHz, DMSO-$d_6$) δ ppm 9.08 (d, J=1.22 Hz, 1H), 8.45-8.49 (m, 2H), 8.24-8.30 (m, 2H), 8.09 (d, J=1.22 Hz, 1H) and 2-(4-nitrophenyl)-2H-1,2,3-triazole (5.8 mmol) MS: ES+ 191.3; $^1$H NMR (400 MHz, DMSO-$d_6$) δ ppm 8.43-8.46 (m, 2H), 8.27-8.30 (m, 4H).

Step b.

To a solution of 1-(4-nitrophenyl)-1H-1,2,3-triazole (5.78 mmol) in ethanol (8 ml) and water (4 ml) was added Fe power (34.73 mmol) and acetic acid (34.74 mmol) at rt. The reaction mixture was stirred at 80° C. for 1 h. The resulting reaction mixture was allowed to cool to rt and poured into a mixture of DCM (20 ml) and water (10 ml). The obtained emulsion was filtered through celite hyflow. Organic layer was separated from the obtained filtrate and the aqueous layer was back extracted with DCM (10 ml). The combined organic phase was collected, dried over Na$_2$SO$_4$, filtered and concentrated under reduced pressure yielding 4-(1H-1,2,3-triazol-1-yl)aniline (5.6 mmol). The material was used directly for the next step without further purification. MS: ES+ 161.10

2-(4-Nitrophenyl)-2H-1,2,3-triazole was processed in a similar manner to afford 4-(2H-1,2,3-triazol-2-yl)aniline. MS: ES+ 161.10

Step c.

To a solution of 4-(1H-1,2,3-triazol-1-yl)aniline (3.43 mmol) in acetic acid (5 ml) was added ammonium thiocyanate (8.59 mmol) at rt and the reaction mixture was then cooled to 10° C. Bromine (3.43 mmol) in acetic acid (2 ml) was added dropwise to the above reaction mixture at 10° C. A thick mass was observed during addition of bromine. The reaction mixture was then stirred well at rt for 3 h. The resulting reaction mixture was poured into chilled water (30 ml) and neutralized using ammonium hydroxide. Obtained yellow precipitates were collected by filtration under reduced pressure, washed with chilled water (2×10 ml), MeOH (2×5 ml) and dried to yield 6-(1H-1,2,3-triazol-1-yl)benzo[d]thiazol-2-amine (2.85 mmol). MS: ES+ 218.13; $^1$H NMR (400 MHz, DMSO-$d_6$) δ ppm 8.73 (d, J=0.92 Hz, 1H), 8.23 (d, J=2.14 Hz, 1H), 7.95 (d, J=0.92 Hz, 1H), 7.75 (s, 2H), 7.71 (dd, J=8.55, 2.44 Hz, 1H), 7.48 (d, J=8.55 Hz, 1H).

4-(2H-1,2,3-triazol-2-yl)aniline was processed in a similar manner to afford 6-(2H-1,2,3-triazol-2-yl)benzo[d]thiazol-2-amine. MS: ES+ 218.13; $^1$H NMR (400 MHz, DMSO-$d_6$) δ ppm 8.35 (s, 1H), 8.08-8.11 (m, 2H), 7.88 (d, J=9.16 Hz, 1H), 7.69 (br s, 2H), 7.45 (d, J=8.85 Hz, 1H).

Intermediate 9
4-(2-aminothiazol-5-yl)-N-methylbenzamide

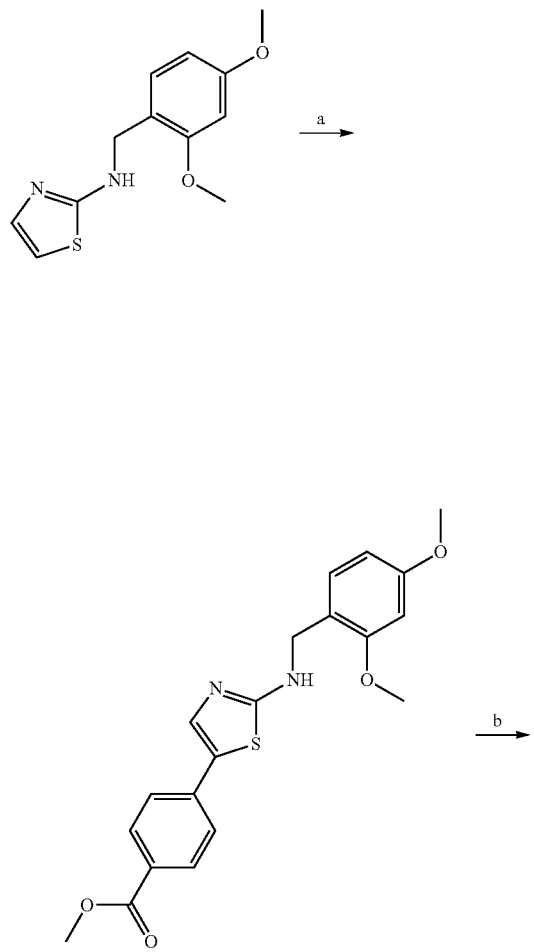

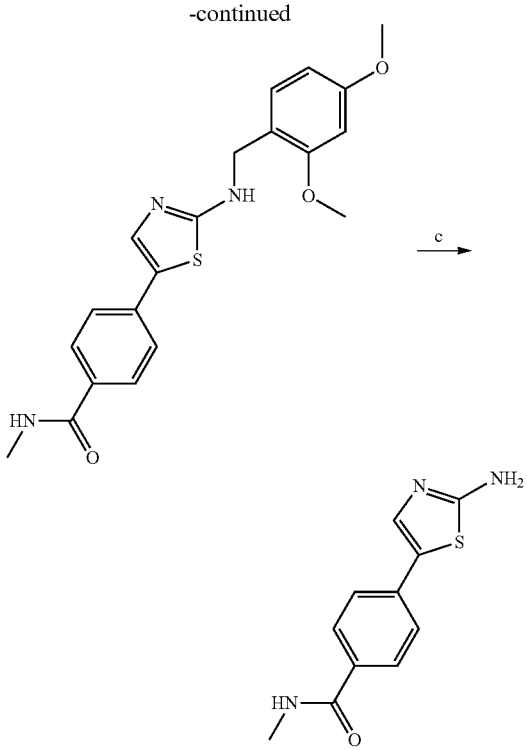

Reagents and conditions: a) methyl 4-bromobenzoate, KOAc, Pd(PPh$_3$)$_4$, DMA, 130° C., 16 h b) trimethylaluminium (2M in toluene), methylamine, DIPEA, toluene, 0° C. 15 min, then at 100° C. 16 h c) TFA, DCM, rt, 48 h.

Step a.

A solution of N-(2,4-dimethoxybenzyl)thiazol-2-amine (7.9 mmol), methyl 4-bromobenzoate (11.9 mmol) and KOAc (23.97 mmol) in DMA (50 ml) was prepared in a glass tube. A stream of nitrogen gas was purged through the reaction mixture at rt for 30 min. Pd(PPh$_3$)$_4$ (0.79 mol) was added to the reaction mixture and the glass tube was tightly sealed. The sealed tube was heated at 140° C. (external temperature) for 16 h. The resulting reaction mixture was poured into water (100 ml) and extracted with EtOAc (2×50 ml). The combined organic phase was collected, dried over Na$_2$SO$_4$, filtered and concentrated under reduced pressure. The resulting residue was purified by column chromatography (25% EtOAc in hexane) yielding methyl 4-(2 ((2,4-dimethoxybenzyl)-amino)thiazol-5-yl)benzoate (3.9 mmol). MS: ES+ 385.68

Step b.

To a solution of methyl 4-(2-((2,4-dimethoxybenzyl)amino)thiazol-5-yl)benzoate (1.8 mmol) and DIPEA (0.9 mmol) in toluene (15 ml) was added trimethylaluminium (2 M in toluene) (9.1 mmol) at 0° C. The reaction mixture was stirred at 0° C. for 15 min. Methylamine (2.18 mmol) was added to the reaction mixture and then heated at 100° C. for 16 h. The resulting reaction mixture was concentrated under reduced pressure and the obtained residue was poured into saturated NaHCO$_3$ solution (30 ml). The resulting mixture was extracted with EtOAc (2×20 ml). The combined organic phase was collected, dried over Na$_2$SO$_4$, filtered and concentrated under reduced pressure yielding 4-(2-((2,4-dimethoxybenzyl)amino)thiazol-5-yl)-N-methylbenzamide (0.86 mmol). MS: ES+ 384.38

Step c.

To a solution of 4-(2-((2,4-dimethoxybenzyl)amino)thiazol-5-yl)-N-methylbenzamide (0.80 mmol) in DCM (5 ml)

was added TFA (3 ml) at 0° C. The reaction mixture was stirred at rt for 48 h. The resulting reaction mixture was poured into water (10 ml) and extracted with EtOAc (2×10 ml). The combined organic phase was collected, dried over Na$_2$SO$_4$, filtered and concentrated under reduced pressure yielding 4-(2-aminothiazol-5-yl)-N-methylbenzamide TFA salt (0.63 mmol). This material was directly used for the next step without further purification. MS: ES+ 234.35

Intermediate 10 5-(2-chlorophenyl)thiazol-2-amine

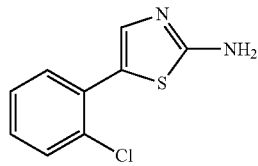 [SMILES: Nc1ncc(-c2ccccc2Cl)s1]

Synthesised using a procedure similar to that described for Intermediate 9 using 1-bromo-2-chlorobenzene (CAS Number 694-80-4) in step a. MS: ES+ 211.13; $^1$H NMR (400 MHz, DMSO-d$_6$) δ ppm 7.55 (dd, J=7.6 Hz, 1.6 Hz, 1H), 7.50 (dd, J=6.0 Hz, 1.2 Hz, 1H), 7.36 (s, 1H), 7.33 (dd, J=6.0 Hz, 1.2 Hz, 1H), 7.25-7.29 (m, 1H), 7.21 (br s, 2H).

Intermediate 11 1-(tert-butoxycarbonyl)-3-(methoxymethyl)pyrrolidine-3-carboxylic Acid

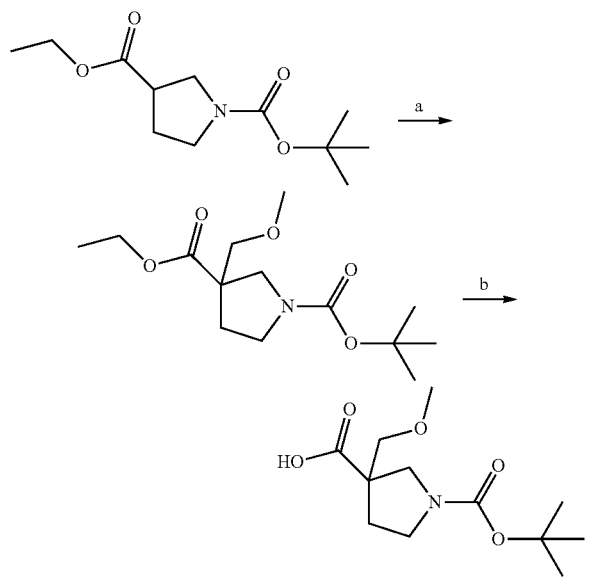

Reagents and conditions: a) bromomethyl methyl ether, freshly prepared LDA, THF, -78° C. 45 min, rt 16 h b) LiOH, THF, water, rt 16 h.

Step a.

A solution of 1-(tert-butyl) 3-ethyl pyrrolidine-1,3-dicarboxylate (2.0 mmol) in THF (5 ml) was cooled to -78° C. Freshly prepared LDA (2.2 mmol) was added dropwise to the reaction mixture at -78° C. The reaction mixture was stirred at -78° C. for 45 min. Bromomethyl methyl ether (2.2 mmol) was added dropwise to the reaction mixture at -78° C. The reaction mixture was stirred at rt for 16 h. The resulting reaction mixture was poured into saturated NH$_4$Cl solution (10 ml) and extracted with EtOAc (3×20 ml). The combined organic phase was collected, dried over Na$_2$SO$_4$, filtered and concentrated under reduced pressure yielding 1-(tert-butyl) 3-ethyl 3-(methoxymethyl)pyrrolidine-1,3-dicarboxylate (quantitative). This material was directly used for the next step without further purification. MS: ES+ 288.70

Step b.

To a solution of 1-(tert-butyl) 3-ethyl 3-(methoxymethyl) pyrrolidine-1,3-dicarboxylate (2.1 mmol) in THF:water (3:1, 10 ml) was added LiOH (8.3 mmol) at rt. The reaction mixture was stirred at rt for 16 h. The resulting reaction mixture was diluted with water (10 ml) and adjusted to pH 3 using saturated aqueous solution of citric acid. The resulting mixture was extracted with DCM (3×20 ml). The combined organic phase was dried over Na$_2$SO$_4$, filtered and concentrated under reduced pressure yielding 1-(tert-butoxycarbonyl)-3-(methoxymethyl)-pyrrolidine-3-carboxylic acid (0.96 mmol). This material was directly used for the next step without further purification. MS: ES- 257.40

Intermediate 12 1-(tert-butoxycarbonyl)-3-cyanopyrrolidine-3-carboxylic Acid

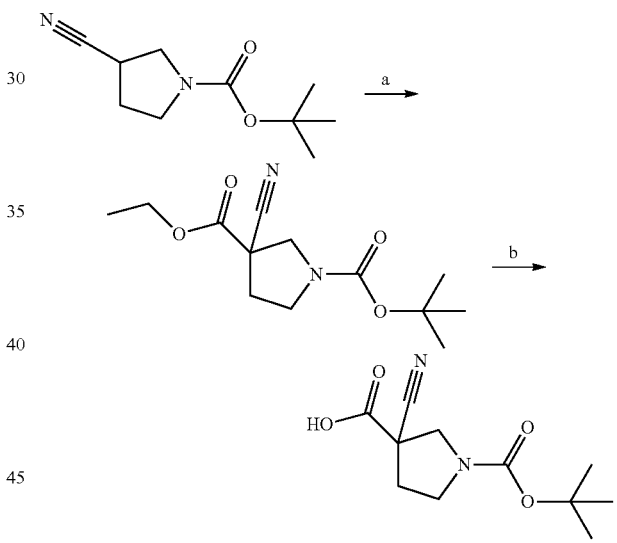

Reagents and conditions: a) Ethyl chloroformate, LiHMDS, THF, -78° C. 30 min, rt, 2 h b) LiOH, THF, water, rt 16 h Step a.

A solution of tert-butyl 3-cyanopyrrolidine-1-carboxylate (2.8 mmol) in THF (5 ml) was cooled to -78° C. LiHMDS (1M in Hexane) (7.0 mmol) was added dropwise to the reaction mixture at -78° C. The reaction mixture was stirred at -78° C. for 30 min. Ethyl chloroformate (8.4 mmol) was added dropwise to the reaction mixture at -78° C. The reaction mixture was stirred at rt for 1 h. The resulting reaction mixture was re-cooled to -78° C. and quenched with saturated NH$_4$Cl solution (10 ml). The resulting mixture was extracted with EtOAc (3×20 ml). The combined organic phase was collected, dried over Na$_2$SO$_4$, filtered and concentrated under reduced pressure yielding 1-(tert-butyl) 3-ethyl 3-cyanopyrrolidine-1,3-dicarboxylate (quantitative). This material was directly used for the next step without further purification. MS: ES+ 269.60

Step b.

To a solution of 1-(tert-butyl) 3-ethyl 3-cyanopyrrolidine-1,3-dicarboxylate (1.8 mmol) in THF:water (3:1, 13 ml) was added LiOH (5.6 mmol) at rt. The reaction mixture was stirred at rt for 16 h. The resulting reaction mixture was diluted with water (10 ml) and adjusted to pH 3 using saturated aqueous solution of citric acid. The resulting mixture was extracted with EtOAc (3×20 ml). The combined organic phase was collected, dried over $Na_2SO_4$, filtered and concentrated under reduced pressure yielding 1-(tert-butoxycarbonyl)-3-cyanopyrrolidine-3-carboxylic acid (0.8 mmol). This material was directly used for the next step without further purification. MS: ES− 239.50

Intermediate 13 tert-butyl (4-methyl-5-(morpholinomethyl)thiazol-2-yl)carbamate

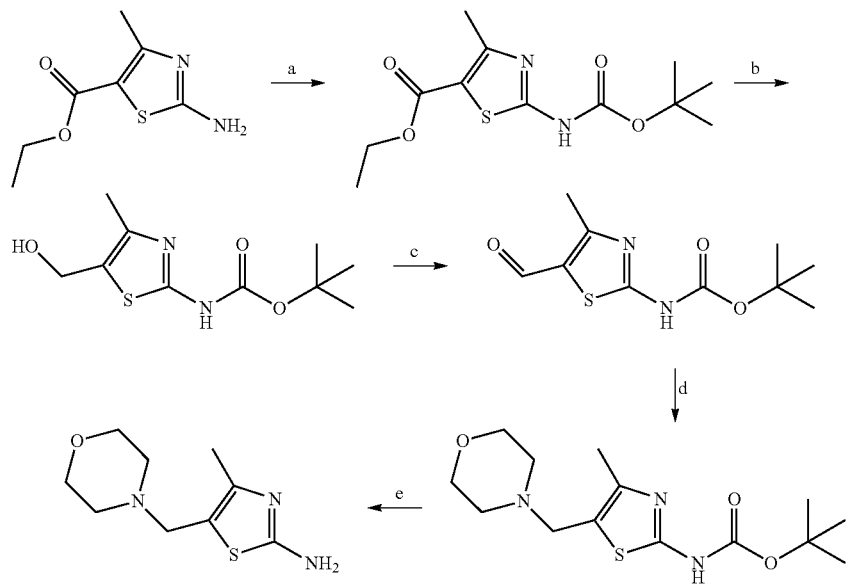

Reagents and conditions: a) (BOC)$_2$O, DMAP, THF, rt 18 h b) 2.0M LiAlH$_4$ in THF, THF, 0° C., rt 2 h c) Dess-Martin periodinane, DCM, rt, 24 h d) morpholine, DCE, 35° C. 3 h, NaBH(OAc)$_3$, 60° C. 5 h e) TFA, DCM, rt 3 h Step a.

To a solution of ethyl 2-amino-4-methylthiazole-5-carboxylate (10.75 mmol) in THF (15 ml) were added (BOC)$_2$O (12.90 mmol), DMAP (1.07 mmol) and TEA (16.13 mmol) at rt. The reaction mixture was stirred at rt for 18 h. The resulting reaction mixture was diluted with EtOAc (180 ml) and washed with 1M HCl (100 ml) and brine (100 ml). The organic phase was collected, dried over $Na_2SO_4$, filtered and concentrated under reduced pressure yielding ethyl 2-((tert-butoxycarbonyl)amino)-4-m ethylthiazole-5-carboxylate (8.39 mmol). This material was used directly for the next step without further purification.

Step b.

To a solution of ethyl 2-((tert-butoxycarbonyl)amino)-4-methylthiazole-5-carboxylate (8.39 mmol) in THF (15 ml) was added LiAlH$_4$ (2.0M in THF) (10.06 mmol) at 0° C. The reaction mixture was stirred at rt for 2 h. The resulting reaction mixture was poured into water (100 ml). The obtained mixture was filtered through celite hyflow and washed with EtOAc (50 ml). The organic layer was separated from the filtrate and the aqueous layer was further extracted with EtOAc (3×150 ml). The combined organic phase was collected, dried over $Na_2SO_4$, filtered and concentrated under reduced pressure yielding tert-butyl (5-(hydroxymethyl)-4-methylthiazol-2-yl)carbamate (7.17 mmol). This material was directly used for the next step without further purification. MS: ES+ 245.33

Step c.

To a solution of tert-butyl (5-(hydroxymethyl)-4-methylthiazol-2-yl) carbamate (7.17 mmol) in DCM (80 ml) was added Dess-Martin periodinane (7.05 mmol) at rt. The reaction mixture was stirred at rt for 24 h. The resulting reaction mixture was poured into water (100 ml). The obtained mixture was neutralized by addition of aqueous solution of saturated $NaHCO_3$. The resulting mixture was extracted with DCM (2×100 ml). The combined organic phase was collected, dried over $Na_2SO_4$, filtered and concentrated under reduced pressure yielding tert-butyl (5-formyl-4-methylthiazol-2-yl) carbamate (4.00 mmol). This material was directly used for the next step without further purification. MS: ES+ 243.48

Step d.

To a solution of tert-butyl (5-formyl-4-methylthiazol-2-yl) carbamate (4.00 mmol) in DCE (5 ml) was added morpholine (8.01 mmol) at rt. The reaction mixture was heated at 35° C. for 3 h. NaBH(OAc)$_3$ (12.02 mmol) was added to the reaction mixture at 35° C. The reaction mixture was then heated at 60° C. for 5 h. The resulting reaction mixture was allowed to cool to rt, poured into ice water (100 ml) and extracted with DCM (3×100 ml). The combined organic phase was collected, dried over $Na_2SO_4$, filtered and concentrated under reduced pressure. The resulting residue was purified by flash chromatography (5% MeOH in DCM) yielding tert-butyl (4-methyl-5-(morpholinomethyl)thiazol-2-yl)carbamate (2.55 mmol). MS: ES+ 314.43

Step e.

To a solution of tert-butyl (4-methyl-5-(morpholinomethyl)thiazol-2-yl)carbamate (2.55 mmol) in DCM (10 ml) was added TFA (25.5 mmol) at 0° C. The reaction mixture was stirred at rt for 3 h. The resulting reaction mixture was concentrated under reduced pressure. The obtained residue was triturated with diethyl ether (2×5 ml) yielding 4-methyl-5-(morpholinomethyl) thiazol-2-amine TFA salt (1.69 mmol). This material was directly used for the next step without further purification. MS: ES+ 214.15

Intermediate 14 ten-butyl (S)-3-((4,5,6,7-tetrahydrothiazolo[5,4-c]pyridin-2-yl)carbamoyl)pyrrolidine-1-carboxylate

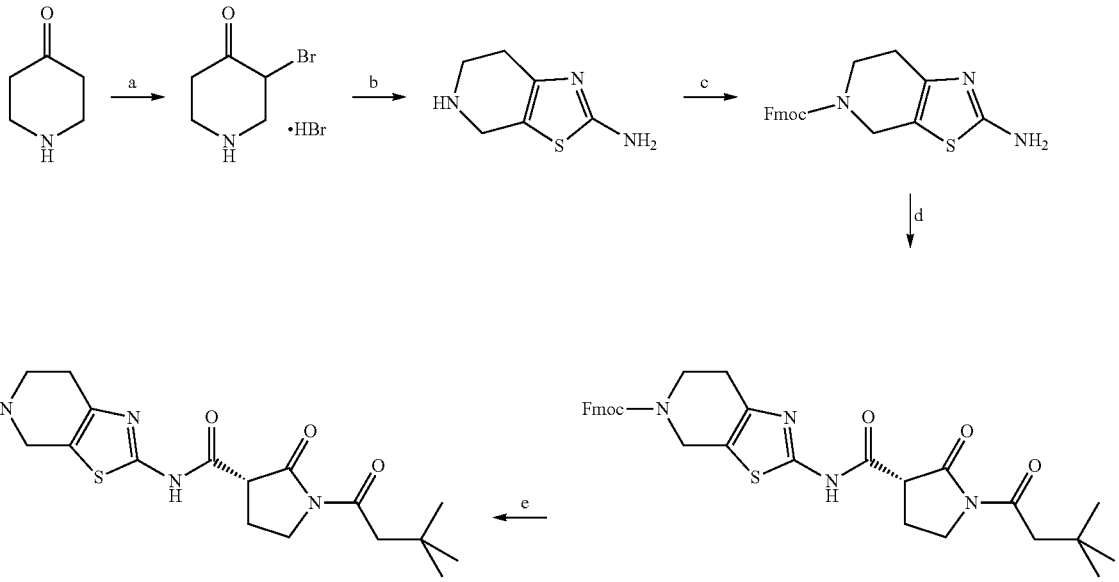

Reagents and conditions: a) 30% HBr in AcOH, 4.8M bromine in AcOH, AcOH, rt 1 h b) thiourea, ethanol, 80° C. 16 h c) FMoc—Cl, K₂CO₃, 1,4-dioxane, water, 0° C., rt 3 h d) T3P (50% in EtOAc), DIPEA, THF, rt 3 h e) piperidine, MeOH, rt 2 h Step a.
To a solution of piperidin-4-one hydrochloride (37.31 mmol) in acetic acid (30 ml) was added 30% HBr in acetic acid (0.47 ml) and 4.8 M bromine in acetic acid (3.0 ml) at rt. The reaction mixture was stirred at rt for 1 h. The resulting reaction mixture was concentrated under reduced pressure to give a residue which was suspended in acetone (100 ml) and refluxed for 1 h. The resulting solid precipitates were collected by filtration under reduced pressure, washed with acetone (30 ml) and dried to yield 3-bromopiperidin-4-one hydrobromide (31.28 mmol). The material was used directly for the next step without further purification. MS: ES+ 178.0, 180.0

Step b.
To a solution of 3-bromopiperidin-4-one hydrobromide (31.39 mmol) in ethanol (100 ml) was added thiourea (32.0 mmol) and the reaction mixture was heated at 80° C. for 16 h. The resulting reaction mixture was allowed to cool to rt. Precipitation was observed in the reaction mixture. The obtained precipitates were collected by filtration under reduced pressure, washed with ethanol (50 ml) and dried to yield 4,5,6,7-tetrahydrothiazolo[5,4-c]pyridin-2-amine hydrobromide (quantitative). The material was used directly for the next step without further purification. MS: ES+ 156.19

Step c.
To a solution of 4,5,6,7-tetrahydrothiazolo[5,4-c]pyridin-2-amine hydrobromide (31.77 mmol) in 1,4-dioxane (47 ml) were added water (75 ml), K₂CO₃ (63.5 mmol) and Fmoc-Cl (47.0 mmol) at 0° C. The reaction mixture was allowed to warm to rt and was stirred for 3 h. The resulting reaction mixture was poured into water (500 ml) and extracted with DCM (3×100 ml). The combined organic phase was collected, dried over Na₂SO₄, filtered and concentrated under reduced pressure. The resulting residue was purified by column chromatography (2% MeOH in DCM) yielding (9H-fluoren-9-yl)methyl-2-amino-6,7-dihydrothiazolo[5,4-c]pyridine-5 (4H)-carboxylate (11.93 mmol). MS: ES+ 378.54; ¹H NMR (400 MHz, DMSO-d₆) δ ppm 7.85-7.90 (m, 2H), 7.63-7.65 (m, 2H), 7.40-7.44 (m, 2H), 7.30-7.34 (m, 2H), 6.83 (br s, 2H), 4.31-4.42 (m, 5H), 3.47-3.60 (m, 2H), 2.29-2.43 (m, 2H).

Step d.
To a solution of (3S)—BOC-1-pyrrolidine-3-carboxylic acid (8.37 mmol) in THF (20 ml) was added T3P (50% in EtOAc) (25.11 mmol) at rt. The reaction mixture was stirred for 20 min. (9H-fluoren-9-yl)methyl 2-amino-6, 7-dihydrothiazolo[5,4-c]pyridine-5 (4H)-carboxylate (10.04 mmol) and DIPEA (25.11 mmol) were added to the reaction mixture and stirred at rt for 3 h. The resulting reaction mixture was poured into water (100 ml) and extracted with EtOAc (3×100 ml). The combined organic phase was collected, dried over Na₂SO₄, filtered and concentrated under reduced pressure. The resulting residue was purified by flash chromatography (2-3% MeOH in DCM) yielding (9H-fluoren-9-yl)methyl (S)-2-(1-(tert-butoxycarbonyl)pyrrolidine-3-carboxamido)-6,7-dihydrothiazolo[5,4-c]pyridine-5 (4H)-carboxylate (3.74 mmol). MS: ES+ 575.74

Step e.
To a solution of (9H-fluoren-9-yl)methyl (S)-2-(1-(tert-butoxycarbonyl)pyrrolidine-3-carboxamido)-6,7-dihydrothiazolo[5,4-c]pyridine-5 (4H)-carboxylate (3.7 mmol) in MeOH (10 ml) was added piperidine (14.9 mmol) at rt. The reaction mixture was stirred at rt for 2 h. The resulting reaction mixture was concentrated under reduced pressure. The resulting residue was purified by flash chromatography (4% MeOH in DCM) yielding the tert-butyl (S)-3-((4,5,6, 7-tetrahydrothiazolo[5,4-c]pyridin-2-yl)carbamoyl)pyrrolidine-1-carboxylate (0.77 mmol). MS: ES+ 353.43

Intermediate 15
6-bromo-5-methylbenzo[d]thiazol-2-amine

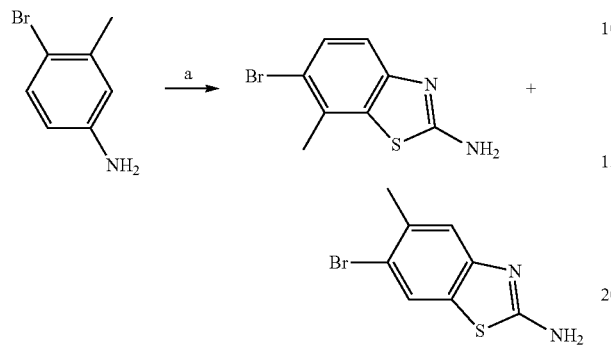

Reagents and conditions: a) ammonium thiocyanate, AcOH, 10° C., rt 1.5 h followed by bromine in AcOH, 10° C. 1.5 h followed by NaOH, water pH = 9

Step a.

To a solution of 4-bromo-3-methyl-aniline (26.88 mmol) in glacial acetic acid (77 ml) was added ammonium thiocyanate (53.68 mmol) at rt. The reaction mixture was allowed to stir until it was almost clear. The reaction mixture was cooled to 10° C. and a solution of bromine (26.88 mmol) in glacial acetic acid (2.5 ml) was added dropwise to the reaction mixture at 10° C. The resulting reaction mixture was stirred at rt for 1.5 h. The resulting precipitates were collected by filtration and washed with cold acetic acid. The obtained off-white cake was taken up in water and adjusted to pH 9 with 1M NaOH solution. The resulting solids were collected by filtration, washed with water (100 ml) and dried under reduced pressure yielding 14.46 mmol of a mixture of 70% 6-bromo-7-methyl-benzothiazol-2-ylamine. MS: ES+ 243.1 (M) 245.1 (M+2); $^1$H NMR (400 MHz, DMSO-$d_6$) δ ppm 7.61 (br s, 2H), 7.40, (d, J=8.8 Hz, 1H), 7.10 (d, J=8.8 Hz, 1H), 2.41 (s, 3H) and 30% 6-bromo-5-methyl-benzothiazol-2-ylamine. MS: ES+ 243.10; $^1$H NMR (400 MHz, DMSO-$d_6$) δ ppm 7.88 (s, 1H), 7.57, (br s, 2H), 7.31 (s, 1H), 2.34 (s, 3H).

Intermediate 16 (6-bromo-5-methylimidazo[1,2-a]pyridin-2-amine)

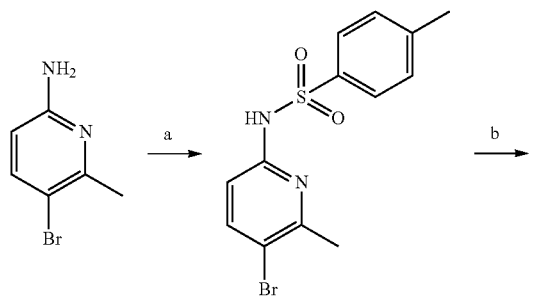

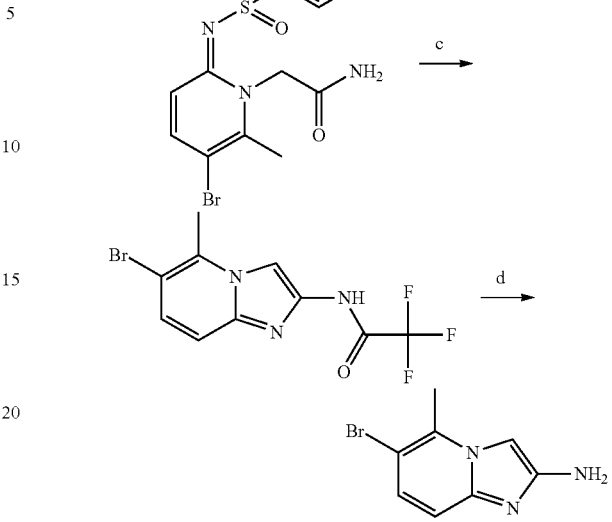

Reagents and conditions: a) pyridine, 4-toluenesulfonyl chloride, 110° C. 3 h b) DIPEA, DMF, 2-bromo acetamide, 80° C. 48 h c) TFAA, DCM, 80° C., 30 min d) LiOH•H$_2$O, THF, water, rt 48 h Step a.

A solution of 5-bromo-6-methylpyridin-2-amine (26.73 mmol) in pyridine (60 ml) was added slowly to 4-toluenesulfonyl chloride (32.08 mmol) at 0° C. The reaction mixture was heated at 110° C. for 3 h. The resulting reaction mixture was concentrated under reduced pressure. The obtained residue was poured into water (300 ml) and stirred for 1 h at rt. The resulting solids were collected by filtration and dried to yield N-(5-bromo-6-methylpyridin-2-yl)-4-methylbenzenesulfonamide (13.19 mmol). This material was directly used for the next step without further purification. MS: ES+ 341.3, 343.28; $^1$H NMR (400 MHz, DMSO-$d_6$) δ ppm 11.14 (s, 1H), 7.82 (t, J=7.6 Hz, 3H), 7.81 (d, J=8.0, 2H), 6.84 (d, J=8.4 Hz, 1H), 2.39 (s, 3H), 2.35 (s, 3H).

Step b.

To a solution of N-(5-bromo-6-methylpyridin-2-yl)-4-methylbenzenesulfonamide (13.19 mmol) in DMF (36 ml) in a glass tube was added 2-bromoacetamide (15.81 mmol) and DIPEA (15.81 mmol) at rt. The reaction mixture was heated at 80° C. for 48 h. The resulting reaction mixture was allowed to cool down to rt and concentrated under reduced pressure. The obtained residue was purified by column chromatography (2% MeOH in DCM) yielding (Z)-2-(5-bromo-6-methyl-2-(tosylimino) pyridin-1 (2H)-yl) acetamide (2.26 mmol). MS: ES+ 398.0, 400.5.

Step c.

To a solution of (Z)-2-(5-bromo-6-methyl-2-(tosylimino) pyridin-1 (2H)-yl) acetamide (2.26 mmol) in DCM (9 ml) was added TFAA (4.5 ml) at rt. The reaction mixture was heated at 80° C. for 30 min. The resulting reaction mixture was allowed to cool down to rt and poured into ice water (150 ml). The obtained mixture was neutralized by addition of aqueous solution of saturated NaHCO$_3$. The resulting mixture was extracted with DCM (3×50 ml). The combined organic phase was collected, dried over Na$_2$SO$_4$, filtered and concentrated under reduced pressure. The resulting residue was purified by column chromatography (1% MeOH in DCM) yielding N-(6-bromo-5-methylimidazo[1,2-a]pyridin-2-yl)-2,2,2-trifluoroacetamide (1.86 mmol). MS: ES+

322.40, 324.38; $^1$H NMR (400 MHz, DMSO-$d_6$) δ ppm 12.57 (br s, 1H), 8.05 (s, 1H), 7.52 (d, J=9.6, 1H), 7.43 (d, J=9.6 Hz, 1H), 2.75 (s, 3H).

Step d.

To a solution of N-(6-bromo-5-methylimidazo trifluoroacetamide (3.11 mmol) in a mixture of THF:water (3:1, 13 ml) was added solid LiOH.H$_2$O (12.44 mmol) portion wise at rt. The reaction mixture was stirred at rt for 48 h. The resulting reaction mixture was poured into water (100 ml) and extracted with EtOAc (3×50 ml). The combined organic phase was collected, dried over Na$_2$SO$_4$, filtered and concentrated under reduced pressure. The resulting residue was purified by column chromatography (7% MeOH in DCM) yielding 6-bromo-5-methylimidazo[1,2-a]pyridin-2-amine (2.47 mmol). MS: ES+ 226.0, 227.90; $^1$H NMR (400 MHz, DMSO-$d_6$) δ ppm 7.20 (d, J=9.20 Hz, 1H), 7.06 (d, J=9.20 Hz, 1H), 6.83 (s, 1H), 5.22 (br s, 2H), 2.59 (s, 3H).

Intermediate 17 (1-[(tert-butoxy)carbonyl]-(±)-trans-4-ethylpyrrolidine-3-carboxylic Acid)

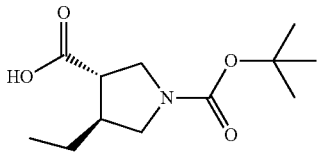 [SMILES: CC[C@@H]1CN(C(=O)OC(C)(C)C)C[C@H]1C(=O)O]

Synthesised using a procedure similar to that described for Intermediate 2 using ethyl (2E)-pent-2-enoate in step a. MS: ES+ (M−56) 188.4, (M−100) 142.2; $^1$H NMR (400 MHz, DMSO-$d_6$) δ ppm 1.27 (br s, 1H), 3.47-3.55 (m, 2H), 2.85-2.93 (m, 1H), 2.64-2.70 (m, 1H), 2.27-2.23 (m, 1H), 1.49-1.56 (m, 1H), 1.39 (s, 9H), 1.27-1.34 (m, 2H), 0.86 (t, J=7.2 Hz, 3H).

Intermediate 18 1-(2-methoxyethyl)-5-(4,4,5,5-tetramethyl-1,3,2-dioxaborolan-2-yl)-1H-indazole

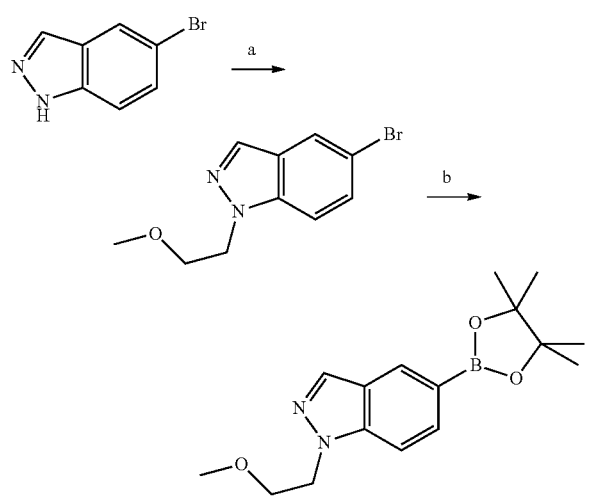

Reagent and conditions: a) 1-bromo-2-methoxyethane, Cs$_2$CO$_3$, DMSO, rt, 30 min b) bis(pinacolato)diboron, Pd(dppf)Cl$_2$•DCM, KOAc, DMF, 80° C., 2 h Step a.

To a solution of 5-bromo-1H-indazole (2.00 g, 10.15 mmol) and 1-bromo-2-methoxyethane (1.69 g, 12.19 mmol) in DMSO (20 ml) was added Cs$_2$CO$_3$ (8.22 g, 25.25 mmol) at rt. The reaction mixture was stirred at rt for 0.5 h. The resulting reaction mixture was diluted with water (50 ml) and extracted with EtOAc (2×50 ml). The combined organic phase was collected, dried over Na$_2$SO$_4$, filtered and concentrated under reduced pressure. The resulting residue was purified by flash chromatography (20% EtOAc in hexane) yielding 5-bromo-1-(2-methoxyethyl)-1H-indazole (1.20 g, 4.72 mmol). LCMS: Method A, 2.28 min, MS: ES+ 255.16.

Step b.

To a solution of 5-bromo-1-(2-methoxyethyl)-1H-indazole (0.30 g, 1.181 mmol) in DMF were added bis(pinacolato)diboron (0.59 g, 2.36 mmol) and potassium acetate (0.57 g, 5.90 mmol) at rt. The reaction mixture was degassed for 30 min. Pd(dppf)Cl$_2$.DCM complex (0.14 g, 0.17 mmol) was added to the reaction mixture at rt. The reaction mixture was heated at 80° C. for 2 h. The resulting reaction mixture was diluted with water (30 ml) and extracted with EtOAc (3×30 ml). The combined organic phase was dried over Na$_2$SO$_4$, filtered and concentrated under reduced pressure. The resulting residue was stirred in hexane (30 ml) for 10 min and the hexane layer was decanted (this process was repeated two more times). The combined hexane layer was concentrated under reduced pressure yielding 1-(2-methoxyethyl)-5-(4,4,5,5-tetramethyl-1,3,2-dioxaborolan-2-yl)-1H-indazole (0.41 g, quantitative). LCMS: Method A, 2.35 min, MS: ES+ 303.37.

Intermediate 19 Regioisomeric Mixture of tert-butyl 4-(4,4,5,5-tetramethyl-1,3,2-dioxaborolan-2-yl)-1H-indazole-1-carboxylate and tert-butyl 4-(4,4,5,5-tetramethyl-1,3,2-dioxaborolan-2-yl)-2H-indazole-2-carboxylate

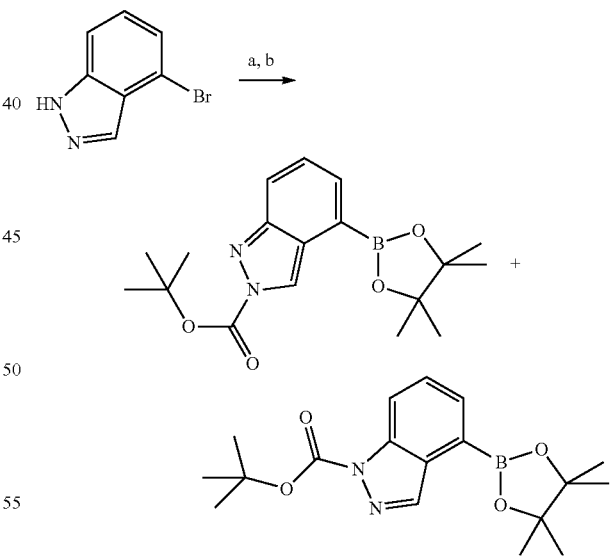

Reagents and conditions: a) BOC anhydride, DMAP, TEA, DCM, rt, 3 h b) bis (pinacolato) diboron, Pd(dppf)Cl$_2$, DMF, 110° C., 1 h Step a.

To a stirred solution of 4-bromo-1H-indazole (3.00 g, 15.22 mmol) in DCM (30 ml) were added DMAP (0.18 g, 1.52 mmol), TEA (1.84 g, 18.27 mmol) and BOC anhydride (3.7 ml, 16.75 mmol) at rt. The reaction mixture stirred at rt for 3 h, poured into water (100 ml) and extracted with DCM (3×30 ml). The combined organic phase was collected, dried over Na$_2$SO$_4$, filtered and concentrated under reduced pressure. The resulting residue was purified by column chromatography (20% EtOAc in hexane) yielding a mixture in approximately 60:40 ratio of regio-isomers tert-butyl 4-bromo-1H-indazole-1-carboxylate and tert-butyl 4-bromo-2H-indazole-2-carboxylate (3.2 g, 10.77 mmol). LCMS: Method A, 2.50 min, 2.61 min, MS: ES+ 297.14.

Step b.

The regioisomeric mixture of tert-butyl 4-bromo-1H-indazole-1-carboxylate and tert-butyl 4-bromo-2H-indazole-2-carboxylate prepared above (0.77 g, 2.59 mmol), bis(pinacolato) diboron (1.31 g, 5.18 mmol) and potassium acetate (1.27 g, 12.96 mmol) in DMF (10 ml) was degassed for 30 min at rt. Pd(dppf)Cl$_2$ (0.09 g, 0.13 mmol) was added to the reaction mixture at rt. The reaction mixture was heated at 110° C. for 2 h. The resulting reaction mixture was poured in to water (50 ml) and extracted with EtOAc (3×30 ml). The combined organic phase was dried over Na$_2$SO$_4$, filtered and concentrated under reduced pressure. The resulting residue was purified by column chromatography (20% EtOAc in hexane) yielding a regioisomeric mixture of tert-butyl 4-(4,4,5,5-tetramethyl-1,3,2-dioxaborolan-2-yl)-1H-indazole-1-carboxylate and tert-butyl 4-(4,4,5,5-tetramethyl-1,3,2-dioxaborolan-2-yl)-2H-indazole-2-carboxylate (0.45 g, 1.30 mmol). LCMS: Method A, 3.03 min, MS: ES+ 345.64.

Intermediate 20 tert-butyl (5-bromothiazol-2-yl)(4-methoxybenzyl)carbamate

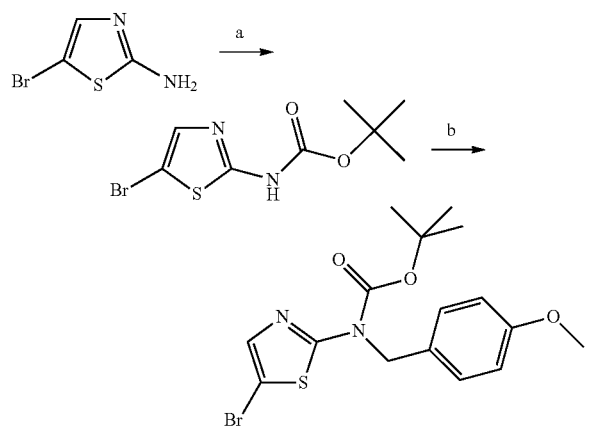

Reagents and conditions: a) (BOC)$_2$O, DMAP, THF, rt, 6 h b) PPh$_3$, DIAD, p-methoxybenzyl alcohol, THF, 0° C. to rt, 2 h Step a.

To a solution of 2-amino-5-bromothiazole (73.06 mmol) and DMAP (3.6 mmol) in THF (130 ml) was added (BOC)$_2$O (73.06 mmol) at rt. The reaction mixture was stirred at rt for 6 h. Excess THF was removed under reduced pressure and the resulting residue was purified by column chromatography (0-5% EtOAc in Hexane) yielding tert-butyl (5-bromothiazol-2-yl)carbamate (52.1 mmol). MS: ES+ 279.08; $^1$H NMR (400 MHz, DMSO-d6) δ ppm 11.75 (s, 1H), 7.44 (s, 1H), 1.48 (s, 9H).

Step b.

A mixture of tert-butyl (5-bromothiazol-2-yl)carbamate (3.6 mmol), PPh$_3$ (7.9 mmol) and p-methoxybenzyl alcohol (7.2 mmol) in THF (10 ml) was cooled at 0° C. DIAD (7.9 mmol) was added dropwise to the reaction mixture at 0° C. The reaction mixture was stirred at 0° C. for 10 min and then at rt for 2 h. The resulting reaction mixture was concentrated under reduced pressure and purified by flash chromatography (0-5% EtOAc in Hexane) yielding tert-butyl (5-bromothiazol-2-yl)(4-methoxybenzyl)carbamate (2.76 mmol). MS: ES-56 343.1; $^1$H NMR (400 MHz, DMSO-d6) δ ppm 7.57 (s, 1H), 7.22 (d, J=8.4 Hz, 2H), 6.89 (d, J=8.4 Hz, 2H), 5.13 (s, 2H), 3.74 (s, 3H), 1.50 (s, 9H).

Intermediate 21 5-(4-fluorophenyl)-4-methylthiazol-2-amine

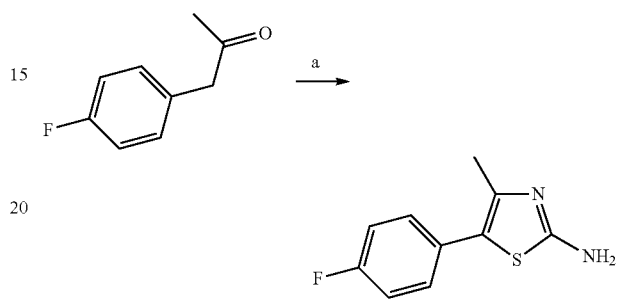

Reagents and conditions: a) thiourea, Cu(OAc)$_2$, I$_2$, methanol, 70° C., 8 h

Step a.

To a stirred solution of 4-fluorophenyl acetone (3.28 mmol) in methanol (5 ml) were added thiourea (4.92 mmol) and Cu(OAc)$_2$ (0.33 mmol) at rt. The reaction mixture was stirred at rt for 30 min. Iodine (3.28 mmol) was added to the reaction mixture at rt and heated to 70° C. for 8 h. The resulting reaction mixture was cooled to rt and concentrated under reduced pressure to remove excess of methanol, saturated Na$_2$S$_2$O$_3$ solution (30 ml) was added to the obtained concentrated mixture. The resulting mixture was extracted with EtOAc (2×15 ml). The combined organic phase was collected, washed with brine (30 ml), dried over Na$_2$SO$_4$, filtered and concentrated under reduced pressure. The obtained residue was triturated with diethyl ether (2×10 ml) yielding 5-(4-fluorophenyl)-4-methylthiazol-2-amine (2.45 mmol). MS: ES+ 209.18; $^1$H NMR (400 MHz, DMSO-d$_6$) δ ppm 7.34-7.37 (m, 2H), 7.21 (t, J=9.2 Hz, 2H), 7.01 (s, 2H), 2.15 (s, 3H).

Intermediate 22 5-(1-phenylethyl) thiazol-2-amine

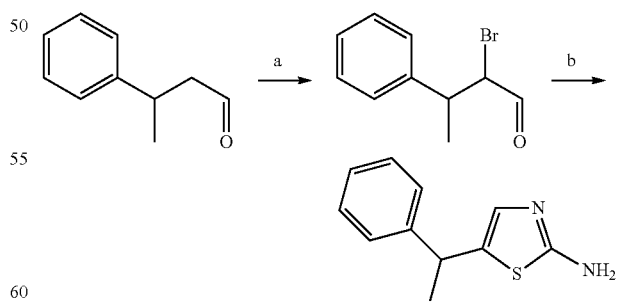

Reagents and conditions: a) Br$_2$, DCM, 0° C. to rt, 16 h b) thiourea, ethanol, reflux, 16 h Step a.

Bromine (2.0 mmol) was added dropwise to a solution of 3-phenylbutanal (2.0 mmol) in DCM (5 ml) at 0° C. The reaction mixture was stirred at rt for 16 h. The resulting reaction mixture was concentrated under reduced pressure yielding 2-bromo-3-phenylbutanal. The obtained material was used immediately for the next step without any further processing.

Step b.

Thiourea (3.5 mmol) was added to a solution of 2-bromo-3-phenylbutanal (1.76 mmol) in EtOH (7 ml) at rt. The reaction mixture was heated at 80° C. for 16 h. The resulting reaction mixture was cooled to rt and concentrated under reduced pressure, water (10 ml) was added to the obtained concentrated mixture. The resulting mixture was extracted with EtOAc (3×20 ml). The combined organic phase was dried over Na₂SO₄, filtered and concentrated under reduced pressure yielding 5-(1-phenylethyl) thiazol-2-amine (1.71 mmol). This material was used for the next step without further purification. MS: ES+ 205.28

Intermediate 23 5-(4-fluorobenzyl)thiazol-2-amine

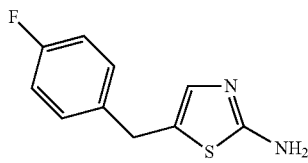 [SMILES: Nc1ncc(Cc2ccc(F)cc2)s1]

Synthesised using a procedure similar to that described for Intermediate 22 using 3-(4-fluorophenyl)propionaldehyde in step a. MS: ES+ 209.18; $^1$H NMR (400 MHz, DMSO-d₆) δ ppm 7.22-7.31 (m, 2H), 7.09-7.15 (m, 2H), 6.72 (br s, 2H), 6.69 (s, 1H), 3.92 (s, 2H).

Intermediate 24 tert-butyl (2'-amino-[4,4'-bipyridin]-2-yl)carbamate

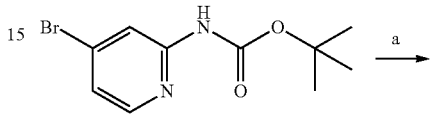

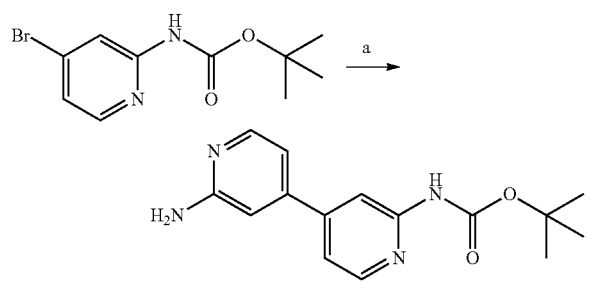

Reagents and conditions: a) 2-aminopyridine-4-boronic acid pinacol ester, PdCl₂(dppf), K₃PO₄, 1,4-dioxane, water, 110° C. (sealed tube), 2 h Step a.

A mixture of tert-butyl (4-bromopyridin-2-yl)carbamate (0.19 g, 0.68 mmol) in 1,4-dioxane:water (8:2) (10 ml) was prepared in a glass vial. The reaction mixture was degassed for 15 min. 2-Aminopyridine-4-boronic acid pinacol ester (0.15 g, 0.68 mmol) and K₃PO₄ (0.43 g, 2.04 mmol) were added to the reaction mixture at rt. The reaction mixture was degassed again for 15 min. Pd(dppf)Cl₂ (0.024 g, 0.034 mmol). The glass vial was sealed and subjected to heating at 110° C. (external temperature) for 2 h. The resulting reaction mixture was combined with one other batch on the same scale prepared by an identical method, poured into water (50 ml) and extracted with EtOAc (2×30 ml). The combined organic phase was washed with brine (20 ml), dried over Na₂SO₄, filtered and concentrated under reduced pressure yielding tert-butyl (2'-amino-[4,4'-bipyridin]-2-yl)carbamate (0.50 g, quantitative). LCMS: Method A, 1.71 min, MS: ES+ 287.48.

Intermediate 25 tert-butyl (2'-amino-[4,4'-bipyridin]-2-yl)(methyl)carbamate

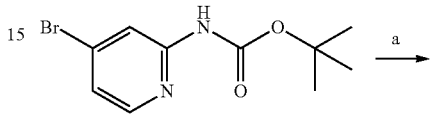

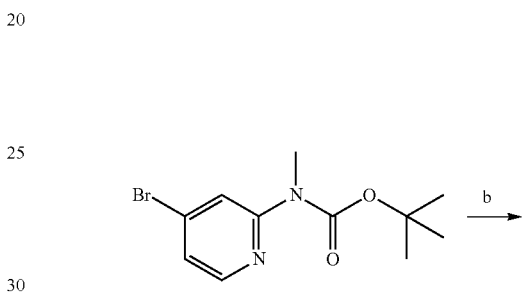

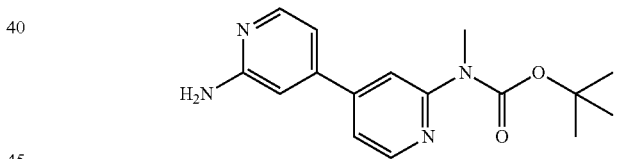

Reagents and conditions: a) NaH, MeI, DMF, 0° C. to rt 1 h b) 2-aminopyridine-4-boronic acid pinacol ester, PdCl₂(dppf), K₃PO₄, 1,4-dioxane, water, 110° C. (sealed tube), 3 h Step a.

To a solution of tert-butyl (4-bromopyridin-2-yl)carbamate (0.25 g, 0.915 mmol) in DMF (5 ml) was added NaH (60% in oil) (0.073 g, 1.83 mmol) at 0° C. The reaction mixture was stirred at 0° C. for 15 min. Methyl iodide (0.26 g, 1.37 mmol) was added to the reaction mixture at 0° C. The reaction mixture was stirred at rt for 1 h, poured into ice cold water (20 ml) and extracted with EtOAc (2×15 ml). The organic layer was washed with brine (20 ml). The organic phase was collected, dried over Na₂SO₄, filtered and concentrated under reduced pressure yielding tert-butyl (4-bromopyridin-2-yl)(methyl)carbamate (0.25 g, 0.87 mmol). This material was directly used for the next step without further purification. LCMS: Method A, 2.50 min, MS: ES+ 230.9; 232.9 (M−56)

Step b.

A procedure similar to that described for Intermediate 24 was used to afford the title compound LCMS: Method A, 1.71 min, MS: ES+ 301.37

Intermediate 26

3-amino-N-methylisoquinoline-6-carboxamide Trifluoracetic Acid Salt

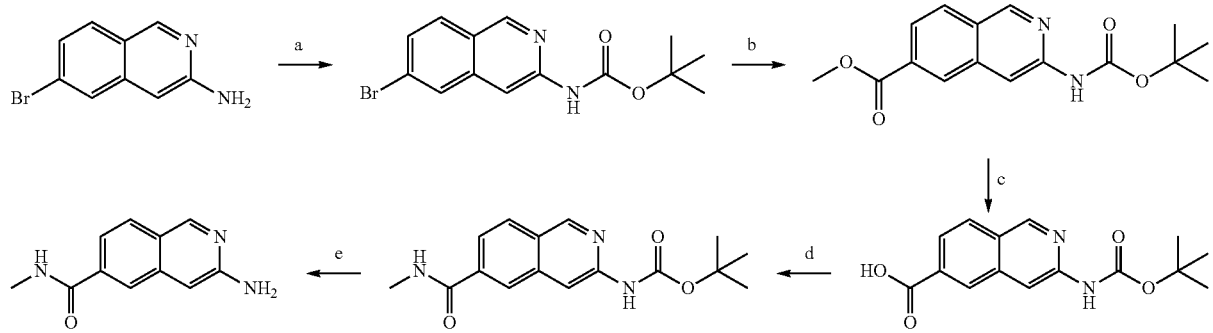

Reagents and conditions: a) LiHMDS, THF -40° C. to 0° C., 30 min, then BOC anhydride, 0° C. to rt, 1 h b) Pd(dppf)Cl$_2$·DCM, NaOAc, MeOH, CO (25 kg/cm$^2$), 85° C., 2 d c) NaOH, water, MeOH, 70° C., 4 h d) methylamine (2M in THF), HATU, DIPEA, THF, rt 18 h e) TFA, DCM, rt, 2 h Step a.

LiHMDS (1M in Hexane) (18 ml, 18.02 mmol) was added dropwise to a stirred solution of 6-bromoisoquinolin-3-amine (2.00 g, 9.01 mmol) in THF (40 ml) at −40° C. The resulting reaction mixture was stirred at 0° C. temperature for 30 min. A solution of BOC anhydride (1.96 g, 9.01 mmol) in THF (10 ml) at 0° C. was added dropwise to the reaction mixture. The reaction mixture was stirred at rt for 1 h and then poured into NH$_4$Cl solution (80 ml) and extracted with EtOAc (3×80 ml). The combined organic phase was collected, dried over Na$_2$SO$_4$, filtered and concentrated under reduced pressure yielding tert-butyl (6-bromoisoquinolin-3-yl)carbamate (2.87 g, 8.91 mmol). LCMS: Method A, 2.64 min, MS: ES+ 323.19.

Step b.

A mixture of tert-butyl (6-bromoisoquinolin-3-yl)carbamate (2.80 g, 8.69 mmol), sodium acetate (3.56 g, 43.48 mmol) and Pd(dppf)Cl$_2$.DCM complex (3.55 g, 4.35 mmol) in MeOH (60 ml) was taken in a pressure vessel. The resulting reaction mixture was stirred at 85° C. under a pressure of CO (25 kg/cm$^2$) for 48 h. The resulting reaction mixture was filtered and the filtrate was concentrated under reduced pressure. The residue was suspended in DCM and filtered. The filtrate was concentrated under reduced pressure and the resulting residue was purified by chromatography (1% MeOH in DCM) yielding methyl 3-((tert-butoxycarbonyl)amino) isoquinoline-6-carboxylate (2.40 g, 7.95 mmol). LCMS: Method A, 2.43 min, MS: ES+ 303.

Step c.

A solution of NaOH (0.70 g, 17.38 mmol) in 50 ml water was added to a solution of methyl 3-((tert-butoxycarbonyl) amino)isoquinoline-6-carboxylate (1.75 g, 5.79 mmol) in methanol (50 ml) at rt. The reaction mixture was heated at 70° C. for 4 h. The resulting reaction mixture was allowed to cool to rt and acidified by slow addition of citric acid solution under continuous stirring. The resulting mixture was extracted with EtOAc (3×100 ml). The combined organic phase was collected dried over Na$_2$SO$_4$, filtered and concentrated under reduced pressure yielding 3-((tert-butoxycarbonyl)amino)isoquinoline-6-carboxylic acid (1.80 g, quantitative). LCMS: Method A, 2.12 min, MS: ES+ 289.33.

Step d.

A mixture of 3-((tert-butoxycarbonyl)amino)isoquinoline-6-carboxylic acid (1.80 g, 6.25 mmol), HATU (3.56 g, 9.37 mmol) and DIPEA (2.15 ml, 12.50 mmol) in THF (50 ml) was prepared at 0° C. The reaction mixture was stirred at rt for 0.5 h. Methyl amine (2M in THF) (6.25 ml, 12.50 mmol) was added in to the reaction mixture at rt. The reaction mixture was stirred at rt for 18 h. The resulting reaction mixture was poured into saturated NaHCO$_3$ solution (100 ml) and extracted with EtOAc (3×100 ml). The combined organic phase was collected, dried over Na$_2$SO$_4$, filtered and concentrated under reduced pressure. The resulting residue was purified by column chromatography (3% MeOH in DCM) yielding tert-butyl (6-(methylcarbamoyl) isoquinolin-3-yl)carbamate (1.35 g, 4.48 mmol). LCMS: Method A, 2.01 min, MS: ES+ 302.38.

Step e.

To a solution of tert-butyl (6-(methylcarbamoyl)isoquinolin-3-yl)carbamate (1.30 g, 4.318 mmol) in DCM (50 ml) was added TFA (13 ml) at 0° C. The reaction mixture was stirred at rt for 2 h. The resulting reaction mixture was concentrated under reduced pressure yielding 3-amino-N-methylisoquinoline-6-carboxamide TFA salt (2.0 g, quantitative). LCMS: Method A, 0.89 min, MS: ES+ 202.13.

Intermediate 27 tert-butyl (2S,3S)-3-((6-(1H-pyrazol-4-yl)isoquinolin-3-yl)carbamoyl)-2-methylpyrrolidine-1-carboxylate

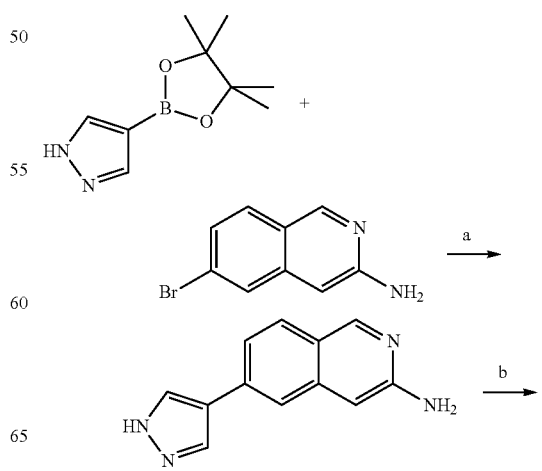

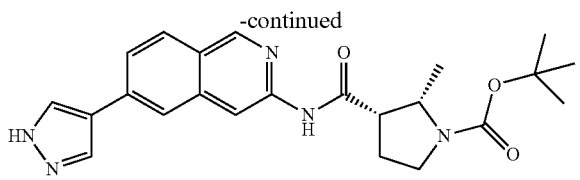

Reagents and conditions: a) Pd(dppf)Cl$_2$, Cs$_2$CO$_3$, DMF, water, sealed tube, microwave, 150° C. 1 h b) Intermediate 1, POCl$_3$, pyridine, DCM, 0° C. to rt, 30 min Step a.

To a solution of 6-bromoisoquinolin-3-amine (0.20 g, 0.89 mmol) and 4-(4,4,5,5-tetramethyl-1,3,2-dioxaborolan-2-yl)-1H-pyrazole (0.19 g, 0.98 mmol) in DMF:water (4:1, 5 ml) was prepared in a microwave glass vial. Cs$_2$CO$_3$ (0.87 g, 2.68 mmol) was added to the reaction mixture at rt. The reaction mixture was degassed at rt for 15 min before adding Pd(dppf)Cl$_2$ (0.06 g, 0.09 mmol) and the glass vial was sealed. The reaction mixture was subjected to microwave heating at 150° C. for 1 h. The resulting reaction mixture was poured into water (50 ml) and extracted with EtOAc (3×50 ml). The combined organic layer was washed with brine solution (50 ml), dried over Na$_2$SO$_4$, filtered and concentrated under reduced pressure. The resulting residue was purified by column chromatography (2.2% MeOH in DCM) yielding 6-(1H-pyrazol-4-yl) isoquinolin-3-amine (0.11 g, 0.52 mmol). LCMS: Method A, 1.47 min, MS: ES+ 211.18.

Step b.

To a solution of 6-(1H-pyrazol-4-yl) isoquinolin-3-amine (0.09 g, 0.42 mmol) and Intermediate 1 (0.10 g, 0.42 mmol) in DCM (2 ml) was added pyridine (0.9 ml g) at 0° C. POCl$_3$ (0.08 g, 0.51 mmol) was added dropwise to the reaction mixture at 0° C. The reaction mixture was stirred at 0° C. for 15 min and then at rt for 30 min. The resulting reaction mixture was diluted with cold water (30 ml) and extracted with EtOAc (3×30 ml). The combined organic layer was washed with saturated aqueous solution of citric acid (30 ml), dried over Na$_2$SO$_4$, filtered and concentrated under reduced pressure. The resulting residue was purified by column chromatography (1.2% MeOH in DCM) yielding tert-butyl (2S,3S)-3-((6-(1H-pyrazol-4-yl)isoquinolin-3-yl)carbamoyl)-2-methylpyrrolidine-1-carboxylate (0.045 g, 0.10 mmol). LCMS: Method A, 1.96 min, MS: ES+ 422.52.

Intermediate 28 6-(oxazol-5-yl)imidazo[1,2-a]pyridin-2-amine

Step a.

To a suspension of LiAlH$_4$ powder (0.165 g, 4.35 mmol) in THF (10 ml) was added a solution of methyl 2-(2,2,2-trifluoroacetamido)imidazo[1,2-a]pyridine-6-carboxylate (0.5 g, 1.74 mmol) in THF (5 ml) dropwise at 0° C. under nitrogen atmosphere. The reaction mixture was stirred at 0° C. under nitrogen atmosphere for 1 h. The resulting reaction mixture was combined with one other batch on the same scale prepared by an identical method and quenched in EtOAc (100 ml). The resulting organic solution was washed with water (50 ml). The emulsion was filtered through celite hyflow. The organic phase was separated from the filtrate. The resulting organic phase was dried over Na$_2$SO$_4$, filtered and concentrated under reduced pressure. The resulting residue was triturated with n-pentane (2×10 ml) and dried to yield 2,2,2-trifluoro-N-(6-(hydroxymethyl)imidazo[1,2-a]pyridin-2-yl)acetamide (0.55 g, 2.12 mmol). LCMS: Method A, 1.57 min, MS: ES+ 260.21.

Step b.

To a solution of 2,2,2-trifluoro-N-(6-(hydroxymethyl)imidazo[1,2-a]pyridin-2-yl)acetamide (0.55 g, 2.12 mmol) in DCM (20 ml) was added Dess-Martin periodinane (3.6 g, 8.49 mmol) at rt. The reaction mixture was stirred at rt for 2 days. The resulting reaction mixture was combined with one other batch which was performed at 0.25 g scale following an identical method. The resulting reaction mixture was carefully filtered through celite hyflow. The resulting filtrate was poured in to water (200 ml), basified with solid NaHCO$_3$ and extracted with EtOAc (2×100 ml). The combined organic phase was collected dried over Na$_2$SO$_4$, filtered and concentrated under reduced pressure. The obtained residue was triturated with n-hexane (3×7 ml) and dried yielding 2,2,2-trifluoro-N-(6-formylimidazo[1,2-a]pyridin-2-yl)acetamide (0.75 g, 2.92 mmol). LCMS: Method A, 1.85 min, MS: ES+ 258.36.

Step c.

A mixture of 2,2,2-trifluoro-N-(6-formylimidazo[1,2-a]pyridin-2-yl)acetamide (0.75 g, 2.92 mmol), 4-toluenesulphonylmethyl isocyanide (0.569 g, 2.92 mmol) and K$_2$CO$_3$ (0.805 g, 5.83 mmol) in MeOH (10 ml) was heated to 70° C. for 3 h. The resulting reaction mixture was poured into water (150 ml) and extracted with EtOAc (3×70 ml). The combined organic phase was dried over Na$_2$SO$_4$, filtered and concentrated under reduced pressure yielding 2,2,2-trifluoro-N-(6-(oxazol-5-yl)imidazo[1,2-a]pyridin-2-yl)acet

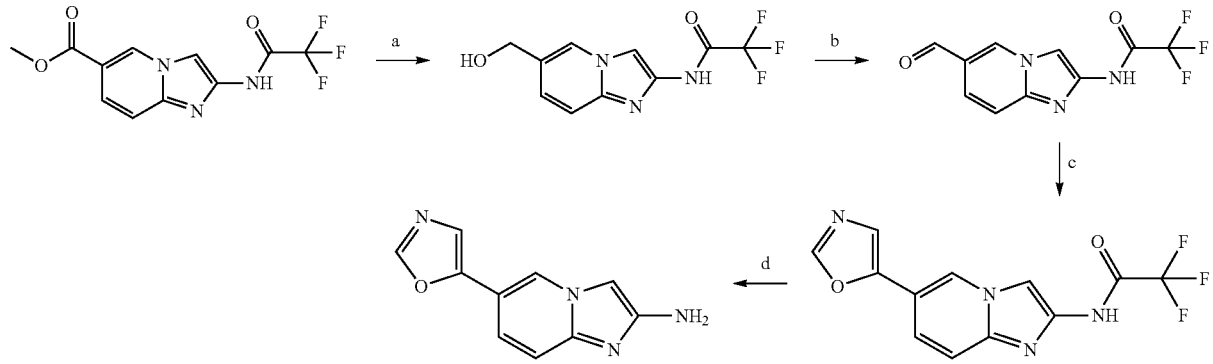

Reagents and conditions: a) LiAlH$_4$, THF, 0° C., 1 h b) Dess-Martin periodinane, DCM, rt, 2 d c) 4-toluenesulphonylmethyl isocyanide, K$_2$CO$_3$, MeOH, 70° C., 3 h d) NaOH, water, rt, 2 h amide (0.55 g, 1.86 mmol). This material was used directly for the next step without further purification. LCMS: Method A, 1.88 min, MS: ES+ 297.38.

Step d.

To a solution of 2,2,2-trifluoro-N-(6-(oxazol-5-yl)imidazo[1,2-a]pyridin-2-yl)acetamide (0.25 g, 0.844 mmol) in water was added NaOH (0.13 g, 3.375 mmol) at rt. The reaction mixture was stirred at rt for 2 h. The resulting reaction mixture was poured into water (120 ml) and extracted with EtOAc (2×20 ml). The combined organic phase was dried over Na₂SO₄, filtered and concentrated under reduced pressure yielding 6-(oxazol-5-yl)imidazo[1,2-a]pyridin-2-amine (0.17 g, 0.84 mmol). This material was used directly for the next step without further purification.

Intermediate 29 6-(isopropylsulfonyl)-5,6,7,8-tetrahydro-4H-thiazolo[4,5-d]azepin-2-amine

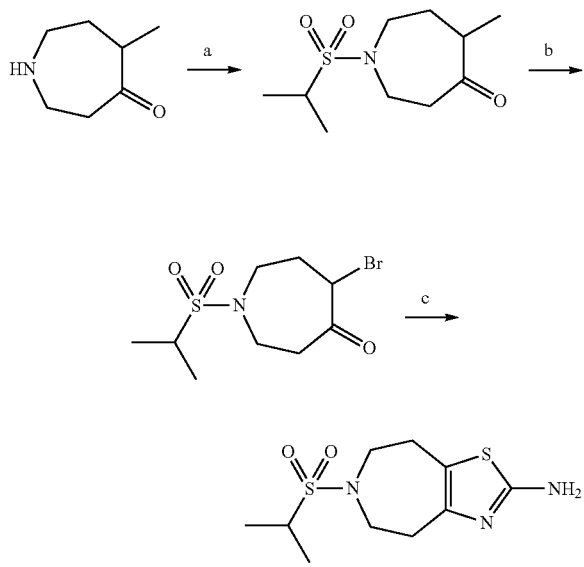

Reagents and conditions: a) isopropylsulfonyl chloride, DIPEA, DCM, rt, 2 h b) Br₂, CHCl₃, 0° C. to rt, 1 h c) thiourea, ethanol, 90° C., 2 h Step a.

To a solution of 4-perhydroazepinone hydrochloride (1 g, 6.68 mmol) in DCM (10 ml) was added DIPEA (3.45 g, 26.73 mmol) at rt for 10 min. Isopropylsulfonyl chloride (1.14 g, 8.02 mmol) was added to the reaction mixture at rt. The reaction mixture was stirred at rt for 2 h. The resulting reaction mixture was poured into water (100 ml) and extracted with DCM (3×40 ml). The organic phase was collected, dried over Na₂SO₄, filtered and concentrated under reduced pressure to 1-(isopropylsulfonyl)azepan-4-one (0.54 g, 2.46 mmol). This material was used directly for the next step without further purification. LCMS: Method A, 1.54 min, MS: ES+ 220.23.

Step b.

To a solution of 1-(isopropylsulfonyl)azepan-4-one (0.54 g, 2.46 mmol) in CHCl₃ (10.8 ml) was added bromine (0.29 g, 3.6 mmol) at 0° C. The reaction mixture was stirred at rt for 1 h. The resulting reaction mixture was poured into sodium metabisulphite solution (60 ml) and extracted with DCM (3×30 ml). The combined organic phase was dried over Na₂SO₄, filtered and concentrated under reduced pressure to yielding 5-bromo-1-(isopropylsulfonyl)azepan-4-one (0.6 g, 2.02 mmol). This material was used directly for the next step without further purification.

Step c.

To a solution of 5-bromo-1-(isopropylsulfonyl)azepan-4-one (0.6 g, 2.02 mmol) in ethanol (9 ml) was added thiourea (0.76 g, 10.10 mmol) at rt. The reaction mixture was heated at 90° C. for 2 h. The resulting reaction mixture was poured into 1M HCl solution (50 ml) and extracted with DCM (2×20 ml). The aqueous layer was neutralised with solid Na₂CO₃ to adjust pH up to 8 and extracted with DCM (3×30 ml). The combined organic phase was dried over Na₂SO₄, filtered and concentrated under reduced pressure. The resulting residue was purified by column chromatography (2% MeOH in DCM) yielding 6-(isopropylsulfonyl)-5,6,7,8-tetrahydro-4H-thiazolo[4,5-d]azepin-2-amine (0.18 g, 0.67 mmol). LCMS: Method C, 3.03 min, MS: ES+ 276.05

Intermediate 30 1-(4-(1-(2-methoxyethyl)-1H-pyrazol-4-yl)phenyl)-1H-imidazol-4-amine

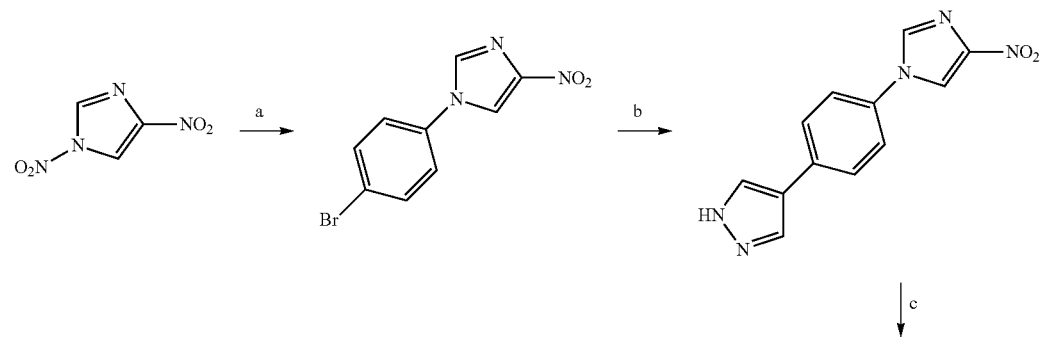

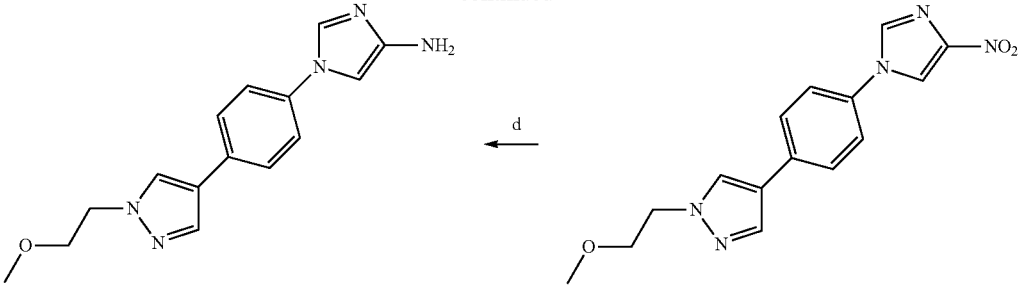

Reagents and conditions: a) 4-bromoaniline, MeOH, rt, 16 h b) 4-(4,4,5,5-tetramethyl-1,3,2-dioxaborolan-2-yl)-1H-pyrazole, Pd(dppf)Cl₂·DCM, DMF, water, 150° C., 1 h c) 1-bromo-2-methoxyethane, K₂CO₃, DMF, 100° C., 16 h d) H₂, 10% Pd/C, THF, rt, 4 h Step a.

To a solution of 1,4-dinitro-1H-imidazole (2.5 g, 15.80 mmol) in MeOH (40 ml) was added 4-bromoaniline (2.70 g, 15.80 mmol) at 0° C. The reaction mixture was stirred at rt for 16 h. The resulting solid precipitates were collected by filtration under reduced pressure and dried yielding 1-(4-bromophenyl)-4-nitro-1H-imidazole (3.5 g, 13.11 mmol). This material was used directly for the next step without further purification. LCMS: Method A, 2.11 min, MS: ES+ 268.20.

Step b.

A solution of 1-(4-bromophenyl)-4-nitro-1H-imidazole (0.30 g, 1.12 mmol) and 4-(4,4,5,5-tetramethyl-1,3,2-dioxaborolan-2-yl)-1H-pyrazole (0.26 g, 1.35 mmol) in DMF:water (9:1, 10 ml) was prepared in a microwave glass vial. Na₂CO₃ (0.23 g, 2.24 mmol) was added to the reaction mixture at rt. The reaction mixture was degassed for 30 min at rt. Pd(dppf)Cl₂. DCM complex (0.10 g, 0.11 mmol) was added to the reaction mixture at rt. The reaction mixture was subjected to microwave heating at 150° C. for 1 h. The resulting reaction mixture was poured into water (20 ml) and extracted with EtOAc (3×20 ml). The combined organic layer was dried over Na₂SO₄, filtered and concentrated under reduced pressure. The crude product was triturated with n-pentane (30 ml) yielding 4-(4-(4-nitro-1H-imidazol-1-yl) phenyl)-1H-pyrazole (0.25 g, 0.98 mmol). This material was used directly for the next step without further purification. LCMS: Method A, 178 min, MS: ES+ 256.41.

Step c.

To a solution of (4-(4-(4-nitro-1H-imidazol-1-yl) phenyl)-1H-pyrazole (0.23 g, 0.90 mmol) in DMF (6 ml) was added K₂CO₃ (0.37 g, 2.70 mmol) at rt. The reaction mixture was stirred at rt for 5 min and treated with 1-bromo-2-methoxyethane (0.19 g, 1.35 mmol). The reaction mixture was heated at 100° C. for 16 h. The resulting reaction mixture allowed to cool to rt, poured into water (15 ml) and extracted with EtOAc (3×10 ml). The combined organic phase was collected, washed with water (2×10 ml), dried over Na2SO4, filtered and concentrated under reduced pressure yielding 1-(2-methoxyethyl)-4-(4-(4-nitro-1H-imidazol-1-yl)phenyl)-1H-pyrazole (0.25 g, 0.79 mmol). This material was used directly for the next step without further purification. LCMS: Method A, 1.91 min, MS: ES+ 314.59.

Step d.

To a solution of 1-(2-methoxyethyl)-4-(4-(4-nitro-1H-imidazol-1-yl)phenyl)-1H-pyrazole (0.25 g, 0.79 mmol) in THF (5 ml) was added 10% Pd/C (0.05 g) at rt. The reaction mixture was purged with H₂ gas at rt for 2 h. The resulting reaction mixture was carefully filtered through celite hyflow. The obtained filtrate was directly used for next acid amine coupling reaction. LCMS: Method A, 1.41 min, MS: ES+ 284.39.

Intermediate 31 (3S,4R)-1-(tert-butoxycarbonyl)-4-(pyridin-3-yl)pyrrolidine-3-carboxylic Acid

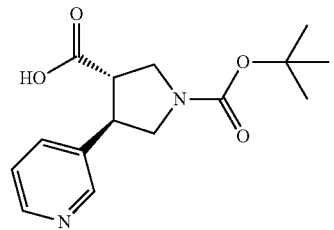 [SMILES: CC(C)(C)OC(=O)N1C[C@@H](C(=O)O)[C@H](c2cccnc2)C1]

Synthesised using a procedure similar to that described for Intermediate 2 using ethyl trans-3-(3-pyridyl)acrylate in step a. LCMS: Method A, 1.51 min, MS: ES+ 293.28; ¹H NMR (400 MHz, DMSO-d6) δ ppm 12.5 (br s, 1H), 8.55 (d, J=2 Hz, 1H), 8.47 (dd, J=1.6 Hz, 4.8 Hz, 1H), 7.84 (d, J=7.6 Hz, 1H), 7.37-7.40 (m, 1H), 3.72-3.80 (m, 2H), 3.48-3.61 (m, 1H), 3.36-3.45 (m, 1H), 3.23-3.28 (m, 1H), 2.64-2.78 (m, 1H), 1.38 (s, 9H).

Intermediate 32 (3S,4R)-1-(tert-butoxycarbonyl)-4-(pyrimidin-5-yl)pyrrolidine-3-carboxylic Acid

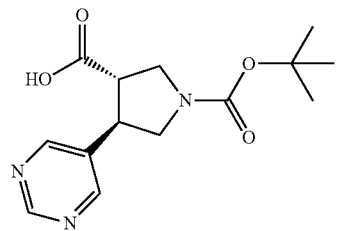 [SMILES: CC(C)(C)OC(=O)N1C[C@@H](C(=O)O)[C@H](c2cncnc2)C1]

Synthesised using a procedure similar to that described for Intermediate 2 using 3-pyrimidin-5-yl-acrylic acid ethyl ester in step a. LCMS: Method A, 1.65 min, MS: ES+ 294.23; ¹H NMR (400 MHz, DMSO-d6) δ ppm 12.47 (br s, 1H), 9.08 (s, 1H), 8.83 (s, 2H), 3.78-3.83 (m, 1H), 3.59-3.53 (m, 2H), 3.51-3.46 (m, 2H), 2.78-2.64 (m, 1H), 1.43 (s, 9H).

Intermediate 33 1-(tert-butoxycarbonyl)-3-methoxy-pyrrolidine-3-carboxylic Acid

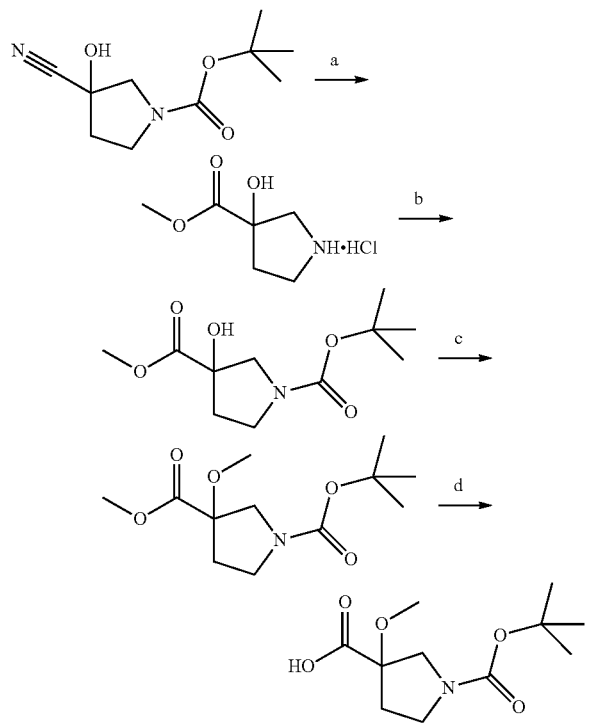

Reagents and conditions: a) 4M HCl in 1,4-dioxane, MeOH, 0° C. to rt 1 h b) BOC anhydride, NaHCO₃, EtOAc, rt 8 h c) MeI, Cs₂CO₃, MeCN, 80° C. 20 h d) LiOH·H₂O, MeOH, rt 2 h Step a.

To a solution of tert-butyl 3-cyano-3-hydroxypyrrolidine-1-carboxylate (0.60 g, 2.83 mmol) in MeOH (15 ml) was added 4M HCl in 1,4-dioxane (6 ml) at 0° C. The reaction mixture was stirred at rt for 1 h. The resulting reaction mixture was concentrated under reduced pressure yielding methyl 3-hydroxypyrrolidine-3-carboxylate HCl salt (0.55 g, quantitative). This material was used directly for next step without further purification. LCMS: Method A, 0.25 min, MS: ES+ 146.08.

Step b.

To the suspension of methyl 3-hydroxypyrrolidine-3-carboxylate HCl (0.55 g, 3.03 mmol) in sat. NaHCO₃ solution (2 ml) and EtOAc (5 ml) was added BOC anhydride (1.32 g, 6.07 mmol) and stirred at rt for 8 h. The resulting reaction mixture was poured into water (15 ml) and extracted with EtOAc (3×10 ml). The combined organic phase was collected, dried over Na₂SO₄, filtered and concentrated under reduced pressure yielding 1-(tert-butyl) 3-methyl 3-hydroxypyrrolidine-1,3-dicarboxylate (0.29 g, 1.18 mmol). This material was used directly for the next step without further purification. LCMS: Method A, 1.88 min, MS: ES+ 246.30.

Step c.

To a solution of methyl 1-(tert-butyl) 3-methyl 3-hydroxypyrrolidine-1,3-dicarboxylate (0.27 g, 1.10 mmol) in MeCN (10 ml) was added Cs₂CO₃ (1.79 g, 5.51 mmol) at rt. The reaction mixture was stirred at rt for 5 min. CH₃I (0.78 g, 5.51 mmol) was added to the reaction mixture at rt. The reaction mixture was heated at 80° C. for 20 h. The resulting reaction mixture was poured into cold water (15 ml) and extracted with EtOAc (3×10 ml). The combined organic phase was collected, dried over Na₂SO₄, filtered and concentrated under reduced pressure. The resulting residue was purified by column chromatography (10% EtOAc in hexane) yielding 1-(tert-butyl) 3-methyl 3-methoxypyrrolidine-1,3-dicarboxylate (0.23 g, 0.88 mmol). LCMS: Method A, 2.13 min, MS: ES+ 260.30.

Step d.

To a solution of 1-(tert-butyl) 3-methyl 3-methoxypyrrolidine-1,3-dicarboxylate (0.23 g, 0.88 mmol) in MeOH (10 ml) was added LiOH·H₂O (0.15 g, 3.55 mmol) at rt. The reaction mixture was stirred at rt for 2 h. The resulting reaction mixture was diluted with water (10 ml) and extracted with EtOAc (2×10 ml). The aqueous layer was acidified to pH 6 using 10% aqueous solution of citric acid. The resulting mixture was extracted with MeOH: EtOAc mixture (1:9, 7×10 ml). The combined organic phase was dried over Na₂SO₄, filtered and concentrated under reduced pressure yielding 1-(tert-butoxycarbonyl)-3-methoxypyrrolidine-3-carboxylic acid (0.20 g, 0.81 mmol). This material was directly used for the next step without further purification. LCMS: Method A, 1.85 min, MS: ES- 244.20.

Intermediate 34 2'-chloro-[4,4'-bipyridin]-2-amine

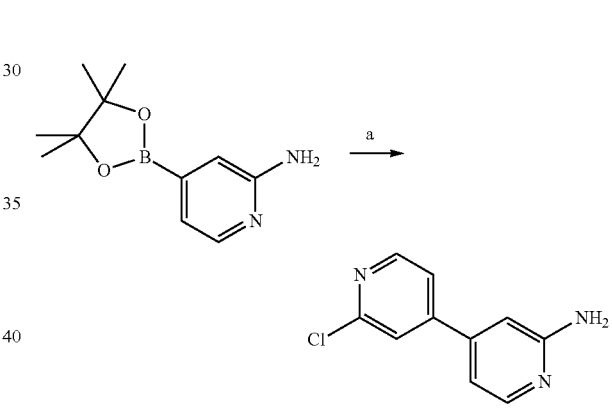

Reagents and conditions: a) 2-chloro-4-iodopyridine, PdCl₂(dppf), K₃PO₄, 1,4-dioxane, water, 100° C., 16 h Step a.

A mixture of 2-chloro-4-iodopyridine (0.75 g, 3.13 mmol), 2-aminopyridine-4-boronic acid pinacol ester (0.76 g, 3.45 mmol) and K₃PO₄ (1.3 g, 6.26 mmol) was prepared in 1,4-dioxane:water (2:1, 3 ml) at rt. The reaction mixture was degassed for 15 min. PdCl₂ (dppf) (0.11 g, 0.16 mmol) was added to the reaction mixture at rt. The reaction mixture was heated at 100° C. for 16 h. The resulting reaction mixture was allowed to cool to rt, poured into brine solution (100 ml) and extracted with EtOAc (3×75 ml). The combined organic phase was washed with DM water (75 ml). The organic phase was separated, dried over Na₂SO₄, filtered and concentrated under reduced pressure. The resulting residue was purified by flash chromatography (75% EtOAc in hexane) yielding 2'-chloro-[4,4'-bipyridin]-2-amine (0.3 g, 1.46 mmol). LCMS: Method A, 1.49 min, MS: ES+ 206.13.

Intermediate 35 4-amino-2-cyclopropylbenzonitrile

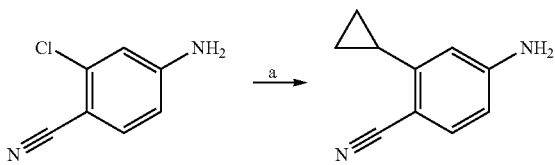

Reagents and conditions: a) cyclopropylboronic acid, Pd(OAc)$_2$, Tricyclohexylphosphene, K$_3$PO$_4$, toluene, water, 80° C., 15 h Step a.

A solution of 4-amino-2-chlorobenzonitrile (0.46 g, 3.00 mmol) and cyclopropylboronic acid (0.39 g, 4.50 mmol) in toluene:water (6:1, 7 ml) was prepared in a glass vial at rt. K$_3$PO$_4$ (2.55 g, 12.01 mmol) and tricyclohexylphosphine (0.34 g, 1.20 mmol) were added to the reaction mixture at rt under nitrogen atmosphere. The reaction mixture was purged with nitrogen for 15 min. Pd(OAc)$_2$ (0.13 g, 0.6 mmol) was added to the reaction mixture at rt under nitrogen atmosphere. The glass vial was sealed and the reaction mixture was heated at 80° C. for 15 h. The resulting reaction mixture was poured into water (200 ml) and extracted with EtOAc (3×100 ml). The combined organic phase was dried over Na$_2$SO$_4$, filtered and concentrated under reduced pressure. The resulting residue was purified by column chromatography (25% EtOAc in Hexane) yielding 4-amino-2-cyclopropylbenzonitrile (0.34 g, 2.15 mmol). LCMS: Method A, 1.90 min, MS: ES+ 159.3.

Example 1 (S)-1-cyano-N-(5-phenylthiazol-2-yl) pyrrolidine-3-carboxamide (Prepared According to Scheme 1)

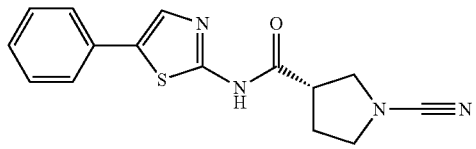 [SMILES: N#CN1CC[C@H](C(=O)Nc2ncc(-c3ccccc3)s2)C1]

Step a.

A solution of 5-phenylthiazol-2-amine (2.6 mmol) and (3S)—BOC-1-pyrrolidine-3-carboxylic acid (2.9 mmol) in THF was stirred at 0° C. for 5 min. To this solution was added T3P (50% in EtOAc) (3.9 mmol) and DIPEA (5.2 mmol) at 0° C. The reaction mixture was stirred at rt for 1 h. The resulting reaction mixture was poured into water (40 ml) and extracted with DCM (40 ml). The organic phase was collected and washed with 1M NaOH solution (30 ml), dried over Na$_2$SO$_4$, filtered and concentrated under reduced pressure. The resulting residue was purified by flash chromatography (2-3% MeOH in DCM) yielding tert-butyl (S)-3-((5-phenylthiazol-2-yl)carbamoyl)pyrrolidine-1-carboxylate (1.2 mmol). MS: ES+ 374.13; $^1$H NMR (400 MHz, DMSO-d$_6$) δ ppm 12.37 (br s, 1H), 7.89 (s, 1H), 7.60-7.62 (m, 2H), 7.40-7.43 (m, 2H), 7.28-7.32 (m, 1H), 3.51-3.53 (m, 1H), 3.36-3.43 (m, 2H), 3.22-3.31 (m, 2H), 2.12-2.18 (m, 1H), 2.01-2.09 (m, 1H), 1.37-1.43 (m, 9H).

Step b.

To a solution of tert-butyl (S)-3-((5-phenylthiazol-2-yl)carbamoyl)pyrrolidine-1-carboxylate (1.2 mmol) in DCM (10 ml) was added 4M HCl in EtOAc (40 mmol) at 0° C. The reaction mixture was stirred at rt for 4 h. The resulting reaction mixture was concentrated under reduced pressure. The obtained residue was triturated with diethyl ether (10 ml) yielding (S)—N-(5-phenylthiazol-2-yl) pyrrolidine-3-carboxamide hydrochloride (1.28 mmol). MS: ES+ 274.13; $^1$H NMR (400 MHz, DMSO-d$_6$) δ ppm 12.55 (br s, 1H), 9.58 (br s, 1H), 9.34 (br s, 1H), 7.91 (s, 1H), 7.60-7.62 (m, 2H), 7.40-7.44 (m, 2H), 7.29-7.33 (m, 1H), 3.38-3.44 (m, 3H), 3.19-3.24 (m, 2H), 2.25-2.33 (m, 1H), 2.08-2.12 (m, 1H).

Step c.

To a solution of (S)—N-(5-phenylthiazol-2-yl) pyrrolidine-3-carboxamide hydrochloride (1.2 mmol) in DCM (5 ml) was added K$_2$CO$_3$ (2.4 mmol) and cyanogen bromide (2.4 mmol) at 0° C. The reaction mixture was stirred at rt for 16 h. The resulting reaction mixture was poured into water (40 ml) and extracted with DCM (50 ml). The organic phase was collected, dried over Na$_2$SO$_4$, filtered and concentrated under reduced pressure. The resulting residue was purified by flash chromatography (1-1.5% MeOH in DCM) yielding the title compound (0.77 mmol). MS: ES+ 299.0; $^1$H NMR (400 MHz, DMSO-d$_6$) δ ppm 12.43 (s, 1H), 7.90 (s, 1H), 7.61-7.63 (m, 2H), 7.40-7.44 (m, 2H), 7.29-7.33 (m, 1H), 3.63-3.66 (m, 1H), 3.53-3.61 (m, 1H), 3.42-3.49 (m, 2H), 3.33-3.40 (m, 1H), 2.16-2.23 (m, 1H), 2.06-2.12 (m, 1H).

Compounds in Table 1 were synthesised using a procedure similar to that described for Example 1 using 1-BOC-pyrrolidine-3-carboxylic acid.

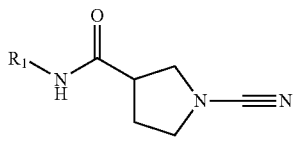

TABLE 1

| Ex | R1 | Name | Amine CAS Number | $^1$H NMR (400 MHz, DMSO-d$_6$) δ ppm | MS |
|---|---|---|---|---|---|
| 2 | | 1-cyano-N-(5-(3-fluorophenyl)thiazol-2-yl)pyrrolidine-3-carboxamide | 438585-95-6 | 12.49 (s, 1H), 8.00 (s, 1H), 7.51-7.56 (m, 1H), 7.41-7.51 (m, 2H), 7.10-7.18 (m, 1H), 3.61-3.67 (m, 1H), 3.53-3.59 (m, 1H), 3.42-3.49 (m, 2H), 3.35-3.41 (m, 1H), 2.16-2.26 (m, 1H), 2.05-2.14 (m, 1H) | ES+ 317.18 |

TABLE 1-continued

| Ex | R1 | Name | Amine CAS Number | $^1$H NMR (400 MHz, DMSO-$d_6$) δ ppm | MS |
|---|---|---|---|---|---|
| 3 | (thiazol-2-yl with 2-fluorophenyl at 5-position) | 1-cyano-N-(5-(2-fluorophenyl)thiazol-2-yl)pyrrolidine-3-carboxamide | 1025927-65-4 | 12.49 (s, 1H), 7.97 (s, 1H), 7.79 (t, J = 7.24 Hz, 1H), 7.33-7.40 (m, 2H), 7.25-7.31 (m, 1H), 3.61-3.67 (m, 1H), 3.54-3.58 (m, 1H), 3.43-3.50 (m, 2H), 3.36-3.41 (m, 1H), 2.17-2.23 (m, 1H), 2.06-2.11 (m, 1H) | ES+ 317.18 |
| 4 | (thiazol-2-yl with 4-chlorophenyl at 5-position) | N-(5-(4-chlorophenyl)thiazol-2-yl)-1-cyano-pyrrolidine-3-carboxamide | 73040-66-1 | 12.47 (s, 1H), 7.95 (s, 1H), 7.65 (d, J = 8.54 Hz, 2H), 7.48 (d, J = 8.54 Hz, 2H), 3.60-3.65 (m, 1H), 3.53-3.57 (m, 1H), 3.42-3.50 (m, 2H), 3.36-3.42 (m, 1H), 2.16-2.23 (m, 1H), 2.05-2.12 (m, 1H) | ES+ 333.13 |
| 5 | (thiazol-2-yl with 3-chlorophenyl at 5-position) | N-(5-(3-chlorophenyl)thiazol-2-yl)-1-cyano-pyrrolidine-3-carboxamide | 1249447-08-2 | 12.50 (s, 1H), 8.02 (s, 1H), 7.74 (t, J = 1.83 Hz, 1H), 7.56 (d, J = 7.60 Hz, 1H), 7.44 (t, J = 8.0 Hz, 1H), 7.36 (d, J = 8.8 Hz, 1H), 3.61-3.67 (m, 1H), 3.53-3.59 (m, 1H), 3.42-3.49 (m, 2H), 3.36-3.42 (m, 1H), 2.16-2.26 (m, 1H), 2.04-2.14 (m, 1H) | ES+ 332.88 |
| 6 | (thiazol-2-yl with 2-chlorophenyl at 5-position) | N-(5-(2-chlorophenyl)thiazol-2-yl)-1-cyano-pyrrolidine-3-carboxamide | Intermediate 10 | 12.49 (s, 1H), 7.81 (s, 1H), 7.66-7.68 (m, 1H), 7.58-7.61 (m, 1H), 7.37-7.45 (m, 2H), 3.60-3.67 (m, 1H), 3.53-3.60 (m, 1H), 3.42-3.50 (m, 2H), 3.32-3.42 (m, 1H), 2.15-2.25 (m, 1H), 2.04-2.15 (m, 1H) | ES+ 332.88 |
| 7 | (5-methylthiazol-2-yl) | 1-cyano-N-(5-methylthiazol-2-yl)pyrrolidine-3-carboxamide | 7305-71-7 | 12.13 (s, 1H), 7.14 (d, J = 1.20 Hz, 1H), 3.58-3.63 (m, 1H), 3.48-3.52 (m, 1H), 3.39-3.47 (m, 2H), 3.25-3.32 (m, 1H), 2.34 (d, J = 1.22 Hz, 3H), 2.13-2.22 (m, 1H), 1.99-2.09 (m, 1H) | ES+ 237.01 |
| 8 | (5-tert-butylthiazol-2-yl) | N-(5-(tert-butyl)thiazol-2-yl)-1-cyano-pyrrolidine-3-carboxamide | 299417-31-5 | 12.13 (s, 1H), 7.17 (s, 1H), 3.60-3.62 (m, 1H), 3.48-3.58 (m, 1H), 3.39-3.47 (m, 2H), 3.25-3.32 (m, 1H), 2.14-2.19 (m, 1H), 2.06-2.09 (m, 1H), 1.32 (s, 9H) | ES+ 279.93 |
| 9 | (4-phenylthiazol-2-yl) | 1-cyano-N-(4-phenylthiazol-2-yl)pyrrolidine-3-carboxamide | 2010-06-2 | 12.50 (s, 1H), 7.89-7.91 (m, 2H), 7.66 (s, 1H), 7.41-7.45 (m, 2H), 7.31-7.35 (m, 1H), 3.60-3.71 (m, 1H), 3.52-3.60 (m, 1H), 3.41-3.52 (m, 2H), 3.32-3.42 (m, 1H), 2.18-2.23 (m, 1H), 2.06-2.13 (m, 1H) | ES+ 299.43 |
| 10 | (2-phenylthiazol-5-yl) | 1-cyano-N-(2-phenylthiazol-5-yl)pyrrolidine-3-carboxamide | 87657-91-8 | 11.69 (s, 1H), 7.85-7.88 (m, 2H), 7.61 (s, 1H), 7.40-7.49 (m, 3H), 3.61-3.65 (m, 1H), 3.52-3.58 (m, 1H), 3.40-3.51 (m, 2H), 3.22-3.32 (m, 1H), 2.16-2.24 (m, 1H), 2.03-2.11 (m, 1H) | ES+ 298.90 |
| 11 | (5-phenyl-1,3,4-thiadiazol-2-yl) | 1-cyano-N-(5-phenyl-1,3,4-thiadiazol-2-yl)pyrrolidine-3-carboxamide | 2002-03-1 | 12.90 (s, 1H), 7.94-7.95 (m, 2H), 7.54-7.55 (m, 3H), 3.56-3.68 (m, 2H), 3.33-3.47 (m, 3H), 2.19-2.25 (m, 1H), 2.08-2.14 (m, 1H) | ES+ 299.96 |

TABLE 1-continued

| Ex | R1 | Name | Amine CAS Number | ¹H NMR (400 MHz, DMSO-d$_6$) δ ppm | MS |
|---|---|---|---|---|---|
| 12 | ethyl-1,3,4-thiadiazole | 1-cyano-N-(5-ethyl-1,3,4-thiadiazol-2-yl)pyrrolidine-3-carboxamide | 14068-53-2 | 13.84 (br s, 1H), 3.84-3.89 (m, 1H), 3.64-3.79 (m, 3H), 3.55-3.61 (m, 1H), 3.07-3.12 (m, 2H), 2.39-2.47 (m, 1H), 2.27-2.36 (m, 1H), 1.45 (t, J = 7.48 Hz, 3H) | ES+ 252.10 |
| 13 | 3-phenylisoxazole | 1-cyano-N-(3-phenylisoxazol-5-yl)pyrrolidine-3-carboxamide | 4369-55-5 | 11.96 (s, 1H), 7.83-7.89 (m, 2H), 7.48-7.55 (m, 3H), 6.77 (s, 1H), 3.54-3.64 (m, 2H), 3.42-3.46 (m, 2H), 3.24-3.33 (m, 1H), 2.16-2.26 (m, 1H), 2.06-2.12 (m, 1H) | ES+ 282.93 |
| 14 | 3-(4-methoxyphenyl)isoxazole | 1-cyano-N-(3-(4-methoxyphenyl)isoxazol-5-yl)pyrrolidine-3-carboxamide | 86685-98-5 | 11.90 (s, 1H), 7.79 (d, J = 9.15 Hz, 2H), 7.04 (d, J = 8.85 Hz, 2H), 6.72 (s, 1H), 3.81 (s, 3H), 3.59-3.66 (m, 1H), 3.52-3.60 (m, 1H), 3.40-3.49 (m, 2H), 3.26-3.21 (m, 1H), 2.14-2.25 (m, 1H), 2.03-2.13 (m, 1H) | ES+ 312.97 |
| 15 | 5-phenylisoxazole | 1-cyano-N-(5-phenylisoxazol-3-yl)pyrrolidine-3-carboxamide | 6455-31-8 | 11.31 (s, 1H), 7.88-7.90 (m, 2H), 7.52-7.57 (m, 3H), 7.39 (s, 1H), 3.59-3.65 (m, 1H), 3.51-3.57 (m, 1H), 3.41-3.49 (m, 2H), 3.25-3.32 (m, 1H), 2.15-2.24 (m, 1H), 2.02-2.12 (m, 1H) | ES+ 282.93 |
| 16 | 5-tert-butylisoxazole | N-(5-tert-butyl)isoxazol-3-yl)-1-cyano-pyrrolidine-3-carboxamide | 55809-36-4 | 11.18 (s, 1H), 6.62 (s, 1H), 3.55-3.61 (m, 1H), 3.46-3.51 (m, 1H), 3.38-3.45 (m, 2H), 3.21-3.24 (m, 1H), 2.12-2.17 (m, 1H), 1.99-2.07 (m, 1H), 1.29 (s, 9H) | ES+ 263.0 |
| 17 | 3-tert-butyl-1H-pyrazole | N-(3-(tert-butyl)-1H-pyrazol-5-yl)-1-cyanopyrrolidine-3-carboxamide | 82560-12-1 | 12.07 (br s, 1H), 10.50 (s, 1H), 6.30 (s, 1H), 3.55-3.58 (m, 1H), 3.33-3.49 (m, 3H), 3.14-3.19 (m, 1H), 2.06-2.16 (m, 1H), 1.94-2.05 (m, 1H), 1.25 (s, 9H) | ES+ 262.04 |
| 18 | benzo[d]thiazole | N-(benzo[d]thiazol-2-yl)-1-cyano-pyrrolidine-3-carboxamide | 136-95-8 | 12.57 (s, 1H), 7.99 (d, J = 7.20 Hz, 1H), 7.76 (d, J = 7.94 Hz, 1H), 7.42-7.47 (m, 1H), 7.30-7.34 (m, 1H), 3.56-3.68 (m, 2H), 3.35-3.50 (m, 3H), 2.19-2.26 (m, 1H), 2.06-2.16 (m, 1H) | ES+ 273.10 |
| 19 | 6-methylbenzo[d]thiazole | 1-cyano-N-(6-methyl-benzo[d]thiazol-2-yl)pyrrolidine-3-carboxamide | 2536-91-6 | 10.32 (br s, 1H), 7.64-7.68 (m, 2H), 7.31 (dd, 8.4 Hz, 1.2 Hz, 1H), 3.76-3.81 (m, 1H), 3.63-3.71 (m, 2H), 3.44-3.50 (m, 1H), 3.17-3.20 (m, 1H), 2.51 (s, 3H), 2.19-2.36 (m, 2H) | ES+ 287.18 |
| 20 | 6-(trifluoromethyl)benzo[d]thiazole | 1-cyano-N-(6-(trifluoromethyl)benzo[d]thiazol-2-yl)pyrrolidine-3-carboxamide | 777-12-8 | 12.84 (s, 1H), 8.54 (s, 1H), 7.93 (d, J = 8.24 Hz, 1H), 7.76 (d, J = 8.85 Hz, 1H), 3.57-3.69 (m, 2H), 3.38-3.50 (m, 3H), 2.19-2.29 (m, 1H), 2.07-2.17 (m, 1H) | ES+ 340.84 |
| 21 | 6-methoxybenzo[d]thiazole | 1-cyano-N-(6-methoxybenzo[d]thiazol-2-yl)pyrrolidine-3-carboxamide | 1747-60-0 | 12.44 (s, 1H), 7.65 (d, J = 8.85 Hz, 1H), 7.59 (d, J = 2.44 Hz, 1H), 7.04 (dd, J = 8.69, 2.59 Hz, 1H), 3.81 (s, 3H), 3.61-3.68 (m, 1H), 3.53-3.60 (m, 1H), 3.41-3.52 (m, 2H), 3.35-3.41 (m, 1H), 2.16-2.28 (m, 1H), 2.03-2.15 (m, 1H) | ES+ 303.10 |

TABLE 1-continued

| Ex | R1 | Name | Amine CAS Number | $^1$H NMR (400 MHz, DMSO-d$_6$) δ ppm | MS |
|---|---|---|---|---|---|
| 22 | 6-bromo-benzo[d]thiazol-2-yl | N-(6-bromo-benzo[d]thiazol-2-yl)-1-cyano-pyrrolidine-3-carboxamide | 15864-32-1 | 12.67 (s, 1H), 8.28 (d, J = 1.98 Hz, 1H), 7.70 (d, J = 8.55 Hz, 1H), 7.59 (dd, J = 8.62, 2.06 Hz, 1H), 3.53-3.69 (m, 2H), 3.36-3.50 (m, 3H), 2.16-2.30 (m, 1H), 2.01-2.13 (m, 1H) | ES+ 350.92 |
| 23 | 1H-benzo[d]imidazol-2-yl | N-(1H-benzo[d]imidazol-2-yl)-1-cyano-pyrrolidine-3-carboxamide | 934-32-7 | 12.12 (br s, 1H), 11.76 (br s, 1H), 7.35-7.51 (m, 2H), 7.06-7.11 (m, 2H), 3.56-3.67 (m, 2H), 3.41-3.52 (m, 2H), 3.30-3.34 (m, 1H), 2.17-2.26 (m, 1H), 2.06-2.16 (m, 1H) | ES+ 255.95 |
| 24 | pyridin-2-yl | 1-cyano-N-(pyridin-2-yl)pyrrolidine-3-carboxamide | 504-29-0 | 10.71 (s, 1H), 8.31-8.36 (m, 1H), 8.08 (d, J = 8.24 Hz, 1H), 7.79 (td, J = 7.86, 1.98 Hz, 1H), 7.12 (ddd, J = 7.33, 4.88, 0.92Hz, 1H), 3.57-3.64 (m, 1H), 3.38-3.53 (m, 3H), 3.29-3.34 (m, 1H), 2.12-2.22 (m, 1H), 1.99-2.10 (m, 1H) | ES+ 216.98 |
| 25 | 5-chloro-pyridin-2-yl | N-(5-chloro-pyridin-2-yl)-1-cyanopyrrolidine-3-carboxamide | 1072-98-6 | 10.89 (s, 1H), 8.38-8.41 (m, 1H), 8.12 (d, J = 8.85 Hz, 1H), 7.92 (dd, J = 8.85, 2.78 Hz, 1H), 3.58-3.64 (m, 1H), 3.33-3.54 (m, 4 H), 2.12-2.22 (m, 1H), 2.00-2.10 (m, 1H) | ES+ 251.23 |
| 26 | 5-methylpyridin-2-yl | 1-cyano-N-(5-methylpyridin-2-yl)pyrrolidine-3-carboxamide | 1603-41-4 | 10.61 (s, 1H), 8.16 (dd, J = 1.52, 0.92 Hz, 1H), 7.98 (d, J = 8.55 Hz, 1H), 7.61 (dd, J = 8.55, 2.14 Hz, 1H), 3.57-3.63 (m, 1H), 3.43-3.52 (m, 2H), 3.37-3.43 (m, 1H), 3.26-3.33 (m, 1H), 2.24 (s, 3H), 2.10-2.20 (m, 1H), 1.97-2.09 (m, 1H) | ES+ 231.03 |
| 27 | 5-methoxypyridin-2-yl | 1-cyano-N-(5-methoxypyridin-2-yl)pyrrolidine-3-carboxamide | 10167-97-2 | 10.57 (s, 1H), 8.00-8.06 (m, 2H), 7.44 (dd, J = 9.16, 3.05 Hz, 1H), 3.81 (s, 3H), 3.57-3.63 (m, 1H), 3.43-3.51 (m, 2H), 3.37-3.43 (m, 1H), 3.26-3.32 (m, 1H), 2.11-2.20 (m, 1H), 1.98-2.08 (m, 1H) | ES+ 247.23 |
| 28 | 5-morpholinopyridin-2-yl | 1-cyano-N-(5-morpholino-pyridin-2-yl)pyrrolidine-3-carboxamide | 571189-78-1 | 10.50 (s, 1H), 8.02 (d, J = 2.78 Hz, 1H), 7.95 (d, J = 9.16 Hz, 1H), 7.42 (dd, J = 9.16, 3.05 Hz, 1H), 3.71-3.78 (m, 4 H), 3.56-3.63 (m, 1H), 3.43-3.50 (m, 2H), 3.37-3.43 (m, 1H), 3.24-3.31 (m, 1H), 3.07-3.14 (m, 4 H), 2.10-2.20 (m, 1H), 1.98-2.07 (m, 1H) | ES+ 301.93 |
| 29 | 5-(piperidin-1-yl)pyridin-2-yl | 1-cyano-N-(5-(piperidin-1-yl)pyridin-2-yl)pyrrolidine-3-carboxamide | 94924-94-4 | 10.45 (s, 1H), 7.99 (d, J = 2.78 Hz, 1H), 7.92 (d, J = 9.16 Hz, 1H), 7.39 (dd, J = 9.16, 3.05 Hz, 1H), 3.56-3.63 (m, 1H), 3.36-3.51 (m, 3H), 3.23-2.30 (m, 1H), 3.06-3.16 (m, 4 H), 2.10-2.18 (m, 1H), 1.97-2.06 (m, 1H), 1.57-1.67 (m, 4 H), 1.48-1.56 (m, 2H) | ES+ 299.96 |
| 30 | 5-(1H-imidazol-1-yl)pyridin-2-yl | N-(5-(1H-imidazol-1-yl)pyridin-2-yl)-1-cyano-pyrrolidine-3-carboxamide | 935547-73-2 | 10.94 (s, 1H), 8.70 (dd, J = 2.75, 0.61 Hz, 1H), 8.29 (s, 1H), 8.18-8.25 (m, 1H), 8.11-8.16 (m, 1H), 7.80 (t, J = 1.22 Hz, 1H), 7.14 (s, 1H), 3.59-3.66 (m, 1H), 3.38-3.55 (m, 4 H), 2.14-2.24 (m, 1H), 2.01-2.12 (m, 1H) | ES+ 282.93 |

TABLE 1-continued

| Ex | R1 | Name | Amine CAS Number | ¹H NMR (400 MHz, DMSO-$d_6$) δ ppm | MS |
|---|---|---|---|---|---|
| 31 | 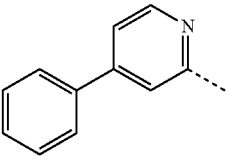 | 1-cyano-N-(4-phenylpyridin-2-yl)pyrrolidine-3-carboxamide | 60781-83-1 | 10.82 (s, 1H), 8.36-8.47 (m, 2H), 7.71-7.75 (m, 2H), 7.40-7.58 (m, 4 H), 3.58-3.67 (m, 1H), 3.46-3.57 (m, 2H), 3.36-3.47 (m, 2H), 2.15-2.19 (m, 1H), 2.02-2.13 (m, 1H) | ES+ 292.92 |
| 32 | 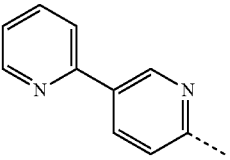 | N-([2,3'-bipyridin]-6'-yl)-1-cyano-pyrrolidine-3-carboxamide | 31860-60-3 | 10.92 (s, 1H), 9.06 (dd, J = 2.44, 0.61 Hz, 1H), 8.66-8.71 (m, 1H), 8.49 (dd, J = 8.85, 2.44 Hz, 1H), 8.21 (d, J = 8.85 Hz, 1H), 8.01-8.05 (m, 1H), 7.91 (td, J = 7.78, 1.83 Hz, 1H), 7.38 (ddd, J = 7.48, 4.88, 1.07 Hz, 1H), 3.60-3.66 (m, 1H), 3.50-3.56 (m, 1H), 3.44-3.50 (m, 1H), 3.34-3.44 (m, 2H), 2.15-2.24 (m, 1H), 2.03-2.13 (m, 1H) | ES+ 293.97 |
| 33 | 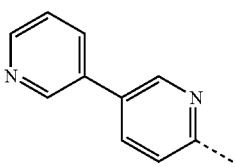 | N-([3,3'-bipyridin]-6-yl)-1-cyano-pyrrolidine-3-carboxamide | 31970-30-6 | 10.88 (s, 1H), 8.96 (d, J = 2.14 Hz, 1H), 8.74 (t, J = 1.68 Hz, 1 H), 8.60 (dd, J = 4.88, 1.53 Hz, 1H), 8.21 (d, J = 1.53 Hz, 2 H), 8.13-8.18 (m, 1H), 7.51 (ddd, J = 7.94, 4.73, 0.76 Hz, 1H), 3.60-3.66 (m, 1H), 3.38-3.56 (m, 4 H), 2.15-2.24 (m, 1H), 2.03-2.12 (m, 1H) | ES+ 294.04 |
| 34 | 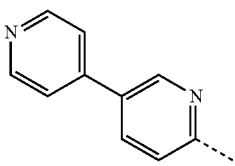 | N-([3,4'-bipyridin]-6-yl)-1-cyano-pyrrolidine-3-carboxamide | 79739-33-6 | 10.94 (s, 1H), 8.84 (dd, J = 2.59, 0.76 Hz, 1H), 8.64-8.68 (m, 2H), 8.26-8.31 (m, 1H), 8.20-8.25 (m, 1H), 7.77-7.82 (m, 2H), 3.60-3.66 (m, 1H), 3.50-3.56 (m, 1H), 3.44-3.50 (m, 1H), 3.35-3.44 (m, 2H), 2.17-2.23 (m, 1H), 2.03-2.12 (m, 1H) | ES+ 294.04 |
| 35 | 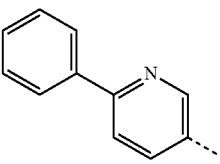 | 1-cyano-N-(6-phenyl-pyridin-3-yl)pyrrolidine-3-carboxamide | 126370-67-0 | 10.44 (br s, 1H), 8.82 (s, 1H), 7.94-8.17 (m, 4H), 7.40-7.47 (m, 3H), 3.41-3.69 (m, 4H), 3.21-3.30 (m, 1H), 2.15-2.27 (m, 1H), 2.04-2.15 (m, 1H) | ES+ 292.99 |
| 36 | 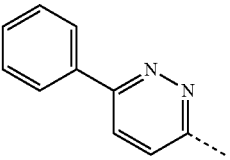 | 1-cyano-N-(6-phenyl-pyridazin-3-yl)pyrrolidine-3-carboxamide | 14966-91-7 | 11.44 (s, 1H), 8.40 (d, J = 9.46 Hz, 1H), 8.26 (d, J = 9.46 Hz, 1H), 8.11 (dd, J = 8.0 Hz, 1.2 Hz, 2H), 7.50-7.58 (m, 3H), 3.61-3.69 (m, 1H), 3.53-3.59 (m, 1H), 3.38-3.52 (m, 3H), 2.17-2.27 (m, 1H), 2.05-2.16 (m, 1H) | ES+ 293.99 |
| 37 | 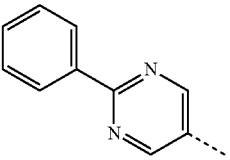 | 1-cyano-N-(2-phenyl-pyrimidin-5-yl)pyrrolidine-3-carboxamide | 59808-52-5 | 10.63 (s, 1H), 9.11 (s, 2H), 8.31-8.39 (m, 2H), 7.48-7.56 (m, 3H), 3.61-3.68 (m, 1H), 3.54-3.60 (m, 1H), 3.41-3.52 (m, 2H), 3.24-3.31 (m, 1H), 2.17-2.27 (m, 1H), 2.05-2.16 (m, 1H) | ES+ 293.91 |
| 38 | 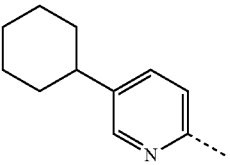 | 1-cyano-N-(5-cyclo-hexylpyridin-2-yl)pyrrolidine-3-carboxamide | Intermediate 6 | 10.62 (s, 1H), 8.19 (d, J = 2.44 Hz, 1H), 7.99 (d, J = 8.55 Hz, 1H), 7.65 (dd, J = 8.55, 2.44 Hz, 1H), 3.57-3.63 (m, 1H), 3.43-3.51 (m, 2H), 3.26-3.42 (m, 3H), 2.11-2.21 (m, 1H), 1.97-2.08 (m, 1H), 1.73-1.82 (m, 4 H), 1.68-1.72 (m, 1H), 1.29-1.47 (m, 4 H), 1.17-1.29 (m, 1H) | ES+ 299.04 |

TABLE 1-continued

| Ex | R1 | Name | Amine CAS Number | ¹H NMR (400 MHz, DMSO-d₆) δ ppm | MS |
|----|----|------|------------------|----------------------------------|-----|
| 39 | | N-(1-benzyl-1H-indazol-5-yl)-1-cyano-pyrrolidine-3-carboxamide | 23856-21-5 | 10.14 (s, 1H), 8.14 (d, J = 1.22 Hz, 1H), 8.07 (d, J = 0.92 Hz, 1H), 7.65 (d, J = 8.85 Hz, 1H), 7.43 (dd, J = 9.16, 1.83 Hz, 1 H), 7.24-7.33 (m, 3H), 7.18-7.22 (m, 2H), 5.63 (s, 2H), 3.59-3.66 (m, 1H), 3.47-3.55 (m, 2H), 3.41-3.47 (m, 1H), 3.18-3.21 (m, 1H), 2.13-2.22 (m, 1H), 2.03-2.11 (m, 1H) | ES+ 346.18 |
| 40 | | 1-cyano-N-(1-propyl-1H-benzo[d]imidazol-5-yl)pyrrolidine-3-carboxamide | 177843-27-5 | 10.08 (s, 1H), 8.19 (s, 1H), 7.98 (d, J = 1.83 Hz, 1H), 7.54 (d, J = 8.85 Hz, 1H), 7.39 (dd, J = 8.85, 1.83 Hz, 1H), 4.18 (t, J = 7.02 Hz, 2H), 3.60-3.66 (m, 1H), 3.41-3.55 (m, 3H), 3.16-3.34 (m, 1H), 2.14-2.23 (m, 1H), 2.02-2.13 (m, 1H), 1.75-1.82 (m, 2H), 0.83 (t, J = 7.48 Hz, 3H) | ES+ 298.23 |

Compounds in Table 2 were synthesised using a procedure similar to that described for Example 1 using (S)-1-(tert-butoxycarbonyl)pyrrolidine-3-carboxylic acid.

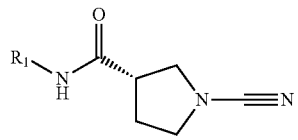

TABLE 2

| Ex | R1 | Name | Amine CAS Number | ¹H NMR (400 MHz, DMSO-d₆) δ ppm | MS |
|----|----|------|------------------|----------------------------------|-----|
| 41 | | (S)-1-cyano-N-(1-phenyl-1H-imidazol-4-yl)pyrrolidine-3-carboxamide | 158688-63-2 | 10.75 (s, 1H), 8.14 (d, J = 1.83 Hz, 1H), 7.72 (d, J = 1.53 Hz, 1H), 7.62-7.64 (m, 2H), 7.50-7.53 (m, 2H), 7.30-7.40 (m, 1H), 3.55-3.65 (m, 1H), 3.25-3.37 (m, 4 H), 2.08-2.19 (m, 1H), 1.95-2.08 (m, 1H) | ES+ 282.33 |
| 42 | | (S)-1-cyano-N-(5-phenyl-1H-pyrazol-3-yl)pyrrolidine-3-carboxamide | 1572-10-7 | 12.90 (s, 1H), 10.70 (s, 1H), 7.71-7.72 (m, 2H), 7.43-7.45 (m, 2H), 7.29-7.38 (m, 1H), 6.93 (d, J = 1.83 Hz, 1 H), 3.58-3.62 (m, 1H), 3.37-3.54 (m, 3H), 3.21-3.25 (m, 1H), 2.13-2.17 (m, 1H), 2.01-2.06 (m, 1H) | ES+ 282.28 |
| 43 | | (S)-1-cyano-N-(5-(tetrahydro-2H-pyran-4-yl)-1H-pyrazol-3-yl)pyrrolidine-3-carboxamide | 1000896-69-4 | 12.13 (s, 1H), 10.52 (s, 1H), 6.32 (s, 1H), 3.87-3.90 (m, 2 H), 3.56-3.59 (m, 1H), 3.37-3.48 (m, 5 H), 3.16-3.20 (m, 1H), 2.81-2.87 (m, 1H), 2.02-2.12 (m, 1H), 1.98-2.00 (m, 1H), 1.78-1.81 (m, 2H), 1.53-1.64 (m, 2H) | ES+ 290.1 |

TABLE 2-continued

| Ex | R1 | Name | Amine CAS Number | ¹H NMR (400 MHz, DMSO-d₆) δ ppm | MS |
|---|---|---|---|---|---|
| 44 | (phenyl-triazolyl) | (S)-1-cyano-N-(1-phenyl-1H-1,2,3-triazol-4-yl)pyrrolidine-3-carboxamide | 2076-64-4 | 11.33 (s, 1H), 8.77 (s, 1H), 7.89-8.00 (m, 2H), 7.55-7.64 (m, 2H), 7.42-7.53 (m, 1H), 3.59-3.70 (m, 1H), 3.38-3.57 (m, 3H), 3.25-3.34 (m, 1H), 2.12-2.25 (m, 1H), 1.98-2.10 (m, 1H) | ES+ 283.28 |
| 45 | (phenyl-pyrazolyl) | (S)-1-cyano-N-(1-phenyl-1H-pyrazol-3-yl)pyrrolidine-3-carboxamide | 1128-56-9 | 10.96 (s, 1H), 8.43 (d, J = 2.74 Hz, 1H), 7.76-7.78 (m, 2H), 7.47-7.51 (m, 2H), 7.25-7.31 (m, 1H), 6.81 (d, J = 2.44 Hz, 1H), 3.59-3.64 (m, 1H), 3.49-3.53 (m, 1H), 3.37-3.47 (m, 2H), 3.21-3.30 (m, 1H), 2.12-2.21 (m, 1H), 2.00-2.10 (m, 1H) | ES+ 282.08 |
| 46 | (4-methylbenzothiazolyl) | (S)-1-cyano-N-(4-methylbenzo[d]thiazol-2-yl)pyrrolidine-3-carboxamide | 1477-42-5 | 12.67 (s, 1H), 7.80 (d, J = 7.63 Hz, 1H), 7.25-7.29 (m, 1H), 7.19-7.25 (m, 1H), 3.62-3.68 (m, 1H), 3.55-3.61 (m, 1H), 3.42-3.52 (m, 2H), 3.36-3.42 (m, 1H), 2.58 (s, 3H), 2.18-2.28 (m, 1H), 2.05-2.16 (m, 1H) | ES+ 286.94 |
| 47 | (7-methylbenzothiazolyl) | (S)-1-cyano-N-(7-methylbenzo[d]thiazol-2-yl)-pyrrolidine-3-carboxamide | 14779-18-1 | 12.58 (br s, 1H), 7.61 (d, J = 7.02 Hz, 1H), 7.38 (t, J = 6.40 Hz, 1H), 7.16 (d, J = 7.01 Hz, 1H), 3.63-3.67 (m, 1H), 3.57-3.60 (m, 1H), 3.43-3.47 (m, 2H), 3.38-3.42 (m, 1H), 2.52 (s, 3H), 2.21-2.23 (m, 1H), 2.08-2.13 (m, 1H) | ES+ 287.33 |
| 48 | (4-bromobenzothiazolyl) | (S)-N-(4-bromobenzo[d]thiazol-2-yl)-1-cyano-pyrrolidine-3-carboxamide | 20358-02-5 | 12.96 (br s, 1H), 8.00 (d, J = 7.32 Hz, 1H), 7.67 (d, J = 7.63 Hz, 1H), 7.22 (t, J = 7.78 Hz, 1H), 3.57-3.67 (m, 2H), 3.42-3.49 (m, 2H), 3.37-3.41 (m, 1H), 2.18-2.27 (m, 1H), 2.08-2.17 (m, 1H) | ES+ 352.87 |
| 49 | (imidazo[1,2-a]pyridinyl) | (S)-1-cyano-N-(imidazo[1,2-a]pyridin-2-yl)-pyrrolidine-3-carboxamide | 39588-26-6 | 10.92 (br s, 1H), 8.54 (d, J = 7.02 Hz, 1H), 8.11 (s, 1H), 7.42 (d, J = 9.16 Hz, 1H), 7.22 (t, J = 6.87 Hz, 1H), 6.87 (t, J = 6.87 Hz, 1H), 3.59-3.66 (m, 1H), 3.45-3.55 (m, 2H), 3.36-3.42 (m, 1H), 3.22-3.32 (m, 1H), 2.12-2.23 (m, 1H), 2.01-2.11 (m, 1H) | ES+ 256.00 |
| 50 | (7-bromoimidazopyridinyl) | (S)-N-(7-bromo-imidazo[1,2-a]pyridin-2-yl)-1-cyanopyrrolidine-3-carboxamide | 865604-33-7, preparation described in WO2005089763 | 11.01 (s, 1H), 8.52 (d, J = 7.02Hz, 1H), 8.16 (s, 1H), 7.75 (d, J = 1.83 Hz, 1H), 7.06 (dd, J = 7.17, 1.98 Hz, 1H), 3.58-3.65 (m, 1H), 3.37-3.52 (m, 3H), 3.25-3.32 (m, 1H), 2.13-2.19 (m, 1H), 2.01-2.08 (m, 1H) | ES+ 334.0, 336.0 |
| 51 | (6-bromoimidazopyridinyl) | (S)-N-(6-bromoimidazo]1,2-a]pyridin-2-yl)-1-cyanopyrrolidine-3-carboxamide | 947248-52-4, preparation described in WO2012174312 | 11.01 (s, 1H), 8.91 (d, J = 1.22 Hz, 1H), 8.13 (s, 1H), 7.40-7.44 (m, 1H), 7.31-7.36 (m, 1H), 3.59-3.64 (m, 1H), 3.36-3.53 (m, 3H), 3.25-3.32 (m, 1H), 2.12-2.22 (m, 1H), 2.01-2.09 (m, 1H) | ES+ 333.9, 335.9 |

TABLE 2-continued

| Ex | R1 | Name | Amine CAS Number | ¹H NMR (400 MHz, DMSO-d₆) δ ppm | MS |
|---|---|---|---|---|---|
| 52 | pyrazolo[1,5-a]pyridin-2-yl | (S)-1-cyano-N-(pyrazolo[1,5-a]pyridin-2-yl)pyrrolidine-3-carboxamide | 51119-05-2, preparation described in WO2012102297 | 11.00 (s, 1H), 8.51 (dd, J = 6.80, 0.80 Hz, 1H), 7.58 (d, J = 8.85 Hz, 1H), 7.19 (t, J = 6.80 Hz, 1H), 6.85 (s, 1H), 6.79-6.83 (m, 1H), 3.60-3.65 (m, 1H), 3.49-3.53 (m, 1H), 3.45-3.47 (m, 1H), 3.42-3.46 (m, 1H), 3.26-3.33 (m, 1H), 2.13-2.22 (m, 1H), 2.01-2.07 (m, 1H) | ES+ 256.63 |
| 53 | 4-methoxypyridin-2-yl | (S)-1-cyano-N-(4-methoxypyridin-2-yl)pyrrolidine-3-carboxamide | 10201-73-7 | 10.68 (s, 1H), 8.13 (d, J = 5.79 Hz, 1H), 7.73 (s, 1H), 6.73 (dd, J = 5.79, 2.44 Hz, 1H), 3.82 (s, 3H), 3.57-3.63 (m, 1H), 3.47-3.52 (m, 1H), 3.38-3.50 (m, 2H), 3.30-3.37 (m, 1H), 2.11-2.21 (m, 1H), 1.99-2.08 (m, 1H) | ES+ 247.06 |
| 54 | 5-phenylpyridin-2-yl | (S)-1-cyano-N-(5-phenylpyridin-2-yl)pyrrolidine-3-carboxamide | 33421-40-8 | 10.84 (s, 1H), 8.67 (d, J = 1.83Hz, 1H), 8.09-8.22 (m, 2H), 7.72 (d, J = 7.32 Hz, 2H), 7.49 (t, J = 7.6 Hz, 2H), 7.40 (t, J = 7.6 Hz, 1H), 3.59-3.65 (m, 1H), 3.34-3.54 (m, 4 H), 2.14-2.26 (m, 1H), 2.02-2.13 (m, 1H) | ES+ 293.23 |
| 55 | 6-phenylpyridin-2-yl | (S)-1-cyano-N-(6-phenylpyridin-2-yl)pyrrolidine-3-carboxamide | 39774-25-9 | 10.74 (s, 1H), 8.03-8.12 (m, 3H), 7.89 (t, J = 7.93 Hz, 1H), 7.69 (d, J = 7.63 Hz, 1H), 7.43-7.52 (m, 3H), 3.61-3.65 (m, 1H), 3.46-3.56 (m, 3H), 3.37-3.44 (m, 1H), 2.15-2.25 (m, 1H), 2.03-2.13 (m, 1H) | ES+ 292.99 |
| 56 | 1,8-naphthyridin-2-yl | (S)-1-cyano-N-(1,8-naphthyridin-2-yl)pyrrolidine-3-carboxamide | 15992-83-3 | 11.36 (s, 1H), 9.01 (dd, J = 4.42, 1.98 Hz, 1H), 8.45-8.49 (m, 1H), 8.39-8.44 (m, 2H), 7.52-7.56 (m, 1H), 3.62-3.68 (m, 1H), 3.54-3.59 (m, 1H), 3.42-3.53 (m, 3H), 2.18-2.27 (m, 1H), 2.04-2.18 (m, 1H) | ES+ 268.28 |
| 57 | 5-benzylthiazol-2-yl | (S)-N-(5-benzylthiazol-2-yl)-1-cyanopyrrolidine-3-carboxamide | 121952-97-4 | 12.18 (s, 1H), 7.29-7.35 (m, 2H), 7.20-7.29 (m, 4 H), 4.08 (s, 2H), 3.55-3.62 (m, 1H), 3.46-3.50 (m, 1H), 3.34-3.43 (m, 2H), 3.25-3.29 (m, 1H), 2.10-2.21 (m, 1H), 1.98-2.06 (m, 1H) | ES+ 313.28 |
| 58 | isoquinolin-3-yl | (S)-1-cyano-N-(isoquinolin-3-yl)pyrrolidine-3-carboxamide | 25475-67-6 | 10.85 (s, 1H), 9.16 (s, 1H), 8.50 (s, 1H), 8.06 (d, J = 7.6 Hz, 1H), 7.91 (d, J = 7.93 Hz, 1H), 7.72 (ddd, J = 8.24, 6.86, 1.06 Hz, 1H), 7.54 (ddd, J = 8.16, 6.94, 1.06 Hz, 1H), 3.62-3.67 (m, 1H), 3.47-3.57 (m, 2H), 3.38-3.46 (m, 2H), 2.16-2.24 (m, 1H), 2.05-2.13 (m, 1H) | ES+ 267.10 |
| 59 | 5-(tetrahydro-2H-pyran-4-yl)thiazol-2-yl | (S)-1-cyano-N-(5-(tetrahydro-2H-pyran-4-yl)thiazol-2-yl)pyrrolidine-3-carboxamide | Intermediate 3 | 12.18 (s, 1H), 7.22 (s, 1H), 3.88-3.91 (m, 2H), 3.58-3.63 (m, 1H), 3.48-3.53 (m, 1H), 3.39-3.45 (m, 3H), 3.28-3.33 (m, 1H), 3.01-3.07 (m, 2H), 2.15-2.19 (m, 1H), 2.01-2.06 (m, 1H), 1.83-1.87 (m, 2H), 1.56-1.66 (m, 2H) | ES+ 307.47 |

TABLE 2-continued

| Ex | R1 | Name | Amine CAS Number | ¹H NMR (400 MHz, DMSO-d₆) δ ppm | MS |
|---|---|---|---|---|---|
| 60 | | (S)-1-cyano-N-(1-methyl-5-phenyl-1H-pyrazol-3-yl)pyrrolidine-3-carboxamide | Intermediate 4 | 10.70 (s, 1H), 7.46-7.51 (m, 5 H), 6.61 (s, 1H), 3.76 (s, 3 H), 3.57-3.61 (m, 1H), 3.35-3.40 (m, 2H), 3.42-3.49 (m, 1H), 3.17-3.24 (m, 1H), 2.10-2.18 (m, 1H), 1.97-2.06 (m, 1H) | ES+ 296.33 |
| 61 | | (S)-1-cyano-N-(5-(4-methoxy-piperidin-1-yl)pyridin-2-yl)pyrrolidine-3-carboxamide | Intermediate 5 | 10.45 (s, 1H), 8.02 (d, J = 2.78 Hz, 1H), 7.92 (d, J = 9.16 Hz, 1H), 7.41 (dd, J = 9.16, 3.05 Hz, 1H), 3.56-3.62 (m, 1H), 3.37-3.50 (m, 6 H), 3.25-3.30 (m, 4 H), 2.84-2.93 (m, 2H), 2.10-2.19 (m, 1H), 1.99-2.07 (m, 1H), 1.91-1.94 (m, 2H), 1.46-1.58 (m, 2H) | ES+ 330.06 |
| 62 | | (S)-N-(6-(1H-1,2,3-triazol-1-yl)benzo[d]thiazol-2-yl)-1-cyanopyrrolidine-3-carboxamide | Intermediate 7 | 12.76 (s, 1H), 8.86 (s, 1H), 8.60 (s, 1H), 7.93-8.01 (m, 3 H), 3.58-3.69 (m, 2H), 3.40-3.52 (m, 3H), 2.22-2.27 (m, 1H), 2.10-2.16 (m, 1H) | ES+ 340.23 |
| 63 | | (S)-N-(6-(2H-1,2,3-triazol-2-yl)benzo[d]thiazol-2-yl)-1-cyanopyrrolidine-3-carboxamide | Intermediate 8 | 12.71 (s, 1H), 8.69 (d, J = 1.83 Hz, 1H), 8.13-8.15 (m, 2H), 8.12 (dd, J = 8.80, 2.00 Hz, 1H), 7.91 (d, J = 8.85 Hz, 1H), 3.57-3.69 (m, 2H), 3.39-3.51 (m, 3H), 2.21-2.28 (m, 1H), 2.07-2.17 (m, 1H) | ES+ 340.28 |
| 64 | | (S)-1-cyano-N-(5-(4-(methylcarbamoyl)phenyl)thiazol-2-yl)pyrrolidine-3-carboxamide | Intermediate 9 | 12.49 (s, 1H), 8.49 (d, J = 4.4 Hz, 1H), 8.03 (s, 1H), 7.87 (d, J = 8.4 Hz, 2H), 7.71 (d, J = 8.4 Hz, 2H), 3.62-3.66 (m, 1H), 3.54-3.58 (m, 1H), 3.43-3.48 (m, 2H), 3.37-3.40 (m, 1H), 2.79 (d, H = 4.4 Hz, 3H), 2.19-2.23 (m, 1H), 2.06-2.11 (m, 1H) | ES+ 354.38 |
| 65 | | (S)-1-cyano-N-(4-methyl-5-(morpholino-methyl)thiazol-2-yl)pyrrolidine-3-carboxamide | Intermediate 13 | 12.14 (br s, 1H), 3.46-3.54 (m, 7 H), 3.44-3.48 (m, 1H), 3.37-3.43 (m, 2H), 3.25-3.29 (m, 1H), 2.37-2.42 (m, 4H), 2.20 (s, 3H), 2.14-2.18 (m, 1H), 2.01-2.06 (m, 1H) | ES+ 336.04 |

Example 66 (S)-1-cyano-N-(5-(4-fluorophenyl)thiazol-2-yl)pyrrolidine-3-carboxamide (Prepared According to Scheme 2)

Step a.

To a solution of 2-aminothiazole (35 mmol) in THF (35 ml) was added TEA (52 mmol) at rt. The resulting reaction mixture cooled to 0° C. Acetic anhydride (52 mmol) was added to the reaction mixture. The reaction mixture was stirred at rt for 2 h. Precipitation of solids was observed in the reaction mixture. The obtained precipitates were filtered off under reduced pressure, washed with ice water (2×20 ml), dried under vacuum yielding N-(thiazol-2-yl)acetamide (16.9 mmol). This material was used directly for the next step without further purification. MS: ES+ 143.19; $^1$H NMR (400 MHz, DMSO-d$_6$) δ ppm 12.09 (br s, 1H), 7.45 (d, J=3.60 Hz, 1H), 7.18 (d, J=3.60 Hz, 1H), 2.14 (s, 3H).

Step b.

A solution of N-(thiazol-2-yl)acetamide (7.9 mmol) and 1-bromo-4-fluorobenzene (118 mmol) in DMF (10 ml) was stirred at rt under nitrogen atmosphere in a microwave glass tube for 5 min. K$_3$PO$_4$ (9.4 mmol) was added to the reaction mixture at rt under nitrogen atmosphere. The reaction mixture was purged with nitrogen for 30 min. Pd(OAc)$_2$ (0.5 mmol) and tricyclohexylphosphine (0.4 mmol) were added to the reaction mixture at rt under nitrogen atmosphere and the glass tube was sealed. The sealed tube was subjected to microwave irradiation at 140° C. for 1.5 h. The resulting reaction mixture was poured into water (30 ml) and extracted with EtOAc (3×30 ml). The combined organic phase was collected, dried over Na$_2$SO$_4$, filtered and concentrated under reduced pressure. The resulting residue was purified by column chromatography (70-80% EtOAc in hexane) yielding N-(5-(4-fluorophenyl)thiazol-2-yl)acetamide (1.3 mmol). MS: ES+ 237.28; $^1$H NMR (400 MHz, DMSO-d$_6$) δ ppm 12.19 (s, 1H), 7.83 (s, 1H), 7.64-7.67 (m, 2H), 7.23-7.28 (m, 2H), 2.16 (s, 3H).

Step c.

To a solution of N-(5-(4-fluorophenyl) thiazol-2-yl)acetamide (1.3 mmol) in 1,4-dioxane (6 ml) was added concentrated HCl (24 ml) at rt. The reaction mixture was heated at 100° C. for 4 h. The resulting reaction mixture was poured into water (30 ml) and basified with aqueous 1M NaOH solution. The obtained precipitates were filtered off under reduced pressure, washed with ice water (3×10 ml) and dried under vacuum yielding 5-(4-fluorophenyl)thiazol-2-amine (0.7 mmol). This material was used directly for the next step without further purification. MS: ES+ 195.18; $^1$H NMR (400 MHz, DMSO-d$_6$) δ ppm 7.43-7.46 (m, 2H), 7.35 (s, 1H), 7.17-7.29 (m, 2H), 7.15 (br s, 2H).

Steps d-f.

The title compound was synthesised from the intermediate above using a procedure similar to that described for Example 1 using (S)-1-(tert-butoxycarbonyl)pyrrolidine-3-carboxylic acid. MS: ES+ 316.91; $^1$H NMR (400 MHz, DMSO-d$_6$) δ ppm 12.43 (br s, 1H), 7.87 (s, 1H), 7.64-7.68 (m, 2H), 7.25-7.29 (m, 2H), 3.61-3.65 (m, 1H), 3.53-3.57 (m, 1H), 3.40-3.50 (m, 3H), 2.16-2.33 (m, 1H), 2.03-2.12 (m, 1H).

Example 67 (S)-1-cyano-N-(5-(3,4-difluorophenyl)thiazol-2-yl)pyrrolidine-3-carboxamide

Synthesised using a procedure similar to that described for Example 66 using 1-bromo-3,4-difluorobenzene. MS: ES+ 334.99; $^1$H NMR (400 MHz, DMSO-d$_6$) δ ppm 12.48 (s, 1H), 7.95 (s, 1H), 7.77-7.82 (m, 1H), 7.43-7.52 (m, 2H), 3.61-3.65 (m, 1H), 3.53-3.57 (m, 1H), 3.37-3.50 (m, 2H), 3.25-3.29 (m, 1H), 2.16-2.25 (m, 1H), 2.04-2.12 (m, 1H).

Example 68 (S)-1-cyano-N-(5-(4-(trifluoromethyl)phenyl)thiazol-2-yl)pyrrolidine-3-carboxamide

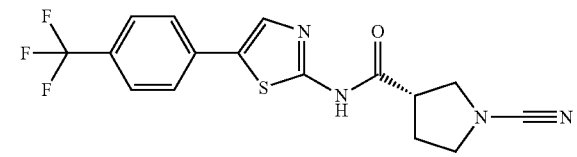 [SMILES: N#CN1CC[C@H](C(=O)Nc2ncc(-c3ccc(C(F)(F)F)cc3)s2)C1]

Synthesised using a procedure similar to that described for Example 66 using 1-bromo-4-(trifluoromethyl)benzene. MS: ES+ 366.87; $^1$H NMR (400 MHz, DMSO-d6) δ ppm 12.55 (br s, 1H), 8.08-8.16 (m, 1H), 7.82-7.90 (m, 2H), 7.74-7.80 (m, 2H), 3.61-3.65 (m, 1H), 3.57-3.58 (m, 1H), 3.33-3.47 (m, 3H), 2.16-2.30 (m, 1H), 2.04-2.15 (m, 1H).

Example 69 (S)-1-cyano-N-(5-(pyridin-4-yl)thiazol-2-yl)pyrrolidine-3-carboxamide

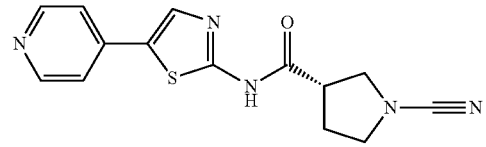 [SMILES: N#CN1CC[C@H](C(=O)Nc2ncc(-c3ccncc3)s2)C1]

Synthesised using a procedure similar to that described for Example 66 using 4-bromopyridine hydrochloride. MS: ES+ 300.07; $^1$H NMR (400 MHz, DMSO-d6) δ ppm 12.68 (s, 1H), 8.61 (d, J=6.0 Hz, 2H), 8.32 (s, 1H), 7.74 (d, J=6.0 Hz, 2H), 3.59-3.66 (m, 1H), 3.55-3.57 (m, 1H), 3.43-3.50 (m, 2H), 3.34-3.41 (m, 1H), 2.19-2.24 (m, 1H), 2.07-2.12 (m, 1H).

Example 70 (S)-1-cyano-N-(5-(pyridin-2-yl)thiazol-2-yl)pyrrolidine-3-carboxamide

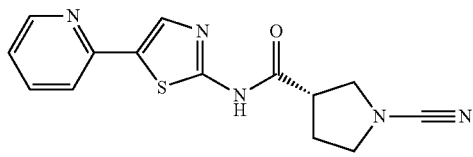

Synthesised using a procedure similar to that described for Example 66 using 2-bromopyridine. MS: ES+ 300.05; $^1$H NMR (400 MHz, DMSO-d6) δ ppm 12.42 (s, 1H), 8.52 (d, J=4.4 Hz, 1H), 8.19 (s, 1H), 7.91-7.95 (m, 1H), 7.80-7.84 (m, 1H), 7.24-7.27 (m, 1H), 3.62-3.66 (m, 1H), 3.54-3.58 (m, 1H), 3.40-3.51 (m, 3H), 2.17-2.28 (m, 1H), 2.04-2.13 (m, 1H).

Example 71 (R)-1-cyano-N-(5-phenylpyridin-2-yl)pyrrolidine-3-carboxamide

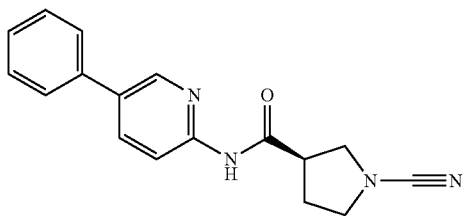 [SMILES: N#CN1CC[C@@H](C(=O)Nc2ccc(-c3ccccc3)cn2)C1]

Synthesised using a procedure similar to that described for Example 1 using (R)-1-(tert-butoxycarbonyl)pyrrolidine-3-carboxylic acid and 2-amino-5-phenylpyridine. MS: ES+ 292.99; $^1$H NMR (400 MHz, DMSO-d$_6$) δ ppm 10.83 (s, 1H), 8.67 (d, J=1.67 Hz, 1H), 8.10-8.20 (m, 2H), 7.70-7.75 (m, 2H), 7.49 (t, J=7.6 Hz, 2H), 7.39 (t, J=7.6 Hz, 1H), 3.59-3.67 (m, 1H), 3.32-3.55 (m, 4H), 2.14-2.24 (m, 1H), 2.02-2.12 (m, 1H).

Example 72 (2S,3S)-1-cyano-2-methyl-N-(5-phenylthiazol-2-yl)pyrrolidine-3-carboxamide

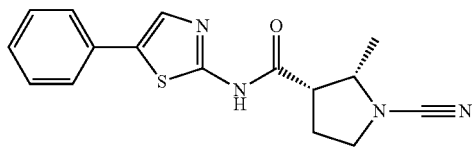 [SMILES: C[C@H]1[C@@H](C(=O)Nc2ncc(-c3ccccc3)s2)CCN1C#N]

Synthesised using a procedure similar to that described for Example 1 using Intermediate 1 and 2-amino-5-phenylthiazole. Purification by preparative HPLC; mobile phase: (A) 100% n-hexane (B) 100% IPA, column: YMC PACKSIL, 250×20 mm, 5 μm, flow rate: 18 ml/min. MS: ES+ 312.90; $^1$H NMR (400 MHz, DMSO-d$_6$) δ ppm 12.41 (br s, 1H), 7.90 (s, 1H), 7.60-7.63 (m, 2H), 7.39-7.45 (m, 2H), 7.27-7.34 (m, 1H), 3.96-4.04 (m, 1H), 3.60-3.68 (m, 1H), 3.40-3.46 (m, 1H), 3.28-3.34 (m, 1H), 2.17-2.24 (m, 1H), 2.03-2.10 (m, 1H), 1.10 (d, J=6.41 Hz, 3H).

Example 73 (2S,3S)-1-cyano-N-(5-(4-fluorophenyl)thiazol-2-yl)-2-methylpyrrolidine-3-carboxamide

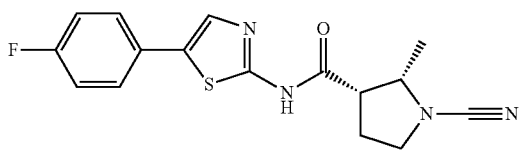 [SMILES: C[C@H]1[C@@H](C(=O)Nc2ncc(-c3ccc(F)cc3)s2)CCN1C#N]

Synthesised using a procedure similar to that described for Example 66 using Intermediate 1. MS: ES+ 331.05; $^1$H NMR (400 MHz, DMSO-d$_6$) δ ppm 12.42 (s, 1H), 7.87 (s, 1H), 7.65-7.69 (m, 2H), 7.25-7.29 (m, 2H), 3.98-4.02 (m, 1H), 3.61-3.66 (m, 1H), 3.40-3.46 (m, 1H), 3.28-3.32 (m, 1H), 2.16-2.23 (m, 1H), 2.06-2.09 (m, 1H), 1.10 (d, J=6.71 Hz, 3H).

Example 74 (2S,3S)-1-cyano-2-methyl-N-(1-phenyl-1H-imidazol-4-yl)pyrrolidine-3-carboxamide

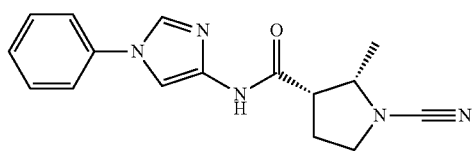 [SMILES: C[C@H]1[C@@H](C(=O)Nc2cn(-c3ccccc3)cn2)CCN1C#N]

Synthesised using a procedure similar to that described for Example 1 using Intermediate 1 and 4-amino-1-phenylimidazole. Purification by preparative HPLC; mobile phase: (A) 100% n-hexane (B) 100% IPA, column: YMC PACKSIL, 250×20 mm, 5 μm, flow rate: 20 ml/min. MS: ES+ 296.09; $^1$H NMR (400 MHz, DMSO-d$_6$) δ ppm 10.69 (s, 1H), 8.14 (d, J=1.83 Hz, 1H), 7.73 (d, J=1.83 Hz, 1H), 7.62-7.66 (m, 2H), 7.50-7.54 (m, 2H), 7.33-7.39 (m, 1H), 3.90-3.98 (m, 1H), 3.59-3.68 (m, 1H), 3.34-3.43 (m, 1H), 3.18-3.23 (m, 1H), 2.09-2.21 (m, 1H), 1.95-2.05 (m, 1H), 1.11 (d, J=6.71 Hz, 3H).

Example 75 (2S,3S)-1-cyano-2-methyl-N-(5-phenyl-1H-pyrazol-3-yl)pyrrolidine-3-carboxamide

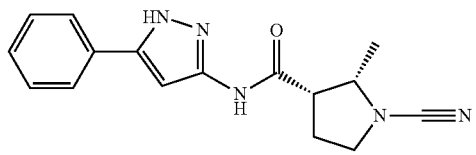 [SMILES: C[C@H]1[C@@H](C(=O)Nc2cc(-c3ccccc3)[nH]n2)CCN1C#N]

Synthesised using a procedure similar to that described for Example 1 using Intermediate 1 and 5-amino-3-phenylpyrazole. Purification by preparative HPLC; mobile phase: (A) 100% n-hexane (B) 100% IPA, column: YMC PACKSIL, 250×20 mm, 5 μm, flow rate: 20 ml/min. MS: ES+ 296.47; $^1$H NMR (400 MHz, DMSO-d$_6$) δ ppm 12.89 (br s, 1H), 10.64 (br s, 1H), 7.70-7.74 (m, 2H), 7.41-7.47 (m, 2H), 7.31-7.37 (m, 1H), 6.94 (br s, 1H), 3.93-3.98 (m, 1H), 3.59-3.67 (m, 1H), 3.38-3.44 (m, 1H), 3.16-3.21 (m, 1H), 2.12-2.20 (m, 1H), 1.97-2.04 (m, 1H), 1.13 (d, J=6.40 Hz, 3H).

Example 76 (2S,3S)-1-cyano-2-methyl-N-(5-(tetrahydro-2H-pyran-4-yl)thiazol-2-yl)pyrrolidine-3-carboxamide

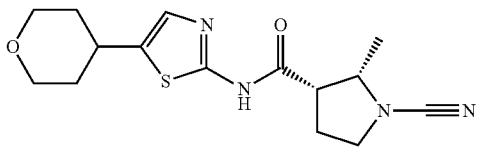 [SMILES: C[C@H]1[C@@H](C(=O)Nc2ncc(C3CCOCC3)s2)CCN1C#N]

Synthesised using a procedure similar to that described for Example 1 using Intermediate 1 and Intermediate 3. MS: ES+ 321.18; $^1$H NMR (400 MHz, DMSO-$d_6$) δ ppm 12.19 (br s, 1H), 7.19 (s, 1H), 3.93-3.98 (m, 1H), 3.86-3.92 (m, 2H), 3.58-3.64 (m, 1H), 3.34-3.44 (m, 3H), 3.17-3.27 (m, 1H), 2.99-3.05 (m, 1H), 2.12-2.19 (m, 1H), 1.99-2.06 (m, 1H), 1.83-1.86 (m, 2H), 1.56-1.86 (m, 2H), 1.05 (d, J=6.4 Hz, 3H).

Example 77 (2S,3S)—N-(5-(2-chlorophenyl)thiazol-2-yl)-1-cyano-2-methylpyrrolidine-3-carboxamide

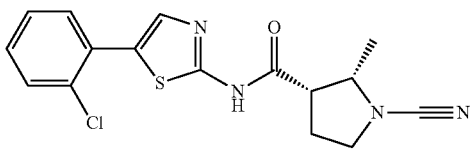

Synthesised using a procedure similar to that described for Example 1 using Intermediate 1 and 5-(2-chlorophenyl)thiazol-2-amine. MS: ES+ 347.63; $^1$H NMR (400 MHz, DMSO-$d_6$) δ ppm 12.43 (br s, 1H), 7.28 (s, 1H), 7.67 (dd, J=7.2 Hz, 1.6 Hz, 1H), 7.59 (dd, J=8.0 Hz, 2.0 Hz, 1H), 7.37-7.44 (m, 2H), 3.97-4.03 (m, 1H), 3.61-3.66 (m, 1H), 3.40-3.46 (m, 1H), 3.29-3.32 (m, 1H), 2.16-2.24 (m, 1H), 2.02-2.09 (m, 1H), 1.10 (d, J=6.4 Hz, 3H).

Example 78 1-cyano-3-methyl-N-(5-phenylthiazol-2-yl)pyrrolidine-3-carboxamide

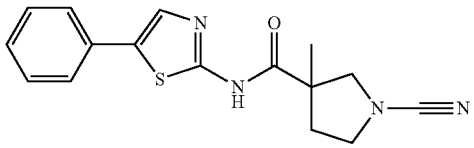

Synthesised using a procedure similar to that described for Example 1 using 1-(tert-butoxycarbonyl)-3-methylpyrrolidine-3-carboxylic acid and 2-amino-5-phenylthiazole. MS: ES+ 312.9; $^1$H NMR (400 MHz, DMSO-$d_6$) δ ppm 12.30 (s, 1H), 7.93 (s, 1H), 7.61-7.63 (m, 2H), 7.44-7.40 (m, 2H), 7.29-7.33 (m, 1H), 3.86-3.89 (m, 1H), 3.48-3.52 (m, 1H), 3.37-3.41 (m, 1H), 3.29-3.33 (m, 1H), 2.38-2.45 (m, 1H), 1.92-1.99 (m, 1H), 1.42 (s, 3H).

Example 79 1-cyano-3-methyl-N-(1-phenyl-1H-imidazol-4-yl)pyrrolidine-3-carboxamide

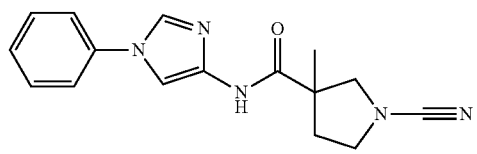

Synthesised using a procedure similar to that described for Example 1 using 1-(tert-butoxycarbonyl)-3-methylpyrrolidine-3-carboxylic acid and 4-bmino-1-phenylimidazole. MS: ES+ 296.53; $^1$H NMR (400 MHz, DMSO-$d_6$) δ ppm 10.52 (s, 1H), 8.16 (d, J=1.6 Hz, 1H), 7.73 (d, J=1.6 Hz, 1H), 7.63-7.65 (m, 2H), 7.50-7.54 (m, 2H), 7.34-7.38 (m, 1H), 3.85 (d, J=9.16 Hz, 1H), 3.36-3.60 (m, 2H), 3.25 (d, J=9.16 Hz, 1H), 2.37-2.42 (m, 1H), 1.89-1.94 (m, 1H), 1.38 (s, 3H).

Example 80 1-cyano-3-(methoxymethyl)-N-(5-phenylthiazol-2-yl)pyrrolidine-3-carboxamide (Prepared According to Scheme 1)

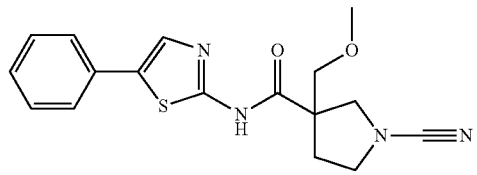 [SMILES: COCC1(C(=O)Nc2ncc(-c3ccccc3)s2)CCN(C#N)C1]

Step a.

To a solution of Intermediate 11 (1.0 mmol) in DMF (5 ml) was added HATU (1.5 mmol) and 5-phenylthiazol-2-amine (1.0 mmol) at rt. The reaction mixture was stirred for 10 min. TEA (2.9 mmol) was added dropwise to the reaction mixture. The reaction mixture was stirred at rt for 6 h. The resulting reaction mixture was poured into water (20 ml) and extracted with EtOAc (3×20 ml). The combined organic phase was collected, dried over Na$_2$SO$_4$, filtered and concentrated under reduced pressure yielding tert-butyl 3-(methoxymethyl)-3-((5-phenylthiazol-2-yl)carbamoyl)pyrrolidine-1-carboxylate (0.5 mmol). This material was directly used for the next step without further purification. MS: ES+ 418.48

Steps b-c.

The title compound was synthesised from the intermediate above using a procedure similar to that described for Example 1 according to Scheme 1 steps b and c. MS: ES+ 343.33; $^1$H NMR (400 MHz, DMSO-$d_6$) δ ppm 12.54 (br s, 1H), 7.87 (s, 1H), 7.59-7.61 (m, 2H), 7.39-7.43 (m, 2H), 7.27-7.30 (m, 1H), 3.92 (d, J=9.60 Hz, 1H), 3.80 (d, J=9.60 Hz, 1H), 3.62 (d, J=9.60 Hz, 1H), 3.45-3.52 (m, 1H), 3.32-3.41 (m, 2H), 3.25 (s, 3H), 2.30-2.36 (m, 1H), 1.98-2.06 (m, 1H).

Example 81 1, 3-dicyano-N-(5-phenylthiazol-2-yl)pyrrolidine-3-carboxamide

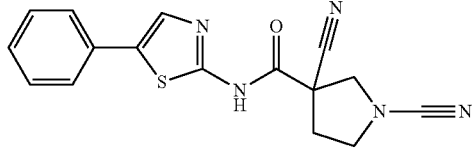 [SMILES: N#CN1CCC(C#N)(C(=O)Nc2ncc(-c3ccccc3)s2)C1]

Synthesised using a procedure similar to that described for Example 1 using 2-amino-5-methylthiazole and Intermediate 12. MS: ES+ 324.48; ¹H NMR (400 MHz, DMSO-d₆) δ ppm 13.49 (s, 1H), 7.96 (s, 1H), 7.61-7.63 (m, 2H), 7.40-7.44 (m, 2H), 7.31-7.33 (m, 1H), 3.93-4.00 (m, 2H), 3.59-3.63 (m, 2H), 2.57-2.67 (m, 2H).

Example 82 (3S,4S)-1-cyano-4-methyl-N-(5-phenylthiazol-2-yl)pyrrolidine-3-carboxamide

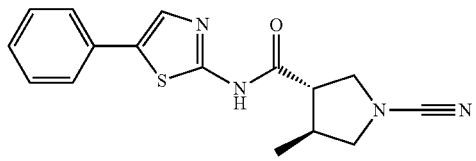 [SMILES: C[C@@H]1CN(C#N)C[C@H]1C(=O)Nc1ncc(-c2ccccc2)s1]

Synthesised using a procedure similar to that described for Example 1 using Intermediate 2 and 2-amino-5-phenylthiazole. Purification by preparative chiral HPLC; mobile phase: (A) 70-50% n-hexane (B) 30-50% IPA, column: Chiralpak IC, 250×10 mm, 5 μm, flow rate: 8 ml/min. MS: ES+ 313.23; ¹H NMR (400 MHz, DMSO-d₆) δ ppm 12.48 (br s, 1H), 7.91 (s, 1H), 7.61-7.63 (m, 2H), 7.39-7.44 (m, 2H), 7.29-7.35 (m, 1H), 3.73-3.77 (m, 1H), 3.59-3.63 (m, 1H), 3.52-3.56 (m, 1H), 3.05-3.10 (m, 1H), 2.94-2.99 (m, 1H), 2.46-2.47 (m, 1H), 1.06 (d, J=6.71 Hz, 3H).

Example 83 (3S,4S)-1-cyano-4-methyl-N-(5-methylthiazol-2-yl)pyrrolidine-3-carboxamide

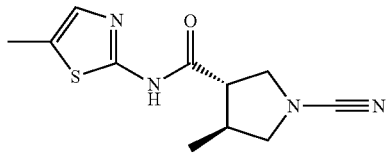 [SMILES: Cc1cnc(NC(=O)[C@@H]2CN(C#N)C[C@H]2C)s1]

Synthesised using a procedure similar to that described for Example 1 using Intermediate 2 and 2-amino-5-methylthiazole. Purification by preparative chiral HPLC; mobile phase: (A) 70-50% n-hexane (B) 30-50% IPA, column: Chiralpak IC, 250×10 mm, 5 μm, flow rate: 8 ml/min. MS: ES+ 251.17; ¹H NMR (400 MHz, DMSO-d₆) δ ppm 12.20 (s, 1H), 7.16 (d, J=1.2 Hz, 1H), 3.69-3.74 (m, 1H), 3.57-3.61 (m, 1H), 3.47-3.52 (m, 1H), 3.03-3.07 (m, 1H), 2.87-2.95 (m, 1H), 2.40-2.48 (m, 1H), 2.35 (s, 3H), 1.03 (d, J=6.71 Hz, 3H).

Example 84 (±)-trans-N-(5-(2-chlorophenyl)thiazol-2-yl)-1-cyano-4-methylpyrrolidine-3-carboxamide

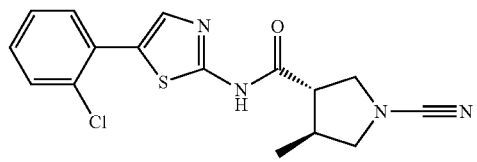

Synthesised using a procedure similar to that described for Example 1 using Intermediate 2 and Intermediate 10. MS: ES+ 347.07; ¹H NMR (400 MHz, DMSO-d₆) δ ppm 12.57 (s, 1H), 7.82 (s, 1H), 7.67 (dd, J=7.2, 1.6 Hz, 1H), 7.59 (dd, J=7.6, 2.0 Hz, 1H), 7.37-7.45 (m, 2H), 3.73-3.77 (m, 1H), 3.59-3.63 (m, 1H) 3.53-3.57 (m, 1H), 3.06-3.10 (m, 1H), 2.94-3.01 (m, 1H), 2.46-2.49 (m, 1H), 1.06 (d, J=6.71 Hz, 3H).

Example 85 (±)-1-cyano-4-methyl-N-(1-phenyl-1H-imidazol-4-yl)pyrrolidine-3-carboxamide

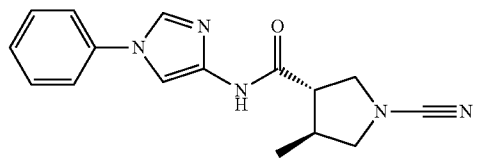 [SMILES: C[C@@H]1CN(C#N)C[C@H]1C(=O)Nc1cn(-c2ccccc2)cn1]

Synthesised using a procedure similar to that described for Example 1 using Intermediate 2 and 4-amino-1-phenylimidazole. MS: ES+ 296.38; ¹H NMR (400 MHz, DMSO-d₆) δ ppm 10.80 (s, 1H), 8.14 (d, J=1.52 Hz, 1H), 7.74 (d, J=1.52 Hz, 1H), 7.64 (d, J=8.0 Hz, 2H), 7.51 (t, J=7.6 Hz, 2H), 7.33-7.39 (m, 1H), 3.67-3.72 (m, 1H), 3.60-3.64 (m, 1H), 3.45-3.50 (m, 1H), 3.01-3.06 (m, 1H), 2.85-2.91 (m, 1H), 2.40-2.45 (m, 1H), 1.03 (d, J=6.71 Hz, 3H).

Example 86 (±)-1-cyano-4-ethyl-N-(5-phenylthiazol-2-yl)pyrrolidine-3-carboxamide

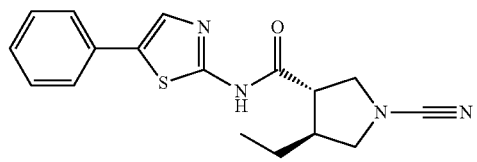 [SMILES: CC[C@@H]1CN(C#N)C[C@H]1C(=O)Nc1ncc(-c2ccccc2)s1]

Synthesised using a procedure similar to that described for Example 1 using Intermediate 17 and 2-amino-5-phenylthiazole. MS: ES+ 327.43; ¹H NMR (400 MHz, DMSO-d₆) δ ppm 12.51 (s, 1H), 7.91 (s, 1H), 7.61-7.64 (m, 2H), 7.40-7.45 (m, 2H), 7.30-7.34 (m, 1H) 3.72-3.76 (m, 1H), 3.62-3.66 (m, 1H), 3.49-3.53 (m, 1H), 3.13-3.17 (m, 1H), 3.01-3.05 (m, 1H), 2.38-2.41 (m, 1H), 1.46-1.51 (m, 1H), 1.36-1.42 (m, 1H), 0.87 (t, J=7.6 Hz, 3H).

Example 87 (±)-1-cyano-4-ethyl-N-(1-phenyl-1H-imidazol-4-yl)pyrrolidine-3-carboxamide

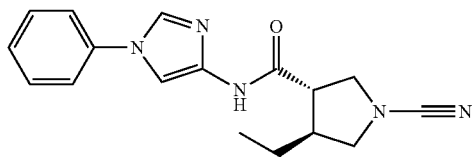 [SMILES: CC[C@@H]1CN(C#N)C[C@H]1C(=O)Nc1cn(-c2ccccc2)cn1]

Synthesised using a procedure similar to that described for Example 1 using Intermediate 17 and 1-phenyl-1H-imidazol-4-amine. MS: ES+ 310.13; ¹H NMR (400 MHz, DMSO-d₆) δ ppm 10.82 (s, 1H), 8.14 (d, J=1.6 Hz, 1H), 7.74 (d, J=1.6 Hz, 1H), 7.62-7.74 (m, 2H), 7.49-7.53 (m, 2H), 7.34-7.39 (m, 1H), 3.63-3.70 (m, 2H), 3.40-3.50 (m, 1H), 3.07-3.12 (m, 1H), 2.91-2.97 (m, 1H), 2.30-2.35 (m, 1H), 1.44-1.49 (m, 1H), 1.29-1.38 (m, 1H), 0.86 (d, J=7.6 Hz, 3H).

Example 88 1-cyano-5-methyl-N-(5-phenylthiazol-2-yl)pyrrolidine-3-carboxamide

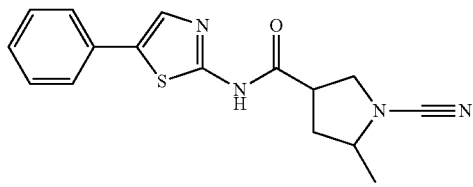 [SMILES: CC1CC(C(=O)Nc2ncc(-c3ccccc3)s2)CN1C#N]

Synthesised using a procedure similar to that described for Example 1 using 1-(tert-butoxycarbonyl)-5-methylpyrrolidine-3-carboxylic acid (prepared according to the method described in WO2010059658) and 2-amino-5-phenylthiazole. The compound was a mixture of diastereomers 86:14, the peaks mentioned in below NMR are just for the major diastereomer. MS: ES+ 313.13; ¹H NMR (400 MHz, DMSO-d₆) δ ppm 12.41 (s, 1H), 7.90 (s, 1H), 7.61-7.63 (m, 2H), 7.40-7.44 (m, 2H), 7.29-7.33 (m, 1H), 3.61-3.72 (m, 3H), 3.33-3.42 (m, 1H), 2.34-2.43 (m, 1H), 1.63-1.72 (m, 1H), 1.27 (d, J=6.10 Hz, 3H).

Example 89 1-cyano-5-methyl-N-(1-phenyl-1H-imidazol-4-yl)pyrrolidine-3-carboxamide

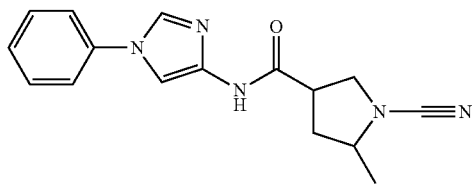 [SMILES: CC1CC(C(=O)Nc2cn(-c3ccccc3)cn2)CN1C#N]

Synthesised using a procedure similar to that described for Example 1 using 1-(tert-butoxycarbonyl)-5-methylpyrrolidine-3-carboxylic acid (prepared according to the method described in WO2010059658) and 4-amino-1-phenylimidazole. The compound was a mixture of diastereomers 89:11, the peaks mentioned in below NMR are just for the major diastereomer. MS: ES+ 296.10; ¹H NMR (400 MHz, DMSO-d₆) δ ppm 10.73 (s, 1H), 8.13 (d, J=1.52 Hz, 1H), 7.70 (d, J=1.52 Hz, 1H), 7.61-7.65 (m, 2H), 7.48-7.54 (m, 2H), 7.33-7.39 (m, 1H), 3.54-3.71 (m, 3H), 3.23-3.33 (m, 1H), 2.28-2.32 (m, 1H), 1.59-1.67 (m, 1H), 1.20-1.27 (m, 3H).

Example 90 1-cyano-5-methyl-N-(5-phenyl-1H-pyrazol-3-yl)pyrrolidine-3-carboxamide

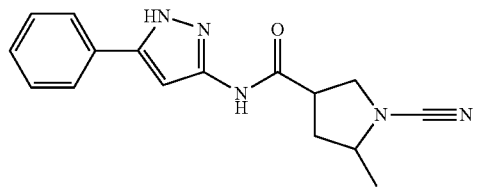 [SMILES: CC1CC(C(=O)Nc2cc(-c3ccccc3)[nH]n2)CN1C#N]

Synthesised using a procedure similar to that described for Example 1 using 1-(tert-butoxycarbonyl)-5-methylpyrrolidine-3-carboxylic acid (prepared according to the method described in WO2010059658) and 5-amino-3-phenylpyrazole. The compound was a mixture of diastereomers 88:12, the peaks mentioned in below NMR are just for the major diastereomer. MS: ES+ 296.08; ¹H NMR (400 MHz, DMSO-d₆) δ ppm 12.89 (br s, 1H), 10.67 (s, 1H), 7.70-7.72 (m, 2H), 7.42-7.47 (m, 2H), 7.31-7.37 (m, 1H), 6.88 (brs, 1H), 3.54-3.73 (m, 3H), 3.20-3.32 (m, 1H), 2.29-2.37 (m, 1H), 1.60-1.68 (m, 1H), 1.27 (d, J=6.40 Hz, 3H).

Example 91 (S)-1-cyano-N-(5-morpholinothiazol-2-yl)pyrrolidine-3-carboxamide (Prepared According to Scheme 3)

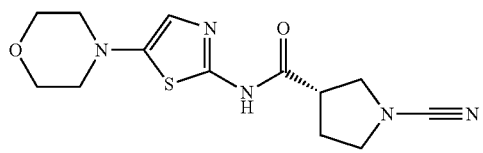 [SMILES: N#CN1CC[C@H](C(=O)Nc2ncc(N3CCOCC3)s2)C1]

Step a.

To a solution of morpholine (11.17 mmol) in MeCN (15 ml) was added Cs₂CO₃ (16.75 mmol) at rt. The reaction mixture was stirred for 5 min. 5-Bromothiazol-2-amine (5.58 mmol) was added to the reaction mixture and stirred at rt for 2 h. The resulting reaction mixture was poured into water (100 ml) and extracted with EtOAc (3×50 ml). The combined organic phase was collected, dried over Na₂SO₄, filtered and concentrated under reduced pressure. The resulting residue was purified by column chromatography (2% MeOH in DCM) yielding 5-morpholinothiazol-2-amine (1.83 mmol). MS: ES+ 186.05; ¹H NMR (400 MHz, DMSO-d₆) δ ppm 6.49 (s, 2H), 6.28 (s, 1H), 3.64-3.67 (m, 4H), 2.79-2.80 (m, 4H).

Steps b-d.

The title compound was synthesised from the intermediate above using a procedure similar to that described for Example 1 using (S)-1-(tert-butoxycarbonyl)pyrrolidine-3-carboxylic acid. MS: ES+ 308.33; $^1$H NMR (400 MHz, DMSO-d$_6$) δ ppm 11.97 (s, 1H), 6.69 (s, 1H), 3.70-3.73 (m, 4H), 3.57-3.63 (m, 1H), 3.39-3.50 (m, 3H), 3.24-3.33 (m, 1H), 2.97-3.00 (m, 4H), 2.10-2.21 (m, 1H), 1.97-2.10 (m, 1H).

Compounds in Table 3 were synthesised using a procedure similar to that described for Example 91 using 1-BOC-pyrrolidine-3-carboxylic acid.

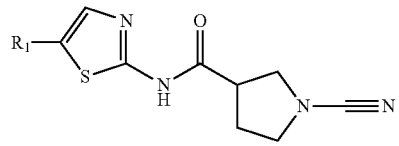

TABLE 3

| Ex | R1 | Name | Amine CAS Number | $^1$H NMR (400 MHz, DMSO-d$_6$) δ ppm | MS |
|---|---|---|---|---|---|
| 92 | (4-methylpiperazin-1-yl) | 1-cyano-N-(5-(4-methylpiperazin-1-yl)thiazol-2-yl)pyrrolidine-3-carboxamide | 109-01-3 | 11.93 (s, 1H), 6.64 (s, 1H), 3.57-3.61 (m, 1H), 3.38-3.52 (m, 3H), 3.24-3.27 (m, 1H), 2.95-3.00 (m, 4H), 2.41-2.46 (m, 4H), 2.23 (s, 3H), 2.13-2.18 (m, 1H), 2.01-2.04 (m, 1H) | ES− 319.15 |
| 93 | (2-(acetamidomethyl)piperidin-1-yl) | N-(5-(2-(acetamidomethyl)piperidin-1-yl)thiazol-2-yl)-1-cyanopyrrolidine-3-carboxamide | 98998-26-6 | 11.93 (s, 1H), 7.86 (br s, 1H), 6.72 (s, 1H), 3.56-3.63 (m, 1H), 3.38-3.52 (m, 3H), 3.13-3.28 (m, 4H), 2.99-3.02 (m, 2H), 2.13-2.17 (m, 1H), 1.99-2.07 (m, 1H), 1.77 (s, 3H), 1.46-1.62 (m, 6H) | ES+ 377.49 |
| 94 | (methyl(phenyl)amino) | 1-cyano-N-(5-(methyl(phenyl)amino)thiazol-2-yl)pyrrolidine-3-carboxamide | 100-61-8 | 12.23 (s, 1H), 7.21-7.28 (m, 3H), 6.82-6.93 (m, 3H), 3.57-3.64 (m, 1H), 3.47-3.54 (m, 1H), 3.38-3.47 (m, 2H), 3.28-3.31 (m, 1H), 3.24 (s, 3H), 2.12-2.22 (m, 1H), 2.01-2.05 (m, 1H) | ES+ 328.28 |
| 95 | (indolin-1-yl) | 1-cyano-N-(5-(indolin-1-yl)thiazol-2-yl)pyrrolidine-3-carboxamide | 496-15-1 | 12.18 (s, 1H), 7.18 (d, J = 7.32Hz, 1H), 7.09-7.14 (m, 2H), 6.88 (d, J = 7.93 Hz, 1H), 6.78 (t, J = 7.47 Hz, 1H), 3.87 (t, J = 8.54 Hz, 2H), 3.59-3.65 (m, 1H), 3.49-3.55 (m, 1H), 3.40-3.49 (m, 2H), 3.27-3.33 (m, 1H), 3.16 (t, J = 8.54 Hz, 2H), 2.14-2.23 (m, 1H), 2.01-2.11 (m, 1H) | ES+ 340.18 |

Compounds in Table 4 were synthesised using a procedure similar to that described for Example 91 using (S)-1-(tert-butoxycarbonyl)pyrrolidine-3-carboxylic acid.

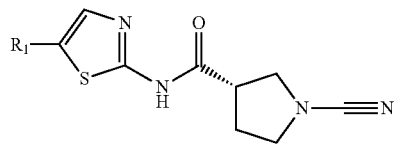

TABLE 4

| Ex | R1 | Name | Amine CAS Number | ¹H NMR (400 MHz, DMSO-d₆) δ ppm | MS |
|---|---|---|---|---|---|
| 96 | piperidin-1-yl | (S)-1-cyano-N-(5-(piperidin-1-yl)thiazol-2-yl)pyrrolidine-3-carboxamide | 110-89-4 | 11.90 (s, 1H), 6.62 (s, 1H), 3.56-3.63 (m, 1H), 3.47-3.51 (m, 1H), 3.38-3.45 (m, 2H), 3.21-3.31 (m, 1H), 2.95-3.00 (m, 4H), 2.10-2.21 (m, 1H), 1.97-2.07 (m, 1H), 1.59-1.65 (m, 4H), 1.46-1.54 (m, 2H) | ES+ 306.27 |
| 97 | isoindolin-2-yl | (S)-1-cyano-N-(5-(isoindolin-2-yl)thiazol-2-yl)pyrrolidine-3-carboxamide | 496-12-8 | 11.93 (s, 1H), 7.37-7.40 (m, 2H), 7.30-7.33 (m, 2H), 6.46 (s, 1H), 4.53 (s, 4H), 3.58-3.64 (m, 1H), 3.38-3.53 (m, 3H), 3.24-3.30 (m, 1H), 2.14-2.19 (m, 1H), 2.01-2.09 (m, 1H) | ES+ 340.10 |
| 98 | 3,4-dihydroisoquinolin-2(1H)-yl | (S)-1-cyano-N-(5-(3,4-dihydroisoquinolin-2(1H)-yl)thiazol-2-yl)pyrrolidine-3-carboxamide | 91-21-4 | 11.97 (s, 1H), 7.17-7.30 (m, 4H), 6.75 (s, 1H), 4.25 (s, 2H), 3.58-3.63 (m, 1H), 3.37-3.52 (m, 5H), 3.24-3.29 (m, 1H), 2.90-2.95 (m, 2H), 2.13-2.20 (m, 1H), 2.00-2.05 (m, 1H) | ES+ 354.15 |
| 99 | (R)-2-(methoxymethyl)pyrrolidin-1-yl | (S)-1-cyano-N-(5-((R)-2-(methoxymethyl)pyrrolidin-1-yl)thiazol-2-yl)pyrrolidine-3-carboxamide | 84025-81-0 | 11.85 (s, 1H), 6.39 (s, 1H), 3.57-3.62 (m, 1H), 3.45-3.53 (m, 3H), 3.36-3.45 (m, 2H), 3.22-3.30 (m, 6H), 2.97-2.99 (m, 1H), 2.13-2.16 (m, 1H), 1.84-2.05 (m, 5H) | ES+ 336.15 |
| 100 | (S)-2-(methoxymethyl)pyrrolidin-1-yl | (S)-1-cyano-N-(5-((S)-2-(methoxymethyl)pyrrolidin-1-yl)thiazol-2-yl)pyrrolidine-3-carboxamide | 63126-47-6 | 11.71 (br s, 1H), 6.33 (s, 1H), 3.69-3.80 (m, 2H), 3.59-3.69 (m, 2H), 3.43-3.57 (m, 3H), 3.33-3.40 (m, 4H), 3.20-3.23 (m, 1H), 3.05-3.17 (m, 1H), 2.24-2.33 (m, 2H), 1.98-2.10 (m, 4H) | ES+ 336.78 |

TABLE 4-continued

| Ex | R1 | Name | Amine CAS Number | ¹H NMR (400 MHz, DMSO-d₆) δ ppm | MS |
|---|---|---|---|---|---|
| 101 | 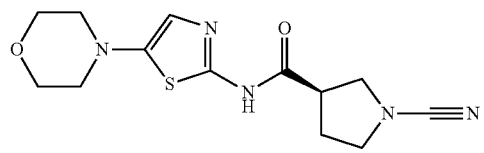 | (S)-1-cyano-N-(5-(5-oxo-1,4-diazepan-1-yl)thiazol-2-yl)pyrrolidine-3-carboxamide | 34376-54-0 | 11.99 (br s, 1H), 7.68 (br s, 1H), 6.62 (s, 1H), 3.57-3.62 (m, 1H), 3.39-3.52 (m, 3H), 3.21-3.33 (m, 7H), 2.51-2.56 (m, 2H), 2.11-2.21 (m, 1H), 1.99-2.08 (m, 1H) | ES+ 335.33 |

Example 102 (R)-1-cyano-N-(5-morpholinothiazol-2-yl)pyrrolidine-3-carboxamide

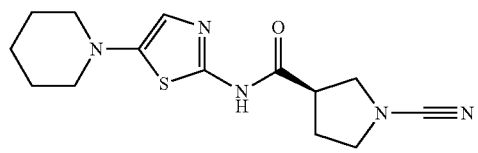 [SMILES: N#CN1CC[C@@H](C(=O)Nc2ncc(N3CCCCC3)s2)C1]

Synthesised using a procedure similar to that described for Example 91 using morpholine and (R)-1-(tert-butoxycarbonyl)pyrrolidine-3-carboxylic acid. MS: ES+ 308.33; ¹H NMR (400 MHz, DMSO-d₆) δ ppm 11.97 (s, 1H), 6.69 (s, 1H), 3.70-3.73 (m, 4H), 3.57-3.63 (m, 1H), 3.39-3.50 (m, 3H), 3.24-3.33 (m, 1H), 2.97-3.00 (m, 4H), 2.10-2.21 (m, 1H), 1.97-2.10 (m, 1H).

Example 103 (R)-1-cyano-N-(5-(piperidin-1-yl)thiazol-2-yl)pyrrolidine-3-carboxamide

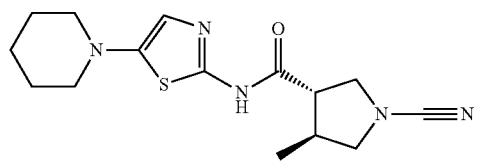 [SMILES: C[C@@H]1CN(C#N)C[C@H]1C(=O)Nc1ncc(N2CCCCC2)s1]

Synthesised using a procedure similar to that described for Example 91 using piperidine and (R)-1-(tert-butoxycarbonyl)pyrrolidine-3-carboxylic acid. MS: ES+ 305.9; ¹H NMR (400 MHz, DMSO-d₆) δ ppm 11.89 (s, 1H), 6.61 (s, 1H), 3.57-3.61 (m, 1H), 3.37-3.50 (m, 3H), 3.23-3.34 (m, 1H), 2.95-3.00 (m, 4H), 2.09-2.21 (m, 1H), 1.97-2.08 (m, 1H), 1.57-1.69 (m, 4H), 1.50 (m, 2H).

Example 104 (±)-trans-1-cyano-4-methyl-N-(5-(piperidin-1-yl)thiazol-2-yl)pyrrolidine-3-carboxamide Synthesised using a procedure similar to that described for Example 91 using piperidine and Intermediate 2. MS: ES+ 320.21; ¹H NMR (400 MHz, DMSO-d₆) δ ppm 11.99 (s, 1H), 6.62 (s, 1H), 3.67-3.72 (m, 1H), 3.57-3.61 (m, 1H), 3.45-3.49 (m, 1H), 3.02-3.06 (m, 1H), 2.96-3.00 (m, 4H), 2.84-2.90 (m, 1H), 2.40-2.46 (m, 1H), 1.59-1.64 (m, 4H), 1.49-1.52 (m, 2H), 1.01 (d, J=6.71 Hz, 3H).

Example 105 1-cyano-5-methyl-N-(5-(piperidin-1-yl)thiazol-2-yl)pyrrolidine-3-carboxamide

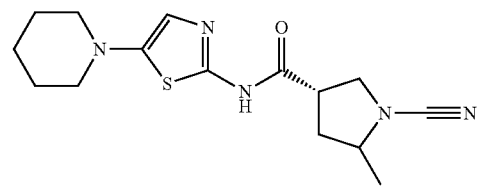 [SMILES: CC1C[C@H](C(=O)Nc2ncc(N3CCCCC3)s2)CN1C#N]

Synthesised using a procedure similar to that described for Example 91 using piperidine and 1-(tert-butoxycarbonyl)-5-methylpyrrolidine-3-carboxylic acid (prepared according to the method described in WO2010059658). MS: ES+ 320.38; ¹H NMR (400 MHz, DMSO-d₆) δ ppm 11.89 (s, 1H), 6.62 (s, 1H), 3.67-3.71 (m, 1H), 3.54-3.63 (m, 2H), 3.23-3.32 (m, 1H), 2.95-3.00 (m, 4H), 2.29-2.35 (m, 1H), 1.56-1.66 (m, 5H), 1.49-1.52 (m, 2H), 1.25 (d, J=6.10 Hz, 3H).

Example 106 (S)-1-cyano-N-(6-(pyrrolidin-1-yl)pyridin-2-yl)pyrrolidine-3-carboxamide

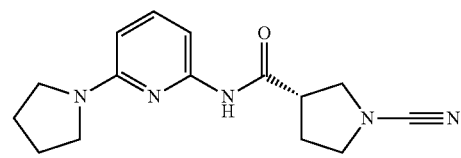 [SMILES: N#CN1CC[C@H](C(=O)Nc2cccc(N3CCCC3)n2)C1]

Synthesised using a procedure similar to that described for Example 91 using 2-amino-6-bromopyridine, pyrrolidine and (S)-1-(tert-butoxycarbonyl)pyrrolidine-3-carboxylic acid. MS: ES+ 286.38; ¹H NMR (400 MHz, DMSO-d₆) δ ppm 10.07 (s, 1H), 7.44 (t, J=7.93 Hz, 1H), 7.27 (d, J=8.24 Hz, 1H), 6.16 (d, J=8.24 Hz, 1H), 3.56-3.62 (m, 1H), 3.42-3.48 (m, 2H), 3.31-3.41 (m, 6H), 2.10-2.19 (m, 1H), 1.98-2.06 (m, 1H), 1.90-1.97 (m, 4H).

Example 107 (S)-1-cyano-N-(4-(pyrrolidin-1-yl) pyridin-2-yl)pyrrolidine-3-carboxamide

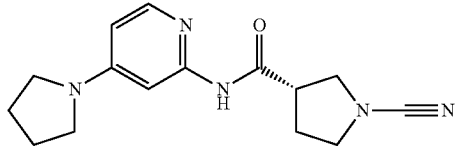 [SMILES: N#CN1CC[C@H](C(=O)Nc2cc(N3CCCC3)ccn2)C1]

Synthesised using a procedure similar to that described for Example 91 using 2-amino-4-bromopyridine, pyrrolidine and (S)-1-(tert-butoxycarbonyl)pyrrolidine-3-carboxylic acid. MS: ES+ 286.33; $^1$H NMR (400 MHz, CDCl$_3$) δ ppm 7.77 (d, J=6.40 Hz, 1H), 7.41 (s, 1H), 6.27 (dd, J=6.4, 2.4 Hz, 1H), 3.59-3.77 (m, 3H), 3.45-3.54 (m, 1H), 3.40-3.48 (m, 4H), 3.23-3.26 (m, 1H), 2.24-2.33 (m, 2H), 2.06-2.11 (m, 4H).

Example 108 (S)-1-cyano-N-(5-(pyrrolidin-1-yl) pyrazin-2-yl)pyrrolidine-3-carboxamide

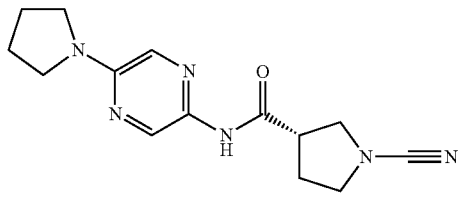 [SMILES: N#CN1CC[C@H](C(=O)Nc2cnc(N3CCCC3)cn2)C1]

Synthesised using a procedure similar to that described for Example 91 using 2-amino-5-bromopyrazine, pyrrolidine and (S)-1-(tert-butoxycarbonyl)pyrrolidine-3-carboxylic acid. MS: ES+ 287.48; $^1$H NMR (400 MHz, DMSO-d$_6$) δ ppm 10.42 (s, 1H), 8.73 (s, 1H), 7.72 (d, J=1.52 Hz, 1H), 3.56-3.65 (m, 1H), 3.45-3.52 (m, 2H), 3.40-3.43 (m, 5H), 3.25-3.29 (m, 1H), 2.13-2.16 (m, 1H), 2.01-2.06 (m, 1H), 1.93-1.96 (m, 4H).

Example 109 N-(5-(2-aminophenyl)thiazol-2-yl)-1-cyanopyrrolidine-3-carboxamide (Prepared According to Scheme 4)

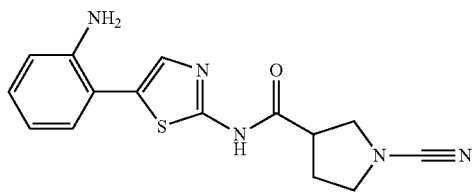 [SMILES: N#CN1CCC(C(=O)Nc2ncc(-c3ccccc3N)s2)C1]

Step a.

A solution of 5-bromothiazol-2-amine (39.3 mmol) and BOC-1-pyrrolidine-3-carboxylic acid (32.5 mmol) in THF (50 ml) was stirred at rt for 5 min. T3P (50% in EtOAc) (65.1 mmol) and TEA (97.6 mmol) were added to the reaction mixture at rt. The reaction mixture was stirred at rt for 16 h. The resulting reaction mixture was poured into water (100 ml) and extracted with EtOAc (3×100 ml). The combined organic phase was collected, dried over Na$_2$SO$_4$, filtered and concentrated under reduced pressure. The resulting residue was purified by flash chromatography (45-50% EtOAc in hexane) yielding tert-butyl 3-((5-bromothiazol-2-yl)carbamoyl)-pyrrolidine-1-carboxylate (12.88 mmol). MS: ES+ 376.23; $^1$H NMR (400 MHz, DMSO-d$_6$) δ ppm 12.54 (s, 1H), 7.58 (s, 1H), 3.50-3.54 (m, 1H), 3.36-3.40 (m, 2H), 3.24-3.34 (m, 2H), 2.12-2.15 (m, 1H), 2.00-2.05 (m, 1H), 1.4 (s, 9H).

Step b.

A solution of tert-butyl 3-((5-bromothiazol-2-yl)carbamoyl)pyrrolidine-1-carboxylate (0.26 mmol) and 2-(4,4,5,5-tetramethyl-1,3,2-dioxaborolan-2-yl)aniline (0.26 mmol) in 1,4-dioxane:water (1:1, 1 ml) was stirred at rt in a glass tube for 5 min. Na$_2$CO$_3$ (1.06 mmol) was added to the reaction mixture and degassed for 30 min. Pd(PPh$_3$)$_4$ (0.026 mol) was added and the glass tube was sealed. The reaction mixture was heated at 110° C. (external temperature) for 24 h. The resulting reaction mixture was poured into water (150 ml) and extracted with EtOAc (3×50 ml). The combined organic phase was dried over Na$_2$SO$_4$, filtered and concentrated under reduced pressure. The resulting residue was purified by column chromatography (45-50% EtOAc in hexane) yielding tert-butyl 3-((5-(2-aminophenyl)thiazol-2-yl)carbamoyl)pyrrolidine-1-carboxylate (quantitative). MS: ES+ 389.30

Step c.

To a solution of tert-butyl 3-((5-(2-aminophenyl)thiazol-2-yl)carbamoyl)pyrrolidine-1-carboxylate (0.38 mmol) in DCM (2 ml) was added 4M HCl in 1,4-dioxane (1.54 mmol) at 0° C. The reaction mixture was stirred at rt for 24 h. The resulting reaction mixture was concentrated under reduced pressure. The obtained residue was triturated with diethyl ether (10 ml) yielding N-(5-(2-aminophenyl)thiazol-2-yl) pyrrolidine-3-carboxamide hydrochloride (0.34 mmol). This material was used directly for the next step without further purification. MS: ES+ 289.23

Step d.

To a solution of N-(5-(2-aminophenyl)thiazol-2-yl)pyrrolidine-3-carboxamide hydrochloride (0.34 mmol) in DCM (2 ml) was added TEA (1.38 mmol) and cyanogen bromide (0.5 mmol) at 0° C. The reaction mixture was stirred at rt for 30 min. The resulting reaction mixture was poured into water (20 ml) and extracted with DCM (3×20 ml). The combined organic phase was collected, dried over Na$_2$SO$_4$, filtered and concentrated under reduced pressure. The resulting residue was purified by column chromatography (3-4% MeOH in DCM) yielding the title compound (0.05 mmol). MS: ES+ 314.16; $^1$H NMR (400 MHz, DMSO-d$_6$) δ ppm 12.35 (s, 1H), 7.56 (s, 1H), 7.13 (dd, J=7.63, 1.52 Hz, 1H), 7.03-7.08 (m, 1H), 6.79 (d, J=7.2 Hz, 1H), 6.59-6.64 (m, 1H), 5.09 (br s, 2H), 3.61-3.66 (m, 1H), 3.52-3.56 (m, 1H), 3.40-3.48 (m, 2H), 3.33-3.38 (m, 1H), 2.18-2.22 (m, 1H), 2.04-2.09 (m, 1H).

Compounds in Table 5 were synthesised using a procedure similar to that described for Example 109 using 1-BOC-pyrrolidine-3-carboxylic acid.

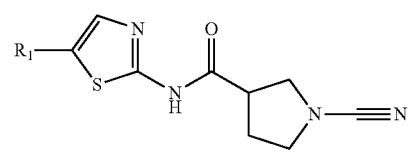

TABLE 5

| Ex | R1 | Name | Boronic acid or boronate ester CAS Number | 1H NMR (400 MHz, DMSO-d6) δ ppm | MS |
|---|---|---|---|---|---|
| 110 | 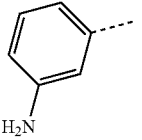 | N-(5-(3-aminophenyl)thiazol-2-yl)-1-cyanopyrrolidine-3-carboxamide | 30418-59-8 | 12.36 (br s, 1H), 7.71 (s, 1 H), 7.05 (t, J = 7.70 Hz, 1H), 6.73-6.80 (m, 2H), 6.47-6.54 (m, 1H), 5.24 (br s, 2H), 3.59-3.67 (m, 1H), 3.52-3.59 (m, 1H), 3.37-3.52 (m, 3H), 2.14-2.26 (m, 1H), 2.03-2.13 (m, 1H) | ES+ 313.89 |
| 111 | 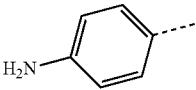 | N-(5-(4-aminophenyl)thiazol-2-yl)-1-cyanopyrrolidine-3-carboxamide | 214360-73-3 | 12.23 (s, 1H), 7.56 (s, 1H), 7.25 (d, J = 8.54 Hz, 2H), 6.58 (d, J = 8.54 Hz, 2H), 5.33 (br s, 2H), 3.58-3.67 (m, 1H), 3.50-3.57 (m, 1H), 3.40-3.49 (m, 2H), 3.28-3.37 (m, 1H), 2.18-2.21 (m, 1H), 2.05-2.10 (m, 1H) | ES+ 313.95 |
| 112 | 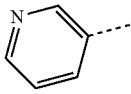 | 1-cyano-N-(5-(pyridin-3-yl)thiazol-2-yl)pyrrolidine-3-carboxamide | 1692-25-7 | 12.53 (s, 1H), 8.87 (d, J = 2.44 Hz, 1H), 8.50 (dd, J = 4.73, 1.68 Hz, 1H), 8.05 (s, 1H), 8.02 (dd, J = 2.44, 1.53 Hz, 1H), 7.42-7.48 (m, 1H), 3.60-3.68 (m, 1H), 3.53-3.59 (m, 1H), 3.40-3.51 (m, 2H), 3.34-3.31 (m, 1H), 2.16-2.29 (m, 1H), 2.05-2.13 (m, 1H) | ES+ 299.96 |
| 113 | 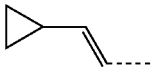 | (E)-1-cyano-N-(5-(2-cyclopropylvinyl)thiazol-2-yl)pyrrolidine-3-carboxamide | 903510-64-5 | 12.26 (br s, 1H), 7.28 (s, 1 H), 6.59 (d, J = 15.57 Hz, 1 H), 5.50 (dd, J = 15.41, 9.00 Hz, 1H), 3.38-3.68 (m, 5H), 2.15-2.20 (m, 1H), 2.01-2.08 (m, 1H), 1.44-1.61 (m, 1H), 0.71-0.82 (m, 2H), 0.48-0.49 (m, 2H) | ES+ 289.18 |
| 114 | 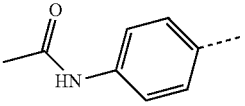 | N-(5-(4-acetamidophenyl)thiazol-2-yl)-1-cyanopyrrolidine-3-carboxamide | 101251-09-6 | 12.38 (s, 1H), 10.06 (s, 1H), 7.80 (s, 1H), 7.61-7.71 (m, 2 H), 7.53-7.58 (m, 2H), 3.60-3.66 (m, 1H), 3.52-3.55 (m, 1H), 3.40-3.50 (m, 2H), 3.30-3.34 (m, 1H), 2.16-2.24 (m, 1H), 1.97-2.12 (m, 4 H) | ES+ 355.89 |
| 115 | 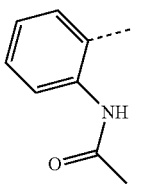 | N-(5-(2-acetamidophenyl)thiazol-2-yl)-1-cyanopyrrolidine-3-carboxamide | 169760-16-1 | 12.38 (s, 1H), 9.63 (s, 1H), 7.75 (s, 1H), 7.61 (d, J = 7.32 Hz, 1H), 7.27-7.39 (m, 3H), 3.61-3.67 (m, 1H), 3.53-3.58 (m, 1H), 3.41-3.47 (m, 2H), 3.30-3.34 (m, 1H), 2.17-2.24 (m, 1H), 2.05-2.12 (m, 1H), 2.02 (s, 3H) | ES+ 356.23 |
| 116 | 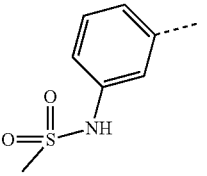 | 1-cyano-N-(5-(3-(methylsulfonamido)phenyl)thiazol-2-yl)pyrrolidine-3-carboxamide | 148355-75-3 | 12.46 (br s, 1H), 9.88 (br s, 1 H), 7.86 (s, 1H), 7.37-7.42 (m, 3H), 7.13-7.17 (m, 1H), 3.60-3.67 (m, 1H), 3.53-3.58 (m, 1H), 3.37-3.48 (m, 2H), 3.32-3.38 (m, 1H), 3.05 (s, 3H), 2.16-2.25 (m, 1 H), 2.03-2.14 (m, 1H) | ES+ 391.79 |

Example 117 (S)-1-cyano-N-(5-(3-cyanophenyl)thiazol-2-yl)pyrrolidine-3-carboxamide

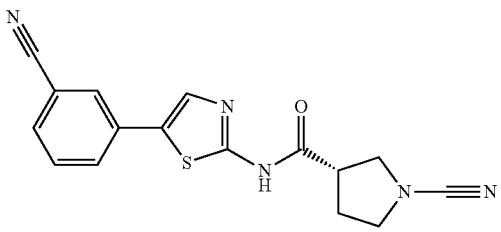 [SMILES: N#Cc1cccc(-c2cnc(NC(=O)[C@H]3CCN(C#N)C3)s2)c1]

Synthesised using a procedure similar to that described for Example 109 using (S)-1-(tert-butoxycarbonyl)pyrrolidine-3-carboxylic acid and 3-cyanophenylboronic acid in step b. MS: ES+ 324.33; $^1$H NMR (400 MHz, DMSO-d$_6$) δ ppm 12.49 (s, 1H), 8.12-8.22 (m, 1H), 8.08 (s, 1H), 7.88-7.96 (m, 1H), 7.72-7.80 (m, 1H), 7.57-7.66 (m, 1H), 3.58-3.66 (m, 1H), 3.50-3.57 (m, 1H), 3.34-3.48 (m, 3H), 2.16-2.30 (m, 1H), 2.00-2.15 (m, 1H).

Example 118 (S)-1-cyano-N-(5-(4-cyanophenyl)thiazol-2-yl)pyrrolidine-3-carboxamide

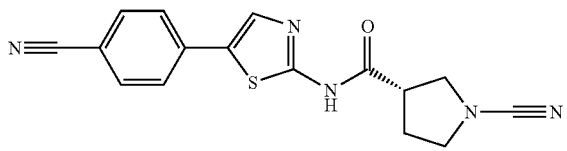 [SMILES: N#Cc1ccc(-c2cnc(NC(=O)[C@H]3CCN(C#N)C3)s2)cc1]

Synthesised using a procedure similar to that described for Example 109 using (S)-1-(tert-butoxycarbonyl)pyrrolidine-3-carboxylic acid and 4-cyanophenylboronic acid. MS: ES+324.48; $^1$H NMR (400 MHz, DMSO-d$_6$) δ ppm 12.60 (s, 1H), 8.15 (s, 1H), 7.86-7.88 (m, 2H), 7.81-7.84 (m, 2H), 3.61-3.66 (m, 1H), 3.54-3.59 (m, 1H), 3.40-3.49 (m, 2H), 3.36-3.40 (m, 1H), 2.17-2.23 (m, 1H), 2.06-2.13 (m, 1H).

Example 119 1-cyano-N-(5-(3,5-dimethylisoxazol-4-yl)benzo[d]thiazol-2-yl)pyrrolidine-3-carboxamide

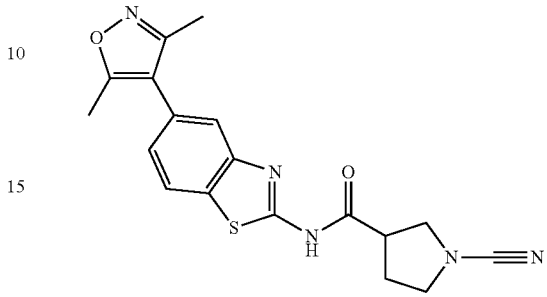

Synthesised using a procedure similar to that described for Example 109 using 2-amino-5-bromobenzothiazole in step a and 3,5-dimethylisoxazole-4-boronic acid in step b. MS: ES+ 367.92; $^1$H NMR (400 MHz, DMSO-d$_6$) δ ppm 12.61 (s, 1H), 8.09 (d, J=8.24 Hz, 1H), 7.75 (s, 1H), 7.33 (d, J=7.94 Hz, 1H), 3.53-3.72 (m, 2H), 3.39-3.49 (m, 3H), 2.44 (s, 3H), 2.21-2.27 (m, 4H), 2.05-2.19 (m, 1H).

Compounds in Table 6 were synthesised using a procedure similar to that described for Example 109 using (S)-1-(tert-butoxycarbonyl)pyrrolidine-3-carboxylic acid and 2-amino-6-bromobenzothiazole.

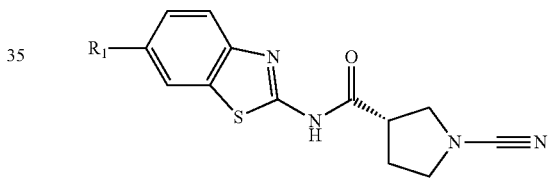

TABLE 6

| Ex | R1 | Name | Boronic acid or boronate ester CAS Number | $^1$H NMR (400 MHz, DMSO-d$_6$) δ ppm | MS |
|---|---|---|---|---|---|
| 120 | 3,5-dimethylisoxazol-4-yl | (S)-1-cyano-N-(6-(3,5-dimethylisoxazol-4-yl)benzo[d]thiazol-2-yl)pyrrolidine-3-carboxamide | 16114-47-9 | 12.65 (s, 1H), 8.07 (d, J = 1.53 Hz, 1H), 7.83 (d, J = 8.24 Hz, 1H), 7.44 (dd, J = 8.00, 2.00 Hz, 1H), 3.55-3.70 (m, 2H), 3.39-3.51 (m, 3H), 2.44 (s, 3 H), 2.20-2.26 (m, 4 H), 2.02-2.16 (m, 1H) | ES+ 368.23 |
| 121 | 4-methoxyphenyl | (S)-1-cyano-N-(6-(4-methoxyphenyl)benzo[d]thiazol-2-yl)pyrrolidine-3-carboxamide | 5720-07-0 | 12.60 (br s, 1H), 8.26 (s, 1 H), 7.78-7.80 (m, 1H), 7.67-7.71 (m, 3H), 7.05-7.06 (m, 2H), 3.81 (s, 3H), 3.60-3.68 (m, 2H), 3.34-3.48 (m, 3H), 2.20-2.27 (m, 1H), 2.09-2.14 (m, 1H) | ES+ 379.58 |
| 122 | phenyl | (S)-1-cyano-N-(6-phenyl-benzo[d]thiazol-2-yl)pyrrolidine-3-carboxamide | 98-80-6 | 12.62 (br s, 1H), 8.33 (d, J = 1.22 Hz, 1H), 7.82 (d, J = 8.4 Hz, 1H), 7.73-7.76 (m, 3H), 7.47-7.51 (m, 2H), 7.37-7.39 (m, 1H), 3.64-3.68 (m, 1H), 3.57-3.61 (m, 1H), 3.34-3.50 (m, 3H), 2.22-2.27 (m, 1H), 2.09-2.15 (m, 1H) | ES+ 349.38 |

TABLE 6-continued

| Ex | R1 | Name | Boronic acid or boronate ester CAS Number | $^1$H NMR (400 MHz, DMSO-$d_6$) δ ppm | MS |
|---|---|---|---|---|---|
| 123 | | (S)-1-cyano-N-(6-(1-methyl-1H-pyrazol-5-yl)benzo[d]thiazol-2-yl)pyrrolidine-3-carboxamide | 847818-74-0 | 12.68 (s, 1H), 8.21 (d, J = 1.83 Hz, 1H), 7.84 (d, J = 8.54 Hz, 1H), 7.59 (dd, J = 8.24, 1.83 Hz, 1H), 7.49 (d, J = 1.83 Hz, 1H), 6.45 (d, J = 1.83 Hz, 1H), 3.89 (s, 3H), 3.64-3.69 (m, 1H), 3.58-3.62 (m, 1H), 3.34-3.52 (m, 3H), 2.21-2.29 (m, 1H), 2.10-2.16 (m, 1H) | ES+ 353.07 |
| 124 | | (S)-1-cyano-N-(6-(1-methyl-1H-pyrazol-4-yl)benzo[d]thiazol-2-yl)pyrrolidine-3-carboxamide | 761446-44-0 | 12.55 (s, 1H), 8.17-8.19 (m, 2H), 7.91 (s, 1H), 7.72 (d, J = 8.40 Hz, 1H), 7.65 (dd, J = 8.4, 2.0 Hz, 1H), 3.88 (s, 3H), 3.61-3.67 (m, 1H), 3.51-3.60 (m, 1H), 3.43-3.51 (m, 2H), 3.38-3.41 (m, 1H), 2.19-2.26 (m, 1H), 2.08-2.15 (m, 1H) | ES+ 353.00 |
| 125 | | (S)-1-cyano-N-(6-(3,5-dimethyl-1H-pyrazol-4-yl)benzo[d]thiazol-2-yl)pyrrolidine-3-carboxamide | 1162262-39-6 | 12.55 (s, 1H), 12.31 (br s, 1H), 7.90 (s, 1H), 7.76 (d, J = 8.4 Hz, 1H), 7.35 (d, J = 8.4 Hz, 1H), 3.56-3.66 (m, 2H), 3.35-3.47 (m, 3H), 2.22 (s, 6H), 2.15-2.21 (m, 1H), 2.07-2.13 (m, 1H) | ES+ 366.94 |
| 126 | | (S)-1-cyano-N-(6-(5-methylisoxazol-4-yl)benzo[d]thiazol-2-yl)pyrrolidine-3-carboxamide | 1346808-41-0 | 12.63 (s, 1H), 8.92 (s, 1H), 8.2 (d, J = 1.6 Hz, 1H), 7.82 (d, J = 4.4 Hz, 1H), 7.61 (dd, J = 8.8 Hz, 2.0 Hz, 1H), 3.57-3.68 (m, 2H), 3.36-3.50 (m, 3H), 2.63 (s, 3H), 2.16-2.26 (m, 1H), 2.09-2.14 (m, 1H) | ES+ 354.53 |

Example 127 (S)-1-cyano-N-(7-(3,5-dimethylisoxazol-4-yl)imidazo[1,2-a]pyridin-2-yl)pyrrolidine-3-carboxamide

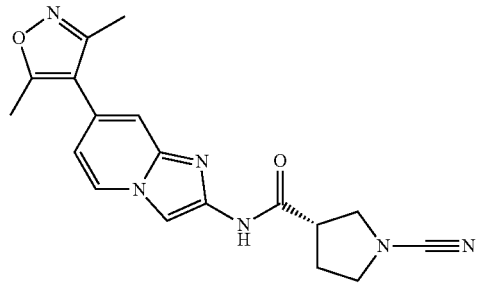 [SMILES: Cc1noc(C)c1-c1ccn2cc(NC(=O)[C@H]3CCN(C#N)C3)nc2c1]

Synthesised using a procedure similar to that described for Example 109 using (S)-1-(tert-butoxycarbonyl)pyrrolidine-3-carboxylic acid, 2-amino-7-bromoimidazo[1,2-a]pyridine (prepared according to the method described in WO2005089763) and 3,5-dimethylisoxazole-4-boronic acid. MS: ES+ 351.08; $^1$H NMR (400 MHz, DMSO-$d_6$) δ ppm 10.94 (s, 1H), 8.62 (d, J=7.02 Hz, 1H), 8.16 (s, 1H), 7.45 (s, 1H), 6.94 (dd, J=7.02, 1.83 Hz, 1H), 3.61-3.66 (m, 1H), 3.44-3.54 (m, 2H), 3.40-3.43 (m, 1H), 3.30-3.33 (m, 1H), 2.47 (s, 3H), 2.29 (s, 3H), 2.16-2.21 (m, 1H), 2.05-2.10 (m, 1H).

Example 128 (S)-1-cyano-N-(6-(3,5-dimethylisoxazol-4-yl)imidazo[1,2-a]pyridin-2-yl)pyrrolidine-3-carboxamide

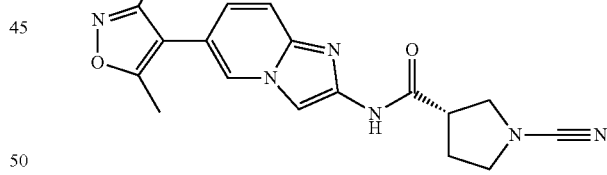

Synthesised using a procedure similar to that described for Example 109 using (S)-1-(tert-butoxycarbonyl)pyrrolidine-3-carboxylic acid, 2-amino-6-bromoimidazo[1,2-a]pyridine (prepared according to the method described in WO2012174312) and 3,5-dimethylisoxazole-4-boronic acid. MS: ES+ 351.09; $^1$H NMR (400 MHz, DMSO-$d_6$) δ ppm 11.00 (br s, 1H), 8.66 (s, 1H), 8.15 (s, 1H), 7.52 (d, J=9.20 Hz, 1H), 7.26 (dd, J=9.16, 1.53 Hz, 1H), 3.49-3.52 (m, 1H), 3.44-3.48 (m, 1H), 3.38-3.42 (m, 2H), 3.28-3.31 (m, 1H), 2.43 (s, 3H), 2.20 (s, 3H), 2.14-2.22 (m, 1H), 2.01-2.10 (m, 1H).

Example 129 (S)-1-cyano-N-(6-cyclopropylimidazo[1,2-a]pyridin-2-yl)pyrrolidine-3-carboxamide (Prepared According to Scheme 4)

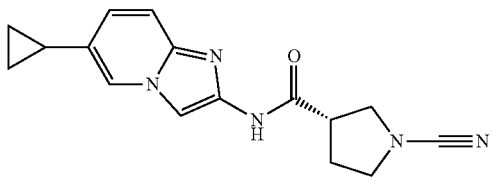 [SMILES: N#CN1CC[C@H](C(=O)Nc2cn3cc(C4CC4)ccc3n2)C1]

Step b.

A solution of tert-butyl (S)-3-((6-bromoimidazo[1,2-a]pyridin-2-yl)carbamoyl)pyrrolidine-1-carboxylate (0.98 mmol) [prepared using a procedure similar to that described for Example 109 using (S)-1-(tert-butoxycarbonyl)pyrrolidine-3-carboxylic acid and 2-amino-7-bromoimidazo[1,2-a]pyridine (prepared according to the method described in WO2005089763) in step a] and potassium cyclopropyl trifluoroborate (1.96 mmol) in toluene:water (8:1, 9 ml) was mixed in a glass tube. $K_3PO_4$ (1.96 mmol) was added to the reaction mixture at rt and degassed for 10 min. Pd(dppf)$Cl_2.CH_2Cl_2$ (0.098 mmol) was added to the reaction mixture at rt and the glass tube was tightly sealed and heated to 100° C. for 18 h. The resulting reaction mixture was poured into water (100 ml) and extracted with EtOAc (2×100 ml). The combined organic phase was dried over $Na_2SO_4$, filtered and concentrated under reduced pressure. The resulting residue was purified by column chromatography (4% MeOH in DCM) yielding tert-butyl (S)-3-((6-cyclopropylimidazo[1,2-a]pyridin-2-yl)carbamoyl) pyrrolidine-1-carboxylate (0.45 mmol). MS: ES+ 371.5

Steps c-d.

The title compound was synthesised from the intermediate above using a procedure similar to that described for Example 109, steps c and d. MS: ES+ 296.38; $^1$H NMR (400 MHz, DMSO-$d_6$) δ ppm 10.87 (s, 1H), 8.37 (d, J=0.9 Hz, 1H), 7.99 (s, 1H), 7.32 (d, J=9.6 Hz, 1H), 6.97 (dd, J=9.6, 2.0 Hz, 1H), 3.59-3.61 (m, 1H), 3.40-3.51 (m, 2H), 3.26-3.34 (m, 2H), 2.13-2.19 (m, 1H), 2.01-2.08 (m, 1H), 1.90-1.94 (m, 1H), 0.88-0.95 (m, 2H), 0.66-0.70 (m, 2H).

Example 130 1-cyano-N-(6-cyclopropylbenzo[d]thiazol-2-yl)pyrrolidine-3-carboxamide

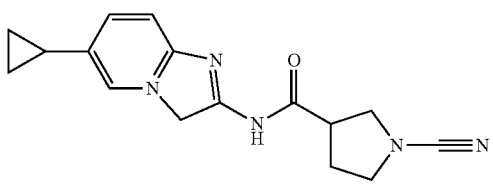

Synthesised using a procedure similar to that described for Example 129 using 2-amino-6-bromobenzothiazole and potassium cyclopropyltrifluoroborate. MS: ES+ 312.90; $^1$H NMR (400 MHz, CD$_3$OD) δ ppm 7.63 (d, J=8.40 Hz, 1H), 7.59 (d, J=1.60 Hz, 1H), 7.19 (dd, J=8.40, 1.60 Hz, 1H), 3.70-3.74 (m, 2H), 3.50-3.64 (m, 3H), 2.18-2.39 (m, 2H), 2.00-2.10 (m, 1H), 0.97-1.06 (m, 2H), 0.71-0.78 (m, 2H).

Example 131 (S)-1-cyano-N-(6-(3,6-dimethoxypyridazin-4-yl)imidazo[1,2-a]pyridin-2-yl)pyrrolidine-3-carboxamide (Prepared According to Scheme 4)

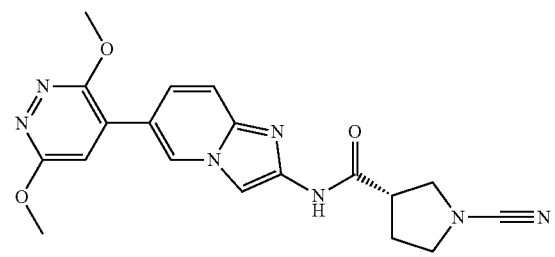 [SMILES: COc1cc(-c2ccc3nc(NC(=O)[C@H]4CCN(C#N)C4)cn3c2)c(OC)nn1]

Step b.

A solution of tert-butyl (3S)-3-[(6-bromoimidazo[1,2-c]pyridin-2-yl)carbamoyl]pyrrolidine-1-carboxylate (0.61 mmol) [prepared using a procedure similar to that described for Example 109 using (S)-1-(tert-butoxycarbonyl)pyrrolidine-3-carboxylic acid and 2-amino-7-bromoimidazo[1,2-a]pyridine (prepared according to the method described in WO2005089763) in step a] and 3,6-dimethoxylpyridazine-4-boronic acid (1.22 mmol) in 1,4-dioxane:water (4:1, 5 ml) was stirred at rt in a glass tube for 5 min. CsF (1.83 mmol) was added to the reaction mixture at rt and degassed for 30 min. Pd(dppf)$Cl_2.CH_2Cl_2$ (0.06 mol) was added to the reaction mixture at rt and the glass tube was sealed. The resulting reaction mixture was heated at 100° C. for 2 h. The resulting reaction mixture was poured into water (20 ml) and extracted with EtOAc (3×20 ml). The combined organic phase was dried over $Na_2SO_4$, filtered and concentrated under reduced pressure. The resulting residue was purified by column chromatography (100% DCM) yielding tert-butyl (S)-3-((6-(3,6-dimethoxypyridazin-4-yl)imidazo[1,2-a]pyridin-2-yl)carbamoyl) pyrrolidine-1-carboxylate (0.44 mmol). MS: ES+ 469.91. $^1$H NMR (400 MHz, DMSO-$d_6$) δ ppm 10.94 (br s, 1H) 9.01 (s, 1H), 8.17 (s, 1H), 7.50-7.57 (m, 2H), 7.39 (s, 1H), 4.02 (s, 3H), 4.06 (s, 3H), 3.51-3.53 (m, 1H), 3.35-3.43 (m, 2H), 3.23-3.28 (m, 2H), 2.09-2.11 (m, 1H), 2.03-2.04 (m, 1H), 1.41 (s, 9H).

Steps c-d.

The title compound was synthesised from the intermediate above using a procedure similar to that described for Example 109, steps c and d. MS: ES+ 394.11; $^1$H NMR (400 MHz, DMSO-$d_6$) δ ppm 11.01 (s, 1H), 9.02 (s, 1H), 8.19 (s, 1H), 7.49-7.57 (m, 2H), 7.40 (s, 1H), 4.04 (s, 3H), 4.00 (s, 3H), 3.59-3.69 (m, 1H), 3.46-3.54 (m, 2H), 3.40-3.44 (m, 2H), 2.14-2.21 (m, 1H), 1.99-2.10 (m, 1H).

Example 132 (S)-1-cyano-N-(6-(3,6-dimethoxy-pyridazin-4-yl)benzo[d]thiazol-2-yl)pyrrolidine-3-carboxamide

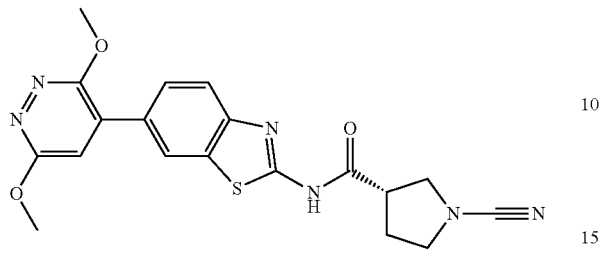

Synthesised using a procedure similar to that described for Example 131 using 2-amino-5-bromobenzothiazole and 3,6-dimethoxylpyridazine-4-boronic acid. MS: ES+ 411.06; $^1$H NMR (400 MHz, DMSO-d$_6$) δ ppm 12.69 (s, 1H), 8.34 (d, J=1.52 Hz, 1H), 7.83 (d, J=8.4 Hz, 1H), 7.75 (dd, J=2.0, 8.8 Hz, 1H), 7.31 (s, 1H), 4.01 (s, 3H), 4.00 (s, 3H) 3.57-3.68 (m, 2H), 3.37-3.51 (m, 3H), 2.19-2.33 (m, 1H), 2.07-2.16 (m, 1H).

Example 133 (2S,3S)-1-cyano-N-(6-(3,5-dimethyl-isoxazol-4-yl)benzo[d]thiazol-2-yl)-2-methyl-pyrrolidine-3-carboxamide

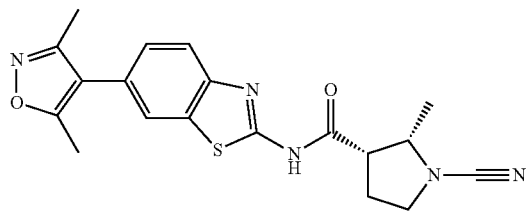 [SMILES: Cc1noc(C)c1-c1ccc2nc(NC(=O)[C@H]3CCN(C#N)[C@H]3C)sc2c1]

Synthesised using a procedure similar to that described for Example 109 using Intermediate 1, 2-amino-6-bromobenzothiazole and 3,5-dimethylisoxazole-4-boronic acid. Purification by preparative HPLC; mobile phase: (A) 100% n-hexane (B) 50% IPA/MeOH, column: YMC PACKSIL, 250×20 mm, 5 μm, flow rate: 15 ml/min. MS: ES+ 382.10; $^1$H NMR (400 MHz, DMSO-d$_6$) δ ppm 12.64 (s, 1H), 8.05 (d, J=1.52 Hz, 1H), 7.83 (d, J=8.24 Hz, 1H), 7.44 (dd, J=8.4, 2.0 Hz, 1H), 4.01-4.06 (m, 1H), 3.61-3.67 (m, 1H), 3.41-3.48 (m, 1H), 3.34-3.47 (m, 1H), 2.43 (s, 3H), 2.26 (s, 3H), 2.20-2.24 (m, 1H), 2.05-2.14 (m, 1H), 1.14 (d, J=6.71 Hz, 3H).

Example 134 1-cyano-N-(5-(p-tolyl)pyridin-2-yl)pyrrolidine-3-carboxamide

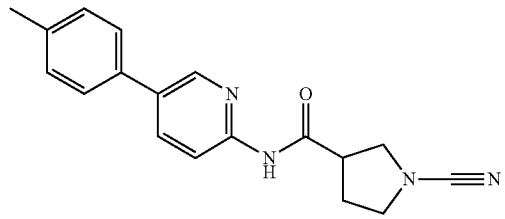 [SMILES: Cc1ccc(-c2ccc(NC(=O)C3CCN(C#N)C3)nc2)cc1]

Synthesised using a procedure similar to that described for Example 109 using 2-amino-5-bromo-pyridine and 4-methylphenylboronic acid. MS: ES+ 307.23; $^1$H NMR (400 MHz, DMSO-d$_6$) δ ppm 10.82 (s, 1H), 8.64 (d, J=2.0 Hz, 1H), 8.13-8.20 (m, 1H), 8.07-8.12 (m, 1H), 7.62 (d, J=8.24 Hz, 2H), 7.29 (d, J=7.94 Hz, 2H), 3.59-3.66 (m, 1H), 3.38-3.55 (m, 4H), 2.35 (s, 3H), 2.14-2.23 (m, 1H), 2.01-2.11 (m, 1H).

Example 135 1-cyano-N-(5-(m-tolyl)pyridin-2-yl)pyrrolidine-3-carboxamide

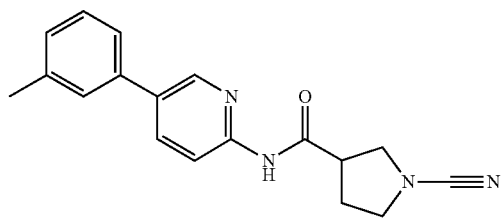 [SMILES: Cc1cccc(-c2ccc(NC(=O)C3CCN(C#N)C3)nc2)c1]

Synthesised using a procedure similar to that described for Example 109 using 2-amino-5-bromo-pyridine and 3-methylphenylboronic acid. MS: ES+ 307.23; $^1$H NMR (400 MHz, DMSO-d$_6$) δ ppm 10.84 (s, 1H), 8.66 (dd, J=2.44, 0.61 Hz, 1H), 8.14-8.20 (m, 1H), 8.08-8.13 (m, 1H), 7.49-7.55 (m, 2H), 7.37 (t, J=7.63 Hz, 1H), 7.21 (d, J=7.33 Hz, 1H), 3.59-3.66 (m, 1H), 3.38-3.55 (m, 4H), 2.38 (s, 3H), 2.16-2.21 (m, 1H), 2.02-2.12 (m, 1H).

Example 136 1-cyano-N-(5-(o-tolyl)pyridin-2-yl)pyrrolidine-3-carboxamide

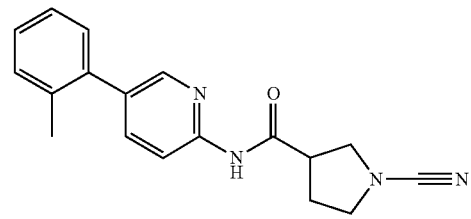 [SMILES: Cc1ccccc1-c1ccc(NC(=O)C2CCN(C#N)C2)nc1]

Synthesised using a procedure similar to that described for Example 109 using 2-amino-5-bromo-pyridine and 2-methylphenylboronic acid. MS: ES+ 307.23; $^1$H NMR (400 MHz, DMSO-d$_6$) δ ppm 10.81 (s, 1H), 8.31 (d, J=2.44 Hz, 1H), 8.16 (d, J=8.55 Hz, 1H), 7.82 (dd, J=8.55, 2.44 Hz, 1H), 7.28-7.38 (m, 3H), 7.23-7.27 (m, 1H), 3.59-3.67 (m, 1H), 3.36-3.56 (m, 4H), 2.25 (s, 3H), 2.14-2.23 (m, 1H), 2.03-2.13 (m, 1H).

Example 137 (S)-1-cyano-N-(6-(3,5-dimethylisoxazol-4-yl)-5-methylimidazo[1,2-a]pyridin-2-yl)pyrrolidine-3-carboxamide

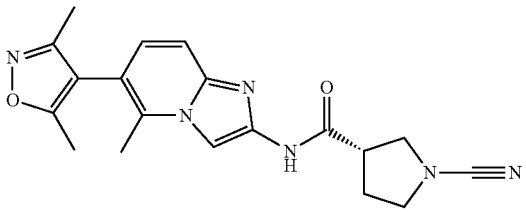 [SMILES: Cc1noc(C)c1-c1ccc2nc(NC(=O)[C@H]3CCN(C#N)C3)cn2c1C]

Synthesised using a procedure similar to that described for Example 109 using (S)-1-(tert-butoxycarbonyl)pyrrolidine-3-carboxylic acid, Intermediate 16 and 3, 5-dimethylisoxazole-4-boronic acid. MS: ES+ 365.23; $^1$H NMR (400 MHz, DMSO-$d_6$) δ ppm 11.02 (s, 1H), 7.95 (s, 1H), 7.44 (d, J=9.2, 1H), 7.15 (d, J=9.2, 1H), 3.62-3.66 (m, 1H), 3.42-3.54 (m, 3H), 3.30-3.34 (m, 1H), 2.41 (s, 3H), 2.27 (s, 3H), 2.15-2.23 (m, 1H), 2.09 (s, 3H), 2.02-2.08 (m, 1H).

Example 138 (S)-1-cyano-N-(6-(3,5-dimethylisoxazol-4-yl)-7-methylbenzo[d]thiazol-2-yl)pyrrolidine-3-carboxamide (Prepared According to Scheme 5)

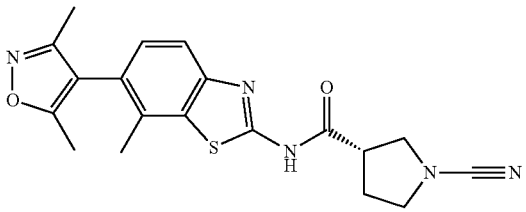 [SMILES: Cc1noc(C)c1-c1ccc2nc(NC(=O)[C@H]3CCN(C#N)C3)sc2c1C]

Step a.

A solution of Intermediate 15 (1.23 mmol) and 3,5-dimethylisoxazole-4-boronic acid (2.46 mmol) in ethanol:toluene:water (1:2:1, 10 ml) was stirred at rt in a glass tube for 5 min. $Na_2CO_3$ (2.46 mmol) was added to the reaction mixture and purged using nitrogen for 20 min. Pd(PPh$_3$)$_4$ (0.12 mmol) was added to the reaction mixture and the glass tube was sealed. The resulting reaction mixture was heated at 100° C. (external temperature) for 3 h. The resulting reaction mixture was poured into water (100 ml) and extracted with EtOAc (2×80 ml). The combined organic phase was dried over $Na_2SO_4$, filtered and concentrated under reduced pressure. The resulting residue was purified by flash chromatography (40% EtOAc in hexane) yielding a 75:25 mixture of 6-(3,5-dimethyl-1,2-oxazol-4-yl)-7-methyl-1,3-benzothiazol-2-amine & 6-(3, 5-dimethyl-1,2-oxazol-4-yl)-5-methyl-1,3-benzothiazol-2-amine (0.54 mmol). MS: ES+ 260.33.

Step b.

To a solution of (3S)—BOC-1-pyrrolidine-3-carboxylic acid (0.97 mmol) and DIPEA (1.62 mmol) in DCM (5 ml) was added HBTU (1.2 mmol) at rt and the reaction mixture was stirred for 30 mins. A solution of 75:25 mixture of 6-(3,5-dimethyl-1,2-oxazol-4-yl)-7-methyl-1,3-benzothiazol-2-amine & 6-(3,5-dimethyl-1,2-oxazol-4-yl)-5-methyl-1,3-benzothiazol-2-amine (0.81 mmol) in DCM (5 ml) was added dropwise to the reaction mixture and stirred at rt for 2 h. The resulting reaction mixture was poured into water (100 ml) and basified using solid $NaHCO_3$. The resulting mixture was extracted with EtOAc (2×80 ml). The combined organic phase was collected, dried over $Na_2SO_4$, filtered and concentrated under reduced pressure. The resulting residue was purified by flash chromatography (38% EtOAc in hexane) yielding a 80:20 mixture of tert-butyl (S)-3-((6-(3,5-dimethylisoxazol-4-yl)-7-methylbenzo[d]thiazol-2-yl)carbamoyl)pyrrolidine-1-carboxylate & tert-butyl (S)-3-((6-(3,5-dimethylisoxazol-4-yl)-5-methylbenzo[d]thiazol-2-yl)carbamoyl)pyrrolidine-1-carboxylate (1.24 mmol). MS: ES+ 456.91.

Step c.

To a solution of a 80:20 mixture of tert-butyl (S)-34 (6-(3,5-dimethylisoxazol-4-yl)-7-methylbenzo[d]thiazol-2-yl)carbamoyl)pyrrolidine-1-carboxylate & tert-butyl (S)-3-((6-(3,5-dimethylisoxazol-4-yl)-5-methylbenzo[d]thiazol-2-yl)carbamoyl)pyrrolidine-1-carboxylate (0.43 mmol) in DCM (5 ml) was added TFA (1 ml) at 0° C. The reaction mixture was stirred at rt for 1 h. The resulting reaction mixture was concentrated under reduced pressure. The obtained residue was azetropically distilled using DCM to yielding a 80:20 mixture of (S)—N-(6-(3,5-dimethylisoxazol-4-yl)-7-methylbenzo[d]thiazol-2-yl)pyrrolidine-3-carboxamide & (S)—N-(6-(3,5-dimethylisoxazol-4-yl)-5-methylbenzo[d]thiazol-2-yl)pyrrolidine-3-carboxamide TFA salt (quantitative). This material was used directly for the next step without further purification. MS: ES+ 357.48.

Step d.

To a solution of a 80:20 mixture of (S)—N-(6-(3,5-dimethylisoxazol-4-yl)-7-methylbenzo[d]thiazol-2-yl)pyrrolidine-3-carboxamide & (S)—N-(6-(3,5-dimethylisoxazol-4-yl)-5-methylbenzo[d]thiazol-2-yl)pyrrolidine-3-carboxamide TFA salt (0.71 mmol) in THF (5 ml) was added $K_2CO_3$ (7.1 mmol) at rt. Cyanogen bromide (0.56 mmol) was added to the reaction mixture at 0° C. and stirred for 10 min. The resulting reaction mixture was poured into water (150 ml) and extracted with EtOAc (2×80 ml). The combined organic phase was collected, dried over $Na_2SO_4$, filtered and concentrated under reduced pressure. The resulting residue was purified by flash chromatography (72% EtOAc in hexane) yielding 70:30 mixture of (3S)-1-cyano-N-[6-(3,5-dimethyl-1,2-oxazol-4-yl)-7-methyl-1,3-benzothiazol-2-yl]pyrrolidine-3-carboxamide & (3S)-1-cyano-N-[6-(3,5-dimethyl-1,2-oxazol-4-yl)-5-methyl-1,3-benzothiazol-2-yl]pyrrolidine-3-carboxamide (0.17 mmol). The regio-isomers were separated by preparative chiral HPLC; mobile phase: (A) 75-70% 10 mM aq $NH_4OAc$ (B) 25-30% MeCN, column: Sunfire C18, 250×19 mm, 5 μm, flow rate: 19 ml/min, yielding the title compound (0.057 mmol). MS: ES+ 382.43; $^1$H NMR (400 MHz, DMSO-$d_6$) δ ppm 12.64 (br s, 1H), 7.60 (d, J=8.0 Hz, 1H), 7.22 (d, J=8.4 Hz, 1H), 3.57-3.66 (m, 2H), 3.42-3.47 (m, 2H), 3.32-3.36 (m, 1H), 2.28 (s, 3H), 2.23 (s, 3H), 2.18-2.22 (m, 1H), 2.10-2.13 (m, 1H), 2.05 (s, 3H).

Example 139 (S)-1-cyano-N-(7-methyl-6-(1-methyl-1H-pyrazol-4-yl)benzo[d]thiazol-2-yl)pyrrolidine-3-carboxamide

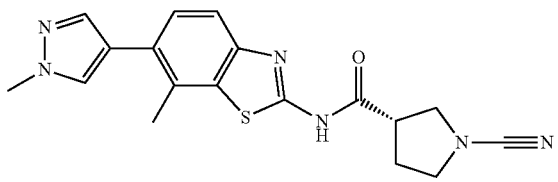 [SMILES: Cc1c(-c2cnn(C)c2)ccc2nc(NC(=O)[C@H]3CCN(C#N)C3)sc12]

Synthesised using a procedure similar to that described for Example 138 using 1-methyl-1H-pyrazole-4-boronic acid pinacol ester. MS: ES+ 366.3; ¹H NMR (400 MHz, DMSO-d₆) δ ppm 12.56 (s, 1H), 7.97 (s, 1H), 7.68 (s, 1H), 7.61 (d, J=8.4 Hz, 1H), 7.44 (d, J=8.4 Hz, 1H), 3.90 (s, 3H), 3.63-3.68 (m, 1H), 3.56-3.60 (m, 1H), 3.43-3.49 (m, 2H), 3.37-3.42 (m, 1H), 2.55 (s, 3H), 2.21-2.28 (m, 1H), 2.07-2.19 (m, 1H).

Example 140 1-cyano-N-(5-(morpholinomethyl) thiazol-2-yl)pyrrolidine-3-carboxamide (Prepared According to Scheme 6)

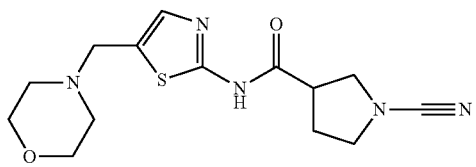 [SMILES: N#CN1CCC(C(=O)Nc2ncc(CN3CCOCC3)s2)C1]

Step a.

A solution of 2-amino-5-formylthiazole (15.6 mmol), 1-(tert-butoxycarbonyl)pyrrolidine-3-carboxylic acid (19.5 mmol) and HOAt (18.7 mmol) in DMF (20 ml) was stirred at rt for 5 min. DIPEA (21.8 mmol) and EDC.HCl (18.7 mmol) were added to the reaction mixture and stirred for a further 3 h at rt. The resulting reaction mixture was poured into water (200 ml) and extracted with EtOAc (2×50 ml). The combined organic phase was collected, dried over Na₂SO₄, filtered and concentrated under reduced pressure. The resulting residue was purified by flash chromatography (60% EtOAc in hexane) yielding tert-butyl 3-((5-formylthiazol-2-yl)carbamoyl)pyrrolidine-1-carboxylate (4.6 mmol). MS: ES+ 326.20; ¹H NMR (400 MHz, DMSO-d₆) δ ppm 12.91 (s, 1H), 9.97 (s, 1H), 8.44 (s, 1H), 3.63-4.02 (m, 1H), 3.27-3.36 (m, 4H), 2.11-2.22 (m, 1H), 1.99-2.10 (m, 1H), 1.45 (s, 9H).

Step b.

To a solution of 3 ((5-formylthiazol-2-yl)carbamoyl)pyrrolidine-1-carboxylate (1.5 mmol) and morpholine (0.8 mmol) in DCE (10 ml) was added sodium triacetoxyborohydride (1.5 mmol) at rt and stirred for 3 h. The resulting reaction mixture was poured into water (50 ml) and extracted with EtOAc (2×25 ml). The combined organic phase dried over Na₂SO₄, filtered and concentrated under reduced pressure. The resulting residue was purified by flash chromatography (25% EtOAc in hexane) yielding tert-butyl 3-((5-(morpholinomethyl)thiazol-2-yl)carbamoyl) pyrrolidine-1-carboxylate (1.2 mmol). MS: ES+397.33; ¹H NMR (400 MHz, DMSO-d₆) δ ppm 12.16 (s, 1H), 7.30 (s, 1H), 3.49-3.62 (m, 6H), 3.35-3.39 (s, 3H), 3.19-3.31 (m, 2H), 2.31-2.37 (m, 4H), 2.05-2.15 (m, 1H), 1.92-2.01 (m, 1H), 1.40 (s, 9H).

Step c.

To a solution of tert-butyl 3-((5-(morpholinomethyl)thiazol-2-yl)carbamoyl)pyrrolidine-1-carboxylate (1.2 mmol) in DCM (4 ml) was added TFA (0.6 ml) at 0° C. The reaction mixture was stirred at rt for 40 min. The resulting reaction mixture was concentrated under reduced pressure. The obtained residue was azeotropically distilled using DCM yielding N-(5-(morpholinomethyl)thiazol-2-yl)pyrrolidine-3-carboxamide TFA salt (1.0 mmol). This material was used directly for the next step without further purification.

Step d.

To a solution of N-(5-(morpholinomethyl)thiazol-2-yl) pyrrolidine-3-carboxamide TFA salt (1.0 mmol) in THF (4 ml) was added K₂CO₃ (3.0 mmol) at 0° C. The reaction mixture was stirred at 0° C. for 30 min. Cyanogen bromide (1.1 mmol) was added to the reaction mixture at 0° C. The reaction mixture was then stirred at rt for 2 h. The resulting reaction mixture was poured into water (30 ml) and extracted with EtOAc (20 ml). The organic phase was collected, dried over Na₂SO₄, filtered and concentrated under reduced pressure. The resulting residue was purified by flash chromatography (7-8% MeOH in DCM) yielding the title compound (0.08 mmol). MS: ES+ 322.23; ¹H NMR (400 MHz, DMSO-d₆) δ ppm 12.20 (br s, 1H), 7.30 (s, 1H), 3.56-3.63 (m, 3H), 3.46-3.60 (m, 4H), 3.40-3.44 (m, 2H), 3.20-3.30 (m, 2H), 2.30-2.48 (m, 4H), 2.15-2.18 (m, 1H), 2.02-2.07 (m, 1H).

Example 141 1-cyano-N-(5-(pyrrolidin-1-ylmethyl) thiazol-2-yl)pyrrolidine-3-carboxamide

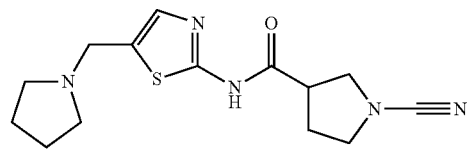 [SMILES: N#CN1CCC(C(=O)Nc2ncc(CN3CCCC3)s2)C1]

Synthesised using a procedure similar to that described for Example 140 using pyrrolidine. MS: ES+ 306.38; ¹H NMR (400 MHz, DMSO-d₆) δ ppm 12.29 (s, 1H), 7.29 (s, 1H), 3.72 (s, 2H), 3.59-3.63 (m, 1H), 3.49-3.53 (m, 1H), 3.40-3.46 (m, 2H), 3.29-3.34 (m, 1H), 2.45 (m, 4H), 2.12-2.23 (m, 1H), 2.01-2.12 (m, 1H), 1.69 (m, 4H).

Example 142 (3S)-1-cyano-N-(54 (2,6-dimethylmorpholino)methyl)thiazol-2-yl)pyrrolidine-3-carboxamide

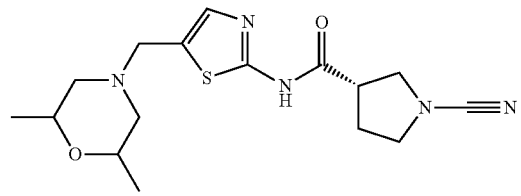 [SMILES: CC1CN(Cc2cnc(NC(=O)[C@H]3CCN(C#N)C3)s2)CC(C)O1]

Synthesised using a procedure similar to that described for Example 140 using (S)-1-(tert-butoxycarbonyl)pyrrolidine-3-carboxylic acid and 2,6-dimethyl-morpholine. MS: ES+350.43; ¹H NMR (400 MHz, DMSO-d₆) δ ppm 12.22 (br s, 1H), 7.30 (s, 1H), 3.62 (m, 4H), 3.28-3.55 (m, 5H), 2.67-2.70 (m, 2H), 2.11-2.27 (m, 1H), 2.05-2.07 (m, 1H), 1.64 (t, J=10.84 Hz, 2H), 1.03 (d, J=6.41 Hz, 6H).

Example 143 (S)-1-cyano-N-(5-(((R)-2-(methoxymethyl)pyrrolidin-1-yl)methyl)thiazol-2-yl)pyrrolidine-3-carboxamide

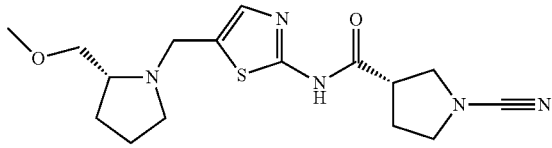 [SMILES: COC[C@H]1CCCN1Cc1cnc(NC(=O)[C@H]2CCN(C#N)C2)s1]

Synthesised using a procedure similar to that described for Example 140 using (S)-1-(tert-butoxycarbonyl)pyrrolidine-3-carboxylic acid and (R)-2-(methoxymethyl)pyrrolidine. MS: ES+ 349.98; ¹H NMR (400 MHz, DMSO-d₆) δ ppm 12.19 (s, 1H), 7.27 (s, 1H), 4.10 (d, J=14.04 Hz, 1H), 3.50-3.67 (m, 2H), 3.42-3.46 (m, 1H), 3.37-3.45 (m, 2H), 3.20-3.32 (m, 6H), 2.79-2.87 (m, 1H), 2.65-2.74 (m, 1H), 2.09-2.27 (m, 2H), 1.97-2.10 (m, 1H), 1.77-1.87 (m, 1H), 1.56-1.68 (m, 2H), 1.48 (m, 1H).

Example 144 (S)-1-cyano-N-(5-(((S)-2-(methoxymethyl)pyrrolidin-1-yl)methyl)thiazol-2-yl)pyrrolidine-3-carboxamide

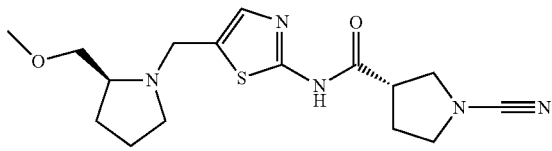 [SMILES: COC[C@@H]1CCCN1Cc1cnc(NC(=O)[C@H]2CCN(C#N)C2)s1]

Synthesised using a procedure similar to that described for Example 140 using (S)-1-(tert-butoxycarbonyl)pyrrolidine-3-carboxylic acid and (S)-2-(methoxymethyl)pyrrolidine. MS: ES+ 349.98; ¹H NMR (400 MHz, DMSO-d₆) δ ppm 12.19 (s, 1H), 7.27 (s, 1H), 4.10 (d, J=14.04 Hz, 1H), 3.59-3.68 (m, 2H), 3.49-3.53 (m, 1H), 3.37-3.47 (m, 3H), 3.20-3.31 (m, 5H), 2.73-2.89 (m, 1H), 2.60-2.75 (m, 1H), 2.08-2.27 (m, 2H), 1.99-2.08 (m, 1H), 1.75-1.87 (m, 1H), 1.54-1.71 (m, 2H), 1.45-1.48 (m, 1H).

Example 145 (2S,3S)-1-cyano-N-(5-(((R)-2-(methoxymethyl)pyrrolidin-1-yl)methyl)thiazol-2-yl)-2-methylpyrrolidine-3-carboxamide (Prepared According to Scheme 7)

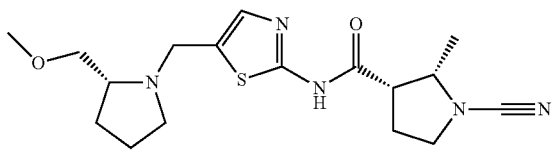 [SMILES: COC[C@H]1CCCN1Cc1cnc(NC(=O)[C@H]2CCN(C#N)[C@H]2C)s1]

Step a.

To a solution of 2-aminothiazole-5-carbaldehyde (3.9 mmol) in THF (10 ml) was added DMAP (5.85 mmol) and (BOC)₂O (5.85 mmol) at 0° C. The reaction mixture was stirred at rt for 1 h. The resulting reaction mixture was poured into water (50 ml) and extracted with EtOAc (3×100 ml). The combined organic phase was collected, dried over Na₂SO₄, filtered and concentrated under reduced pressure. The resulting residue was purified by flash chromatography (40% EtOAc in hexane) yielding tert-butyl (5-formylthiazol-2-yl) carbamate (2.63 mmol). This material was used directly for the next step without further purification. MS: ES+ 229.05.

Step b.

To a solution of tert-butyl (5-formylthiazol-2-yl) carbamate (2.19 mmol) and (R)-2-(methoxymethyl) pyrrolidine (4.83 mmol) in MeOH (5 ml) was added sodium triacetoxyborohydride (3.28 mmol) at rt. The reaction mixture was heated at 80° C. for 2 h. The resulting reaction mixture was poured into aqueous 1M HCl (50 ml) and extracted with EtOAc (2×25 ml). The organic layer was discarded. The aqueous layer was basified with solid Na₂CO₃. The resulting mixture was extracted with EtOAc (2×50 ml). The combined organic phase was collected, dried over Na₂SO₄, filtered and concentrated under reduced pressure yielding tert-butyl (R)-(5-((2-(methoxymethyl) pyrrolidin-1-yl) methyl) thiazol-2-yl) carbamate (1.56 mmol). This material was used directly for the next step without further purification. MS: ES+ 328.48; ¹H NMR (400 MHz, DMSO-d₆) δ ppm 11.29 (s, 1H), 7.14 (s, 1H), 4.06 (d, J=14.4 Hz, 1H), 3.62 (d, J=14.4 Hz, 1H), 3.34-3.38 (m, 1H), 3.23-3.29 (m, 3H), 3.19-3.22 (m, 1H), 2.82-2.86 (m, 1H), 2.67-2.70 (m, 1H), 2.18-2.24 (m, 1H), 1.77-1.85 (m, 1H), 1.57-1.63 (m, 3H), 1.47 (s, 9H).

Step c.

To a solution of tert-butyl (R)-(5-((2-(methoxymethyl) pyrrolidin-1-yl) methyl) thiazol-2-yl) carbamate (1.56 mmol) in DCM (6 ml) was added TFA (2.5 ml) at 0° C. The reaction mixture was stirred at rt for 1 h. The resulting reaction mixture was concentrated under reduced pressure. The obtained residue was neutralized by aqueous solution of saturated NaHCO₃. The resulting mixture was extracted with DCM (2×100 ml). The combined organic phase was collected, dried over Na₂SO₄, filtered and concentrated under reduced pressure yielding (R)-5-((2-(methoxymethyl) pyrrolidin-1-yl) methyl)thiazol-2-amine (quantitative). This material was used directly for the next step without further purification. MS: ES+ 228.04.

Step d.

To a solution of (2S,3S)-1-(tert-butoxycarbonyl)-2-methylpyrrolidine-3-carboxylic acid (1.74 mmol) in THF (6 ml) was added T3P (50% in EtOAc) (5.24 mmol) at rt. The reaction mixture was stirred for 30 min and then cooled to 0° C. (R)-5-((2-(methoxymethyl) pyrrolidin-1-yl)methyl) thiazol-2-amine (1.57 mmol) and DIPEA (5.24 mmol) were added and the reaction mixture was stirred at rt for 1 h. The resulting reaction mixture was poured into saturated NaHCO₃ (25 ml) and extracted with EtOAc (3×50 ml). The combined organic phase was collected, dried over Na₂SO₄, filtered and concentrated under reduced pressure yielding tert-butyl (2S,3S)-3-((5-(((R)-2-(methoxymethyl) pyrrolidin-1-yl) methyl) thiazol-2-yl) carbamoyl)-2-methylpyrrolidine-1-carboxylate (0.52 mmol). This material was used directly for the next step without further purification. MS: ES+ 439.25; ¹H NMR (400 MHz, DMSO-d₆) δ ppm 12.09 (br s, 1H), 7.26 (s, 1H), 4.18-4.22 (m, 1H), 4.08-4.11 (m, 1H), 3.63-3.66 (m, 1H), 3.34-3.39 (m, 2H), 3.26 (s, 3H), 3.16-3.22 (m, 3H), 2.81-2.93 (m, 1H), 2.67-2.69 (m, 1H), 2.19-2.25 (m, 2H), 1.90-1.93 (m, 1H), 1.80-1.85 (m, 1H), 1.58-1.63 (m, 2H), 1.47-1.50 (m, 1H), 1.47 (s, 9H), 0.90 (d, J=5.2 Hz, 3H).

Step e.

To a solution of tert-butyl (2S,3S)-3-((5-(((R)-2-(methoxymethyl)pyrrolidin-1-yl)methyl)thiazol-2-yl) carbamoyl)-2-methylpyrrolidine-1-carboxylate (0.52 mmol) in DCM (10 ml) was added TFA (1.0 ml) at 0° C. The reaction mixture was stirred at rt for 1 h. The resulting reaction mixture was concentrated under reduced pressure. The obtained residue was triturated with diethyl ether (10 ml) yielding (2S,3S)—N-(5-(((R)-2-(methoxymethyl) pyrrolidin-1-yl) methyl) thiazol-2-yl)-2-methylpyrrolidine-3-carboxamide TFA salt (0.409 mmol). This material was used directly for the next step without further purification. MS: ES+ 339.10.

Step f.

To a solution of (2S,3S)—N-(5-(((R)-2-(methoxymethyl) pyrrolidin-1-yl)methyl)thiazol-2-yl)-2-methylpyrrolidine-3-carboxamide TFA salt (0.409 mmol) in THF (6 ml) was added $K_2CO_3$ (1.2 mmol) at 0° C. The reaction mixture was stirred at 0° C. for 30 min. Cyanogen bromide (0.60 mmol) was added to the reaction mixture at 0° C. The reaction mixture was stirred at rt for 1 h. The resulting reaction mixture was poured into water (30 ml). The resulting solid precipitates were collected by filtration under reduced pressure and dried yielding the title compound (0.09 mmol). MS: ES+ 364.15; $^1$H NMR (400 MHz, DMSO-$d_6$) δ ppm 12.16 (br s, 1H), 7.27 (s, 1H), 4.08-4.12 (m, 1H), 3.97-4.01 (m, 1H), 3.63-3.67 (m, 2H), 3.35-3.42 (m, 4H), 3.26 (s, 3H), 2.83-2.87 (m, 1H), 2.62-2.69 (m, 1H), 2.15-2.28 (m, 2H), 2.03-2.11 (m, 1H), 1.75-1.83 (m, 1H), 1.55-1.70 (m, 2H), 1.49-1.51 (m, 1H), 0.87 (d, J=5.2 Hz, 3H).

Example 146 (S)—N-(1-benzyl-M-imidazol-4-yl)-1-cyanopyrrolidine-3-carboxamide (Prepared According to Scheme 8, Steps c, f, h, i, j)

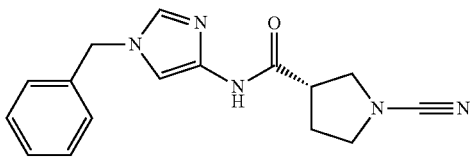 [SMILES: N#CN1CC[C@H](C(=O)Nc2cn(Cc3ccccc3)cn2)C1]

Step c.

To a solution of 4-nitro-1H-imidazole (4.42 mmol) in DMSO (5 ml) were added KOH pellets (6.6 mmol) at rt. The reaction mixture was cooled to 0° C. and treated with benzyl bromide (5.31 mmol). The reaction mixture was stirred at rt for 3 h. The resulting reaction mixture was poured into water (50 ml) and extracted with EtOAc (3×50 ml). The combined organic phase was collected, dried over $Na_2SO_4$, filtered and concentrated under reduced pressure. The resulting residue was purified by column chromatography (1.5-2.5% MeOH in DCM) yielding 1-benzyl-4-nitro-1H-imidazole (3.2 mmol). $^1$H NMR (400 MHz, DMSO-$d_6$) δ ppm 8.50 (d, J=1.2 Hz, 1H), 8.01 (d, J=1.2 Hz, 1H), 7.34-7.43 (m, 5H), 5.31 (s, 2H).

Step f.

A solution of 1-benzyl-4-nitro-1H-imidazole (2.46 mmol) in MeOH:water (1:1, 12 ml) was stirred at rt for 5 min. Fe powder (12.3 mmol) and $NH_4Cl$ (4.9 mmol) were added to the reaction mixture. The reaction mixture was heated at 80° C. for 2 h. The resulting reaction mixture was allowed to cool to rt and poured into water (30 ml). The obtained mixture was filtered through celite hyflow and washed with EtOAc (20 ml). The organic layer was separated and the aqueous layer was extracted with EtOAc (3×20 ml). The combined organic phase was collected, washed with saturated $NaHCO_3$ solution (20 ml), dried over $Na_2SO_4$, filtered and concentrated under reduced pressure yielding 1-benzyl-1H-imidazol-4-amine (1.4 mmol). This material was immediately used for the next step without further purification. MS: ES+ 174.24.

Step h.

A solution of 1-benzyl-1H-imidazol-4-amine (1.4 mmol) and (3S)—BOC-1-pyrrolidine-3-carboxylic acid (1.4 mmol) in THF (3 ml) was stirred at 0° C. for 5 min. T3P (50% in EtOAc) (2.1 mmol) and TEA (4.3 mmol) was added to the reaction mixture and stirred at rt for 2 h. The resulting reaction mixture was poured into water (40 ml) and extracted with EtOAc (3×20 ml). The combined organic phase was dried over $Na_2SO_4$, filtered and concentrated under reduced pressure. The resulting residue was purified by flash chromatography (2-3% MeOH in DCM) yielding tert-butyl (S)-3-((1-benzyl-1H-imidazol-4-yl)carbamoyl) pyrrolidine-1-carboxylate (0.80 mmol). MS: ES+ 371.33

Step i.

To a solution of tert-butyl (S)-3-((1-benzyl-1H-imidazol-4-yl)carbamoyl)pyrrolidine-1-carboxylate (0.80 mmol) in DCM (6 ml) was added 4M HCl in 1,4-dioxane (24 mmol) at 0° C. The reaction mixture was stirred at rt for 1 h. The resulting reaction mixture was concentrated under reduced pressure. The obtained residue was triturated with diethyl ether (10 ml) yielding (S)—N-(1-benzyl-1H-imidazol-4-yl) pyrrolidine-3-carboxamide hydrochloride (0.65 mmol). This material was used directly for the next step without further purification. MS: ES+ 271.33.

Step j.

To a solution of (S)—N-(1-benzyl-1H-imidazol-4-yl)pyrrolidine-3-carboxamide hydrochloride (0.65 mmol) in DMF (4 ml) was added $K_2CO_3$ (1.95 mmol) and cyanogen bromide (0.78 mmol) at 0° C. The reaction mixture was stirred at rt for 30 min. The resulting reaction mixture was poured into water (40 ml) and extracted with EtOAc (3×20 ml). The combined organic phase was collected, dried over $Na_2SO_4$, filtered and concentrated under reduced pressure. The resulting residue was purified by flash chromatography (2.5-3.5% MeOH in DCM) yielding the title compound (0.14 mmol). MS: ES+ 296.01; $^1$H NMR (400 MHz, DMSO-$d_6$) δ ppm 10.53 (s, 1H), 7.60 (d, J=1.2 Hz, 1H), 7.35-7.38 (m, 2H), 7.27-7.33 (m, 3H), 7.21 (d, J=1.2 Hz, 1H), 5.14 (s, 2H), 3.52-3.56 (m, 1H), 3.34-3.46 (m, 3H), 3.15-3.21 (m, 1H), 2.04-2.10 (m, 1H), 1.93-2.00 (m, 1H).

Example 147 (S)-1-cyano-N-(1-phenethyl-1H-imidazol-4-yl)pyrrolidine-3-carboxamide

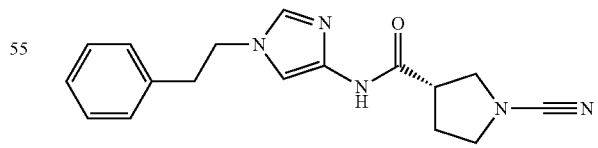

Synthesised using a procedure similar to that described for Example 146 using (2-bromoethyl)benzene in step c. MS: ES+ 310.01; $^1$H NMR (400 MHz, DMSO-$d_6$) δ ppm 10.47 (s, 1H), 7.27-7.30 (m, 4H), 7.19-7.23 (m, 3H), 4.16 (t, J=7.32 Hz, 2H), 3.53-3.60 (m, 1H), 3.36-3.48 (m, 3H), 3.15-3.23 (m, 1H), 3.01 (t, J=7.32 Hz, 2H), 2.06-2.15 (m, 1H), 1.97-2.05 (m, 1H).

Example 148 (S)-1-cyano-N-(1-isobutyl-1H-imidazol-4-yl)pyrrolidine-3-carboxamide

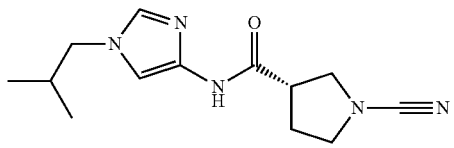 [SMILES: CC(C)Cn1cnc(NC(=O)[C@H]2CCN(C#N)C2)c1]

Synthesised using a procedure similar to that described for Example 146 using 1-bromo-2-methylpropane in step c. MS: ES+ 262.04; ¹H NMR (400 MHz, DMSO-d₆) δ ppm 10.51 (s, 1H), 7.41 (d, J=1.52 Hz, 1H), 7.20 (d, J=1.52 Hz, 1H), 3.72 (d, J=7.32 Hz, 2H), 3.54-3.58 (m, 1H), 3.36-3.49 (m, 3H), 3.17-3.21 (m, 1H), 2.05-2.15 (m, 1H), 1.92-2.04 (m, 2H), 0.82 (d, J=6.71 Hz, 6H).

Example 149 (2S,3S)—N-(1-benzyl-1H-imidazol-4-yl)-1-cyano-2-methylpyrrolidine-3-carboxamide

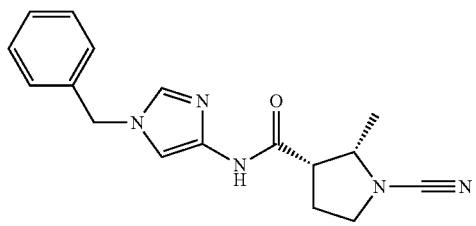 [SMILES: C[C@H]1[C@@H](C(=O)Nc2cn(Cc3ccccc3)cn2)CCN1C#N]

Synthesised using a procedure similar to that described for Example 146 using benzyl bromide and Intermediate 1. Purification by preparative HPLC; mobile phase: (A) 100% n-hexane (B) 50% IPA/MeOH, column: YMC PACKSIL, 250×20 mm, 5 µm, flow rate: 20 ml/min. MS: ES+ 310.15; ¹H NMR (400 MHz, DMSO-d₆) δ ppm 10.48 (s, 1H), 7.60 (d, J=1.60 Hz, 1H), 7.35-7.39 (m, 2H), 7.29-7.33 (m, 3H), 7.22 (d, J=1.60 Hz, 1H), 5.13 (s, 2H), 3.87-3.90 (m, 1H), 3.55-3.59 (m, 1H), 3.36-3.39 (m, 1H), 3.12-3.14 (m, 1H), 2.06-2.09 (m, 1H), 1.92-1.96 (m, 1H), 1.04 (d, J=6.40 Hz, 3H).

Example 150 (S)-1-cyano-N-(1-(4-fluorophenyl)-1H-imidazol-4-yl)pyrrolidine-3-carboxamide (Prepared According to Scheme 8, Steps a, b, g, h, i, j)

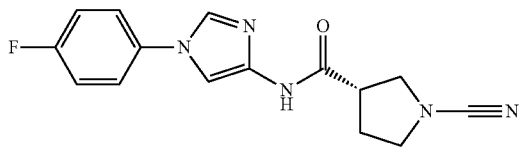 [SMILES: N#CN1CC[C@H](C(=O)Nc2cn(-c3ccc(F)cc3)cn2)C1]

Step a.
A solution of 4-nitro-1H-imidazole (8.84 mmol) in acetic acid (18 ml) was cooled to 0° C. Fuming HNO₃ (4.3 ml) was added dropwise to the reaction mixture. After completion of addition, acetic anhydride (12 ml) was added dropwise to the reaction mixture at 0° C. The reaction mixture was stirred at rt for 2 h. The resulting reaction mixture was slowly poured into ice water (100 ml) and extracted with EtOAc (3×50 ml). The combined organic phase was slowly washed with saturated K₂CO₃ solution (50 ml) (Exothermic Process), brine (50 ml) dried over Na₂SO₄, filtered and concentrated under reduced pressure yielding 1,4-dinitro-1H-imidazole (8.8 mmol). This material was used directly for the next step without further purification. ¹H NMR (400 MHz, CDCl₃) δ ppm 8.53 (d, J=1.5 Hz, 1H), 8.40 (d, J=1.5 Hz, 1H).

Step b.
To a solution of 1,4-dinitro-1H-imidazole (1.25 mmol) in MeOH:water (1:1, 8 ml) was added 4-fluoroaniline (1.32 mmol) at rt. The reaction mixture was stirred at rt for 2 h. The resulting solid precipitates were collected by filtration under reduced pressure and dried yielding 1-(4-fluorophenyl)-4-nitro-1H-imidazole (0.96 mmol). This material was used directly for the next step without further purification. MS: ES+ 208.23.

Step g.
To a solution of 1-(4-fluorophenyl)-4-nitro-1H-imidazole (0.97 mmol) in MeOH (5 ml) was added 10% Pd/C (0.5% w/w) at rt. The reaction mixture was purged with H₂ gas for 2 h at rt. The resulting reaction mixture was carefully filtered through celite hyflow and concentrated under reduced pressure to yield 1-(4-fluorophenyl)-1H-imidazol-4-amine (0.90 mmol). This material was used immediately for the next step without further purification. MS: ES+: 177.96

Step h-j.
The title compound was synthesised from the intermediate above using a procedure similar to that described for Example 146 according to Scheme 8 steps h, i and j. MS: ES+300.23; ¹H NMR (400 MHz, DMSO-d₆) δ ppm 10.73 (s, 1H), 8.08 (d, J=1.2 Hz, 1H), 7.66-7.70 (m, 3H), 7.33-7.38 (m, 2H), 3.58-3.62 (m, 1H), 3.44-3.50 (m, 2H), 3.37-3.43 (m, 1H), 3.21-3.28 (m, 1H), 2.10-2.18 (m, 1H), 1.98-2.07 (m, 1H).

Example 151 (S)-1-cyano-N-(1-(3-fluorophenyl)-1H-imidazol-4-yl)pyrrolidine-3-carboxamide

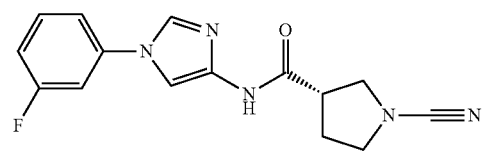 [SMILES: N#CN1CC[C@H](C(=O)Nc2cn(-c3cccc(F)c3)cn2)C1]

Synthesised using a procedure similar to that described for Example 150 using 3-fluoroaniline in step b. MS: ES+ 300.28; ¹H NMR (400 MHz, DMSO-d₆) δ ppm 10.75 (s, 1H), 8.21 (d, J=1.52 Hz, 1H), 7.78 (d, J=1.52 Hz, 1H), 7.62-7.67 (m, 1H), 7.50-7.59 (m, 2H), 7.16-7.23 (m, 1H), 3.58-3.63 (m, 1H), 3.37-3.51 (m, 3H), 3.23-3.34 (m, 1H), 2.10-2.20 (m, 1H), 1.98-2.08 (m, 1H).

Example 152 (S)-1-cyano-N-(1-(2-fluorophenyl)-1H-imidazol-4-yl)pyrrolidine-3-carboxamide

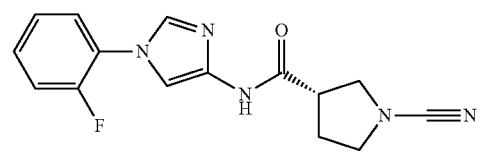 [SMILES: N#CN1CC[C@H](C(=O)Nc2cn(-c3ccccc3F)cn2)C1]

Synthesised using a procedure similar to that described for Example 150 using 2-fluoroaniline in step b. MS: ES+ 300.23; $^1$H NMR (400 MHz, DMSO-$d_6$) δ ppm 10.75 (br s, 1H), 8.22 (s, 1H), 7.78 (s, 1H), 7.63-7.65 (m, 1H), 7.50-7.58 (m, 2H), 7.19-7.20 (m, 1H), 3.58-3.62 (m, 1H), 3.29-3.58 (m, 3H), 3.22-3.29 (m, 1H), 2.10-2.19 (m, 1H), 1.98-2.08 (m, 1H).

Example 153 (S)-1-cyano-N-(1-(4-(trifluoromethyl)phenyl)-1H-imidazol-4-yl)pyrrolidine-3-carboxamide

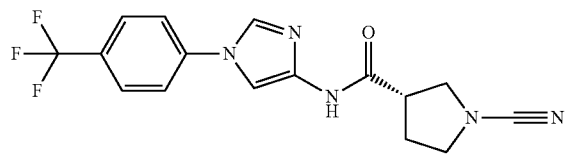 [SMILES: N#CN1CC[C@H](C(=O)Nc2cn(-c3ccc(C(F)(F)F)cc3)cn2)C1]

Synthesised using a procedure similar to that described for Example 150 using 4-(trifluoromethyl)aniline. MS: ES+ 350.1; $^1$H NMR (400 MHz, DMSO-$d_6$) δ ppm 10.77 (s, 1H), 8.31 (d, J=1.6 Hz, 1H), 7.84-7.92 (m, 5H), 3.58-3.63 (m, 1H), 3.38-3.50 (m, 3H), 3.22-3.50 (m, 1H), 2.11-2.19 (m, 1H), 1.99-2.08 (m, 1H).

Example 154 (S)-1-cyano-N-(1-(3-(trifluoromethyl)phenyl)-1H-imidazol-4-yl)pyrrolidine-3-carboxamide

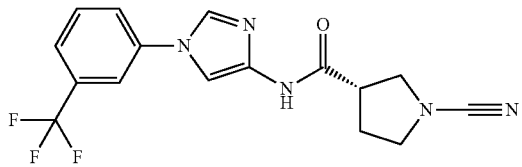 [SMILES: N#CN1CC[C@H](C(=O)Nc2cn(-c3cccc(C(F)(F)F)c3)cn2)C1]

Synthesised using a procedure similar to that described for Example 150 using 3-(trifluoromethyl)aniline. MS: ES+ 350.13; $^1$H NMR (400 MHz, DMSO-$d_6$) δ ppm 10.76 (s, 1H), 8.30 (d, J=1.6 Hz, 1H), 8.35-8.47 (m, 1H), 7.98 (d, J=7.2 Hz, 1H), 7.86 (d, J=1.2 Hz, 1H), 7.69-7.76 (m, 2H), 3.58-3.63 (m, 1H), 3.38-3.50 (m, 3H), 3.24-3.29 (m, 1H), 2.11-2.17 (m, 1H), 2.01-2.07 (m, 1H).

Example 155 (S)-1-cyano-N-(1-(4-(methylcarbamoyl)phenyl)-1H-imidazol-4-yl)pyrrolidine-3-carboxamide

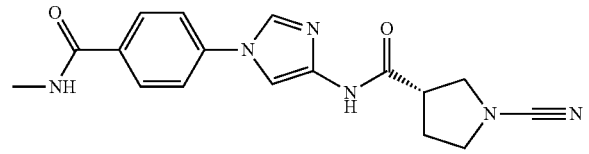 [SMILES: CNC(=O)c1ccc(-n2cnc(NC(=O)[C@H]3CCN(C#N)C3)c2)cc1]

Synthesised using a procedure similar to that described for Example 150 using 4-amino-N-methylbenzamide. MS: ES+ 339.23; $^1$H NMR (400 MHz, DMSO-$d_6$) δ ppm 10.77 (s, 1H), 8.53 (d, J=4.8 Hz, 1H), 8.25 (d, J=1.6 Hz, 1H), 7.96 (d, J=8.8 Hz, 2H), 7.81 (d, J=1.6 Hz, 1H), 7.76 (d, J=8.8 Hz, 2H), 3.58-3.62 (m, 1H), 3.44-3.49 (m, 2H), 3.37-3.41 (m, 1H), 3.24-3.27 (m, 1H), 2.79 (d, J=4.8 Hz, 3H), 2.12-2.17 (m, 1H), 2.00-2.05 (m, 1H).

Example 156 (S)-1-cyano-N-(1-(3-(methylcarbamoyl)phenyl)-1H-imidazol-4-yl)pyrrolidine-3-carboxamide

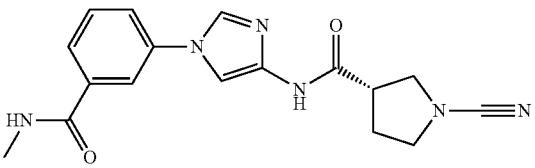 [SMILES: CNC(=O)c1cccc(-n2cnc(NC(=O)[C@H]3CCN(C#N)C3)c2)c1]

Synthesised using a procedure similar to that described for Example 150 using 3-amino-N-methylbenzamide. MS: ES+ 339.18; $^1$H NMR (400 MHz, DMSO-$d_6$) δ ppm 10.76 (s, 1H), 8.65 (d, J=4.8 Hz, 1H), 8.20 (d, J=1.6 Hz, 1H), 8.02 (s, 1H), 7.85 (d, J=1.6 Hz, 1H), 7.79-7.83 (m, 2H), 7.59 (t, J=8.0 Hz, 1H), 3.59-3.63 (m, 1H), 3.37-3.50 (m, 3H), 3.16-3.28 (m, 1H), 2.81 (d, 4.4 Hz, 3H), 2.13-2.18 (m, 1H), 2.01-2.06 (m, 1H).

Example 157 (S)-1-cyano-N-(1-(2-(methylcarbamoyl)phenyl)-1H-imidazol-4-yl)pyrrolidine-3-carboxamide

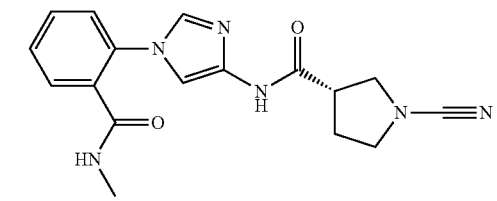 [SMILES: CNC(=O)c1ccccc1-n1cnc(NC(=O)[C@H]2CCN(C#N)C2)c1]

Synthesised using a procedure similar to that described for Example 150 using 2-amino-N-methylbenzamide. MS: ES+ 339.18; $^1$H NMR (400 MHz, DMSO-$d_6$) δ ppm 10.67 (s, 1H), 8.36-8.39 (m, 1H), 7.62 (d, J=1.6 Hz, 1H), 7.55-7.59 (m, 1H), 7.46-7.50 (m, 3H), 7.41 (d, J=1.6 Hz, 1H), 3.57-3.61 (m, 1H), 3.36-3.49 (m, 3H), 3.20-3.27 (m, 1H), 2.64 (d, J=4.8 Hz, 3H), 2.09-2.18 (m, 1H), 1.97-2.06 (m, 1H).

Example 158 (S)-1-cyano-N-(1-(4-((2-methoxyethyl)carbamoyl)phenyl)-1H-imidazol-4-yl)pyrrolidine-3-carboxamide

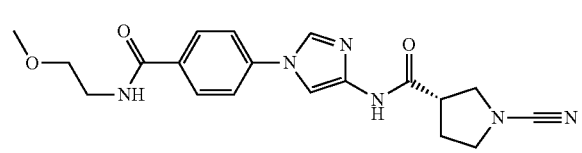 [SMILES: COCCNC(=O)c1ccc(-n2cnc(NC(=O)[C@H]3CCN(C#N)C3)c2)cc1]

Synthesised using a procedure similar to that described for Example 150 using 4-amino-N-(2-methoxyethyl)benzamide. MS: ES+ 383.28; $^1$H NMR (400 MHz, DMSO-$d_6$) δ ppm 10.77 (s, 1H), 8.63 (t, J=4.4 Hz, 1H), 8.27 (d, J=1.6 Hz, 1H), 7.98 (d, J=8.8 Hz, 2H), 7.81 (d, J=1.6 Hz, 1H), 7.76 (d, J=8.8 Hz, 2H), 3.58-3.62 (m, 1H), 3.42-3.50 (m, 5H), 3.37-3.39 (m, 2H), 3.27 (s, 3H), 3.22-3.26 (m, 1H), 2.11-2.17 (m, 1H), 1.98-2.05 (m, 1H).

Example 159 (S)-1-cyano-N-(1-(4-methoxyphenyl)-1H-imidazol-4-yl)pyrrolidine-3-carboxamide

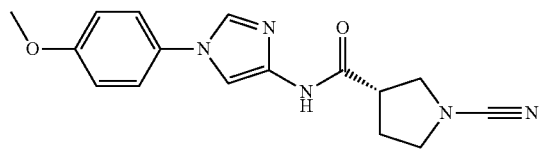 [SMILES: COc1ccc(-n2cnc(NC(=O)[C@H]3CCN(C#N)C3)c2)cc1]

Synthesised using a procedure similar to that described for Example 150 using 4-methoxyaniline. MS: ES+ 312.18; $^1$H NMR (400 MHz, DMSO-$d_6$) δ ppm 10.70 (s, 1H), 7.99 (d, J=1.6 Hz, 1H), 7.62 (d, J=1.2 Hz, 1H), 7.54 (d, J=8.8 Hz, 2H), 7.06 (d, J=9.2 Hz, 2H), 3.80 (s, 3H), 3.57-3.62 (m, 1H), 3.44-3.48 (m, 2H), 3.37-3.42 (m, 1H), 3.22-3.26 (m, 1H), 2.11-2.16 (m, 1H), 1.99-2.04 (m, 1H).

Example 160 (S)-1-cyano-N-(1-(2-methoxyphenyl)-1H-imidazol-4-yl)pyrrolidine-3-carboxamide

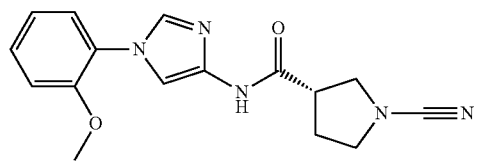 [SMILES: COc1ccccc1-n1cnc(NC(=O)[C@H]2CCN(C#N)C2)c1]

Synthesised using a procedure similar to that described for Example 150 using 2-methoxyaniline. MS: ES+ 312.18; $^1$H NMR (400 MHz, DMSO-$d_6$) δ ppm 10.68 (s, 1H), 7.75 (d, J=1.6 Hz, 1H), 7.39-7.45 (m, 3H), 7.25 (d, J=8.0 Hz, 1H), 7.05-7.07 (m, 1H), 3.83 (s, 3H), 3.57-3.61 (m, 1H), 3.44-3.49 (m, 2H), 3.34-3.42 (m, 1H), 3.22-3.26 (m, 1H), 2.09-2.17 (m, 1H), 1.99-2.06 (m, 1H).

Example 161 (S)-1-cyano-N-(1-(tetrahydro-2H-pyran-4-yl)-1H-imidazol-4-yl)pyrrolidine-3-carboxamide

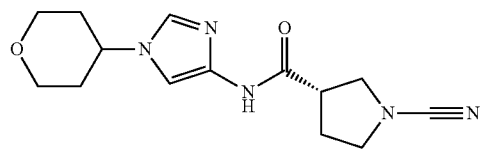 [SMILES: N#CN1CC[C@H](C(=O)Nc2cn(C3CCOCC3)cn2)C1]

Synthesised using a procedure similar to that described for Example 150 using 4-amino-tetrahydropyran. MS: ES+ 290.53; $^1$H NMR (400 MHz, DMSO-$d_6$) δ ppm 10.51 (s, 1H), 7.56 (d, J=1.60 Hz, 1H), 7.29 (d, J=1.60 Hz, 1H), 4.21-4.27 (m, 1H), 3.93-3.97 (m, 2H), 3.54-3.58 (m, 1H), 3.37-3.48 (m, 5H), 3.17-3.21 (m, 1H), 2.06-2.12 (m, 1H), 1.82-2.03 (m, 5H).

Example 162 (S)-1-cyano-N-(1-cyclohexyl-1H-imidazol-4-yl)pyrrolidine-3-carboxamide

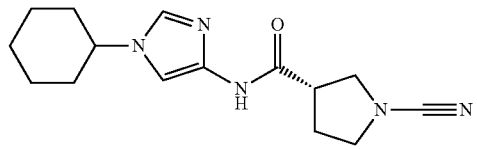 [SMILES: N#CN1CC[C@H](C(=O)Nc2cn(C3CCCCC3)cn2)C1]

Synthesised using a procedure similar to that described for Example 150 using cyclohexylamine. MS: ES+ 288.15; $^1$H NMR (400 MHz, DMSO-$d_6$) δ ppm 10.51 (s, 1H), 7.53 (d, J=1.2 Hz, 1H), 7.28 (d, J=1.6 Hz, 1H), 3.94-3.98 (m, 1H), 3.54-3.58 (m, 1H), 3.36-3.48 (m, 3H), 3.17-3.21 (m, 1H), 2.08-2.12 (m, 1H), 1.93-2.01 (m, 3H), 1.75-1.85 (m, 2H), 1.56-1.66 (m, 4H), 1.31-1.41 (m, 2H).

Example 163 (S)-1-cyano-N-(1-cyclohexyl-1H-imidazol-4-yl)pyrrolidine-3-carboxamide

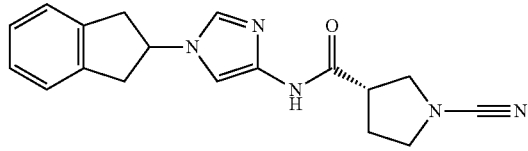 [SMILES: N#CN1CC[C@H](C(=O)Nc2cn(C3Cc4ccccc4C3)cn2)C1]

Synthesised using a procedure similar to that described for Example 150 using (±)-1-aminoindane. MS: ES+ 322.58; $^1$H NMR (400 MHz, DMSO-$d_6$) δ ppm 10.54 (s, 1H), 7.59 (d, J=1.2 Hz, 1H), 7.37 (d, J=7.6 Hz, 1H), 7.31 (t, J=7.2 Hz, 1H), 7.22 (t, J=7.2 Hz, 1H), 7.07 (d, J=7.6 Hz, 1H), 7.00 (d, J=1.2 Hz, 1H), 5.79 (t, J=6.8 Hz, 1H), 3.51-3.56 (m, 1H), 3.36-3.43 (m, 3H), 3.15-3.18 (m, 1H), 3.07-3.13 (m, 1H), 2.89-2.97 (m, 1H), 2.60-2.67 (m, 1H), 2.13-2.19 (m, 1H), 2.05-2.10 (m, 1H), 1.92-1.98 (m, 1H).

Example 164 (S)-1-cyano-N-(1-(2,3-dihydro-1H-inden-2-yl)-1H-imidazol-4-yl)pyrrolidine-3-carboxamide Synthesised using a procedure similar to that described for Example 150 using 2,3-dihydro-1H-inden-2-amine. MS: ES+ 322.58; $^1$H NMR (400 MHz, DMSO-$d_6$) δ ppm 10.51 (s, 1H), 7.54 (d, J=1.60 Hz, 1H), 7.30 (dd, J=5.20, 3.20 Hz, 2H), 7.23 (dd, J=5.20, 2.00 Hz, 2H), 7.10 (d, J=1.60 Hz, 1H), 5.01-5.10 (m, 1H), 3.51-3.57 (m, 1H), 3.36-3.47 (m, 5H), 3.08-3.18 (m, 3H), 2.05-2.10 (m, 1H), 1.93-1.99 (m, 1H).

Example 165 (S)-1-cyano-N-(1-((tetrahydro-2H-pyran-4-yl)methyl)-1H-imidazol-4-yl)pyrrolidine-3-carboxamide

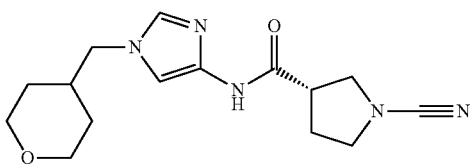 [SMILES: N#CN1CC[C@H](C(=O)Nc2cn(CC3CCOCC3)cn2)C1]

Synthesised using a procedure similar to that described for Example 150 using 4-(aminomethyl)tetrahydropyran. MS: ES+ 304.25; $^1$H NMR (400 MHz, DMSO-$d_6$) δ ppm 10.52 (s, 1H), 7.43 (s, 1H), 7.23 (s, 1H), 3.81-3.83 (m, 4H), 3.54-3.58 (m, 1H), 3.43-3.46 (m, 2H), 3.17-3.26 (m, 4H), 2.08-2.11 (m, 1H), 1.96-2.01 (m, 1H), 1.89-1.90 (m, 1H), 1.36-1.39 (m, 2H), 1.13-1.24 (m, 2H).

Example 166 (S)-1-cyano-N-(1-((S)-1-phenylethyl)-1H-imidazol-4-yl)pyrrolidine-3-carboxamide

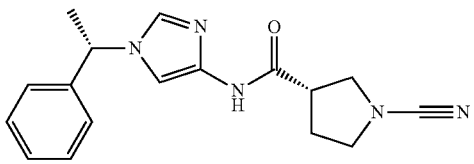 [SMILES: C[C@@H](c1ccccc1)n1cnc(NC(=O)[C@H]2CCN(C#N)C2)c1]

Synthesised using a procedure similar to that described for Example 150 using (S)-(−)-1-methylbenzylamine in step b. The reduction step was performed as described in Example 146 (Fe, NH$_4$Cl, MeOH, H$_2$O, 80° C.). MS: ES+ 310.10; $^1$H NMR (400 MHz, DMSO-$d_6$) δ ppm 10.54 (s, 1H), 7.66 (d, J=1.22 Hz, 1H), 7.34-7.39 (m, 2H), 7.28-7.32 (m, 3H), 7.22 (d, J=1.52 Hz, 1H), 5.47 (q, J=6.91 Hz, 1H), 3.51-3.57 (m, 1H), 3.35-3.48 (m, 3H), 3.13-3.21 (m, 1H), 2.04-2.13 (m, 1H), 1.92-2.02 (m, 1H), 1.77 (d, J=7.01 Hz, 3H).

Example 167 (S)-1-cyano-N-(1-((R)-1-phenylethyl)-1H-imidazol-4-yl)pyrrolidine-3-carboxamide

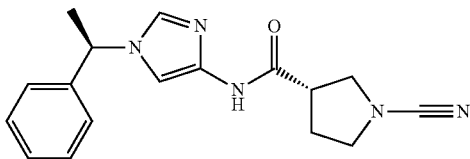 [SMILES: C[C@H](c1ccccc1)n1cnc(NC(=O)[C@H]2CCN(C#N)C2)c1]

Synthesised using a procedure similar to that described for Example 150 using (R)-(−)-1-methyl-benzylamine. MS: ES+ 310.23; $^1$H NMR (400 MHz, DMSO-$d_6$) δ ppm 10.54 (s, 1H), 7.66 (d, J=1.22 Hz, 1H), 7.34-7.39 (m, 2H), 7.28-7.32 (m, 3H), 7.22 (d, J=1.52 Hz, 1H), 5.47 (q, J=6.91 Hz, 1H), 3.51-3.57 (m, 1H), 3.35-3.48 (m, 3H), 3.13-3.21 (m, 1H), 2.04-2.13 (m, 1H), 1.92-2.02 (m, 1H), 1.77 (d, J=7.01 Hz, 3H).

Example 168 (S)-1-cyano-N-(1-(pyridin-2-ylmethyl)-1H-imidazol-4-yl)pyrrolidine-3-carboxamide

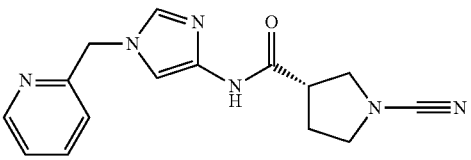 [SMILES: N#CN1CC[C@H](C(=O)Nc2cn(Cc3ccccn3)cn2)C1]

Synthesised using a procedure similar to that described for Example 150 using 2-(chloromethyl)-pyridine hydrochloride. The reduction step was performed as described in Example 146 (10% Pd/C, MeOH, H$_2$, rt). MS: ES+ 297.53; $^1$H NMR (400 MHz, DMSO-$d_6$) δ ppm 10.54 (s, 1H), 8.54 (dd, J=4.52, 1.12 Hz, 1H), 7.78-7.83 (m, 1H), 7.59 (d, J=1.20 Hz, 1H), 7.32-7.35 (m, 1H), 7.21-7.25 (m, 2H), 5.24 (s, 2H), 3.53-3.57 (m, 1H), 3.37-3.50 (m, 3H), 3.15-3.22 (m, 1H), 2.05-2.13 (m, 1H), 1.94-2.01 (m, 1H).

Example 169 (S)-1-cyano-N-(1-(pyridin-3-ylmethyl)-1H-imidazol-4-yl)pyrrolidine-3-carboxamide

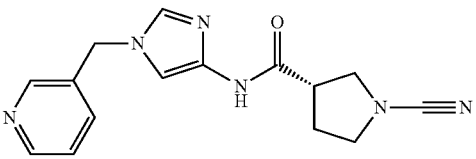 [SMILES: N#CN1CC[C@H](C(=O)Nc2cn(Cc3cccnc3)cn2)C1]

Synthesised using a procedure similar to that described for Example 146 using 3-(chloromethyl)-pyridine hydrochloride. The reduction step was performed as described in Example 150 (10% Pd/C, MeOH, H$_2$, rt). MS: ES+ 297.43; $^1$H NMR (400 MHz, DMSO-$d_6$) δ ppm 10.56 (s, 1H), 8.53-8.57 (m, 2H), 7.65-7.71 (m, 2H), 7.39-7.42 (m, 1H), 7.26 (s, 1H), 5.20 (s, 2H), 3.52-3.56 (m, 1H), 3.34-3.46 (m, 3H), 3.15-3.19 (m, 1H), 2.04-2.10 (m, 1H), 1.93-2.00 (m, 1H).

Example 170 (S)-1-cyano-N-(1-(pyridin-4-ylmethyl)-1H-imidazol-4-yl)pyrrolidine-3-carboxamide

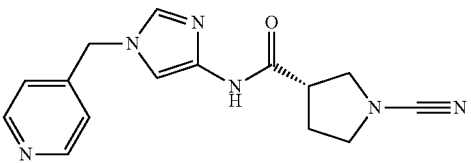 [SMILES: N#CN1CC[C@H](C(=O)Nc2cn(Cc3ccncc3)cn2)C1]

Synthesised using a procedure similar to that described for Example 146 using 4-(chloromethyl)-pyridine hydrochloride. The reduction step was performed as described in Example 150 (10% Pd/C, MeOH, H$_2$, rt). MS: ES+ 297.48; $^1$H NMR (400 MHz, DMSO-$d_6$) δ ppm 10.59 (s, 1H), 8.55 (dd, J=4.40, 1.60 Hz, 2H), 7.63 (d, J=1.20 Hz, 1H), 7.25 (d, J=1.20 Hz, 1H), 7.18 (dd, J=4.36, 1.32 Hz, 2H), 5.23 (s, 2H), 3.53-3.58 (m, 1H), 3.37-3.47 (m, 3H), 3.17-3.20 (m, 1H), 2.05-2.12 (m, 1H), 1.95-2.01 (m, 1H).

Example 171 (S)-1-cyano-N-(1-((3,5-dimethylisoxazol-4-yl)methyl)-1H-imidazol-4-yl)pyrrolidine-3-carboxamide

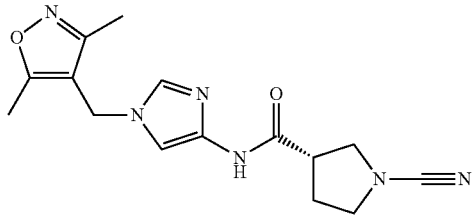 [SMILES: Cc1noc(C)c1Cn1cnc(NC(=O)[C@H]2CCN(C#N)C2)c1]

Synthesised using a procedure similar to that described for Example 146 using 4-(chloromethyl)-3,5-dimethylisoxazole. The reduction step was performed as described in Example 150 (10% Pd/C, MeOH, H$_2$, rt). MS: ES+ 315.38; $^1$H NMR (400 MHz, DMSO-d$_6$) δ ppm 10.55 (s, 1H), 7.54 (d, J=1.00 Hz, 1H), 7.13 (d, J=1.00 Hz, 1H), 5.00 (s, 2H), 3.53-3.57 (m, 1H), 3.37-3.46 (m, 3H), 3.16-3.21 (m, 1H), 2.39 (s, 3H), 2.08 (s, 3H), 2.06-2.16 (m, 1H), 1.92-2.00 (m, 1H).

Example 172 (2S,3S)-1-cyano-2-methyl-N-(1-((S)-1-phenylethyl)-1H-imidazol-4-yl)pyrrolidine-3-carboxamide

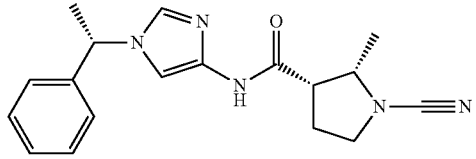

Synthesised using a procedure similar to that described for Example 150 using (S)-(−)-1-methyl-benzylamine and Intermediate 1. The reduction step was performed as described in Example 146 (Fe, NH$_4$Cl, MeOH, H$_2$O, 80° C.). MS: ES+ 324.38; $^1$H NMR (400 MHz, DMSO-d$_6$) δ ppm 10.47 (s, 1H), 7.65 (s, 1H), 7.23-7.63 (m, 5H), 7.25 (s, 1H), 5.47-5.48 (m, 1H), 3.86-3.90 (m, 1H), 3.55-3.62 (m, 1H), 3.36-3.42 (m, 1H), 3.13-3.16 (m, 1H), 2.07-2.09 (m, 1H), 1.91-1.99 (m, 1H), 1.78 (d, J=7.01 Hz, 3H), 1.06 (d, J=6.71 Hz, 3H).

Example 173 (3S,4S)-1-cyano-4-methyl-N-(1-((S)-1-phenylethyl)-1H-imidazol-4-yl)pyrrolidine-3-carboxamide

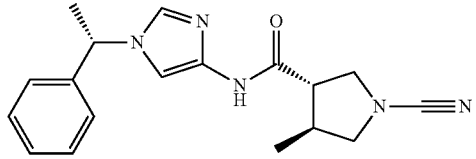 [SMILES: C[C@@H]1CN(C#N)C[C@H]1C(=O)Nc1cn([C@@H](C)c2ccccc2)cn1]

Synthesised using a procedure similar to that described for Example 150 using (S)-(−)-1-methyl-benzylamine and Intermediate 2. The reduction step was performed as described in Example 146 (Fe, NH$_4$Cl, MeOH, H$_2$O, 80° C.). MS: ES+ 324.43; $^1$H NMR (400 MHz, DMSO-d$_6$) δ ppm 10.59 (s, 1H), 7.67 (s, 1H), 7.28-7.38 (m, 5H), 7.24-7.25 (m, 1H), 5.46-5.48 (m, 1H), 3.55-3.65 (m, 2H), 3.36-3.40 (m, 1H), 2.97-3.01 (m, 1H), 2.76-2.83 (m, 1H), 2.33-2.38 (m, 1H), 1.78 (d, J=7.02 Hz, 3H), 0.98 (d, J=6.10 Hz, 3H).

Example 174 (S)-1-cyano-N-(1-(4-methylpyridin-2-yl)-1H-imidazol-4-yl)pyrrolidine-3-carboxamide (Prepared According to Scheme 8, Steps d, g, h, i, j)

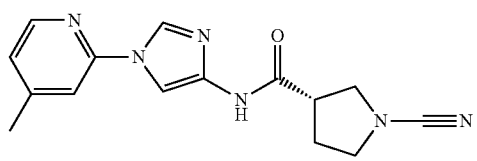 [SMILES: Cc1ccnc(-n2cnc(NC(=O)[C@H]3CCN(C#N)C3)c2)c1]

Step d.

A solution of 2-fluoro-4-methylpyridine (9.0 mmol), K$_2$CO$_3$ (27.0 mmol) and KI (9.0 mmol) in DMF (10 ml) was stirred at rt for 5 min. 4-Nitroimidazole (9.0 mmol) was added to the reaction mixture and then heated at 100° C. for 72 h. The resulting reaction mixture was poured into water (50 ml) and extracted with EtOAc (3×100 ml). The combined organic phase was dried over Na$_2$SO$_4$, filtered and concentrated under reduced pressure. The resulting residue was purified by flash chromatography (90-100% EtOAc in hexane) yielding 4-methyl-2-(4-nitro-1H-imidazol-1-yl)pyridine (1.34 mmol). MS: ES+ 205.23; $^1$H NMR (400 MHz, DMSO-d$_6$) δ ppm 9.07 (d, J=1.2 Hz, 1H), 8.69 (d, J=1.2 Hz, 1H), 8.44 (d, J=5.2 Hz, 1H), 7.93 (s, 1H), 7.38 (d, J=5.2 Hz, 1H), 2.44 (s, 3H).

Step g.

To a solution of 4-methyl-2-(4-nitro-1H-imidazol-1-yl)pyridine (2.4 mmol) in MeOH (15 ml) was added 10% Pd/C (0.10% w/w) at rt. The reaction mixture was purged with H$_2$ gas for 2 h at rt. The resulting reaction mixture was carefully filtered through celite hyflow and concentrated under reduced pressure to yield 1-(4-methylpyridin-2-yl)-1H-imidazol-4-amine (2.4 mmol). MS: ES+ 175.1

Steps h-j.

The title compound was synthesised from the intermediate above using a procedure similar to that described for Example 146 according to Scheme 8 steps h, i and j. MS: ES+ 297.0; $^1$H NMR (400 MHz, DMSO-d$_6$) δ ppm 10.76 (s, 1H), 8.40 (d, J=1.53 Hz, 1H), 8.34 (d, J=5.19 Hz, 1H), 7.99 (d, J=1.53 Hz, 1H), 7.69 (s, 1H), 7.20 (d, J=4.88 Hz, 1H), 3.57-3.64 (m, 1H), 3.38-3.52 (m, 3H), 3.24-3.27 (m, 1H), 2.41 (s, 3H), 2.10-2.21 (m, 1H), 1.98-2.08 (m, 1H).

Example 175 (S)-1-cyano-N-(1-(6-methylpyridin-2-yl)-1H-imidazol-4-yl)pyrrolidine-3-carboxamide

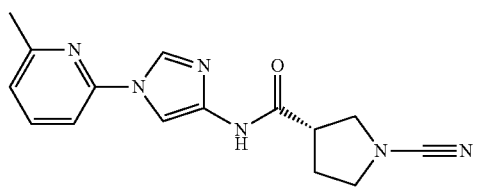 [SMILES: Cc1cccc(-n2cnc(NC(=O)[C@H]3CCN(C#N)C3)c2)n1]

Synthesised using a procedure similar to that described for Example 174 using 2-fluoro-6-methylpyridine in step d. MS: ES+ 297.0; $^1$H NMR (400 MHz, DMSO-d$_6$) δ ppm 10.76 (s, 1H), 8.40 (d, J=1.53 Hz, 1H), 7.99 (d, J=1.53 Hz, 1H), 7.86 (t, J=7.94 Hz, 1H), 7.60 (d, J=7.94 Hz, 1H), 7.22 (d, J=7.63 Hz, 1H), 3.57-3.63 (m, 1H), 3.44-3.51 (m, 2H), 3.37-3.44 (m, 1H), 3.23-3.27 (m, 1H), 2.51 (s, 3H), 2.10-2.20 (m, 1H), 1.98-2.08 (m, 1H).

Example 176 (S)-1-cyano-N-(1-(2-methylpyrimidin-4-yl)-1H-imidazol-4-yl)pyrrolidine-3-carboxamide

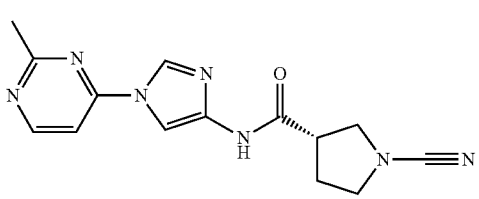 [SMILES: Cc1nccc(-n2cnc(NC(=O)[C@H]3CCN(C#N)C3)c2)n1]

Synthesised using a procedure similar to that described for Example 174 using 4-chloro-2-methylpyrimidine in step d. MS: ES+ 297.98; $^1$H NMR (400 MHz, DMSO-d$_6$) δ ppm 10.87 (s, 1H), 8.77 (d, J=5.80 Hz, 1H), 8.60 (d, J=1.53 Hz, 1H), 8.06 (d, J=1.53 Hz, 1H), 7.77 (d, J=5.49 Hz, 1H), 3.57-3.63 (m, 1H), 3.37-3.51 (m, 3H), 3.22-3.31 (m, 1H), 2.64 (s, 3H), 2.11-2.20 (m, 1H), 1.99-2.08 (m, 1H).

Example 177 (S)-1-cyano-N-(1-(4-cyanophenyl)-1H-imidazol-4-yl)pyrrolidine-3-carboxamide

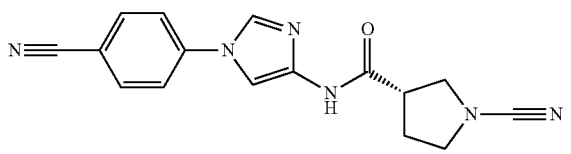 [SMILES: N#Cc1ccc(-n2cnc(NC(=O)[C@H]3CCN(C#N)C3)c2)cc1]

Synthesised using a procedure similar to that described for Example 174 using 4-fluorobenzonitrile in step d. MS: ES+ 307.43; $^1$H NMR (400 MHz, DMSO-d$_6$) δ ppm 10.81 (s, 1H), 8.35 (d, J=1.83 Hz, 1H), 7.97-8.04 (m, 2H), 7.88-7.93 (m, 2H), 7.87 (d, J=1.83 Hz, 1H), 3.58-3.62 (m, 1H), 3.37-3.54 (m, 3H), 3.21-3.30 (m, 1H), 2.09-2.21 (m, 1H), 1.96-2.08 (m, 1H).

Example 178 (S)—N-(1-benzyl-2-methyl-1H-imidazol-4-yl)-1-cyanopyrrolidine-3-carboxamide

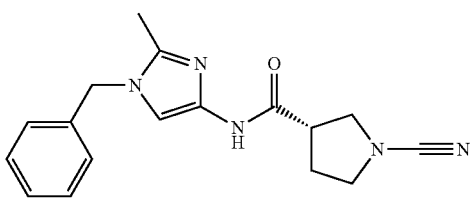 [SMILES: Cc1nc(NC(=O)[C@H]2CCN(C#N)C2)cn1Cc1ccccc1]

Synthesised using a procedure similar to that described for Example 174 using 2-methyl-4 (5)-nitroimidazole and benzyl chloride. MS: ES+ 310.47; $^1$H NMR (400 MHz, DMSO-d$_6$) δ ppm 10.43 (s, 1H), 7.35-7.38 (m, 2H), 7.27-7.31 (m, 1H), 7.17-7.18 (m, 2H), 7.14 (s, 1H), 5.09 (s, 2H), 3.53-3.55 (m, 1H), 3.35-3.46 (m, 3H), 3.12-3.20 (m, 1H), 2.22 (s, 3H), 2.06-2.13 (m, 1H), 1.91-1.99 (m, 1H).

Example 179 (S)-1-cyano-N-(1-(2-(3,5-dimethyl-isoxazol-4-yl)ethyl)-1H-imidazol-4-yl)pyrrolidine-3-carboxamide

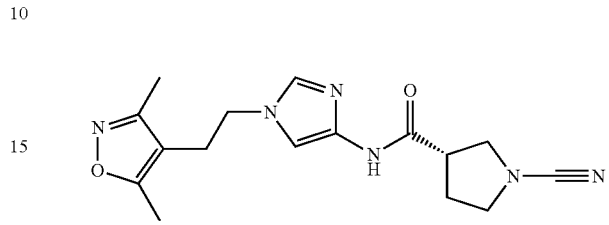

Synthesised using a procedure similar to that described for Example 174 using 4-(2-chloro-ethyl)-3,5-dimethyl-isoxazole. MS: ES+ 329.43; $^1$H NMR (400 MHz, DMSO-d$_6$) δ ppm 10.47 (s, 1H), 7.30 (s, 1H), 7.25 (s, 1H), 4.0 (t, J=8.0 Hz, 2H), 3.55-3.59 (m, 1H), 3.38-3.46 (m, 3H), 3.15-3.22 (m, 1H), 2.71 (t, J=6.8 Hz, 2H), 2.08-2.15 (m, 1H), 2.09 (s, 3H), 2.05 (s, 3H), 1.97-2.02 (m, 1H).

Example 180 (S)-1-cyano-N-(1-(3-cyanophenyl)-1H-imidazol-4-yl)pyrrolidine-3-carboxamide (Prepared According to Scheme 8, Steps d, f, h, i, j)

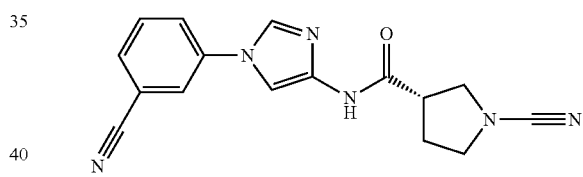

Step f.

To a solution of 3-(4-nitro-1H-imidazol-1-yl)benzonitrile [prepared using a procedure similar to that described for Example 174 using 3-fluorobenzonitrile in step d] (0.65 mmol) in MeOH (8 ml) was added Zn dust (1.96 mmol) and saturated solution of NH$_4$Cl (0.5 ml) at rt. The reaction mixture was stirred at 60° C. for 1 h. The resulting reaction mixture was allowed to cool to rt and poured into water (50 ml) and extracted with EtOAc (2×50 ml). The combined organic phase was dried over Na$_2$SO$_4$, filtered and concentrated under reduced pressure yielding 3-(4-amino-1H-imidazol-1-yl) benzonitrile (0.46 mmol). This material was used immediately for the next step without further purification. MS: ES+ 185.29

Steps h-j.

The title compound was synthesised from the intermediate above using a procedure similar to that described for Example 146 according to Scheme 8 steps h, i and j. MS: ES+ 307.28; $^1$H NMR (400 MHz, DMSO-d$_6$) δ ppm 10.76 (s, 1H), 8.27 (m, 2H), 8.02 (dd, J=8.00 Hz, 1.2 Hz, 1H), 7.87 (d, J=1.53 Hz, 1H), 7.81 (d, J=7.94 Hz, 1H), 7.66-7.75 (m, 1H), 3.58-3.61 (m, 1H), 3.44-3.50 (m, 2H), 3.38-3.40 (m, 1H), 3.23-3.29 (m, 1H), 2.09-2.21 (m, 1H), 1.97-2.08 (m, 1H).

Example 181 (S)-1-cyano-N-(1-(pyridin-3-yl)-1H-imidazol-4-yl)pyrrolidine-3-carboxamide (Prepared According to Scheme 8, Steps e, g, h, i, j)

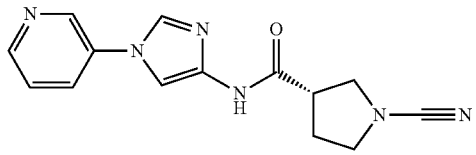

Step e.

To a solution of 4-nitroimidazole (17.6 mmol), pyridine-3-boronic acid (35.3 mmol) and CuCl$_2$ in MeOH (40 ml) was added NaOH (35.3 mmol) at rt and the reaction mixture was stirred for 5 min. A slow stream of O$_2$ gas was purged into the reaction mixture. The reaction mixture was heated at 80° C. for 18 h whilst continuing the slow purging of O$_2$ gas throughout the reaction time. The resulting reaction mixture was allowed to cool to rt and the purging of O$_2$ gas was removed. The reaction mixture was then concentrated under reduced pressure. The obtained crude material was poured in to water (100 ml) and extracted with EtOAc (2×100 ml). The combined organic phase was dried over Na$_2$SO$_4$, filtered and concentrated under reduced pressure yielding 3-(4-nitro-1H-imidazol-1-yl)pyridine (3.89 mmol). This material was directly used for the next step without further purification. MS: ES+ 191.1

Step g.

To a solution of 3-(4-nitro-1H-imidazol-1-yl)pyridine (3.68 mmol) in MeOH:THF (1:1, 10 ml) was added 10% Pd/C (0.25% w/w) at rt. The reaction mixture was purged with H$_2$ gas for 2 h at rt. The resulting reaction mixture was carefully filtered through celite hyflow and concentrated under reduced pressure to yield 1-(pyridin-3-yl)-1H-imidazol-4-amine (3.12 mmol). This material was directly used for the next step without further purification.

Steps h-j.

The title compound was synthesised from the intermediate above using a procedure similar to that described for Example 146 according to Scheme 8 steps h, i and j. MS: ES+ 283.48; $^1$H NMR (400 MHz, DMSO-d$_6$) δ ppm 10.78 (s, 1H), 8.94 (d, J=2.78 Hz, 1H), 8.56 (dd, J=4.58, 1.22 Hz, 1H), 8.24 (d, J=1.53 Hz, 1H), 8.09-8.12 (m, 1H), 7.81 (d, J=1.53 Hz, 1H), 7.53-7.57 (m, 1H), 3.56-3.65 (m, 1H), 3.36-3.52 (m, 3H), 3.22-3.31 (m, 1H), 2.11-2.19 (m, 1H), 1.99-2.07 (m, 1H).

Example 182 (S)-1-cyano-N-(1-(pyridin-4-yl)-1H-imidazol-4-yl)pyrrolidine-3-carboxamide

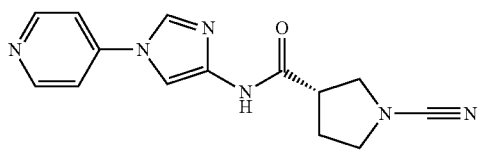

Synthesised using a procedure similar to that described for Example 181 using pyridine-4-boronic acid. MS: ES+ 283.43; $^1$H NMR (400 MHz, DMSO-d$_6$) δ ppm 10.83 (s, 1H), 8.63-8.65 (m, 2H), 8.45 (d, J=1.6 Hz, 1H), 7.91 (d, J=1.6 Hz, 1H), 7.75-7.77 (m, 2H), 3.59-3.63 (m, 1H), 3.42-3.51 (m, 2H), 3.35-3.40 (m, 1H), 3.21-3.31 (m, 1H), 2.09-2.18 (m, 1H), 1.99-2.07 (m, 1H).

Example 183 (S)-1-cyano-N-(1-(3-methoxyphenyl)-1H-imidazol-4-yl)pyrrolidine-3-carboxamide

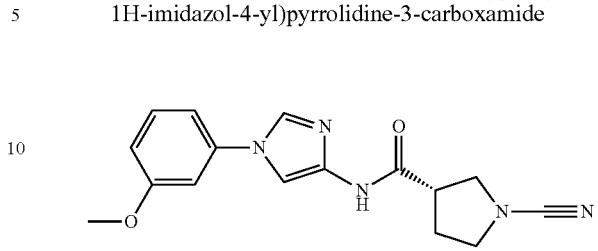

Synthesised using a procedure similar to that described for Example 181 using 3-methoxy-phenylboronic acid. MS: ES+ 312.43; $^1$H NMR (400 MHz, DMSO-d$_6$) δ ppm 10.73 (s, 1H), 8.15 (d, J=1.6 Hz, 1H), 7.72 (d, J=1.6 Hz, 1H), 7.38-7.43 (m, 1H), 7.17-7.19 (m, 2H), 6.92 (dd, J=6.0 Hz, 2.0 Hz, 1H), 3.84 (s, 3H), 3.58-3.61 (m, 1H), 3.45-3.50 (m, 2H), 3.37-3.44 (m, 1H), 3.21-3.28 (m, 1H), 2.07-2.16 (m, 1H), 1.98-2.05 (m, 1H).

Example 184 (3S)—N-(1-(1-benzoylpiperidin-3-yl)-1H-imidazol-4-yl)-1-cyanopyrrolidine-3-carboxamide (Prepared According to Scheme 9)

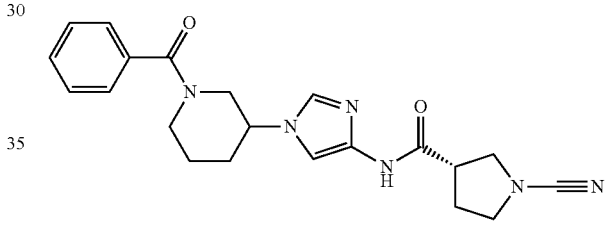

Step b.

To a solution of 1,4-dinitro-1H-imidazole (15.82 mmol) [prepared using a procedure described for Example 150 in step a] in MeOH:water (1:1, 40 ml) was added 1-BOC-3-aminopiperidine (15.82 mmol) at rt. The reaction mixture was stirred at rt for 16 h. The resulting reaction mixture was subjected to evaporation under reduced pressure in order to remove the majority of the MeOH. The obtained mixture was diluted with water (100 ml) and extracted with EtOAc (2×60 ml). The combined organic phase was collected, dried over Na$_2$SO$_4$, filtered and concentrated under reduced pressure. The resulting residue was purified by flash chromatography (60% EtOAc in hexane) yielding tert-butyl 3-(4-nitro-1H-imidazol-1-yl)piperidine-1-carboxylate (9.12 mmol). MS: ES+ 297.43; $^1$H NMR (400 MHz, DMSO-d$_6$) δ ppm 8.55 (d, J=1.2 Hz, 1H) 8.00 (d, J=1.2 Hz, 1H), 4.26-4.33 (m, 1H), 4.00-4.05 (m, 1H), 3.71-3.76 (m, 1H), 2.91-2.98 (m, 1H), 2.07-2.11 (m, 1H), 1.99-2.02 (m, 1H), 1.68-1.74 (m, 1H), 1.44-1.50 (m, 2H), 1.40 (s, 9H).

Step c.

To a solution of tert-butyl 3-(4-nitro-1H-imidazol-1-yl)piperidine-1-carboxylate (9.12 mmol) in DCM (30 ml) was added TFA (10 ml) at rt. The reaction mixture was stirred at rt for 10 min. The resulting reaction mixture was concentrated under reduced pressure. The obtained residue was azeotropically distilled using DCM and further triturated with n-hexane to yield 3-(4-nitro-1H-imidazol-1-yl)piperidine TFA salt (quantitative). This material was used directly for the next step without further purification. MS: ES+ 197.10; ¹H NMR (400 MHz, DMSO-d₆) δ ppm 9.35 (br s, 1H), 9.03 (br s, 1H), 8.61 (d, J=1.4 Hz, 1H), 8.01 (d, J=1.4 Hz, 1H), 4.51-4.59 (m, 1H), 3.59-3.62 (m, 1H), 3.30-3.40 (m, 2H), 2.79-2.89 (m, 1H), 2.15-2.18 (m, 1H), 1.95-2.08 (m, 2H), 1.69-1.80 (m, 1H).

Step i.

To a solution of benzoic acid (2.04 mmol) and TEA (3.07 mmol) in dry THF (5 ml) was added T3P (50% in EtOAc) (4.5 mmol) at rt. A solution of 3-(4-nitro-1H-imidazol-1-yl)piperidine TFA salt (1.63 mmol) in THF (2 ml) was added dropwise and the reaction mixture was stirred at rt for 16 h. The reaction mixture was poured into water (200 ml), basified with solid NaHCO₃ and extracted with EtOAc (2×100 ml). The combined organic phase was collected, dried over Na₂SO₄, filtered and concentrated under reduced pressure yielding [3-(4-nitro-1H-imidazol-1-yl)piperidin-1-yl](phenyl)methanone (quantitative). This material was used directly for the next step without further purification. MS: ES+ 301.38.

Step j.

To a solution of [3-(4-nitro-1H-imidazol-1-yl)piperidin-1-yl](phenyl)methanone (1.0 mmol) in MeOH (20 ml) was added 10% Pd/C (0.3 w/w) at rt. The reaction mixture was purged with H₂ gas for 30 min at rt. The resulting reaction mixture was carefully filtered through celite hyflow and concentrated under reduced pressure to yield [3-(4-amino-1H-imidazol-1-yl)piperidin-1-yl](phenyl)methanone (quantitative). This material was immediately used for the next step without further purification.

Steps f-h.

The title compound was synthesised from the intermediate above using a procedure similar to that described for Example 1 using (S)-1-(tert-Butoxycarbonyl)pyrrolidine-3-carboxylic acid. MS: ES+ 393.19; ¹H NMR (400 MHz, DMSO-d₆) δ ppm 10.58 (br s, 1H), 7.61 (br s, 1H), 7.40-7.46 (m, 5H), 7.24 (br s, 1H), 4.35-4.47 (m, 1H), 4.22-4.27 (m, 1H), 3.54-3.64 (m, 2H), 3.37-3.50 (m, 3H), 3.19-3.30 (m, 2H), 2.89-2.98 (m, 1H), 1.90-2.2 (m, 4H), 1.45-1.75 (m, 2H).

Example 185 (3S)—N-(1-(1-benzoylpyrrolidin-3-yl)-1H-imidazol-4-yl)-1-cyanopyrrolidine-3-carboxamide

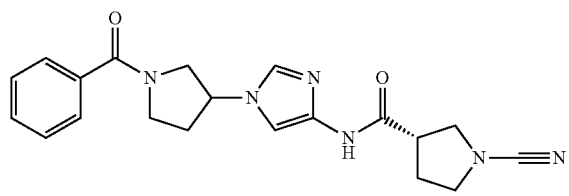 [SMILES: N#CN1CC[C@H](C(=O)Nc2cn(C3CCN(C(=O)c4ccccc4)C3)cn2)C1]

Synthesised using a procedure similar to that described for Example 184 using 1-BOC-3-aminopyrrolidine. MS: ES+ 379.58; ¹H NMR (400 MHz, DMSO-d₆) δ ppm 10.58 (br s, 1H), 7.62 (s, 1H), 7.43-7.54 (m, 5H), 7.28 (s, 1H), 4.88-4.93 (m, 1H), 4.79-4.83 (m, 1H), 3.95-3.99 (m, 1H), 3.84-3.89 (m, 1H), 3.69-3.72 (m, 1H), 3.52-3.62 (m, 3H), 3.42-3.46 (m, 2H), 3.17-3.22 (m, 2H), 2.13-2.16 (m, 1H), 2.07-2.10 (m, 1H).

Example 186 (3S)—N-(1-(1-benzylpiperidin-3-yl)-1H-imidazol-4-yl)-1-cyanopyrrolidine-3-carboxamide (Prepared According to Scheme 9)

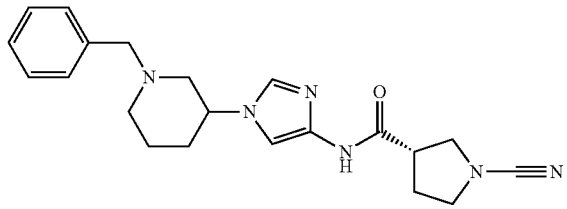 [SMILES: N#CN1CC[C@H](C(=O)Nc2cn(C3CCCN(Cc4ccccc4)C3)cn2)C1]

Step d.

To a solution of 3-(4-nitro-1H-imidazol-1-yl)piperidine TFA salt (prepared in Example 184) (2.25 mmol) and K₂CO₃ (6.77 mmol) in THF (8 ml) was added benzyl bromide (1.8 mmol) at rt. The reaction mixture was heated to 80° C. for 16 h. The resulting reaction mixture was poured into water (70 ml) and extracted with EtOAc (2×50 ml). The combined organic phase was collected, dried over Na₂SO₄, filtered and concentrated under reduced pressure to yield 1-benzyl-3-(4-nitro-1H-imidazol-1-yl)piperidine (quantitative). This material was directly used for the next step without further purification. MS: ES+287.43.

Step e.

A solution of 1-benzyl-3-(4-nitro-1H-imidazol-1-yl)piperidine (1.39 mmol) in THF:water (1:1, 10 ml) was stirred at rt for 5 min. Fe power (13.98 mmol) and NH₄Cl (13.98 mmol) were added and the reaction mixture was heated at 80° C. for 0.5 h. The resulting reaction mixture was allowed to cool to rt and filtered through celite hyflow. The filtrate was poured into water (20 ml) and extracted with EtOAc (2×5 ml). The combined organic phase was dried over Na₂SO₄, filtered and the resulting solution was immediately used for the next step without evaporation.

Steps f-h.

The title compound was synthesised from the previous intermediate using a procedure similar to that described for Example 1 using (S)-1-(tert-butoxycarbonyl)pyrrolidine-3-carboxylic acid. MS: ES+ 379.24; ¹H NMR (400 MHz, DMSO-d₆) δ ppm 10.50 (s, 1H), 7.55 (s, 1H), 7.24-7.33 (m, 6H), 4.15-4.25 (m, 1H), 3.52-3.57 (m, 3H), 3.38-3.50 (m, 2H), 3.16-3.22 (m, 1H), 2.86-2.89 (m, 1H), 2.66-2.73 (m, 1H), 2.25-2.35 (m, 1H), 2.11-2.17 (m, 2H), 1.93-2.07 (m, 2H), 1.60-1.68 (m, 2H), 1.54-1.57 (m, 2H).

Example 187 (3S)-1-cyano-N-(1-(1-methylpiperidin-3-yl)-1H-imidazol-4-yl)pyrrolidine-3-carboxamide (Prepared According to Scheme 9)

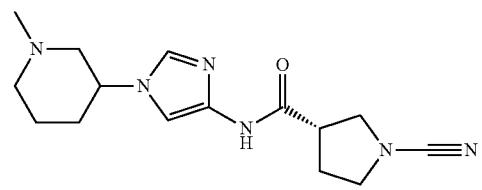 [SMILES: CN1CCCC(n2cnc(NC(=O)[C@H]3CCN(C#N)C3)c2)C1]

Step k.

To a solution of 3-(4-nitro-1H-imidazol-1-yl)piperidine TFA salt (prepared in Example 184) (2.58 mmol) and 37% aqueous formaldehyde solution (10 ml) in MeOH (20 ml) was added sodium cyanoborohydride (3.87 mmol) at rt. Acetic acid (6.19 mmol) was added dropwise to the reaction mixture and stirred at rt for 16 h. The resulting reaction mixture was concentrated under reduced pressure. The obtained residue was poured into water (100 ml), basified with solid NaHCO$_3$ and extracted with EtOAc (2×100 ml). The combined organic phase was collected, dried over Na$_2$SO$_4$, filtered and concentrated under reduced pressure to yield 1-methyl-3-(4-nitro-1H-imidazol-1-yl)piperidine (quantitative). MS: ES+ 211.04; $^1$H NMR (400 MHz, DMSO-d$_6$) δ ppm 8.56 (s, 1H), 8.01 (s, 1H), 4.33-4.40 (m, 1H), 2.86-2.89 (m, 1H), 2.51-2.57 (m, 1H), 2.20-2.36 (m, 1H), 2.22 (s, 3H), 2.05-2.10 (m, 1H), 1.95-1.99 (m, 1H), 1.67-1.79 (m, 2H), 1.54-1.60 (m, 1H).

Step j.

To a solution of 1-methyl-3-(4-nitro-1H-imidazol-1-yl)piperidine (1.90 mmol) in MeOH (50 ml) was added 10% Pd/C (0.25 w/w) at rt. The reaction mixture was purged with H$_2$ gas at rt for 0.5 h. The resulting reaction mixture was carefully filtered through celite hyflow and concentrated under reduced pressure to yield 1-(1-methylpiperidin-3-yl)-1H-imidazol-4-amine (quantitative). This material was immediately used for the next step without further purification. MS: ES+ 378.98; $^1$H NMR (400 MHz, DMSO-d$_6$) δ ppm 10.46 (br s, 1H), 7.56 (s, 1H), 7.29 (s, 1H), 4.10-4.21 (m, 1H), 3.40-3.52 (m, 2H), 3.18-3.38 (m, 4H), 3.07-3.19 (m, 1H), 2.80-2.91 (m, 1H), 2.59-2.68 (m, 1H), 2.20 (S, 3H), 2.08-2.18 (m, 2H), 1.87-1.90 (m, 2H), 1.51-1.73 (m, 2H), 1.39 (s, 9H).

Steps f-h.

The title compound was synthesised from the intermediate above using a procedure similar to that described for Example 1 using (S)-1-(tert-butoxycarbonyl)pyrrolidine-3-carboxylic acid. MS: ES+ 303.04; $^1$H NMR (400 MHz, DMSO-d$_6$) δ ppm 10.58 (br s, 1H), 7.58 (s, 1H), 7.37 (s, 1H), 4.57-4.62 (m, 1H), 3.51-3.60 (m, 1H), 3.34-3.50 (m, 4H), 3.20-3.26 (m, 2H), 3.01-3.14 (m, 2H), 2.50 (s, 3H), 2.07-2.17 (m, 2H), 1.95-2.07 (m, 2H), 1.70-1.80 (m, 2H).

Example 188 (3S)-1-cyano-N-(1-(1-methylpyrrolidin-3-yl)-1H-imidazol-4-yl)pyrrolidine-3-carboxamide

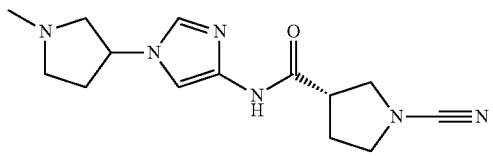 [SMILES: CN1CCC(n2cnc(NC(=O)[C@H]3CCN(C#N)C3)c2)C1]

Synthesised using a procedure similar to that described for Example 187 using 1-BOC-3-aminopyrrolidine. MS: ES+ 289.18; $^1$H NMR (400 MHz, DMSO-d$_6$) δ ppm 10.52 (s, 1H), 7.50 (s, 1H), 7.33 (s, 1H), 4.71-4.82 (m, 1H), 3.54-3.58 (m, 1H), 3.42-3.46 (m, 2H), 3.17-3.22 (m, 1H), 2.87-2.88 (m, 1H), 2.67-2.70 (m, 1H), 2.52-2.61 (m, 1H), 2.33-2.41 (m, 2H), 2.28 (s, 3H), 2.23-2.26 (m, 1H), 2.06-2.12 (m, 1H), 1.96-2.02 (m, 1H), 1.82-1.84 (m, 1H).

Example 189 (S)—N-(5-acetyl-4,5,6,7-tetrahydrothiazolo[5,4-c]pyridin-2-yl)-1-cyanopyrrolidine-3-carboxamide (Prepared According to Scheme 10)

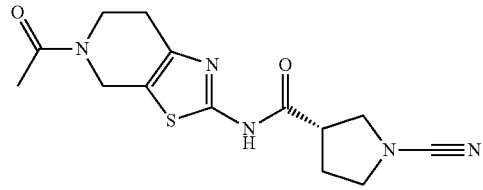 [SMILES: CC(=O)N1CCc2nc(NC(=O)[C@H]3CCN(C#N)C3)sc2C1]

Step a.

To a solution of Intermediate 14 (0.7 mmol) in DCM (2 ml) was added TEA (1.42 mmol) and acetyl chloride (0.85 mmol) at 0° C. The reaction mixture was stirred at rt for 1 h. The resulting reaction mixture was poured into ice cold water (30 ml) and extracted with DCM (3×30 ml). The combined organic phase was collected, dried over Na$_2$SO$_4$, filtered and concentrated under reduced pressure. The resulting residue was purified by flash chromatography (2% MeOH in DCM) yielding the tert-butyl (S)-34 (5-acetyl-4,5,6,7-tetrahydrothiazolo[5,4-c]pyridin-2-yl)carbamoyl)pyrrolidine-1-carboxylate (0.55 mmol). MS: ES+ 395.60.

Step f.

4M HCl in 1,4-dioxane (5 ml) was added to tert-butyl (S)-3-((5-acetyl-4,5,6,7-tetrahydrothiazolo[5,4-c]pyridin-2-yl)carbamoyl) pyrrolidine-1-carboxylate (0.55 mmol) and stirred at rt for 1 h. The resulting reaction mixture was concentrated under reduced pressure. The obtained residue was neutralized by aqueous solution of saturated NaHCO$_3$. The resulting mixture was extracted with DCM (3×100 ml). The combined organic phase was collected, dried over Na$_2$SO$_4$, filtered and concentrated under reduced pressure. The obtained residue was triturated with diethyl ether (10 ml) yielding (S)—N-(5-acetyl-4,5,6,7-tetrahydrothiazolo[5,4-c]pyridin-2-yl) pyrrolidine-3-carboxamide (0.49 mmol). The material was used directly for the next step without further purification. MS: ES+ 295.28.

Step g.

To a solution of (S)—N-(5-acetyl-4,5,6,7-tetrahydrothiazolo[5,4-c]pyridin-2-yl) pyrrolidine-3-carboxamide (0.5 mmol) in CHCl$_3$ (5 ml) was added DIPEA (1.5 mmol) at 0° C. The reaction mixture was stirred at 0° C. for 15 min. Cyanogen bromide (0.7 mmol) was added and the reaction mixture was stirred at 0° C. for 30 min. The resulting reaction mixture was poured into ice cold water (50 ml) and extracted with DCM (2×30 ml). The combined organic phase was collected, dried over Na$_2$SO$_4$, filtered and concentrated under reduced pressure. The resulting residue was purified by flash chromatography (2% MeOH in DCM). The material obtained after chromatography was further triturated with diethyl ether (5 ml) yielding the title compound (0.13 mmol). MS: ES+ 320.3; $^1$H NMR (run at 80° C., 400 MHz, DMSO-d$_6$) δ ppm 11.99 (br s, 1H), 4.62 (s, 2H), 3.72-3.85 (m, 2H), 3.60-3.65 (m, 1H), 3.49-3.56 (m, 1H), 3.38-3.48 (m, 2H), 3.28-3.37 (m, 1H), 2.60-2.80 (m, 2H), 2.16-2.28 (m, 1H), 2.05-2.10 (m, 4H).

Example 190 (S)-1-cyano-N-(5-isobutyryl-4,5,6,7-tetrahydrothiazolo[5,4-c]pyridin-2-yl)pyrrolidine-3-carboxamide

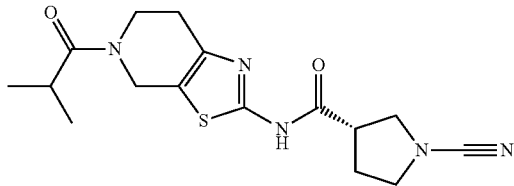 [SMILES: CC(C)C(=O)N1CCc2nc(NC(=O)[C@H]3CCN(C#N)C3)sc2C1]

Synthesised using a procedure similar to that described for Example 189 using 2-methylpropanoyl chloride. MS: ES+ 348.48; $^1$H NMR (run at 80° C., 400 MHz, DMSO-d$_6$) δ ppm 12.00 (br s, 1H), 4.65 (s, 2H), 3.79-3.82 (m, 2H), 3.60-3.64 (m, 1H), 3.51-3.54 (m, 1H), 3.40-3.45 (m, 2H), 3.33-3.38 (m, 1H), 2.95-2.98 (m, 1H), 2.67-2.72 (m, 2H), 2.16-2.23 (m, 1H), 2.05-2.12 (m, 1H), 1.04 (d, J=6.40 Hz, 6H).

Example 191 (S)—N-(5-benzoyl-4,5,6,7-tetrahydrothiazolo[5,4-c]pyridin-2-yl)-1-cyanopyrrolidine-3-carboxamide

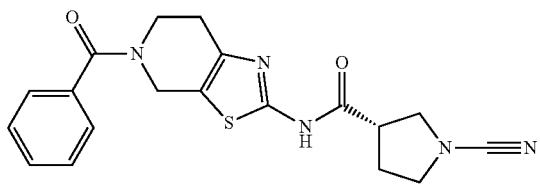 [SMILES: N#CN1CC[C@H](C(=O)Nc2nc3c(s2)CN(C(=O)c2ccccc2)CC3)C1]

Synthesised using a procedure similar to that described for Example 189 using benzoyl chloride. MS: ES+ 382.38; $^1$H NMR (400 MHz, DMSO-d$_6$) δ ppm 12.27 (br s, 1H), 7.41-7.62 (m, 5H), 4.76 (s, 2H), 3.92-3.94 (m, 1H), 3.34-3.61 (m, 6H), 2.66-2.73 (m, 2H), 2.21-2.28 (m, 1H), 2.04-2.11 (m, 1H).

Example 192 (S)-1-cyano-N-(5-(2-methoxybenzoyl)-4,5,6,7-tetrahydrothiazolo[5,4-c]pyridin-2-yl)pyrrolidine-3-carboxamide

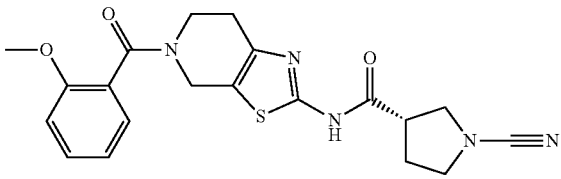 [SMILES: COc1ccccc1C(=O)N1CCc2nc(NC(=O)[C@H]3CCN(C#N)C3)sc2C1]

Synthesised using a procedure similar to that described for Example 189 using 2-methoxybenzoyl chloride. MS: ES+ 412.43; $^1$H NMR (run at 80° C., 400 MHz, DMSO-d$_6$) δ ppm 12.03 (br s, 1H), 7.42 (t, J=7.6 Hz, 1H), 7.11-7.23 (m, 2H), 7.01-7.04 (m, 1H), 4.78 (s, 2H), 4.29-4.39 (m, 1H), 3.94-4.08 (m, 1H), 3.81 (s, 3H), 3.60-3.62 (m, 1H), 3.38-3.47 (m, 3H), 3.31-3.36 (m, 1H), 2.73-2.79 (m, 1H), 2.58-2.65 (m, 1H), 2.19-2.22 (m, 1H), 2.06-2.11 (m, 1H).

Example 193 (S)-1-cyano-N-(5-picolinoyl-4,5,6,7-tetrahydrothiazolo[5,4-c]pyridin-2-yl)pyrrolidine-3-carboxamide (Prepared According to Scheme 10)

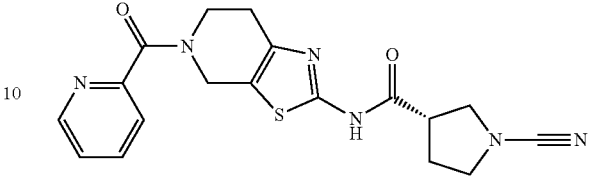

Step b.

To a solution of 2-pyridine carboxylic acid (0.406 mmol) in THF (2 ml) was added T3P (50% in EtOAc) (13.95 mmol) at rt. The reaction mixture was stirred at rt for 15 min. Intermediate 14 (0.41 mmol) and DIPEA (1.23 mmol) were added to the reaction mixture. The reaction mixture was stirred at rt for 1 h. The resulting reaction mixture was poured into water (50 ml) and extracted with EtOAc (3×50 ml). The combined organic phase was collected, dried over Na$_2$SO$_4$, filtered and concentrated under reduced pressure. The resulting residue was purified by flash chromatography (4% MeOH in DCM) yielding tert-butyl (S)-3-((5-picolinoyl-4,5,6,7-tetrahydrothiazolo[5,4-c]pyridin-2-yl) carbamoyl) pyrrolidine-1-carboxylate (0.32 mmol). MS: ES+ 458.66.

Step f.

To a solution of tert-butyl (S)-34 (5-picolinoyl-4,5,6,7-tetrahydrothiazolo[5,4-c]pyridin-2-yl)carbamoyl)pyrrolidine-1-carboxylate (0.32 mmol) in DCM (4 ml) was added TFA (1.31 mmol) at 0° C. The reaction mixture was stirred at rt for 2 h. The resulting reaction mixture was concentrated under reduced pressure. The obtained residue was neutralized by aqueous solution of saturated NaHCO$_3$ and extracted with DCM (3×50 ml). The combined organic phase was collected, dried over Na$_2$SO$_4$, filtered and concentrated under reduced pressure yielding (S)—N-(5-picolinoyl-4,5,6,7-tetrahydrothiazolo[5,4-c]pyridin-2-yl) pyrrolidine-3-carboxamide (0.31 mmol). This material was directly used for the next step without further purification. MS: ES+ 358.43.

Step g.

To a solution of (S)—N-(5-picolinoyl-4,5,6,7-tetrahydrothiazolo[5,4-c]pyridin-2-yl) pyrrolidine-3-carboxamide (0.31 mmol) in THF (6 ml) was added K$_2$CO$_3$ (0.92 mmol) at 0° C. The reaction mixture was stirred at 0° C. for 30 min. Cyanogen bromide (0.46 mmol) was added and the reaction mixture was then stirred at rt for 30 min. The resulting reaction mixture was poured into ice-water (100 ml) extracted with EtOAc (3×50 ml). The combined organic phase was collected, dried over Na$_2$SO$_4$, filtered and concentrated under reduced pressure. The resulting residue was purified by flash chromatography (4% MeOH in DCM) yielding the title compound (0.14 mmol). MS: ES+ 383.63; $^1$H NMR (run at 80° C., 400 MHz, DMSO-d$_6$) δ ppm 11.99 (br s, 1H), 8.62 (d, J=4.58 Hz, 1H), 7.94 (t, J=7.48 Hz, 1H), 7.62 (d, J=7.33 Hz, 1H), 7.49-7.52 (m, 1H), 4.80 (s, 2H), 3.97-4.07 (m, 1H), 3.88-3.94 (m, 1H), 3.60-3.65 (m, 1H), 3.47-3.53 (m, 1H), 3.37-3.45 (m, 2H), 3.31-3.35 (m, 1H), 2.71-2.81 (m, 2H), 2.15-2.22 (m, 1H), 2.04-2.13 (m, 1H).

Example 194 (S)-1-cyano-N-(5-(1-methyl-1H-pyrazole-3-carbonyl)-4,5,6,7-tetrahydrothiazolo[5,4-c]pyridin-2-yl)pyrrolidine-3-carboxamide

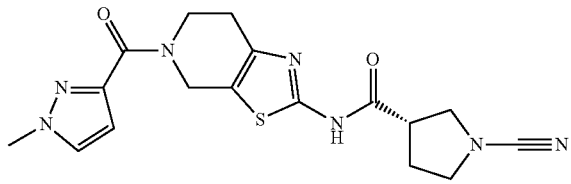 [SMILES: Cn1ccc(C(=O)N2CCc3nc(NC(=O)[C@H]4CCN(C#N)C4)sc3C2)n1]

Synthesised using a procedure similar to that described for Example 193 using 1-methyl-1H-pyrazole-3-carboxylic acid. MS: ES+ 386.43; $^1$H NMR (run at 80° C., 400 MHz, DMSO-$d_6$) δ ppm 11.98 (br s, 1H), 7.74 (s, 1H), 6.57 (s, 1H), 4.89 (s, 2H), 4.06-4.19 (m, 2H), 3.93 (s, 3H), 3.60-3.64 (m, 1H), 3.51-3.55 (m, 1H), 3.43-3.49 (m, 2H), 3.31-3.37 (m, 1H), 2.74-2.77 (m, 2H), 2.19-2.25 (m, 1H), 2.04-2.11 (m, 1H).

Example 195 (S)-1-cyano-N-(5-(1-methyl-2-oxo-1,2-dihydropyridine-3-carbonyl)-4,5,6,7-tetrahydrothiazolo[5,4-c]pyridin-2-yl)pyrrolidine-3-carboxamide

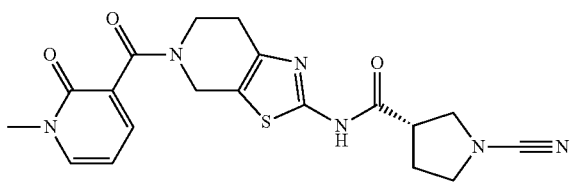 [SMILES: Cn1cccc(C(=O)N2CCc3nc(NC(=O)[C@H]4CCN(C#N)C4)sc3C2)c1=O]

Synthesised using a procedure similar to that described for Example 193 using 1-methyl-2-oxo-1,2-dihydropyridine-3-carboxylic acid. MS: ES+ 413.15; $^1$H NMR (run at 80° C., 400 MHz, DMSO-$d_6$) δ ppm 11.99 (br s, 1H), 7.78 (dd, J=6.71, 2.14 Hz, 1H), 7.47-7.49 (m, 1H), 6.28 (t, J=6.714 Hz, 1H), 4.71 (s, 2H), 3.72-3.79 (m, 1H), 3.60-3.67 (m, 1H), 3.50-3.54 (m, 2H), 3.47 (s, 3H), 3.38-3.45 (m, 2H), 3.29-3.36 (m, 1H), 2.70-2.73 (m, 2H), 2.17-2.23 (m, 1H), 2.07-2.13 (m, 1H).

Example 196 (S)-1-cyano-N-(5-nicotinoyl-4,5,6,7-tetrahydrothiazolo[5,4-c]pyridin-2-yl)pyrrolidine-3-carboxamide

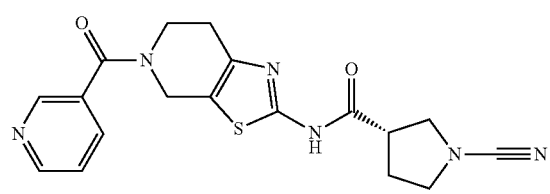 [SMILES: N#CN1CC[C@H](C(=O)Nc2nc3c(s2)CN(C(=O)c2cccnc2)CC3)C1]

Synthesised using a procedure similar to that described for Example 193 using nicotinic acid. MS: ES+ 383.20; $^1$H NMR (run at 80° C., 400 MHz, DMSO-$d_6$) δ ppm 12.00 (br s, 1H), 8.66-8.69 (m, 2H), 7.87 (d, J=8.0 Hz, 1H), 7.48-7.51 (m, 1H), 4.72 (s, 2H), 3.73-3.89 (m, 1H), 3.60-3.65 (m, 1H), 3.51-3.55 (m, 2H), 3.41-3.48 (m, 2H), 3.31-3.37 (m, 1H), 2.75-2.77 (m, 2H), 2.19-2.25 (m, 1H), 2.04-2.11 (m, 1H).

Example 197 (S)-1-cyano-N-(5-(dimethylglycyl)-4,5,6,7-tetrahydrothiazolo[5,4-c]pyridin-2-yl)pyrrolidine-3-carboxamide

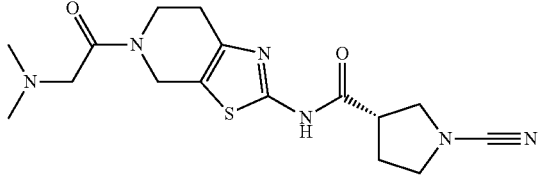 [SMILES: CN(C)CC(=O)N1CCc2nc(NC(=O)[C@H]3CCN(C#N)C3)sc2C1]

Synthesised using a procedure similar to that described for Example 193 using N,N-dimethylglycine. MS: ES+ 363.23; $^1$H NMR (400 MHz, CD$_3$OD) δ ppm 4.72-4.77 (m, 2H), 3.86-3.98 (m, 2H), 3.61-3.65 (m, 2H), 3.51-3.62 (m, 2H), 3.32-3.42 (m, 2H), 2.72-2.84 (m, 2H), 2.38 (s, 3H), 2.32 (s, 3H), 2.15-2.30 (m, 3H).

Example 198 methyl (S)-2-(1-cyanopyrrolidine-3-carboxamido)-6,7-dihydrothiazolo[5,4-c]pyridine-5 (4H)-carboxylate

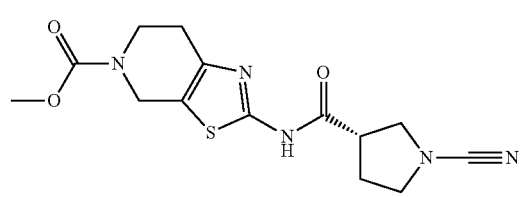 [SMILES: COC(=O)N1CCc2nc(NC(=O)[C@H]3CCN(C#N)C3)sc2C1]

Synthesised using a procedure similar to that described for Example 189 using methyl chloroformate. MS: ES+ 336.43; $^1$H NMR (400 MHz, DMSO-$d_6$) δ ppm 12.24 (br s, 1H), 4.55 (s, 2H), 3.67-3.70 (m, 2H), 3.64 (s, 3H), 3.59-3.61 (m, 1H), 3.48-3.53 (m, 1H), 3.38-3.46 (m, 2H), 3.28-3.32 (m, 1H), 2.65-2.68 (m, 2H), 2.08-2.20 (m, 1H), 2.01-2.08 (m, 1H).

Example 199 2-methoxyethyl (S)-2-(1-cyanopyrrolidine-3-carboxamido)-6,7-dihydrothiazolo[5,4-c]pyridine-5 (4H)-carboxylate

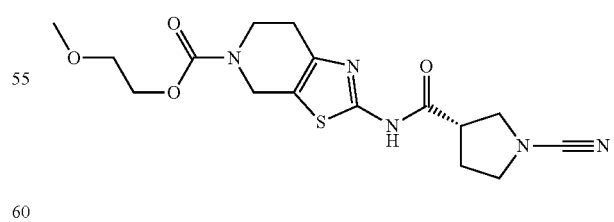

Synthesised using a procedure similar to that described for Example 189 using 2-methoxyethyl chloroformate. MS: ES+ 380.38; $^1$H NMR (400 MHz, DMSO-$d_6$) δ ppm 12.24 (s, 1H), 4.55 (s, 2H), 4.15-4.17 (m, 2H), 3.68-3.70 (m, 2H), 3.59-3.63 (m, 1H), 3.51-3.54 (m, 2H), 3.38-3.45 (m, 3H), 3.29-3.31 (m, 1H), 3.26 (s, 3H), 2.65-2.67 (m, 2H), 2.14-2.22 (m, 1H), 1.99-2.08 (m, 1H).

Example 200 (S)-1-cyano-N-(5-methyl-4,5,6,7-tetrahydrothiazolo[5,4-c]pyridin-2-yl)pyrrolidine-3-carboxamide (Prepared According to Scheme 10)

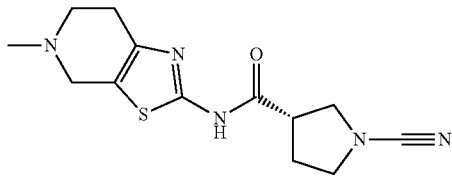 [SMILES: CN1CCc2nc(NC(=O)[C@H]3CCN(C#N)C3)sc2C1]

Step d.

To a solution of Intermediate 14 (0.56 mmol) in MeOH (5 ml) were added 37% aq formaldehyde (1.70 mmol) and acetic acid (3 drops) at 0° C. The reaction mixture was stirred at 0° C. for 30 min, NaCNBH$_3$ (1.12 mmol) was added to the reaction mixture at 0° C. The reaction mixture was stirred at rt for 3 h. The resulting reaction mixture was poured in to ice water (10 ml) and extracted with DCM (3×25 ml). The combined organic phase was collected, dried over Na$_2$SO$_4$, filtered and concentrated under reduced pressure. The resulting residue was purified by flash chromatography (3% MeOH in DCM) yielding tert-butyl (S)-3-((5-methyl-4,5,6,7-tetrahydrothiazolo[5,4-c]pyridin-2-yl)carbamoyl) pyrrolidine-1-carboxylate (0.35 mmol). MS: ES+ 367.3.

Step f.

To a solution of tert-butyl (S)-3-((5-methyl-4,5,6,7-tetrahydrothiazolo[5,4-c]pyridin-2-yl)carbamoyl)pyrrolidine-1-carboxylate (0.35 mmol) in DCM (10 ml) was added TFA (1.4 mmol) at 0° C. The reaction mixture was stirred at rt for 3 h. The resulting reaction mixture was concentrated under reduced pressure. The obtained residue was triturated with diethyl ether (10 ml) yielding (S)—N-(5-methyl-4,5,6,7-tetrahydrothiazolo[5,4-c]pyridin-2-yl)pyrrolidine-3-carboxamide TFA salt (0.21 mmol). The material was used directly for the next step without further purification. MS: ES+ 267.0.

Step g.

To a solution of (S)—N-(5-methyl-4,5,6,7-tetrahydrothiazolo[5,4-c]pyridin-2-yl)pyrrolidine-3-carboxamide TFA salt (0.21 mmol) in DCM (2 ml) was added TEA (0.63 mmol) at 0° C. The reaction mixture was stirred at 0° C. for 10 min. Cyanogen bromide (0.24 mmol) was added to the reaction mixture at 0° C. The reaction mixture was stirred at 0° C. for 30 min. The resulting reaction mixture was poured into ice water (10 ml) and extracted with DCM (3×25 ml). The combined organic phase was collected, dried over Na$_2$SO$_4$, filtered and concentrated under reduced pressure. The resulting residue was purified by flash chromatography (5% MeOH in DCM) to yield the title compound (0.07 mmol). MS: ES+ 292.08; $^1$H NMR (400 MHz, DMSO-d$_6$) δ ppm 12.20 (br s, 1H), 3.55-3.68 (m, 3H), 3.48-3.54 (m, 1H), 3.39-3.47 (m, 2H), 3.25-3.31 (m, 1H), 2.79 (m, 2H), 2.68 (m, 2H), 2.43 (s, 3H), 2.16-2.20 (m, 1H), 2.00-2.08 (m, 1H).

Example 201 (S)—N-(5-benzyl-4,5,6,7-tetrahydrothiazolo[5,4-c]pyridin-2-yl)-1-cyanopyrrolidine-3-carboxamide (Prepared According to Scheme 10)

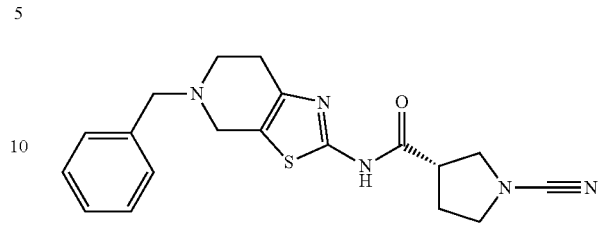

Step e.

To a solution of Intermediate 14 (0.85 mmol) in MeOH (5 ml) was added benzaldehyde (1.70 mmol) and acetic acid (3 drops) at 0° C. The reaction mixture was stirred at 0° C. for 30 min. NaCNBH$_3$ (1.70 mmol) was added to the reaction mixture at 0° C. The reaction mixture was stirred at rt for 3 h. The resulting reaction mixture was poured into ice water (10 ml) and extracted with DCM (3×25 ml). The combined organic phase was dried over Na$_2$SO$_4$, filtered and concentrated under reduced pressure. The resulting residue was purified by flash chromatography (2% MeOH in DCM) yielding tert-butyl (S)-3-((5-benzyl-4,5,6,7-tetrahydrothiazolo[5,4-c]pyridin-2-yl)carbamoyl)pyrrolidine-1-carboxylate (0.58 mmol). MS: ES+ 443.4.

Steps f-g.

The title compound was synthesised from the intermediate above using a procedure similar to that described for Example 200 according to Scheme 8 steps d and e. MS: ES+368.38; $^1$H NMR (400 MHz, DMSO-d$_6$) δ ppm 12.16 (br s, 1H), 7.34-7.46 (m, 4H), 7.24-7.31 (m, 1H), 3.69 (s, 2H), 3.47-3.65 (m, 4H), 3.37-3.43 (m, 2H), 3.25-3.33 (m, 1H), 2.73-2.79 (m, 2H), 2.63-2.67 (m, 2H), 2.13-2.22 (m, 1H), 1.99-2.07 (m, 1H).

Example 202 (S)-1-cyano-N-(5-(methylsulfonyl)-4,5,6,7-tetrahydrothiazolo[5,4-c]pyridin-2-yl)pyrrolidine-3-carboxamide (Prepared According to Scheme 10)

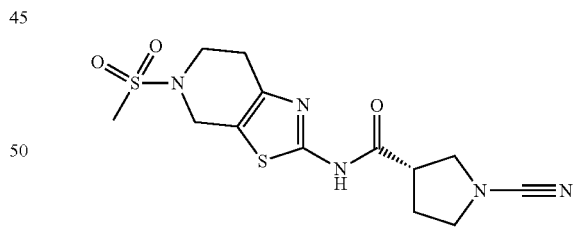

Step c.

To a solution of Intermediate 14 (0.56 mmol) in DCM (2 ml) was added TEA (1.13 mmol) and methanesulfonyl chloride (0.84 mmol) at 0° C. The reaction mixture was stirred at rt for 1 h. The resulting reaction mixture was poured into ice water (10 ml) and extracted with DCM (3×20 ml). The combined organic phase was collected, dried over Na$_2$SO$_4$, filtered and concentrated under reduced pressure. The resulting residue was purified by flash chromatography (2% MeOH in DCM) yielding tert-butyl (S)-3-((5-(methylsulfonyl)-4,5,6,7-tetrahydrothiazolo[5,4-c]pyridin-2-yl)carbamoyl)-pyrrolidine-1-carboxylate (0.43 mmol). MS: ES+ 431.38.

Step f.

4M HCl in 1,4-dioxane (4 mmol) was added to tert-butyl (S)-3-((5-(methylsulfonyl)-4,5,6,7-tetrahydrothiazolo[5,4-c]pyridin-2-yl)carbamoyl) pyrrolidine-1-carboxylate (0.43 mmol) at rt. The reaction mixture was stirred at rt for 1 h. The resulting reaction mixture was concentrated under reduced pressure. The obtained residue was triturated with diethyl ether (10 ml) yielding (S)—N-(5-(methylsulfonyl)-4,5,6,7-tetrahydrothiazolo[5,4-c]pyridin-2-yl)pyrrolidine-3-carboxamide hydrochloride (0.36 mmol). The material was used directly for the next step without further purification. MS: ES+ 331.28.

Step g.

To a solution of (S)—N-(5-(methylsulfonyl)-4,5,6,7-tetrahydrothiazolo[5,4-c]pyridin-2-yl)pyrrolidine-3-carboxamide hydrochloride (0.35 mmol) in $CHCl_3$ (4 ml) was added DIPEA (1.1 mmol) at 0° C. The reaction mixture was stirred at 0° C. for 10 min. Cyanogen bromide (0.53 mmol) was added and the reaction mixture was stirred at 0° C. for 30 min. The resulting reaction mixture was poured into ice-water (10 ml) and extracted with DCM (3×25 ml). The organic phase was collected, dried over $Na_2SO_4$, filtered and concentrated under reduced pressure. The resulting residue was purified by flash chromatography (2% MeOH in DCM) yielding the title compound (0.26 mmol). MS: ES+ 356.39; $^1$H NMR (400 MHz, DMSO-$d_6$) δ ppm 12.28 (s, 1H), 4.40 (s, 2H), 3.59-3.64 (m, 1H), 3.47-3.55 (m, 3H), 3.38-3.47 (m, 2H), 3.26-3.33 (m, 1H), 2.96 (s, 3H), 2.75-2.78 (m, 2H), 2.14-2.23 (m, 1H), 2.00-2.10 (m, 1H).

Example 203 (S)-1-cyano-N-(5-(isopropylsulfonyl)-4,5,6,7-tetrahydrothiazolo[5,4-c]pyridin-2-yl)pyrrolidine-3-carboxamide

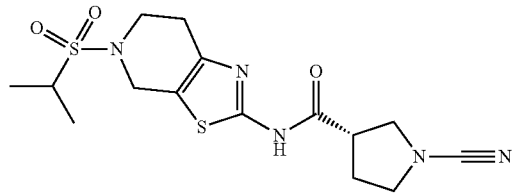 [SMILES: CC(C)S(=O)(=O)N1CCc2nc(NC(=O)[C@H]3CCN(C#N)C3)sc2C1]

Synthesised using a procedure similar to that described for Example 202 using isopropylsulfonyl chloride. MS: ES+ 384.28; $^1$H NMR (400 MHz, DMSO-$d_6$) δ ppm 12.26 (s, 1H), 4.47 (s, 2H), 3.59-3.63 (m, 3H), 3.44-3.53 (m, 1H), 3.37-3.42 (m, 3H), 3.26-3.31 (m, 1H), 2.67-2.71 (m, 2H), 2.14-2.17 (m, 1H), 2.00-2.08 (m, 1H), 1.22 (d, J=6.4 Hz, 6H).

Example 204 (S)-1-cyano-N-(5-(phenylsulfonyl)-4,5,6,7-tetrahydrothiazolo[5,4-c]pyridin-2-yl)pyrrolidine-3-carboxamide

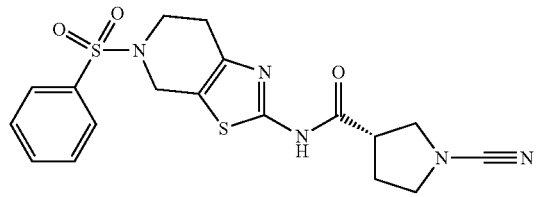 [SMILES: N#CN1CC[C@H](C(=O)Nc2nc3c(s2)CN(S(=O)(=O)c2ccccc2)CC3)C1]

Synthesised using a procedure similar to that described for Example 202 using benzenesulfonyl chloride. MS: ES+ 418.58; $^1$H NMR (400 MHz, DMSO-$d_6$) δ ppm 12.22 (br s, 1H), 7.81-7.83 (m, 2H), 7.68-7.72 (m, 1H), 7.59-7.63 (m, 2H), 4.31 (s, 2H), 3.60-3.62 (m, 1H), 3.47-3.52 (m, 1H), 3.35-3.45 (m, 4H), 3.24-3.29 (m, 1H), 2.61-2.67 (m, 2H), 2.12-2.21 (m, 1H), 1.98-2.07 (m, 1H).

Example 205 (S)-1-cyano-N-(5-(4-ethynylphenyl) thiazol-2-yl)pyrrolidine-3-carboxamide (Prepared According to Scheme 11)

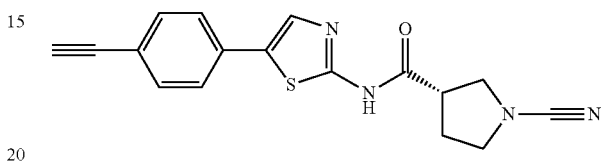

Step a.

To a solution of 2-(4-bromophenyl)ethan-1-ol (4.97 mmol) in DCM (13 ml) was added Dess-Martin periodinane (6.2 mmol) at 0° C. The reaction mixture was stirred at rt for 16 h. The reaction mixture was partially evaporated and the obtained residue was filtered through celite hyflow. The filtrate was concentrated under reduced pressure. The resulting residue was purified by flash chromatography (9-10% EtOAc in hexane) yielding 2-(4-bromophenyl) acetaldehyde (3.51 mmol). MS: ES– 197.10; $^1$H NMR (400 MHz, DMSO-$d^6$) δ ppm 9.68 (s, 1H), 7.54 (d, J=2.0 Hz, 2H), 7.21 (d, J=8.4 Hz, 2H), 3.79 (d, J=0.8 Hz, 2H).

Step b.

Bromine (3.5 mmol) was added dropwise to a solution of 2-(4-bromophenyl) acetaldehyde (3.5 mmol) in DCM (13 ml) at 0° C. The reaction mixture was stirred at rt for 2 h. The resulting reaction mixture was then poured into saturated $NaHCO_3$ solution (20 ml) and extracted with DCM (2×40 ml). The combined organic phase was collected, dried over $Na_2SO_4$, filtered and concentrated under reduced pressure yielding 2-bromo-2-(4-bromophenyl)acetaldehyde. The obtained material was used immediately for the next step without any further processing.

Step c.

Thiourea (7.0 mmol) was added to a solution of 2-bromo-2-(4-bromophenyl) acetaldehyde in EtOH (8 ml) at rt. The reaction mixture was heated at 90° C. for 6 h. The resulting reaction mixture was allowed to cool to rt and was evaporated under reduced pressure. The obtained residue was partitioned between saturated $NaHCO_3$ (20 ml) and DCM (30 ml). The organic layer was separated and the aqueous layer was further extracted with DCM (2×30 ml). The combined organic phase was collected, dried over $Na_2SO_4$, filtered and concentrated under reduced pressure yielding 5-(4-bromophenyl) thiazol-2-amine (2.37 mmol). MS: ES+ 255.1, 257.08; $^1$H NMR (400 MHz, DMSO-$d_6$) δ ppm 7.49-7.52 (m, 2H), 7.46 (s, 1H), 7.36-7.38 (m, 2H), 7.23 (br s, 2H).

Step d.

To a solution of (3S)—BOC-1-pyrrolidine-3-carboxylic acid (0.78 mmol) in THF (2 ml) was added T3P (50% in EtOAc) (1.17 mmol) at 0° C. The reaction mixture was stirred at 0° C. for 15 min. 5-(4-bromophenyl) thiazol-2-amine (0.78 mmol) and TEA (2.3 mmol) were then added to the reaction mixture. The reaction mixture was stirred at rt for 1 h. The resulting reaction mixture was poured into water (50 ml) and extracted with EtOAc (3×30 ml). The combined organic phase was collected, dried over Na$_2$SO$_4$, filtered and concentrated under reduced pressure. The resulting residue was purified by flash chromatography (1-2% MeOH in DCM) yielding tert-butyl (S)-3-((5-(4-bromophenyl)thiazol-2-yl)carbamoyl)pyrrolidine-1-carboxylate (0.37 mmol). MS: ES+ 452.34, 454.28

Step e.

Tert-butyl (S)-3-((5-(4-bromophenyl)thiazol-2-yl)carbamoyl)pyrrolidine-1-carboxylate (0.88 mmol), Pd(PPh$_3$)$_2$Cl$_2$ (0.13 mml) and CuI (0.05 mmol) were mixed in an oven dried glass tube under nitrogen atmosphere. The glass tube was slowly flushed with nitrogen and immediately sealed. Trimethylsilyl acetylene (4.42 mmol) and DIPEA (10 ml) were added to reaction mixture via syringe. A slow stream of nitrogen was again passed in the sealed tube. The tightly sealed glass tube was then subjected to heating at 110° C. (external temperature) for 16 h. The resulting reaction mixture was poured into water (30 ml) and extracted with EtOAc (2×50 ml). The combined organic phase was collected, dried over Na$_2$SO$_4$, filtered and concentrated under reduced pressure. The resulting residue was purified by flash chromatography (30-40% EtOAc in hexane) yielding tert-butyl (S)-3-((5-(4-((trimethylsilyl)ethynyl)phenyl)thiazol-2-yl)carbamoyl)pyrrolidine-1-carboxylate (0.63 mmol). MS: ES+ 470.53

Step f.

A solution of tert-butyl (S)-3-((5-(4-((trimethylsilyl)ethynyl)phenyl)thiazol-2-yl)carbamoyl)pyrrolidine-1-carboxylate (0.63 mmol) in MeOH (10 ml) was stirred at 0° C. for 5 min. 5M aqueous KOH solution (7 ml) was added to the reaction mixture at 0° C. The reaction mixture was stirred at rt for 30 min. The resulting reaction mixture was poured into water (40 ml) and extracted with EtOAc (2×50 ml). The combined organic phase was collected, dried over Na$_2$SO$_4$, filtered and concentrated under reduced pressure. The resulting residue was purified by flash chromatography (60-70% EtOAc in hexane) yielding tert-butyl (S)-3-((5-(4-ethynylphenyl) thiazol-2-yl) carbamoyl) pyrrolidine-1-carboxylate (0.1 mmol). This material was used directly for the next step without further processing.

Step g.

To a solution of tert-butyl (S)-3-((5-(4-ethynylphenyl) thiazol-2-yl) carbamoyl) pyrrolidine-1-carboxylate (0.08 mmol) in DCM (2 ml) was added TFA (0.3 ml) at 0° C. The reaction mixture was stirred at rt for 2 h. The resulting reaction mixture was concentrated under reduced pressure. The obtained residue was triturated with diethyl ether (5 ml) yielding (S)—N-(5-(4-ethynylphenyl) thiazol-2-yl)pyrrolidine-3-carboxamide TFA salt (0.067 mmol). The material was used directly for the next step without further purification. MS: ES+298.38.

Step h.

To a solution of (S)—N-(5-(4-ethynylphenyl) thiazol-2-yl)pyrrolidine-3-carboxamide TFA salt (0.12 mmol) in DCM (2 ml) was added K$_2$CO$_3$ (0.36 mmol) at rt and stirred for 15 min. Cyanogen bromide (0.14 mmol) was added to the reaction mixture at 0° C. The reaction mixture was then stirred at rt for 1 h. The resulting reaction mixture was poured into water (20 ml) and extracted with EtOAc (2×20 ml). The combined organic phase was dried over Na$_2$SO$_4$, filtered and concentrated under reduced pressure. The resulting residue was purified by flash chromatography (1.5-2.5% MeOH in DCM) yielding the title compound (0.01 mmol). MS: ES+ 322.96; $^1$H NMR (400 MHz, DMSO-d$_6$) δ ppm 12.49 (s, 1H), 7.99 (s, 1H), 7.64 (d, J=8.4 Hz, 2H), 7.51 (d, J=8.4 Hz, 2H), 4.29 (s, 1H), 3.61-3.66 (m, 1H), 3.53-3.58 (m, 1H), 3.40-3.48 (m, 3H), 2.16-2.23 (m, 1H), 2.06-2.10 (m, 1H).

Example 206 (S)-1-cyano-N-(5-(3-ethynylphenyl) thiazol-2-yl)pyrrolidine-3-carboxamide

Synthesised using a procedure similar to that described for Example 205 using 3-bromophenethyl alcohol in step a. MS: ES+ 323.06; $^1$H NMR (400 MHz, DMSO-d$_6$) δ ppm 12.48 (s, 1H), 7.99 (s, 1H), 7.61-7.66 (m, 2H), 7.49-7.53 (m, 1H), 7.39-7.46 (m, 1H), 4.29 (s, 1H), 3.61-3.67 (m, 1H), 3.53-3.59 (m, 1H), 3.42-3.50 (m, 2H), 3.36-3.42 (m, 1H), 2.16-2.26 (m, 1H), 2.08-2.12 (m, 1H).

Example 207 (3S)-1-cyano-N-(5-(N-(1-phenylethyl) sulfamoyl)pyridin-2-yl)pyrrolidine-3-carboxamide (Prepared According to Scheme 12)

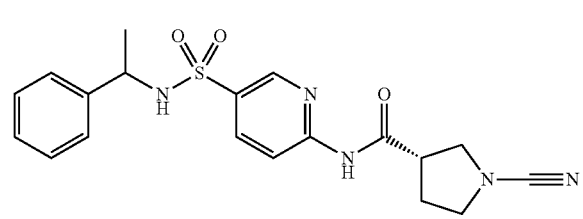 [SMILES: CC(NS(=O)(=O)c1ccc(NC(=O)[C@H]2CCN(C#N)C2)nc1)c1ccccc1]

Step a.

Chlorosulfonic acid (89.2 mmol) was slowly added to 2-aminopyridine (10.6 mmol) under nitrogen atmosphere at 0° C. Upon completion of addition the reaction mixture was allowed to warm to rt and was then heated at 150° C. for 2 h. The resulting reaction mixture was allowed to cool to rt, poured into ice cold water (100 ml) and neutralized by portion-wise addition of solid NaHCO$_3$. The resulting suspension was extracted with EtOAc (2×50 ml). The combined organic phase was dried over Na$_2$SO$_4$, filtered and concentrated under reduced pressure. The obtained crude material was crystallized from diethyl ether: heptane yielding 6-aminopyridine-3-sulfonyl chloride (5.75 mmol). MS: ES+ 193.19; $^1$H NMR (400 MHz, CDCl$_3$) δ ppm 8.71 (d, J=2.75 Hz, 1H), 7.98 (dd, J=9.00, 2.59 Hz, 1H), 6.59 (dd, J=9.16, 0.61 Hz, 1H), 5.41 (br s, 2H).

Step b.

To a solution of 1-phenylethan-1-amine (2.08 mmol) in THF (5 ml) was added TEA (2.5 mmol) at 0° C. and the reaction mixture was stirred for 5 min at 0° C. 6-Aminopyridine-3-sulfonyl chloride (2.08 mmol) was added to the reaction mixture at 0° C. and was then stirred at rt for 30 min. The resulting reaction mixture was poured into water (50 ml) and extracted with EtOAc (2×30 ml). The combined organic phase was collected, dried over Na$_2$SO$_4$, filtered and concentrated under reduced pressure. The resulting residue was purified by column chromatography (25% EtOAc in hexane) yielding 6-amino-N-(1-phenylethyl)pyridine-3-sulfonamide (1.62 mmol). MS: ES+ 278.33; ¹H NMR (400 MHz, DMSO₆) δ ppm 8.12 (dd, J=2.44, 0.61 Hz, 1H), 7.94 (d, J=8.24 Hz, 1H), 7.49 (dd, J=8.85, 2.44 Hz, 1H), 7.18-7.25 (m, 4H), 7.13-7.17 (m, 1H), 6.75 (br s, 2H), 6.35 (dd, J=8.85, 0.61 Hz, 1H), 4.25-4.30 (m, 1H), 1.22 (d, J=7.02 Hz, 3H).

Step c.

A mixture of anhydrous DCM (5 ml) and anhydrous DMF (1.39 mmol) was taken in a glass tube under nitrogen atmosphere at 0° C. Oxalyl chloride (1.39 mmol) was added to the reaction mixture under nitrogen atmosphere at 0° C. Anhydrous pyridine (1.39 mmol) was added to the reaction mixture under nitrogen atmosphere at 0° C. A solution of (S)-1-(tert-butoxycarbonyl)pyrrolidine-3-carboxylic acid (1.39 mmol) in DCM (5 ml) was added dropwise to the reaction mixture under nitrogen atmosphere at 0° C. The resulting reaction mixture was stirred under nitrogen atmosphere at rt for 1 h which resulted in formation of the desired acid chloride. Simultaneously a solution of 6-amino-N-(1-phenylethyl)pyridine-3-sulfonamide in DMF (3 ml) was prepared in another glass tube under nitrogen atmosphere. TEA (1.65 mmol) was added to the reaction mixture in the second glass tube under nitrogen atmosphere at 0° C. Thereafter the acid chloride solution from the first glass tube was carefully collected in a syringe and was added dropwise to the reaction mixture in the second glass tube under nitrogen atmosphere at 0° C. The final reaction mixture was stirred at rt for 16 h. The resulting reaction mixture was concentrated under reduced pressure and the obtained crude material was azeotropically distilled using DCM (2×50 ml). The resulting residue was purified by column chromatography (4% MeOH in DCM) yielding tert-butyl (3S)-3-((5-(N-(1-phenyl ethyl)-sulfamoyl)pyridin-2-yl)carbamoyl)pyrrolidine-1-carboxylate (0.46 mmol). MS: ES+ 475.71

Step d.

To a solution of tert-butyl (3S)-3-((5-(N-(1-phenylethyl) sulfamoyl)pyridin-2-yl)carbamoyl)pyrrolidine-1-carboxylate (0.46 mmol) in DCM (3 ml) was added TFA (2.5 ml) at 0° C. The reaction mixture was stirred at rt for 15 min. The resulting reaction mixture was concentrated under reduced pressure. The obtained residue was azeotropically distilled using DCM (2×15 ml) yielding (3S)—N-(5-(N-(1-phenylethyl)sulfamoyl)pyridin-2-yl)pyrrolidine-3-carboxamide TFA salt (0.37 mmol). This material was used directly for the next step without further purification.

Step e.

To a solution of (3S)—N-(5-(N-(1-phenylethyl)sulfamoyl)pyridin-2-yl)pyrrolidine-3-carboxamide TFA salt (0.37 mmol) in THF (3 ml) was added TEA (1.49 mmol) at 0° C. The reaction mixture was stirred at 0° C. for 5 min. Cyanogen bromide (0.44 mmol) was added to the reaction mixture at 0° C. The reaction mixture was then stirred at rt for 30 min. The resulting reaction mixture was poured into water (30 ml) and extracted with EtOAc (2×20 ml). The combined organic phase was collected, dried over Na₂SO₄, filtered and concentrated under reduced pressure. The resulting residue was purified by flash chromatography (10% MeOH in DCM) yielding the title compound (0.04 mmol). MS: ES+ 399.93; ¹H NMR (400 MHz, DMSO₆) δ ppm 11.07 (br s, 1H), 8.43-8.45 (m, 1H), 8.33-8.35 (m, 1H), 8.07-8.09 (m, 1H), 7.93-7.97 (m, 1H), 7.09-7.21 (m, 5H), 4.35-4.47 (m, 1H), 3.56-3.63 (m, 1H), 3.35-3.53 (m, 4H), 2.14-2.20 (m, 1H), 2.06-2.12 (m, 1H), 1.25-1.27 (m, 3H).

Example 208 (3S)-1-cyano-N-(5-(N-methyl-N-(1-phenylethyl)sulfamoyl)pyridin-2-yl)pyrrolidine-3-carboxamide

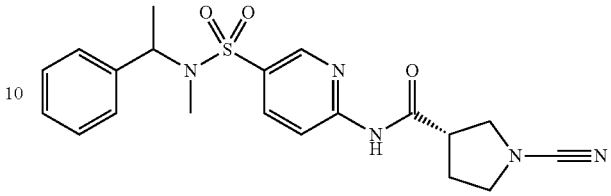

Synthesised using a procedure similar to that described for Example 207 using methyl(1-phenylethyl)amine in step b. MS: ES+ 414.68; ¹H NMR (400 MHz, CD₃OD) δ ppm 8.72-8.73 (m, 1H), 8.33-8.35 (m, 1H), 8.16-8.19 (m, 1H), 7.24-7.37 (m, 5H), 5.29-5.32 (m, 1H), 3.69-3.71 (m, 2H), 3.51-3.60 (m, 2H), 3.32-3.39 (m, 1H), 2.65 (s, 3H), 2.21-2.32 (m, 2H), 1.38-1.40 (m, 3H).

Example 209 (S)-1-cyano-N-(6-(5-methyl-1, 2, 4-oxadiazol-3-yl)imidazo[1,2-a]pyridin-2-yl)pyrrolidine-3-carboxamide (Prepared According to Scheme 13)

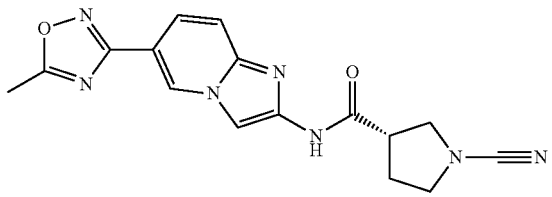 [SMILES: Cc1nc(-c2ccc3nc(NC(=O)[C@H]4CCN(C#N)C4)cn3c2)no1]

Step a.

To a solution of (3S)—BOC-1-pyrrolidine-3-carboxylic acid (4.65 mmol) in THF (20 ml) was added T3P (50% in EtOAc) (13.95 mmol) at 0° C. The reaction mixture was stirred at 0° C. for 15 min. 6-Bromoimidazo[1,2-a]pyridin-2-amine (4.65 mmol) and DIPEA (13.95 mmol) were added to the reaction mixture at 0° C. The reaction mixture was stirred at rt for 1 h. The resulting reaction mixture was poured into water (50 ml) and extracted with EtOAc (3×100 ml). The combined organic phase was collected, dried over Na₂SO₄, filtered and concentrated under reduced pressure yielding tert-butyl (S)-3-((6-bromoimidazo[1,2-a]pyridin-2-yl)carbamoyl)pyrrolidine-1-carboxylate (3.80 mmol). This material was used directly for the next step without further purification. MS: ES+ 409.50, 411.50.

Step b.

A solution of tert-butyl (S)-3-((6-bromoimidazo[1,2-a] pyridin-2-yl)carbamoyl)pyrrolidine-1-carboxylate (2.45 mmol) was prepared in DMF (20 ml) in a glass tube. Zn(CN)₂ (7.35 mmol) and TEA (4.90 mmol) were added to the reaction mixture at rt under nitrogen atmosphere. The reaction mixture was purged with nitrogen gas at rt for 15 min. Pd(dba)₂ (0.24 mol) and 1,1'-bis(diphenylphosphino) ferrocene (0.49 mmol) were added to the reaction mixture at rt under nitrogen atmosphere and the glass tube was sealed. The glass tube was subjected to heating at 100° C. (external temperature) for 24 h. The resulting reaction mixture was allowed to cool down to rt and poured into water (50 ml) and extracted with EtOAc (3×75 ml). The combined organic phase was collected, dried over Na₂SO₄, filtered and concentrated under reduced pressure. The resulting residue was purified by flash chromatography (neat DCM) yielding tert-butyl (S)-3-((6-cyanoimidazo[1,2-a]pyridin-2-yl) carbamoyl) pyrrolidine-1-carboxylate (2.25 mmol). MS: ES+ 356.53.

Step c.

To a solution of (tert-butyl (S)-3-((6-cyanoimidazo[1,2-a]pyridin-2-yl)carbamoyl)pyrrolidine-1-carboxylate (2.25 mmol) in IPA (30 ml) were added hydroxylamine hydrochloride (13.5 mmol) and TEA (15.7 mmol) at rt. The reaction mixture was heated at 70° C. for 3 h. The resulting reaction mixture allowed to cool down to rt and poured into water (50 ml) and extracted with EtOAc (3×75 ml). The combined organic phase was collected, dried over Na₂SO₄, filtered and concentrated under reduced pressure yielding tert-butyl (S)-3-((6-(N-hydroxycarbamimidoyl)imidazo[1,2-a]pyridin-2-yl)carbamoyl) pyrrolidine-1-carboxylate (1.28 mmol). This material was used directly for the next step without further purification. MS: ES+ 389.48.

Step d.

A solution of tert-butyl (S)-3-((6-(N-hydroxycarbamimidoyl)imidazo[1,2-a]pyridin-2-yl)carbamoyl) pyrrolidine-1-carboxylate (1.28 mmol) in N,N-dimethylacetamide dimethylacetal (20 ml) was heated at 100° C. for 1 h. The resulting reaction mixture allowed to cool down to rt and poured into water (25 ml) and extracted with EtOAc (3×25 ml). The combined organic phase was collected, dried over Na₂SO₄, filtered and concentrated under reduced pressure. The resulting residue was purified by flash chromatography (100% DCM) yielding tert-butyl (S)-3-((6-(5-methyl-1,2,4-oxadiazol-3-yl) imidazo[1,2-a]pyridin-2-yl)carbamoyl) pyrrolidine-1-carboxylate (0.70 mmol). This material was used directly for the next step without further purification. MS: ES+ 413.54.

Step e.

To a solution of tert-butyl (S)-3-((6-(5-methyl-1,2,4-oxadiazol-3-yl) imidazo[1,2-a]pyridin-2-yl)carbamoyl) pyrrolidine-1-carboxylate (0.70 mmol) in DCM (6 ml) was added TFA (1.2 ml) at 0° C. The reaction mixture was stirred at rt for 1 hr. The resulting reaction mixture was concentrated under reduced pressure. The obtained residue was triturated with diethyl ether (10 ml) yielding (S)—N-(6-(5-methyl-1,2,4-oxadiazol-3-yl)imidazo[1,2-a]pyridin-2-yl)pyrrolidine-3-carboxamide TFA salt (0.69 mmol). The material was used directly for the next step without further purification. MS: ES+ 313.53.

Step f.

To a solution of (S)—N-(6-(5-methyl-1,2,4-oxadiazol-3-yl)imidazo[1,2-a]pyridin-2-yl)pyrrolidine-3-carboxamide TFA salt (0.69 mmol) in THF (6 ml) was added K₂CO₃ (2.03 mmol) at 0° C. The reaction mixture was stirred at 0° C. for 30 min. Cyanogen bromide (1.03 mmol) was added to the reaction mixture at 0° C. The reaction mixture was then stirred at rt for 1 h. The resulting reaction mixture was poured into water (30 ml). The resulting solid precipitates were collected by filtration under reduced pressure and dried yielding the title compound (0.16 mmol). MS: ES+ 338.10; ¹H NMR (400 MHz, DMSO-d₆) δ ppm 11.06 (br s, 1H), 9.32 (s, 1H), 8.33 (s, 1H), 7.72 (dd, J=9.16, 1.53 Hz, 1H), 7.58 (d, J=9.16 Hz, 1H), 3.61-3.65 (m, 1H), 3.41-3.54 (m, 3H), 3.28-3.32 (m, 1H), 2.69 (s, 3H), 2.14-2.22 (m, 1H), 2.01-2.10 (m, 1H).

Example 210 (±)-trans-1-cyano-N-(6-(3,5-dimethyl-isoxazol-4-yl)imidazo[1,2-a]pyridin-2-yl)-4-(trifluoromethyl)pyrrolidine-3-carboxamide

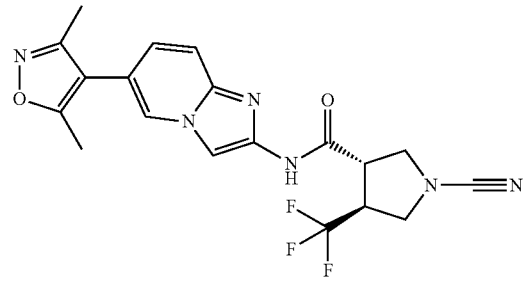 [SMILES: Cc1noc(C)c1-c1ccc2nc(NC(=O)[C@@H]3CN(C#N)C[C@H]3C(F)(F)F)cn2c1]

Synthesised using a procedure similar to that described for Example 109 using trans (±) [4-(trifluoromethyl)pyrrolidine]-1,3-dicarboxylic acid 1-tert-butyl ester, 2-amino-6-bromoimidazo[1,2-a]pyridine (prepared according to the method described in WO2012174312) and 3,5-dimethyl-isoxazole-4-boronic acid. LCMS: Method B, 3.57 min, MS: ES+ 419.31

Example 211 (S)-1-cyano-N-(4-(1-methyl-1H-pyrazol-4-yl)pyridin-2-yl)pyrrolidine-3-carboxamide

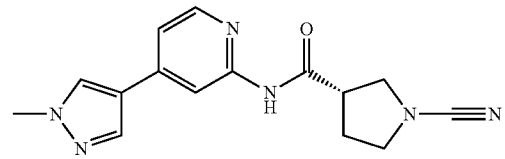 [SMILES: Cn1cc(-c2ccnc(NC(=O)[C@H]3CCN(C#N)C3)c2)cn1]

Synthesised using a procedure similar to that described for Example 138 using 2-amino-4-bromopyridine and 1-methyl-1H-pyrazole-4-boronic acid pinacol ester. LCMS: Method C, 2.96 min, MS: ES+ 297.02

Example 212 (S)-1-cyano-N-(5-(N,N-dimethylsulfamoyl)-4,5,6,7-tetrahydrothiazolo[5,4-c]pyridin-2-yl) pyrrolidine-3-carboxamide (Prepared According to Scheme 10, steps c, f, g)

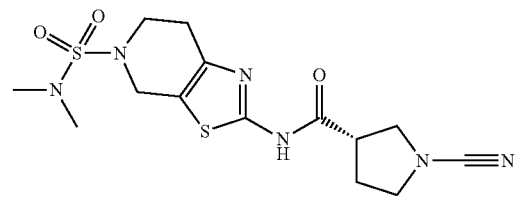 [SMILES: CN(C)S(=O)(=O)N1CCc2nc(NC(=O)[C@H]3CCN(C#N)C3)sc2C1]

Step c.

To a solution of Intermediate 14 (0.48 mmol) in DCM (3 ml) were added TEA (1.44 mmol) and N,N-dimethylaminosulfonyl chloride (0.57 mmol) at 0° C. The reaction mixture was stirred at rt for 2 h. The resulting reaction mixture was poured into water (150 ml) and extracted with EtOAc (3×50 ml). The combined organic phase was collected, washed with saturated NaHCO₃ (50 ml), 10% citric acid (50 ml), brine (50 ml) solution, dried over Na₂SO₄, filtered and concentrated under reduced pressure yielding tert-butyl (S)-3-((5-(N,N-dimethylsulfamoyl)-4,5,6,7-tetrahydrothiazolo[5,4-c]pyridin-2-yl)carbamoyl)pyrrolidine-1-carboxylate (0.39 mmol). This material was used directly for the next step without further purification. MS: ES+ 460.17.

Step f, g.

The title compound was synthesised from the intermediate above using a procedure similar to that described for steps f and g of Example 202. LCMS: Method B, retention time 3.15 min, MS: ES+ 385.14

Example 213 (S)-1-cyano-N-(5-(pyridazin-4-yl)thiazol-2-yl)pyrrolidine-3-carboxamide (Prepared According to scheme 14, Steps a, b, d-g)

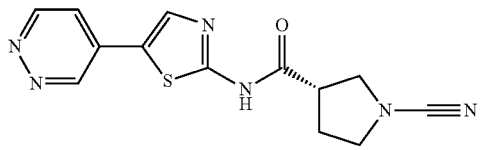 [SMILES: N#CN1CC[C@H](C(=O)Nc2ncc(-c3ccnnc3)s2)C1]

Step a.

A solution of Intermediate 20 (2.5 mmol) in dry THF (15 ml) was cooled at −78° C. 2.4M n-BuLi in Hexane (2.5 mmol) was added dropwise to the reaction mixture at −78° C. The reaction mixture was stirred at −78° C. for 20 min. 4,4,5,5-tetramethyl-1,3,2-dioxaborolane (3.0 mmol) was added to the reaction mixture at −78° C. The reaction mixture was stirred at −78° C. for 30 min. The resulting reaction mixture was allowed to warm to 0° C. and quenched by addition of saturated ammonium chloride solution (100 ml). The resulting mixture was extracted with EtOAc (2×100 ml). The combined organic phase was dried over Na₂SO₄, filtered and concentrated under reduced pressure to give tert-butyl (4-methoxybenzyl)-(5-(4,4,5,5-tetramethyl-1,3,2-dioxaborolan-2-yl)thiazol-2-yl)carbamate (quantitative yield). This material was immediately used for the next step without any purification.

Step b.

In a glass sealed tube a suspension of 4-bromopyridazine hydrobromide (1.25 mmol), tert-butyl (4-methoxybenzyl)-(5-(4,4,5,5-tetramethyl-1,3,2-dioxaborolan-2-yl)thiazol-2-yl)carbamate (2.18 mmol) and Na₂CO₃ (6.25 mmol) in toluene:water (15 ml:3 ml) was degassed with nitrogen for 30 min at rt. PdCl₂(dppf) (0.12 mmol) was added in to the reaction mixture at rt and the glass tube was sealed. The reaction mixture was heated at 100° C. (external) for 1 h. The resulting reaction mixture was cooled to rt, poured into saturated NaHCO₃ solution (300 ml) and extracted with EtOAc (3×150 ml). The combined organic phase was washed with brine solution (250 ml), dried over Na₂SO₄, filtered and concentrated under reduced pressure. The resulting residue was purified by flash chromatography (2.5% MeOH in DCM) yielding tert-butyl (4-methoxybenzyl)(5-(pyridazin-4-yl)thiazol-2-yl)carbamate (1.13 mmol). MS: ES+ 399.35; ¹H NMR (400 MHz, DMSO-d6) δ ppm 9.58-9.60 (m, 1H), 9.15 (dd, J=1.2, 5.6 Hz, 1H), 8.38 (s, 1H), 7.82-7.84 (m, 1H), 7.26 (d, J=8.4 Hz, 2H), 6.90 (d, J=8.8 Hz, 2H), 5.22 (s, 2H), 3.72 (s, 3H), 1.5 (s, 9H).

Step d.

A solution of tert-butyl (4-methoxybenzyl)(5-(pyridazin-4-yl)thiazol-2-yl)carbamate (0.75 mmol) in TFA (15 ml) was heated at 80° C. for 8 h. The resulting reaction mixture was concentrated under reduced pressure and water (75 ml) was added to it. The resulting mixture was extracted with EtOAc (3×50 ml). The obtained aqueous layer was basified by using solid NaHCO₃ and extracted with EtOAc (15×50 ml). The combined organic phase was dried over Na₂SO₄, filtered and concentrated under reduced pressure yielding 5-(pyridazin-4-yl)thiazol-2-amine (0.67 mmol). This material was used for the next step without further purification. MS: ES+ 179.01

Step e.

To a solution of (S)-1-(tert-butoxycarbonyl)pyrrolidine-3-carboxylic acid (1.17 mmol) in THF (7 ml) was added HATU (1.18 mmol) and DIPEA (2.35 mmol) at rt. The reaction mixture was stirred at rt for 2 h. 5-(pyridazin-4-yl)thiazol-2-amine (0.78 mmol) was added to the reaction mixture at rt. The reaction mixture was stirred at rt for 2 h. The resulting reaction mixture was poured into saturated NaHCO₃ solution (100 ml) and extracted with EtOAc (3×50 ml). The combined organic phase was dried over Na₂SO₄, filtered and concentrated under reduced pressure. The resulting residue was purified by flash chromatography (3.5% MeOH in DCM) yielding tert-butyl (S)-3-((5-(pyridazin-4-yl)thiazol-2-yl)carbamoyl)pyrrolidine-1-carboxylate (0.46 mmol). MS: ES+ 376.29; ¹H NMR (400 MHz, DMSO-d6) δ ppm 12.68 (s, 1H), 9.58-9.60 (m, 1H), 9.16 (dd, J=1.2, 5.6 Hz, 1H), 8.48 (s, 1H), 7.81-7.83 (m, 1H), 3.53-3.54 (m, 1H), 3.28-3.44 (m, 4H), 2.15-2.17 (m, 1H), 2.01-2.09 (m, 1H), 1.45 (s, 9H).

Step f, g.

The title compound was synthesised from the intermediate above using a procedure similar to that described for steps c and d of Example 140. LCMS: Method C, 1.87 min, MS: ES+ 300.88; 1H NMR (400 MHz, DMSO-d6) δ ppm 12.78 (s, 1H), 9.58-9.60 (m, 1H), 9.16 (d, J=5.6, 1H), 8.41 (s, 1H), 7.82-7.84 (m, 1H), 3.62-3.66 (m, 1H), 3.55-3.59 (m, 1H), 3.41-3.47 (m, 2H), 3.37-3.39 (m, 1H), 2.17-2.26 (m, 1H), 2.05-2.13 (m, 1H).

Compounds in Table 7 were synthesised using a procedure similar to that described for Example 213.

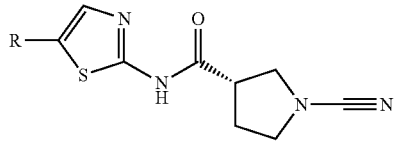

TABLE 7

| Ex | R | Name | Aryl halide CAS Number | LCMS Method RT (min) MS ES+ |
|---|---|---|---|---|
| 214 | 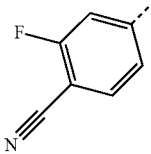 | (S)-1-cyano-N-(5-(4-cyano-3-fluorophenyl)thiazol-2-yl)pyrrolidine-3-carboxamide | 105942-08-3 | B 3.85 342.23 |
| 215 | 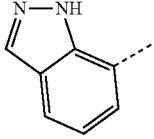 | (S)-N-(5-(1H-indazol-7-yl)thiazol-2-yl)-1-cyanopyrrolidine-3-carboxamide | 53857-58-2 | B 3.56 339.33 |
| 216 | 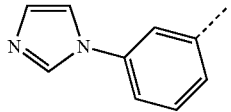 | (S)-N-(5-(3-(1H-imidazol-1-yl)phenyl)thiazol-2-yl)-1-cyanopyrrolidine-3-carboxamide | 25372-02-5 | C 2.77 364.88 |
| 217 | 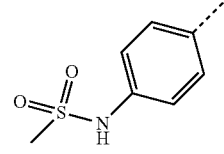 | (S)-1-cyano-N-(5-(4-(methylsulfonamido)phenyl)thiazol-2-yl)pyrrolidine-3-carboxamide | 4284-50-8 | B 3.27 392.37 |
| 218 | 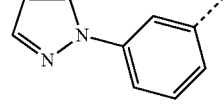 | (S)-N-(5-(3-(1H-pyrazol-1-yl)phenyl)thiazol-2-yl)-1-cyanopyrrolidine-3-carboxamide | 294877-33-1 | C 3.40 364.95 |
| 219 | 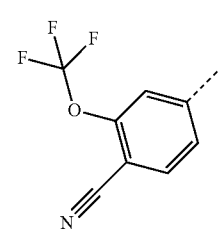 | (S)-1-cyano-N-(5-(4-cyano-3-(trifluoromethoxy)phenyl)thiazol-2-yl)pyrrolidine-3-carboxamide | 1187983-97-6 | C 3.63 407.93 |
| 220 | 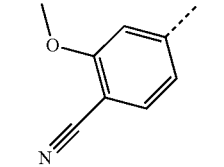 | (S)-1-cyano-N-(5-(4-cyano-3-methoxyphenyl)thiazol-2-yl)pyrrolidine-3-carboxamide | 330793-38-9 | C 3.03 353.90 |
| 221 | 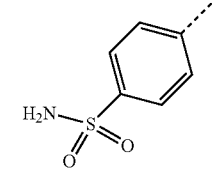 | (S)-1-cyano-N-(5-(4-sulfamoylphenyl)thiazol-2-yl)pyrrolidine-3-carboxamide | 701-34-8 | C 2.26 377.79 |
| 222 | 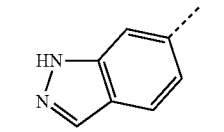 | (S)-N-(5-(1H-indazol-6-yl)thiazol-2-yl)-1-cyanopyrrolidine-3-carboxamide | 79762-54-2 | C/ 2.82/ 338.93 |

TABLE 7-continued

| Ex | R | Name | Aryl halide CAS Number | LCMS Method RT (min) MS ES+ |
|---|---|---|---|---|
| 223 | 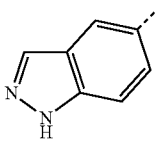 | (S)-N-(5-(1H-indazol-5-yl)thiazol-2-yl)-1-cyanopyrrolidine-3-carboxamide | 53857-57-1 | C 2.69 338.93 |
| 224 | 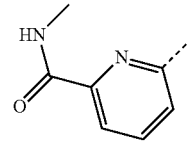 | (S)-6-(2-(1-cyanopyrrolidine-3-carboxamido)thiazol-5-yl)-N-methylpicolinamide | 337535-94-1 | C 2.46 356.96 |
| 225 | 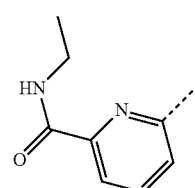 | (S)-6-(2-(1-cyanopyrrolidine-3-carboxamido)thiazol-5-yl)-N-ethylpicolinamide | 337535-98-5 | C 2.65 371.00 |
| 226 | 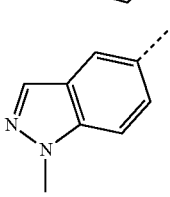 | (S)-1-cyano-N-(5-(1-methyl-1H-indazol-5-yl)thiazol-2-yl)pyrrolidine-3-carboxamide | 465529-57-1 | C 3.10 352.97 |

Example 227 (S)-1-cyano-N-(5-(1-(2-methoxyethyl)-1H-indazol-5-yl)thiazol-2-yl)pyrrolidine-3-carboxamide (Prepared According to Scheme 14, Steps c-g)

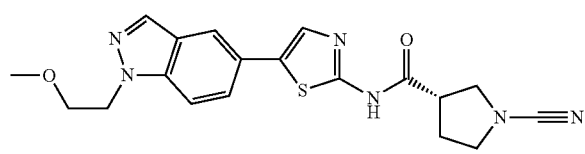 [SMILES: COCCn1ncc2cc(-c3cnc(NC(=O)[C@H]4CCN(C#N)C4)s3)ccc21]

Step c.

A mixture of Intermediate 20 (0.50 g, 1.25 mmol), Intermediate 18 (0.38 g, 1.25 mmol) and Cs$_2$CO$_3$ (0.77 g, 2.37 mmol) in 1,4-dioxane:water (9:1) (5 ml) was prepared in a glass vial. The reaction mixture was degassed for 30 min. Pd(dppf)Cl$_2$ (0.03 g, 0.03 mmol) was added to the reaction mixture at rt. The glass vial was sealed and subjected to heating at 80° C. (external temperature) for 2 h. The resulting reaction mixture was diluted with water (50 ml) and extracted with DCM (3×30 ml). The combined organic phase was collected, dried over Na$_2$SO$_4$, filtered and concentrated under reduced pressure. The resulting residue was purified by flash chromatography (25% EtOAc in hexane) yielding tert-butyl (4-methoxybenzyl)(5-(1-(2-methoxyethyl)-1H-indazol-5-yl)thiazol-2-yl)carbamate (0.37 g, 0.74 mmol). LCMS: Method A, 2.93 min, MS: ES+ 495.6.

Step d-g.

The title compound was synthesised from the intermediate above using a procedure similar to that described for steps d-g of Example 213. LCMS: Method C, 3.24 min, MS: ES+ 397.02

Example 228 (S)-1-cyano-N-(5-(2-oxoindolin-7-yl)thiazol-2-yl)pyrrolidine-3-carboxamide

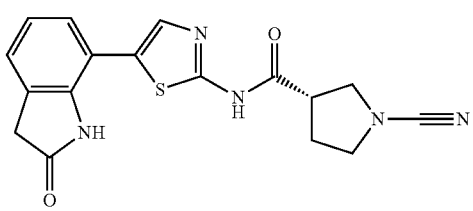 [SMILES: N#CN1CC[C@H](C(=O)Nc2ncc(-c3cccc4c3NC(=O)C4)s2)C1]

Synthesised using a procedure similar to that described for Example 227 using CAS number 1150271-45-6 in step c. LCMS: Method C, 2.82 min, MS: ES+ 353.90

Example 229 (S)-1-cyano-N-(5-(3-methyl-1H-indazol-5-yl)thiazol-2-yl)pyrrolidine-3-carboxamide

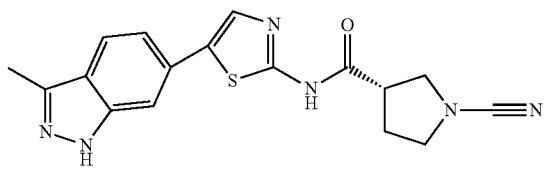 [SMILES: Cc1n[nH]c2cc(-c3cnc(NC(=O)[C@H]4CCN(C#N)C4)s3)ccc12]

Synthesised using a procedure similar to that described for Example 227 using CAS number 864771-17-5 in step c. LCMS: Method B, 3.31 min, MS: ES+ 353.57

Example 230 (S)—N-(5-(1H-indazol-4-yl)thiazol-2-yl)-1-cyanopyrrolidine-3-carboxamide

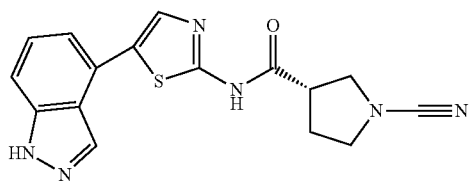 [SMILES: N#CN1CC[C@H](C(=O)Nc2ncc(-c3cccc4[nH]ncc34)s2)C1]

Synthesised using a procedure similar to that described for Example 227 using Intermediate 19 in step c. LCMS: Method A, 1.82 min, MS: ES+ 339.54

Example 231 (S)-1-cyano-N-(5-(4-fluoro-3-(methylcarbamoyl)phenyl)thiazol-2-yl) pyrrolidine-3-carboxamide (Prepared According to Scheme 15)

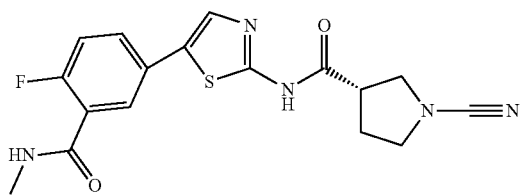 [SMILES: CNC(=O)c1cc(-c2cnc(NC(=O)[C@H]3CCN(C#N)C3)s2)ccc1F]

Step a.

This was carried out using a procedure similar to that described for Example 213 step a. LCMS: Method A, 3.21 min, MS: ES+ 473.40

Step b.

To a solution of methyl 5-(2-((tert-butoxycarbonyl)(4-methoxybenzyl)amino)thiazol-5-yl)-2-fluorobenzoate (0.23 g, 0.48 mmol), triazabicyclodecene (0.13 g, 0.97 mmol) in THF (5 ml) was added $CH_3NH_2$ (2M in THF) (1.21 ml, 2.43 mmol) at 0° C. The reaction mixture was stirred at rt for 4 h. The resulting reaction mixture was poured into water (25 ml) and extracted with EtOAc (3×25 ml). The combined organic layer was dried over $Na_2SO_4$, filtered and concentrated under reduced pressure. The resulting residue was purified by column chromatography (35% EtOAc in hexane) yielding tert-butyl (5-(4-fluoro-3-(methylcarbamoyl)phenyl)thiazol-2-yl)(4-methoxybenzyl)carbamate (0.13 g, 0.27 mmol). LCMS: Method A, 2.87 min, MS: ES+ 472.45

Steps c-f.

The title compound was synthesised from the intermediate above using a procedure similar to that described for Example 213 steps b-e. LCMS: Method A, 1.81 min, MS: ES+ 374.35

Compounds in Table 8 were synthesised using a procedure similar to that described for Example 231.

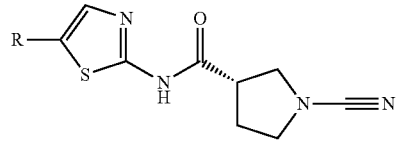

TABLE 8

| Ex | R | Name | Aryl halide CAS Number | LCMS Method RT (min) MS ES+ |
|---|---|---|---|---|
| 232 | ![structure] H₂N-C(=O)-phenyl- | (S)-N-(5-(3-carbamoylphenyl)thiazol-2-yl)-1-cyanopyrrolidine-3-carboxamide | 618-89-3 | B 2.88 342.32 |
| 233 | ![structure] CH₃-NH-C(=O)-phenyl- | (S)-1-cyano-N-(5-(3-(methylcarbamoyl)phenyl)thiazol-2-yl)pyrrolidine-3-carboxamide | 618-89-3 | C 2.59 356.07 |

TABLE 8-continued

| Ex | R | Name | Aryl halide CAS Number | LCMS Method RT (min) MS ES+ |
|---|---|---|---|---|
| 234 | ![structure] | (S)-1-cyano-N-(5-(3-(ethylcarbamoyl)phenyl)thiazol-2-yl)pyrrolidine-3-carboxamide | 618-89-3 | B 3.18 370.27 |
| 235 | ![structure] | (S)-1-cyano-N-(5-(3-(dimethylcarbamoyl)phenyl)thiazol-2-yl)pyrrolidine-3-carboxamide | 618-89-3 | B 3.12 370.27 |
| 236 | ![structure] | (S)-N-(5-(3-carbamoyl-4-fluorophenyl)thiazol-2-yl)-1-cyanopyrrolidine-3-carboxamide | 82702-31-6 | C 2.49 359.89 |
| 237 | ![structure] | (S)-N-(5-(3-carbamoyl-4-chlorophenyl)thiazol-2-yl)-1-cyanopyrrolidine-3-carboxamide | 107947-17-1 | A 1.77 376.30 |
| 238 | ![structure] | (S)-N-(5-(4-chloro-3-(methylcarbamoyl)phenyl)thiazol-2-yl)-1-cyanopyrrolidine-3-carboxamide | 107947-17-1 | A 1.82 390.35 |
| 239 | ![structure] | (S)-N-(5-(4-chloro-3-(prop-2-yn-1-ylcarbamoyl)phenyl)thiazol-2-yl)-1-cyanopyrrolidine-3-carboxamide | 107947-17-1 | B 3.59 414.59 |

Example 240 (S)-1-cyano-N-(5-(isopropylsulfonyl)-4,5,6,7-tetrahydropyrazolo[1,5-a]pyrazin-2-yl)pyrrolidine-3-carboxamide (Prepared According to Scheme 16, Steps a-j)

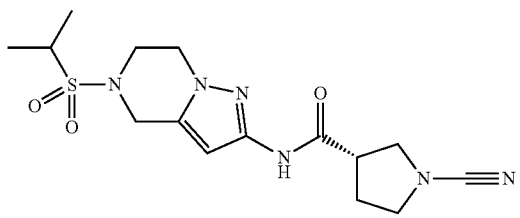 [SMILES: CC(C)S(=O)(=O)N1CCn2nc(NC(=O)[C@H]3CCN(C#N)C3)cc2C1]

Step a.

A solution of 3-nitro-1H-pyrazole-5-carboxylic acid (63.66 mmol) in MeOH (100 ml) and catalytic amount of DMF (0.05 ml) was stirred at 0° C. for 10 min. SOCl$_2$ (165.52 mmol) was added dropwise to the reaction mixture at 0° C. The reaction mixture was allowed to warm up to rt and then heated at 70° C. for 4 h. The resulting reaction mixture was concentrated under reduced pressure. The obtained residue was azeotropically distilled using MeOH (100 ml) yielding methyl 3-nitro-1H-pyrazole-5-carboxylate (quantitative). MS: ES-170.12.

Step b.

A solution of methyl 3-nitro-1H-pyrazole-5-carboxylate (65.27 mmol) and K$_2$CO$_3$ (326.4 mmol) in acetone (335 ml) was stirred at rt for 20 min. 1,2-Dibromoethane (195.81 mmol) was added to the reaction mixture at rt and then stirred at 60° C. for 1 h. The reaction mixture was filtered and the filtrate was concentrated under reduced pressure. The resulting residue was purified by column chromatography (9-10% EtOAc in hexane) yielding methyl 1-(2-bromoethyl)-3-nitro-1H-pyrazole-5-carboxylate (41.10 mmol) MS: ES+ 278.05 (M) 280 (M+2); $^1$H NMR (400 MHz, DMSO-d$_6$) δ ppm 7.63 (s, 1H), 5.01-5.05 (m, 2H), 3.92-3.96 (m, 2H), 3.90 (s, 3H).

Step c.

To a solution of methyl 1-(2-bromoethyl)-3-nitro-1H-pyrazole-5-carboxylate (41.11 mmol) in THF (171 ml) was added LiBH$_4$ (3.0M in THF) (82.21 mmol) at 0° C. The reaction mixture was stirred at rt for 2 h. EtOAc (125 ml) was added to the resulting reaction mixture followed by the addition of water (120 ml). The organic layer was separated and the aqueous layer was further extracted with EtOAc (3×60 ml). The combined organic phase was collected, washed with brine (60 ml) dried over Na$_2$SO$_4$, filtered and concentrated under reduced pressure to yield (1-(2-bromoethyl)-3-nitro-1H-pyrazol-5-yl)methanol (39.46 mmol). This material was directly used for the next step without further purification. MS: ES+ 250 (M) 252 (M+2); $^1$H NMR (400 MHz, DMSO-d$_6$) δ ppm 6.99 (s, 1H), 5.68 (t, J=5.2 Hz, 1H), 4.61-4.67 (m, 4H), 3.91 (t, J=6.4 Hz, 2H).

Step d.

A solution of (1-(2-bromoethyl)-3-nitro-1H-pyrazol-5-yl)methanol (39.43 mmol) in chloroform (394.4 ml) was added PBr$_3$ (39.43 mmol) dropwise at 0° C. The reaction mixture was stirred at rt for 2 h. The resulting reaction mixture was cooled to 0° C. and DCM (1000 ml) added. The mixture was basified with saturated NaHCO$_3$ solution (400 ml). The organic layer was separated and aqueous layer further extracted with DCM (3×400 ml). The combined organic phase was collected, washed with brine (650 ml), dried over Na$_2$SO$_4$, filtered and concentrated under reduced pressure. The resulting residue was purified by column chromatography (15% EtOAc in hexane) yielding 1-(2-bromoethyl)-5-(bromomethyl)-3-nitro-1H-pyrazole (18.27 mmol). $^1$H NMR (400 MHz, DMSO-d$_6$) δ ppm 7.22 (s, 1H), 4.91 (s, 2H), 4.71 (t, J=6.0 Hz, 2H), 3.93 (t, J=6.0 Hz, 2H).

Step e.

To a solution of 1-(2-bromoethyl)-5-(bromomethyl)-3-nitro-1H-pyrazole (18.27 mmol), aqueous ammonia (257 ml) in THF (68 ml) was stirred at rt for 72 h. The reaction mixture was concentrated under reduced pressure. The resulting residue was dissolved in THF (50 ml) and a saturated solution of K$_2$CO$_3$ (5 ml) added (to neutralise residual HBr). The mixture was concentrated under reduced pressure and the resulting residue was purified by column chromatography (4% MeOH in DCM) yielding 2-nitro-4,5,6,7-tetrahydropyrazolo[1,5-a]pyrazine (13.54 mmol). MS: ES+ 169.04.

Step f.

To a solution of 2-nitro-4,5,6,7-tetrahydropyrazolo[1,5-a]pyrazine (1.78 mmol) in DCM (9 ml) was added TEA (3.56 mmol) and the mixture stirred at rt for 15 min. Methanesulfonyl chloride (1.96 mmol) was added at rt and the reaction mixture was stirred at rt for 4 h. The reaction mixture was concentrated under reduced pressure. The resulting residue was purified by flash chromatography (40% EtOAc in Hexane) yielding 5-(isopropylsulfonyl)-2-nitro-4,5,6,7-tetrahydropyrazolo[1,5-a]pyrazine (1.51 mmol). MS: ES+275.5.

Step g.

To a solution of 5-(isopropylsulfonyl)-2-nitro-4,5,6,7-tetrahydropyrazolo[1,5-a]pyrazine (1.45 mmol) in MeOH (16 ml) was added 10% Pd/C (0.5% w/w) at rt. The reaction mixture was purged with H$_2$ gas at rt for 3 h. The resulting reaction mixture was carefully filtered through celite hyflow and concentrated under reduced pressure to yield 5-(isopropylsulfonyl)-4,5,6,7-tetrahydropyrazolo[1,5-a]pyrazin-2-amine (1.27 mmol). The material was immediately used for the next step. MS: ES+ 245.2.

Step h.

To a solution of (3S)—BOC-1-pyrrolidine-3-carboxylic acid (1.47 mmol) in THF (9 ml) was added T3P (50% in EtOAc) (3.65 mmol) at rt. The reaction mixture was stirred for 10 min. 5-(Isopropylsulfonyl)-4,5,6,7-tetrahydropyrazolo[1,5-a]pyrazin-2-amine (1.22 mmol) and DIPEA (3.68 mmol) were added to the reaction mixture and stirred at rt for 1 h. The resulting reaction mixture was poured into water (100 ml) and extracted with EtOAc (3×100 ml). The combined organic phase was washed with saturated NaHCO$_3$ (100 ml) and brine (100 ml) collected, dried over Na$_2$SO$_4$, filtered and concentrated under reduced pressure. The resulting residue was purified by flash chromatography (3% MeOH in DCM) yielding tert-butyl (S)-3-((5-(isopropylsulfonyl)-4,5,6,7-tetrahydropyrazolo[1,5-a]pyrazin-2-yl)carbamoyl)pyrrolidine-1-carboxylate (0.9 mmol). MS: ES+ 442.4.

Step i, j.

The title compound was synthesised from the intermediate above using a procedure similar to that described for steps c and d of Example 140. LCMS: Method C, 2.554 min, MS: ES+ 367.15; $^1$H NMR (400 MHz, DMSO-d6) δ ppm 10.63 (s, 1H), 6.39 (s, 1H), 4.53 (s, 2H), 4.00 (t, J=5.2 Hz, 2H), 3.79 (t, J=5.2 Hz, 2H), 3.55-3.59 (m, 1H), 3.37-3.50 (m, 4H), 3.67-3.33 (m, 1H), 2.10-2.15 (m, 1H), 1.96-2.01 (m, 1H), 1.23 (d, J=6.8 Hz, 6H).

Example 241 (S)-1-cyano-N-(5-phenyl-4,5,6,7-tetrahydropyrazolo[1,5-a]pyrazin-2-yl)pyrrolidine-3-carboxamide (Prepared According to Scheme 16, Steps a-e and g-j).

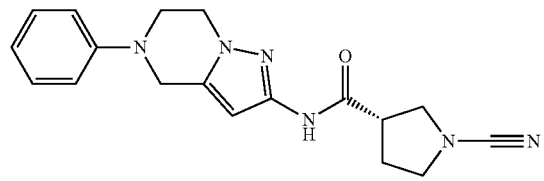 [SMILES: N#CN1CC[C@H](C(=O)Nc2cc3n(n2)CCN(c2ccccc2)C3)C1]

Steps a-e were carried out as described in Example 240

Step f.

A solution of 2-nitro-4,5,6,7-tetrahydropyrazolo[1,5-a]pyrazine (2.97 mmol), iodobenzene (3.56 mmol), Xantphos (0.44 mmol), Cs$_2$CO$_3$ (8.92 mmol) in 1,4-dioxane (15 ml) was stirred at rt under nitrogen atmosphere in a 25 ml glass vial. The reaction mixture was purged with nitrogen for 30 min. Pd(OAc)$_2$ (0.29 mmol) was added to the reaction mixture at rt under nitrogen atmosphere and the glass vial was sealed. The sealed vial was subjected to heat at 100° C. for 2 h. The resulting reaction mixture was cooled and poured into water (100 ml) and extracted with EtOAc (3×100 ml). The combined organic phase was washed with brine solution (100 ml), dried over Na$_2$SO$_4$, filtered and concentrated under reduced pressure. The resulting residue was purified by column chromatography (20% EtOAc in hexane) yielding 2-nitro-5-phenyl-4,5,6,7-tetrahydropyrazolo[1,5-a]pyrazine (Quantitative). MS: ES+ 245.43.

Steps g-j.

The title compound was synthesised from the intermediate above using a procedure similar to that described for Example 240 according to Scheme 16 steps g-j. LCMS: Method B, 3.511 min, MS: ES+ 337.78; $^1$H NMR (400 MHz, DMSO-d6) δ ppm 10.6 (s, 1H), 7.26 (t, J=8.4 Hz, 2H), 7.06 (d, J=8.0 Hz, 2H), 6.83 (t, J=7.6 Hz, 1H), 6.41 (s, 1H), 4.22 (s, 2H), 4.04 (t, J=5.6 Hz, 2H), 3.77 (t, J=5.4 Hz, 2H), 3.57 (t, J=7.6 Hz, 1H), 3.72-3.47 (m, 3H), 3.15-3.22 (m, 1H), 2.10-2.17 (m, 1H), 1.91-2.02 (m, 1H).

Example 242 (S)—N-(5-benzyl-4,5,6,7-tetrahydro-pyrazolo[1,5-a]pyrazin-2-yl)-1-cyanopyrrolidine-3-carboxamide (Prepared According to Scheme 16, Steps a-e and g-j).

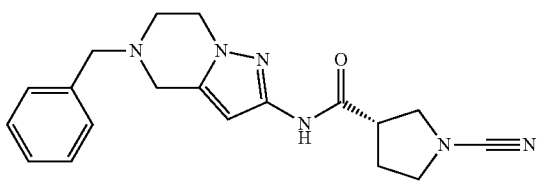 [SMILES: N#CN1CC[C@H](C(=O)Nc2cc3n(n2)CCN(Cc2ccccc2)C3)C1]

Steps a-e were carried out as described in Example 240

Step f.

To a solution of 2-nitro-4,5,6,7-tetrahydropyrazolo[1,5-a]pyrazine (2.08 mmol) in MeOH (14 ml) was added benzaldehyde (4.16 mmol) and acetic acid (5 drops) at 0° C. The reaction mixture was stirred at 0° C. for 1 h. NaCNBH₃ (4.16 mmol) was added to the reaction mixture at 0° C. The reaction mixture was stirred at rt for 1 h. The resulting reaction mixture was poured into water (100 ml) and extracted with EtOAc (3×100 ml). The combined organic phase was washed with brine (100 ml), dried over Na₂SO₄, filtered and concentrated under reduced pressure yielding 5-benzyl-2-nitro-4,5,6,7-tetrahydropyrazolo[1,5-a]pyrazine (quantitative). MS: ES+ 259.48.

Steps g-j.

The title compound was synthesised from the intermediate above using a procedure similar to that described for Example 240 according to Scheme 16 steps g-j. LCMS: Method C, 3.52 min, MS: ES+ 351.23; ¹H NMR (400 MHz, DMSO-d6) δ ppm 10.55 (s, 1H), 7.28-7.36 (m, 5H), 6.25 (s, 1H), 3.91 (t, J=5.6 Hz, 2H), 3.67 (s, 2H), 3.57 (s, 2H), 3.54 (s, 1H), 3.38-3.47 (m, 3H), 3.15-3.19 (m, 1H), 2.87 (t, J=5.2 Hz, 2H), 2.09-2.14 (m, 1H), 1.95-2.00 (m, 1H).

Example 243 (S)-1-cyano-N-(1-(4-cyano-3-(2-methoxyethoxy)phenyl)-1H-imidazol-4-yl)pyrrolidine-3-carboxamide

Example 244 (S)-1-cyano-N-(1-(2-cyano-5-(2-methoxyethoxy)phenyl)-1H-imidazol-4-yl)pyrrolidine-3-carboxamide (Prepared According to Scheme 17)

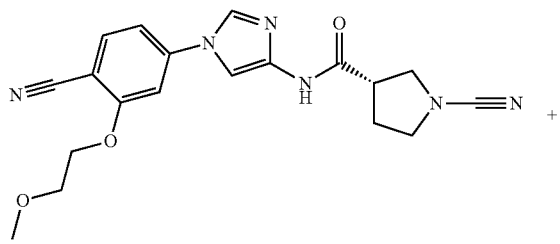
243

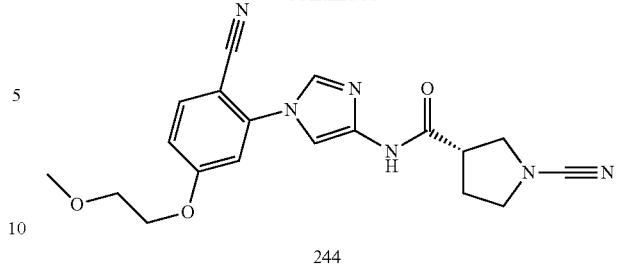
244

Step a.

To a solution of 2-methoxyethanol (1.08 g, 14.19 mmol) in THF (20 ml) was added NaH (60% in mineral oil) (0.56 g, 14.91 mmol) at 0° C. The reaction mixture was stirred at rt for 6 h. The reaction mixture was cooled to 0° C. and a solution of 2,4-difluorobenzonitrile (2.0 g, 14.19 mmol) in dioxane (20 ml) was added dropwise. The reaction mixture was stirred at rt for 16 h. The resulting reaction mixture was diluted with water (100 ml) and extracted with EtOAc (3×100 ml). The combined organic phase was dried over Na₂SO₄, filtered and concentrated under reduced pressure. The resulting residue was purified by flash chromatography (10% EtOAc in hexane) yielding a regio-isomeric mixture of 2-fluoro-4-(2-methoxyethoxy)benzonitrile and 4-fluoro-2-(2-methoxyethoxy)benzonitrile (1.5 g, 7.69 mmol). MS: ES+ 213.20

Step b.

To a solution of 2-fluoro-4-(2-methoxyethoxy)benzonitrile and 4-fluoro-2-(2-methoxyethoxy)benzonitrile (0.7 g, 3.59 mmol) in DMF (10 ml) was added K₂CO₃ (1.48 g, 10.77 mmol) at rt under nitrogen in a microwave tube. KI (0.06 g, 0.36 mmol) was added to the reaction mixture at rt. The reaction mixture was heated at 140° C. for 2 h in a microwave. The resulting reaction mixture was poured in to water (50 ml) and extracted with EtOAc (2×100 ml). The combined organic phase was washed with brine solution (50 ml). The organic phase was collected dried over Na₂SO₄, filtered and concentrated under reduced pressure. The resulting residue was purified by flash chromatography (30-40% EtOAc in hexane) yielding a regio-isomeric mixture of 2-(2-methoxyethoxy)-4-(4-nitro-1H-imidazol-1-yl)benzonitrile and 4-(2-methoxyethoxy)-2-(4-nitro-1H-imidazol-1-yl)benzonitrile (0.55 g, 1.91 mmol). MS: ES+ 289.20

Step c.

To a solution of 2-(2-methoxyethoxy)-4-(4-nitro-1H-imidazol-1-yl)benzonitrile and 4-(2-methoxyethoxy)-2-(4-nitro-1H-imidazol-1-yl)benzonitrile (0.5 g, 1.74 mmol) in THF (30 ml) was added 10% dry Pd/C (0.5 g) at rt. The reaction mixture was purged with H₂ gas at rt for 1 h. The resulting reaction mixture was carefully filtered through celite hyflow. The filtrate containing a regio-isomeric mixture of 4-(4-amino-1H-imidazol-1-yl)-2-(2-methoxyethoxy) benzonitrile and 2-(4-amino-1H-imidazol-1-yl)-4-(2-methoxyethoxy) benzonitrile was used immediately for the next step without distillation.

Step d.

To a solution of (S)-1-(tert-butoxycarbonyl)pyrrolidine-3-carboxylic acid (0.42 g, 1.95 mmol) in THF (20 ml) was added HATU (0.89 g, 2.34 mmol) and DIPEA (0.68 ml, 3.91 mmol) at rt. The reaction mixture was stirred at rt for 1 h. The filtrate obtained in step c containing regio-isomeric mixture of 4-(4-amino-1H-imidazol-1-yl)-2-(2-methoxyethoxy)benzonitrile and 2-(4-amino-1H-imidazol-1-yl)-4-(2-methoxyethoxy)benzonitrile (0.4 g, 1.56 mmol) in THF (40 ml) was added dropwise at rt. and stirred for 2 h. The resulting reaction mixture was poured into a saturated solution of NaHCO₃ (50 ml) and extracted with EtOAc (3×50 ml). The combined organic phase was dried over Na₂SO₄, filtered and concentrated under reduced pressure yielding a regio-isomeric mixture of tert-butyl (S)-3-((1-(4-cyano-3-(2-methoxyethoxy)phenyl)-1H-imidazol-4-yl)carbamoyl)pyrrolidine-1-carboxylate and tert-butyl (S)-3-((1-(2-cyano-5-(2-methoxyethoxy)phenyl)-1H-imidazol-4-yl)carbamoyl)pyrrolidine-1-carboxylate (0.81 g, 1.78 mmol). This material was used directly for the next step without further purification. LCMS: Method B, 4.02 min, 4.09 min, MS: ES+ 456.83

Step e, f.

The title compound was synthesised from the intermediate above using a procedure similar to that described for steps c and d of Example 140, providing a regioisomeric mixture of (S)-1-cyano-N-(1-(4-cyano-3-(2-methoxyethoxy)phenyl)-1H-imidazol-4-yl)pyrrolidine-3-carboxamide and (S)-1-cyano-N-(1-(2-cyano-5-(2-methoxyethoxy)phenyl)-1H-imidazol-4-yl)pyrrolidine-3-carboxamide (0.47 g, 1.24 mmol). LCMS: Method C, 3.44 min, 3.51 min, MS: ES+ 381.05

The regio-isomers were separated by preparative HPLC; mobile phase: (A) 100% water (B) 100% Acetonitrile, column: Sunfire C18, 250×19 mm, 5 μm, flow rate: 15 ml/min; to give(S)-1-cyano-N-(1-(4-cyano-3-(2-methoxyethoxy)phenyl)-1H-imidazol-4-yl)pyrrolidine-3-carboxamide. LCMS: Method C, 3.44 min, MS: ES+ 381.05; 1H NMR (400 MHz, DMSO-d6) δ ppm 10.79 (s, 1H), 8.36 (d, J=1.6 Hz, 1H), 7.92 (d, J=1.6 Hz, 1H), 7.85 (d, J=8.4 Hz, 1H), 7.50 (d, J=1.6 Hz, 1H), 7.41 (dd, J=2.0 Hz, 8.4 Hz, 1H), 4.43 (t, J=4.4 Hz, 2H), 3.75 (t, J=4.4 Hz, 2H), 3.58-3.63 (m, 1H), 3.46-3.50 (m, 2H), 3.38-3.44 (m, 1H), 3.33 (s, 3H), 3.24-3.29 (m, 1H), 2.13-2.17 (m, 1H), 2.00-2.07 (m, 1H) and (S)-1-cyano-N-(1-(2-cyano-5-(2-methoxyethoxy)phenyl)-1H-imidazol-4-yl)pyrrolidine-3-carboxamide LCMS: Method C, 3.35 min, MS: ES+ 381.05; 1H NMR (400 MHz, DMSO-d6) δ ppm 10.81 (s, 1H), 8.01 (d, J=1.6 Hz, 1H), 7.94 (d, J=8.8 Hz, 1H), 7.69 (d, J=1.6 Hz, 1H), 7.28 (d, J=2.4, 1H), 7.18 (dd, J=2.4, 8.4 Hz, 1H), 4.28-4.31 (m, 2H), 3.67-3.70 (m, 2H), 3.58-3.67 (m, 1H), 3.46-3.50 (m, 2H), 3.37-3.44 (m, 1H), 3.34 (s, 3H), 3.24-3.17 (m, 1H), 2.13-2.17 (m, 1H), 2.00-2.07 (m, 1H).

Example 245 (S)-1-cyano-N-(1-(4-cyano-3-(3-morpholinopropoxy)phenyl)-1H-imidazol-4-yl)pyrrolidine-3-carboxamide Example 246 (S)-1-cyano-N-(1-(2-cyano-5-(3-morpholinopropoxy)phenyl)-1H-imidazol-4-yl)pyrrolidine-3-carboxamide

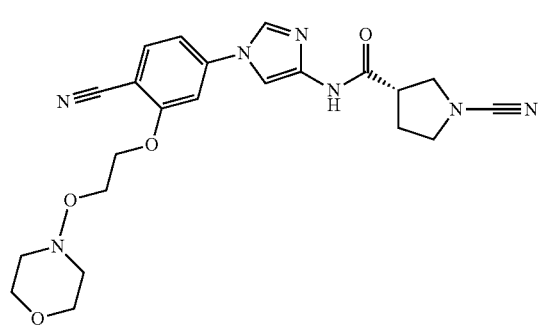

245

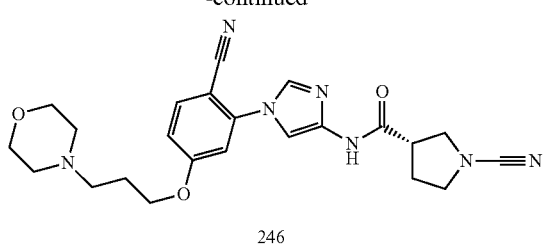

246

The title compound was synthesised as a mixture of regioisomers using a procedure similar to that described for Example 243/244 and separated after the final step by preparative HPLC; mobile phase: (A) 0.1% FA in water (B) Acetonitrile:Methanol (50:50), column: Sunfire C18, 250× 19 mm, 5 μm, flow rate: 15 ml/min to give (S)-1-cyano-N-(1-(4-cyano-3-(3-morpholinopropoxy)phenyl)-1H-imidazol-4-yl)pyrrolidine-3-carboxamide LCMS: Method B, 2.79 min, MS: ES+ 450.94; ¹H NMR (400 MHz, DMSO-d₆) δ ppm 10.82 (s, 1H), 8.36 (d, J=1.6 Hz, 1H), 7.91 (d, J=1.2 Hz, 1H), 7.84 (d, J=8.4 Hz, 1H), 7.48 (d, J=2.0 Hz, 1H), 7.40 (dd, J=2.0, 8.4 Hz, 1H), 4.32 (t, J=6.0 Hz, 2H), 3.58-3.62 (m, 5H), 3.40-3.49 (m, 4H), 3.23-3.35 (m, 2H), 2.43 (br s, 4H), 2.12-2.17 (m, 1H), 1.99-2.05 (m, 1H), 1.94-1.97 (m, 2H), and (S)-1-cyano-N-(1-(2-cyano-5-(3-morpholinopropoxy)phenyl)-1H-imidazol-4-yl)pyrrolidine-3-carboxamide LCMS: Method B, 2.58 min, MS: ES+ 450.74; ¹H NMR (400 MHz, DMSO-d₆) δ ppm 10.79 (s, 1H), 8.01 (d, J=1.2 Hz, 1H), 7.93 (d, J=8.8 Hz, 1H), 7.68 (d, J=1.2 Hz, 1H), 7.25 (d, J=2.4 Hz, 1H), 7.16 (dd, J=2.4, 8.8 Hz, 1H), 4.19 (t, J=6.4 Hz, 2H), 3.55-3.58 (m, 5H), 3.41-3.49 (m, 4H), 3.22-3.35 (m, 2H), 2.36 (br s, 4H), 2.12-2.17 (m, 1H), 2.00-2.07 (m, 1H), 1.87-1.93 (m, 2H).

Example 247 (S)-1-cyano-N-(1-(4-cyano-3-(((S)-tetrahydrofuran-3-yl)oxy)phenyl)-1H-imidazol-4-yl)pyrrolidine-3-carboxamide Example 248 (S)-1-cyano-N-(1-(2-cyano-5-(((S)-tetrahydrofuran-3-yl)oxy)phenyl)-1H-imidazol-4-yl)pyrrolidine-3-carboxamide

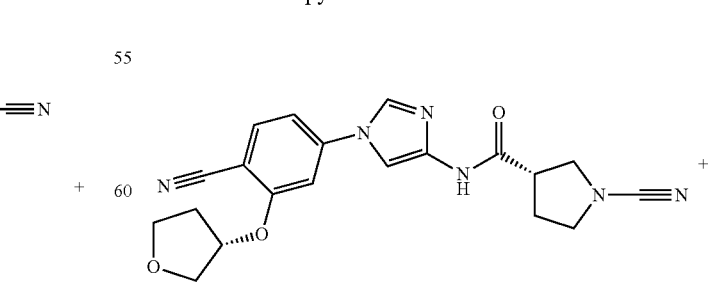

247

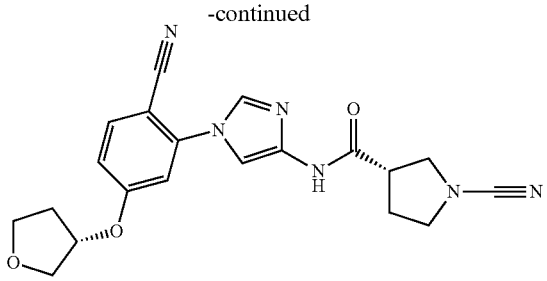

248

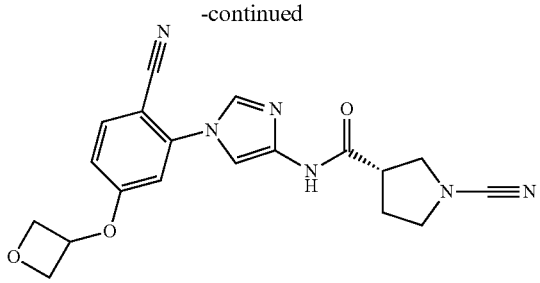

250

The title compound was synthesised as a mixture of regioisomers using a procedure similar to that described for Example 243/244 and separated after the final step by preparative HPLC; Mobile phase: (A) 100% hexane (B) IPA: Methanol (50:50), column: YMC PACKSIL, 250×20 mm, 5 μm, flow rate: 15 ml/min to give (S)-1-cyano-N-(1-(4-cyano-3-4 (S)-tetrahydrofuran-3-yl)oxy)phenyl)-1H-imidazol-4-yl)pyrrolidine-3-carboxamide, LCMS: Method B, 3.20 min, MS: ES+ 393.59; $^1$H NMR (400 MHz, DMSO-$d_6$) δ ppm 10.79 (s, 1H), 8.36 (d, J=1.6 Hz, 1H), 7.92 (d, J=1.6 Hz, 1H), 7.86 (d, J=8.4 Hz, 1H), 7.48 (d, J=1.6 Hz, 1H), 7.42 (dd, J=2.0, 8.4 Hz, 1H), 5.48 (s, 1H), 3.86-3.96 (m, 3H), 3.77-3.83 (m, 1H), 3.58-3.62 (m, 1H), 3.40-3.49 (m, 3H), 3.24-3.29 (m, 1H), 2.28-2.32 (m, 1H), 2.12-2.17 (m, 1H), 2.05-2.07 (m, 2H), and (S)-1-cyano-N-(1-(2-cyano-5-(((S)-tetrahydrofuran-3-yl)oxy)phenyl)-1H-imidazol-4-yl)pyrrolidine-3-carboxamide, LCMS: Method B, 3.38 min, MS: ES+ 393.19; $^1$H NMR (400 MHz, DMSO-$d_6$) δ ppm 10.81 (s, 1H), 8.00 (d, J=2.0 Hz, 1H), 7.95 (d, J=8.4 Hz, 1H), 7.67 (d, J=2.0 Hz, 1H), 7.25 (d, J=2.4 Hz, 1H), 7.17 (dd, J=2.4, 8.4 Hz, 1H), 5.28 (t, J=4.0 Hz, 1H), 3.83-3.91 (m, 3H), 3.76-3.79 (m, 1H), 3.58-3.62 (m, 1H), 3.24-3.49 (m, 4H), 2.27-2.33 (m, 1H), 2.14-2.18 (m, 1H), 1.98-2.05 (m, 1H), 1.88-1.92 (m, 1H).

Example 249 (S)-1-cyano-N-(1-(4-cyano-3-(oxetan-3-yloxy)phenyl)-1H-imidazol-4-yl)pyrrolidine-3-carboxamide Example 250 (S)-1-cyano-N-(1-(2-cyano-5-(oxetan-3-yloxy)phenyl)-1H-imidazol-4-yl)pyrrolidine-3-carboxamide

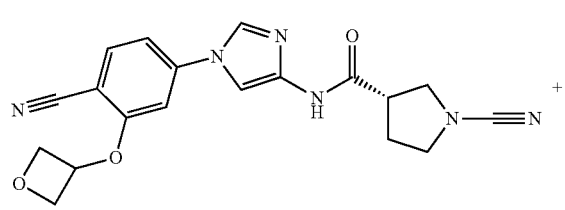

249

The title compound was synthesised as a mixture of regioisomers using a procedure similar to that described for Example 243/244 and separated after the final step by preparative HPLC; mobile phase: (A) 100% water (B) 100% Acetonitrile, column: X-bridge C18, 150×19 mm, 5 μm, flow rate: 13 ml/min, to give (S)-1-cyano-N-(1-(4-cyano-3-(oxetan-3-yloxy)phenyl)-1H-imidazol-4-yl)pyrrolidine-3-carboxamide, LCMS: Method B, 3.31 min, MS: ES+ 379.26; $^1$H NMR (400 MHz, DMSO-$d_6$) δ ppm 10.79 (s, 1H), 8.34 (s, 1H), 7.92 (s, 1H), 7.90 (s, 1H), 7.45 (d, J=8.0 Hz, 1H), 7.11 (s, 1H), 5.67 (t, J=4.8 Hz, 1H), 5.00 (t, J=6.8 Hz, 2H), 4.60 (t, J=6.4 Hz, 2H), 3.58-3.62 (m, 1H), 3.4-3.49 (m, 3H), 3.23-3.27 (m, 1H), 2.12-2.16 (m, 1H), 2.03-2.05 (m, 1H), and (S)-1-cyano-N-(1-(2-cyano-5-(oxetan-3-yloxy)phenyl)-1H-imidazol-4-yl)pyrrolidine-3-carboxamide, LCMS: Method B, 3.24 min, MS: ES+ 379.26; $^1$H NMR (400 MHz, DMSO-$d_6$) δ ppm 10.81 (s, 1H), 7.96-7.99 (m, 2H), 7.67 (d, J=1.6 Hz, 1H), 7.13 (d, J=2.4 Hz, 1H), 7.07 (dd, J=2.4, 8.4 Hz, 1H), 5.5 (t, J=5.2 Hz, 1H), 4.96 (t, J=6.8 Hz, 2H), 4.55-4.58 (m, 2H), 3.58-3.62 (m, 1H), 3.39-3.49 (m, 3H), 3.24-3.29 (m, 1H), 2.12-2.16 (m, 1H), 2.00-2.05 (m, 1H).

Example 251 (S)-1-cyano-N-(4-(pyrazolo[1,5-a]pyrimidin-7-yl)pyridin-2-yl)pyrrolidine-3-carboxamide (Prepared According to Scheme 18)

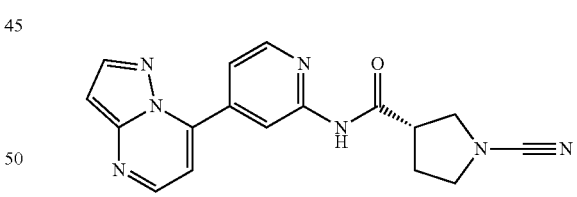

Step a.

To a solution of 2-amino-4-bromo pyridine (2.50 g, 14.45 mmol) and (S)-1-N—BOC-beta-proline (3.72 g, 17.34 mmol) in pyridine (50 ml) was stirred at rt for 15 min, phosphorous oxychloride (2.67 ml, 28.90 mmol) was added dropwise to the reaction mixture at 0° C. and then stirred at rt for 1 h. The resulting reaction mixture was poured into water (100 ml) and extracted with EtOAc (3×30 ml). The combined organic phase was dried over $Na_2SO_4$, filtered and concentrated under reduced pressure. The resulting residue was purified by flash chromatography (20% EtOAc in hexane) yielding tert-butyl (S)-3-((4-bromopyridin-2-yl)carbamoyl)pyrrolidine-1-carboxylate (5.0 g, 13.55 mmol). LCMS: Method A, 2.39 min, MS: ES+ 370.1, 372.1

Step b.

To a solution of tert-butyl (S)-3-((4-bromopyridin-2-yl)carbamoyl)pyrrolidine-1-carboxylate (5.0 g, 13.50 mmol) in 1,4-dioxane were added bis (pinacolato) diboron (5.14 g, 20.26 mmol) and potassium acetate (2.64 g, 27.01 mmol) at rt. The reaction mixture was degassed for 30 min at rt. Pd$_2$(dba)$_3$ (0.61 g, 0.67 mmol) and X-phos (0.64 g, 1.35 mmol) were added to the reaction mixture at rt. The reaction mixture was heated at 110° C. for 2 h. The resulting reaction mixture was filtered through celite and washed with MeOH (100 ml). The organic phase was concentrated under reduced pressure yielding tert-butyl (S)-3-((4-(4,4,5,5-tetramethyl-1,3,2-dioxaborolan-2-yl)pyridin-2-yl)carbamoyl)pyrrolidine-1-carboxylate (11.7 g, quantitative). This material was used directly for the next step without further purification. LCMS: Method A, 1.71 min, MS: ES+ 336.5; 280.38

ES+ 334.37; $^1$H NMR (400 MHz, DMSO-d$_6$) δ ppm 10.92 (s, 1H), 9.28 (dd, J=7.6 Hz, 0.8 Hz, 1H), 8.91 (s, 1H), 8.52 (d, J=4.8 Hz, 1H), 8.33 (d, J=2.4 Hz, 1H), 7.88 (dd, J=5.2 Hz, 1.6 Hz, 1H), 7.67 (d, J=7.2 Hz, 1H), 6.92 (dd, J=2.4 Hz, 0.8 Hz, 1H), 3.61-3.65 (m, 1H), 3.53-3.57 (m, 1H), 3.37-3.50 (m, 3H), 2.18-2.21 (m, 1H), 2.09-2.12 (m, 1H).

Compounds in Table 9 were synthesised using a procedure similar to that described for Example 251.

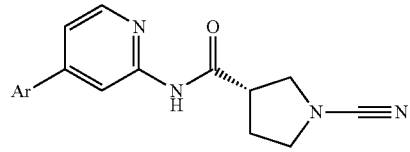

TABLE 9

| Ex | R1 | Name | Aryl halide CAS Number | LCMS Method RT (min) MS ES+ |
|---|---|---|---|---|
| 252 | imidazo[1,2-a]pyrimidin-5-yl | (S)-1-cyano-N-(4-(imidazo[1,2-a]pyrimidin-5-yl)pyridin-2-yl)pyrrolidine-3-carboxamide | 944896-82-6 | B 2.46 334.12 |
| 253 | imidazo[1,2-a]pyridin-5-yl | (S)-1-cyano-N-(4-(imidazo[1,2-a]pyridin-5-yl)pyridin-2-yl)pyrrolidine-3-carboxamide | 69214-09-1 | C 3.07 333.14 |
| 254 | imidazo[1,2-a]pyrazin-6-yl | (S)-1-cyano-N-(4-(imidazo[1,2-a]pyrazin-6-yl)pyridin-2-yl)pyrrolidine-3-carboxamide | 912773-24-1 | C 2.85 334.21 |
| 255 | imidazo[1,2-a]pyrimidin-6-yl | (S)-1-cyano-N-(4-(imidazo[1,2-a]pyrimidin-6-yl)pyridin-2-yl)pyrrolidine-3-carboxamide | 865156-68-9 | C 2.69 334.14 |

Step c.

A solution of 7-chloropyrazolo[1,5-a]pyrimidine (0.18 g, 1.17 mmol), tert-butyl (S)-3-((4-(4,4,5,5-tetramethyl-1,3,2-dioxaborolan-2-yl)pyridin-2-yl)carbamoyl)pyrrolidine-1-carboxylate (2.43 g, 5.86 mmol) and K$_2$CO$_3$ (0.48 g, 3.52 mmol) in DMF (10 ml) was prepared in a glass vial. The reaction mixture was degassed for 20 min. Pd(dppf)Cl$_2$ (0.06 g, 0.093 mmol) was added and the reaction mixture was heated at 80° C. for 2 h. The resulting reaction mixture was cooled to rt and poured into water (50 ml). The obtained mixture was extracted with EtOAc (2×50 ml). The combined organic phase was washed with water (100 ml), dried over Na$_2$SO$_4$, filtered and concentrated under reduced pressure. The resulting residue was purified by flash chromatography (60% EtOAc in hexane) yielding tert-butyl (S)-3-((4-(pyrazolo[1,5-a]pyrimidin-7-yl)pyridin-2-yl)carbamoyl)pyrrolidine-1-carboxylate (0.28 g, 0.68 mmol). LCMS: Method A, 2.14 min, MS: ES+ 409.28.

Steps d,e.

The title compound was synthesised from the intermediate above using a procedure similar to that described for Example 193 steps f,g. LCMS: Method B, 3.23 min, MS:

Example 256 (S)-1-cyano-N-(1,7-naphthyridin-6-yl)pyrrolidine-3-carboxamide (Prepared According to Scheme 1)

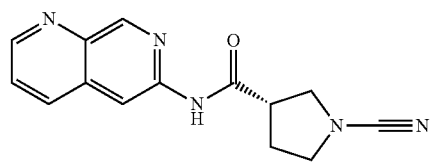 [SMILES: N#CN1CC[C@H](C(=O)Nc2cc3cccnc3cn2)C1]

Step a.

To a solution of 1,7-naphthyridin-6-amine (0.22 g, 0.98 mmol) and (3S)—BOC-1-pyrrolidine-3-carboxylic acid (0.21 g, 0.98 mmol) in DCM (10 ml) was added pyridine (0.95 ml, 11.78 mmol) at 0° C. Phosphorous oxychloride (0.75 ml, 7.86 mmol) was added dropwise to the reaction mixture at 0° C. and then stirred at rt for 20 min. The resulting reaction mixture was poured into saturated NaHCO₃ solution (50 ml) and extracted with DCM (3×50 ml). The combined organic phase was collected, washed with brine (25 ml), dried over Na₂SO₄, filtered and concentrated under reduced pressure. The resulting residue was purified by column chromatography (70-80% EtOAc in n-hexane) yielding tert-butyl (S)-3-((1, 7-naphthyridin-6-yl)carbamoyl)pyrrolidine-1-carboxylate (0.12 g, 0.35 mmol). LCMS: Method A, 1.90 min, MS: ES+ 343.34.

Step b, c.

The title compound was synthesised from the intermediate above using a procedure similar to that described for steps c and d of Example 140. LCMS: Method B, 2.72 min, MS: ES+ 268.11

Compounds in Table 10 were synthesised using a procedure similar to that described for Example 256.

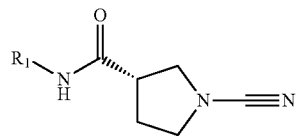

TABLE 10

| Ex | R1 | Name | Amine CAS Number | LCMS Method RT (min) MS ES+ |
|---|---|---|---|---|
| 257 | (3-chlorophenyl-pyrimidin-4-yl) | (S)-N-(6-(3-chlorophenyl)pyrimidin-4-yl)-1-cyanopyrrohdine-3-carboxamide | 1192814-53-1 | B 4.01 328.17 |
| 258 | (2-amino-[4,4'-bipyridin]-2-yl) | (S)-N-(2'-amino-[4,4'-bipyridin]-2-yl)-1-cyanopyrrolidine-3-carboxamide | Intermediate 24 | C 2.82 308.99 |
| 259 | (2'-(methylamino)-[4,4'-bipyridin]-2-yl) | (S)-1-cyano-N-(2'-(methylamino)-[4,4'-bipyridin]-2-yl)pyrrolidine-3-carboxamide | Intermediate 25 | C 3.10 323.03 |
| 260 | (N-methylisoquinoline-6-carboxamide) | (S)-3-(1-cyanopyrrolidine-3-carboxamido)-N-methylisoquinohne-6-carboxamide | Intermediate 26 | A 1.67 324.39 |

Example 261 (S)-1-cyano-N-(6-(3,5-dimethylisoxazol-4-yl)isoquinolin-3-yl)pyrrolidine-3-carboxamide (Prepared According to Scheme 5)

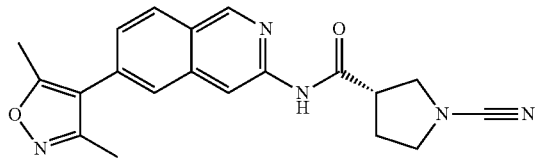 [SMILES: Cc1noc(C)c1-c1ccc2cnc(NC(=O)[C@H]3CCN(C#N)C3)cc2c1]

Step a.

This was carried out using a procedure similar to that described for Example 138 using 6-bromoisoquinolin-3-amine and 3,5-dimethylisoxazole-4-boronic acid pinacol ester. LCMS: Method A, 1.69 min, MS: ES+ 240.15.

Step b.

To a solution of 6-(3,5-dimethylisoxazol-4-yl)isoquinolin-3-amine (0.30 g, 1.25 mmol) and (3S)—BOC-1-pyrrolidine-3-carboxylic acid (0.30 g, 1.38 mmol) in DCM (15 ml) was added pyridine (1.10 ml, 13.81 mmol) at 0° C. The reaction mixture was stirred for 20 min at 0° C. Phosphorous oxychloride (1.20 ml, 12.547 mmol) was added dropwise to the reaction mixture at 0° C. and then stirred at rt for 2 hr. The resulting reaction mixture was poured into water (30 ml) and extracted with DCM (3×25 ml). The combined organic phase was collected, washed with 10% citric acid solution (25 ml) then washed with saturated NaHCO$_3$ solution (2×30 ml), dried over Na$_2$SO$_4$, filtered and concentrated under reduced pressure. The resulting residue was purified by flash chromatography (1% MeOH in DCM) yielding tert-butyl (S)-3-((6-(3,5-dimethylisoxazol-4-yl)isoquinolin-3-yl)carbamoyl) pyrrolidine-1-carboxylate (0.20 g, 0.46 mmol). LCMS: Method A, 2.32 min, MS: ES+437.46.

Step c, d.

The title compound was synthesised from the intermediate above using a procedure similar to that described for steps c and d of Example 138. LCMS: Method B, 4.62 min, MS: ES+ 362.34.

Example 262 (S)—N-(4-(1H-indazol-4-yl)pyridin-2-yl)-1-cyanopyrrolidine-3-carboxamide

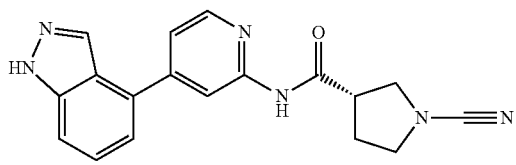 [SMILES: N#CN1CC[C@H](C(=O)Nc2cc(-c3cccc4[nH]ncc34)ccn2)C1]

Synthesised using a procedure similar to that described for Example 261 using 1-BOC-4-bromo-1H-indazole and 2-aminopyridine-4-boronic acid pinacol ester. LCMS: Method C, 3.30 min, MS: ES+ 332.94.

Example 263 (S)-1-cyano-N-(6-ethynylisoquinolin-3-yl)pyrrolidine-3-carboxamide (Prepared According to Scheme 191

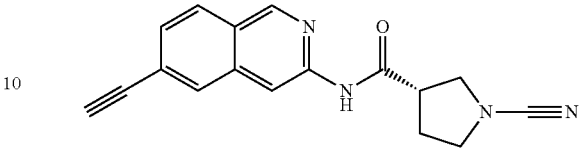

Step a.

To a solution of 6-bromoisoquinolin-3-amine (0.40 g, 1.79 mmol) and (3S)—BOC-1-pyrrolidine-3-carboxylic acid (0.42 g, 1.97 mmol) in DCM (5 ml) was added pyridine (4 ml) at 0° C. POCl$_3$ (0.34 g, 2.15 mmol) was added dropwise to the reaction mixture at 0° C. and stirred for 30 min. The resulting reaction mixture was diluted with water (100 ml) and extracted with EtOAc (3×100 ml). The combined organic layer was washed with 10% aqueous solution of citric acid (2×50 ml), dried over Na$_2$SO$_4$, filtered and concentrated under reduced pressure. The resulting residue was purified by column chromatography (2% MeOH in DCM) yielding tert-butyl (S)-3-((6-bromoisoquinolin-3-yl)carbamoyl)pyrrolidine-1-carboxylate (0.39 g, 0.92 mmol). LCMS: Method A, 2.63 min, MS: ES+ 420.28; 422.3

Step b.

The solution of tert-butyl (S)-3-((6-bromoisoquinolin-3-yl)carbamoyl)pyrrolidine-1-carboxylate (0.25 g, 0.59 mmol) and CuI (0.005 g, 0.03 mmol) in diisopropylamine (5 ml) was degassed at rt for 15 min. Pd(PPh$_3$)$_2$Cl$_2$ (0.06 g, 0.09 mmol) and trimethylsilyl acetylene (0.29 g, 2.99 mmol) were added to reaction mixture at rt. The reaction mixture was heated at 120° C. for 30 min. The resulting reaction mixture was concentrated under reduce pressure. The resulting residue was purified by column chromatography (20-25% EtOAc in hexane) yielding tert-butyl (S)-3-((6-((trimethyl silyl)ethynyl)isoquinolin-3-yl)carbamoyl)pyrrolidine-1-carboxylate (0.31 g, quantitative). LCMS: Method A, 2.90 min, MS: ES+ 438.72.

Step c.

A solution of tert-butyl (S)-3-((6-((trimethylsilyl)ethynyl)isoquinolin-3-yl)carbamoyl)pyrrolidine-1-carboxylate (0.30 g, 0.68 mmol) in MeOH (5 ml) was added K$_2$CO$_3$ (0.24 g, 1.71 mmol) at 0° C. The reaction mixture was stirred at rt for 1 h. The resulting reaction mixture was filtered to remove unreacted K$_2$CO$_3$, washed with MeOH (10 ml). The combined filtrate was concentrated under reduced pressure. The resulting residue was purified by flash chromatography (25-30% EtOAc in hexane) yielding tert-butyl (S)-3-((6-ethynylisoquinolin-3-yl)carbamoyl)pyrrolidine-1-carboxylate (0.24 g, 0.65 mmol). LCMS: Method A, 2.46 min, MS: ES+ 366.28.

Steps d,e.

The title compound was synthesised from the intermediate above using a procedure similar to that described for Example 193 steps f,g. LCMS: Method C, 4.07 min, MS: ES+ 291.10; $^1$H NMR (400 MHz, DMSO-d$_6$) δ ppm 10.89 (s, 1H), 9.17 (s, 1H), 8.48 (s, 1H), 8.05-8.08 (m, 2H), 7.53 (dd, J=8.40 Hz, 1.20 Hz, 1H), 4.47 (s, 1H), 3.62-3.66 (m, 1H), 3.48-3.56 (m, 2H), 3.34-3.47 (m, 2H), 2.16-2.24 (m, 1H), 2.04-2.13 (m, 1H).

Example 264 (2S,3S)-1-cyano-N-(6-ethynylisoquinolin-3-yl)-2-methylpyrrolidine-3-carboxamide

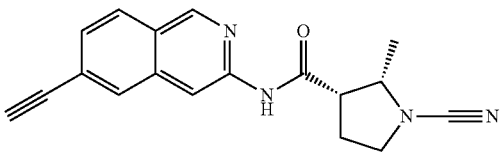 [SMILES: C#Cc1ccc2cnc(NC(=O)[C@H]3CCN(C#N)[C@H]3C)cc2c1]

Synthesised using a procedure similar to that described for Example 263 using Intermediate 1. LCMS: Method C, 4.22 min, MS: ES+ 305.14; $^1$H NMR (400 MHz, DMSO-$d_6$) δ ppm 10.87 (s, 1H), 9.17 (s, 1H), 8.49 (s, 1H), 8.05-8.09 (m, 2H), 7.53 (dd, J=8.40 Hz, 1.20 Hz, 1H), 4.48 (s, 1H), 3.97-4.04 (m, 1H), 3.62-3.68 (m, 1H), 3.36-3.45 (m, 2H), 2.17-2.25 (m, 1H), 1.99-2.07 (m, 1H), 1.15 (d, J=6.40 Hz, 3H).

Example 265 (S)-3-(1-cyanopyrrolidine-3-carboxamido)isoquinoline-6-carboxamide (Prepared According to Scheme 20)

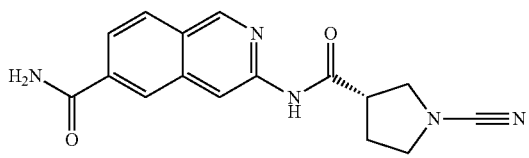 [SMILES: N#CN1CC[C@H](C(=O)Nc2cc3cc(C(N)=O)ccc3cn2)C1]

Step a.

To a solution of methyl 3-((tert-butoxycarbonyl)amino)isoquinoline-6-carboxylate (prepared according to steps a-b of the method described for the synthesis of Intermediate 26, 0.36 g, 1.19 mmol) in DCM (15 ml) was added TFA (3.6 ml) at 0° C. The reaction mixture was stirred at rt for 3 h. The resulting reaction mixture was concentrated under reduced pressure. The resulting residue was triturated with Et$_2$O (10 ml) and dried to yield methyl 3-aminoisoquinoline-6-carboxylate TFA salt (0.37 g, 1.15 mmol). LCMS: Method A, 1.66 min, MS: ES+ 203.18. This material was used directly for the next step without further purification.

Step b.

To a solution of methyl 3-aminoisoquinoline-6-carboxylate TFA salt (0.35 g, 1.11 mmol) and (3S)—BOC-1-pyrrolidine-3-carboxylic in DCM (20 ml) was added pyridine (1.34 ml, 16.61 mmol) at 0° C. Phosphorous oxychloride (1.06 ml, 11.07 mmol) was added dropwise to the reaction mixture at 0° C. The reaction mixture was stirred at rt for 20 min. The resulting reaction mixture was poured into saturated NaHCO$_3$ solution (50 ml) and extracted with DCM (2×50 ml). The combined organic phase was collected, dried over Na$_2$SO$_4$, filtered and concentrated under reduced pressure. The resulting residue was purified by column chromatography (2% MeOH in DCM) yielding methyl (S)-3-(1-(tert-butoxycarbonyl)pyrrolidine-3-carboxamido)isoquinoline-6-carboxylate (0.27 g, 0.68 mmol). LCMS: Method A, 2.26 min, MS: ES+ 400.42.

Step c.

A solution of LiOH (0.26 g, 6.26 mmol) in 5 ml water was added to a solution of methyl (S)-3-(1-(tert-butoxycarbonyl)pyrrolidine-3-carboxamido)isoquinoline-6-carboxylate (0.25 g, 0.63 mmol) in MeOH (10 ml) at rt. The reaction mixture was heated at 60° C. for 3 h. The resulting reaction mixture was allowed to cool to rt. The resulting reaction mixture was concentrated under reduced pressure to remove the organic solvent. The resulting aqueous layer was poured in to the citric acid solution (50 ml) under continuous stirring. The resulting mixture was extracted with EtOAc (3×50 ml). The combined organic phase was collected dried over Na$_2$SO$_4$, filtered and concentrated under reduced pressure yielding (S)-3-(1-(tert-butoxycarbonyl)pyrrolidine-3-carboxamido)isoquinoline-6-carboxylic acid (0.21 g, 0.54 mmol). LCMS: Method A, 2.04 min, MS: ES+ 386.5.

Step d.

A mixture of (S)-3-(1-(tert-butoxycarbonyl)pyrrolidine-3-carboxamido)isoquinoline-6-carboxylic acid (0.2 g, 0.52 mmol), HATU (0.30 g, 0.78 mmol) and DIPEA (0.18 ml, 1.04 mmol) in THF (5 ml) was prepared at 0° C. The reaction mixture was stirred at rt for 0.5 h. Ammonium bicarbonate (0.08 g, 1.04 mmol) was added in to the reaction mixture at rt. The reaction mixture was stirred at rt for 42 h. The resulting reaction mixture was poured into saturated NaHCO$_3$ solution (40 ml) and extracted with EtOAc (2×50 ml). The combined organic phase was collected, dried over Na$_2$SO$_4$, filtered and concentrated under reduced pressure. The resulting residue was purified by column chromatography (3% MeOH in DCM) yielding tert-butyl (S)-3-((6-carbamoylisoquinolin-3-yl)carbamoyl)pyrrolidine-1-carboxylate (0.065 g, 0.17 mmol). LCMS: Method A, 1.92 min, MS: ES+ 385.55.

Steps e,f.

The title compound was synthesised from the intermediate above using a procedure similar to that described for Example 193 steps f,g. LCMS: Method B, 2.73 min, MS: ES+310.5

Example 266 (2S,3S)—N-(6-(1H-pyrazol-4-yl)isoquinolin-3-yl)-1-cyano-2-methylpyrrolidine-3-carboxamide

Synthesised using a procedure similar to that described for Example 193, steps f,g, using Intermediate 27. LCMS: Method C, 3.29 min, MS: ES+ 347.58; $^1$H NMR (400 MHz, DMSO-$d_6$) δ ppm 13.12 (br s, 1H), 10.75 (s, 1H), 9.05 (s, 1H), 8.43-8.47 (m, 2H), 8.13-8.16 (m, 2H), 8.02 (d, J=8.40 Hz, 1H), 7.83 (d, J=8.40 Hz, 1H), 3.97-4.04 (m, 1H), 3.63-3.68 (m, 1H), 3.34-3.45 (m, 2H), 2.18-2.27 (m, 1H), 1.99-2.07 (m, 1H), 1.16 (d, J=6.40 Hz, 3H).

Compounds in Table 11 were synthesised using a procedure similar to that described for Example 1.

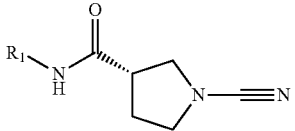

TABLE 11

| Ex | R1 | Name | Amine CAS Number | LCMS Method RT (min) MS ES+ |
|---|---|---|---|---|
| 267 | pyrazolo[1,5-a]pyridin-2-yl | (S)-1-cyano-N-(pyrazolo[1,5-a]pyridin-2-yl)pyrrolidine-3-carboxamide | 51119-05-2 | B 3.00 256.63 |
| 268 | 4-phenylpyridin-2-yl | (S)-1-cyano-N-(4-phenylpyridin-2-yl)pyrrolidine-3-carboxamide | 60781-83-1 | B 3.52 293.33 |
| 269 | 5-(pyridin-3-yl)thiazol-2-yl | (S)-1-cyano-N-(5-(pyridin-3-yl)thiazol-2-yl)pyrrolidine-3-carboxamide | 372096-52-1 | B 2.56 300.18 |
| 270 | 6-(trifluoromethyl)imidazo[1,2-a]pyridin-2-yl | (S)-1-cyano-N-(6-(trifluoromethyl)imidazo[1,2-a]pyridin-2-yl)pyrrolidine-3-carboxamide | 1005785-87-4 | B 3.42 324.22 |
| 271 | 1-methyl-5-(m-tolyl)-1H-pyrazol-3-yl | (S)-1-cyano-N-(1-methyl-5-(m-tolyl)-1H-pyrazol-3-yl)pyrrolidine-3-carboxamide | 1505611-26-6 | C 4.04 310.14 |
| 272 | quinolin-3-yl | (S)-1-cyano-N-(quinolin-3-yl)pyrrolidine-3-carboxamide | 580-17-6 | C 3.30 267.10 |
| 273 | 4-(tert-butyl)pyridin-2-yl | (S)-N-(4-(tert-butyl)pyridin-2-yl)-1-cyanopyrrolidine-3-carboxamide | 33252-26-5 | B 3.25 273.25 |
| 274 | 6-(pyridin-4-yl)pyrimidin-4-yl | (S)-1-cyano-N-(6-(pyridin-4-yl)pyrimidin-4-yl)pyrrolidine-3-carboxamide | 1192814-38-2 | B 2.35 295.23 |
| 275 | 5-phenylpyridazin-3-yl | (S)-1-cyano-N-(5-phenylpyridazin-3-yl)pyrrolidine-3-carboxamide | 105537-97-1 | C 3.43 293.96 |

TABLE 11-continued

| Ex | R1 | Name | Amine CAS Number | LCMS Method RT (min) MS ES+ |
|---|---|---|---|---|
| 276 | | (S)-1-cyano-N-(6-(oxazol-5-yl)imidazo[1,2-a]pyridin-2-yl)pyrrolidine-3-carboxamide | Intermediate 28 | C 2.90 323.03 |
| 277 | | (S)-1-cyano-N-(6-(isopropylsulfonyl)-5,6,7,8-tetrahydro-4H-thiazolo[4,5-d]azepin-2-yl)pyrrolidine-3-carboxamide | Intermediate 29 | B 3.27 398.32 |
| 278 | | (S)-1-cyano-N-(1-(4-(1-(2-methoxyethyl)-1H-pyrazol-4-yl)phenyl)-1H-imidazol-4-yl)pyrrolidine-3-carboxamide | Intermediate 30 | B 3.23 406.65 |

Compounds in Table 12 were synthesised using a procedure similar to that described for Example 1 using 2-amino-5-phenylthiazole.

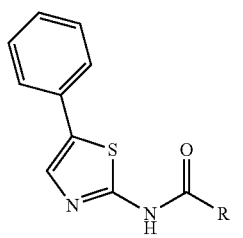

TABLE 12

| Ex | -R | Name | Acid CAS Number | LCMS Method RT (min) MS ES+ |
|---|---|---|---|---|
| 279 | | 3-cyano-N-(5-phenylthiazol-2-yl)-3-azabicyclo[3.1.0]hexane-1-carboxamide | 1363381-55-8 | B 3.93 311.10 |
| 280 | | 2-cyano-N-(5-phenylthiazol-2-yl)-2-azabicyclo[3.1.0]hexane-4-carboxamide | 1258652-53-7 | C 3.61 and 3.81 311.10 |

TABLE 12-continued

| Ex | -R | Name | Acid CAS Number | LCMS Method RT (min) MS ES+ |
|---|---|---|---|---|
| 281 | | (3S,4S)-1-cyano-N-(5-phenylthiazol-2-yl)-4-(trifluoromethyl)pyrrohdine-3-carboxamide | 1212064-03-3 | B 4.28 367.30 |
| 282 | | trans-1-cyano-N-(5-phenylthiazol-2-yl)-4-(pyridin-3-yl)pyrrolidine-3-carboxamide | Intermediate 31 | C 3.17 375.95 |
| 283 | | trans-1-cyano-N-(5-phenylthiazol-2-yl)-4-(pyrimidin-5-yl)pyrrolidine-3-carboxamide | Intermediate 32 | C 2.84 376.93 |
| 284 | | 1-cyano-3-methoxy-N-(5-phenylthiazol-2-yl)pyrrolidine-3-carboxamide | Intermediate 33 | C 3.14 328.95 |

Compounds in Table 13 were synthesised using a procedure similar to that described for Example 109.

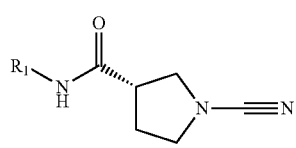

TABLE 13

| Ex | R1 | Name | Aryl halide/Aryl Boronate CAS Number | LCMS Method RT (min) MS ES+ |
|---|---|---|---|---|
| 285 | | (S)-1-cyano-N-(6-(3,5-dimethylisorazol-4-yl)thiazolo[4,5-b]pyridin-2-yl)pyrrolidine-3-carboxamide | 857970-06-0/ 16114-47-9 | C 2.45 368.98 |

TABLE 13-continued

| Ex | R1 | Name | Aryl halide/Aryl Boronate CAS Number | LCMS Method RT (min) MS ES+ |
|---|---|---|---|---|
| 286 | | (S)-1-cyano-N-(5-(3,5-dimethylisoxazol-4-yl)thiazolo[5,4-b]pyridin-2-yl)pyrrolidine-3-carboxamide | 934266-82-7/ 16114-47-9 | C 2.03 369.49 |
| 287 | | (S)-1-cyano-N-(6-(2,6-dimethylphenyl)benzo[d]thiazol-2-yl)pyrrolidine-3-carboxamide | 15864-32-1/ 100379-00-8 | C 4.31 377.13 |
| 288 | | (S)-1-cyano-N-(6-(1,3-dimethyl-1H-pyrazol-4-yl)benzo[d]thiazol-2-yl)pyrrolidine-3-carboxamide | 15864-32-1/ 1046832-21-6 | C 2.86 367.0 |
| 289 | | (S)-1-cyano-N-(6-(5-(trifluoromethyl)-1H-pyrazol-4-yl)isoquinolin-3-yl)pyrrolidine-3-carboxamide | 891785-28-7/ 1218790-40-9 | B 3.70 401.51 |
| 290 | | (S)-1-cyano-N-(4-(3-(5-methylisoxazol-4-yl)phenyl)pyridin-2-yl)pyrrolidine-3-carboxamide | 1369139-84-3/ 1346808-41-0 | C 4.08 373.99 |
| 291 | | (S)-N-(4-(1H-pyrazol-4-yl)pyridin-2-yl)-1-cyanopyrrolidine-3-carboxamide | 84249-14-9/ 269410-08-4 | B 2.25 283.28 |
| 292 | | (S)-N-(6-(1H-pyrazol-4-yl)benzo[d]thiazol-2-yl)-1-cyanopyrrolidine-3-carboxamide | 15864-32-1/ 269410-08-4 | B 3.09 339.28 |

TABLE 13-continued

| Ex | R1 | Name | Aryl halide/Aryl Boronate CAS Number | LCMS Method RT (min) MS ES+ |
|---|---|---|---|---|
| 293 | | (S)-N-(6-(1H-pyrazol-4-yl)isoquinolin-3-yl)-1-cyanopyrrolidine-3-carboxamide | 891785-28-7/ 269410-08-4 | B 2.94 333.30 |
| 294 | | (S)-N-(1-(4-(1H-pyrazol-4-yl)phenyl)-1H-imidazol-4-yl)-1-cyanopyrrolidine-3-carboxamide | 1368048-03-6/ 269410-08-4 | C 2.91 348.04 |
| 295 | | (S)-1-cyano-N-(4-(5-methyl-1H-pyrazol-4-yl)pyridin-2-yl)pyrrolidine-3-carboxamide | 84249-14-9/ 936250-20-3 | C 2.77 297.02 |
| 296 | | (S)-1-cyano-N-(6-(3,5-dimethylisoxazol-4-yl)thiazolo[4,5-c]pyridin-2-yl)pyrrolidine-3-carboxamide | 1244058-73-8/ 16114-47-9 | C 2.45 369.02 |
| 297 | | (S)-1-cyano-N-(2'-(5-methylisoxazol-4-yl)-[4,4'-bipyridin]-2-yl)pyrrolidine-3-carboxamide | Intermediate 34/ 1346808-41-0 | B 3.67 375.49 |

Compounds in Table 14 were synthesised using a procedure similar to that described for Example 150.

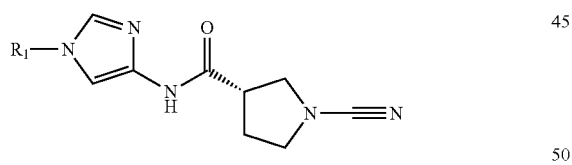

TABLE 14

| Ex | R1 | Name | Amine CAS Number | LCMS Method RT (min) MS ES+ |
|---|---|---|---|---|
| 298 | | (S)-1-cyano-N-(1-(1,3-dimethyl-1H-indazol-5-yl)-1H-imidazol-4-yl)pyrrolidine-3-carboxamide | 5757-85-7 | C 3.27 350.04 |

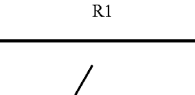

TABLE 14-continued

| Ex | R1 | Name | Amine CAS Number | LCMS Method RT (min) MS ES+ |
|---|---|---|---|---|
| 299 | (3-methyl-1H-indazol-6-yl) | (S)-1-cyano-N-(1-(3-methyl-1H-indazol-6-yl)-1H-imidazol-4-yl)pyrrolidine-3-carboxamide | 79173-62-9 | B 2.87 336.22 |
| 300 | (1H-indazol-5-yl) | (S)-N-(1-(1H-indazol-5-yl)-1H-imidazol-4-yl)-1-cyanopyrrolidine-3-carboxamide | 19335-11-6 | C 2.78 321.97 |
| 301 | (1H-indazol-6-yl) | (S)-N-(1-(1H-indazol-6-yl)-1H-imidazol-4-yl)-1-cyanopyrrolidine-3-carboxamide | 6967-12-0 | C 2.97 321.97 |
| 302 | (4-fluoro-3-methoxyphenyl) | (S)-1-cyano-N-(1-(4-fluoro-3-methoxyphenyl)-1H-imidazol-4-yl)pyrrolidine-3-carboxamide | 64465-53-8 | C 3.67 329.95 |
| 303 | (1H-indazol-4-yl) | (S)-N-(1-(1H-indazol-4-yl)-1H-imidazol-4-yl)-1-cyanopyrrolidine-3-carboxamide | 41748-71-4 | C 2.93 321.97 |
| 304 | (4-cyano-3-cyclopropylphenyl) | (S)-1-cyano-N-(1-(4-cyano-3-cyclopropylphenyl)-1H-imidazol-4-yl)pyrrolidine-3-carboxamide | Intermediate 35 | C 3.86 347.18 |

Compounds in Table 15 were synthesised using a procedure similar to that described for Example 174.

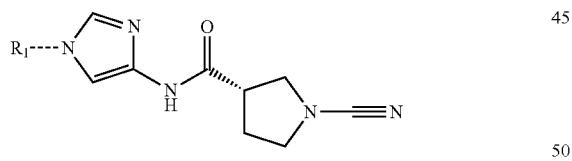

TABLE 15

| Ex | R1 | Name | Aryl halide CAS Number | LCMS Method RT (min) MS ES+ |
|---|---|---|---|---|
| 305 | quinolin-4-yl | (S)-1-cyano-N-(1-(quinolin-4-yl)-1H-imidazol-4-yl)pyrrolidine-3-carboxamide | 3964-04-3 | C 3.17 332.94 |

TABLE 15-continued

| Ex | R1 | Name | Aryl halide CAS Number | LCMS Method RT (min) MS ES+ |
|----|----|------|------------------------|------------------------------|
| 306 | 2-cyano-5-cyclopropylphenyl | (S)-1-cyano-N-(1-(2-cyano-5-cyclopropylphenyl)-1H-imidazol-4-yl)pyrrolidine-3-carboxamide | 1394068-31-5 | C 3.90 346.98 |
| 307 | 4-cyano-3-methoxyphenyl | (S)-1-cyano-N-(1-(4-cyano-3-methoxyphenyl)-1H-imidazol-4-yl)pyrrolidine-3-carboxamide | 191014-55-8 | B 3.25 337.30 |
| 308 | 4-cyano-3-methylphenyl | (S)-1-cyano-N-(1-(4-cyano-3-methylphenyl)-1H-imidazol-4-yl)pyrrolidine-3-carboxamide | 147754-12-9 | C 3.52 320.97 |
| 309 | 4-cyano-3-(trifluoromethyl)phenyl | (S)-1-cyano-N-(1-(4-cyano-3-(trifluoromethyl)phenyl)-1H-imidazol-4-yl)pyrrolidine-3-carboxamide | 194853-86-6 | C 3.92 374.99 |
| 310 | 4-cyano-3-(trifluoromethoxy)phenyl | (S)-1-cyano-N-(1-(4-cyano-3-(trifluoromethoxy)phenyl)-1H-imidazol-4-yl)pyrrolidine-3-carboxamide | 1323966-32-0 | C 3.99 390.96 |

Biological Activity of Compounds of the Invention

Abbreviations

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin In Vitro UCHL1 Inhibition Assay Expression and Purification of UCHL1

The UCHL1 construct was PCR amplified and cloned into a pFLAG-CMV-6a vector (Sigma-Aldrich) with an N-terminal FLAG tag. HEK293T cells were transfected with FLAG-UCHL1 using TransIT-LT1 transfection reagent (Mirus) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM beta-mercaptoethanol, protease inhibitors (complete mini, Roche) and phosphatase inhibitors (PhosSTOP mini, Roche). Lysates were incubated for 30 min on ice and centrifuged at 1200 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM beta-mercaptoethanol) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM beta-mercaptoethanol, protease inhibitors (complete mini, Roche) and phosphatase inhibitors (PhosSTOP mini, Roche). To elute the bound UCHL1, elution buffer (10 mM Tris, pH 7.5, 150 mM NaCl, 0.5 mM EDTA, 10% glycerol, 0.5% NP40, 5 mM beta-mercaptoethanol, 0.15 mg/ml 3xFLAG peptide (Sigma-Aldrich)) was added to the resin and incubated at 4° C. for 2.5 hours rotating. The resin was centrifuged at 4000 rpm for 30 seconds, and the supernatant containing purified FLAG-UCHL1 was removed and stored at −80° C.

UCHL1 Biochemical Kinetic Assay

Reactions were performed in duplicate in black 384 well plates (small volume, Greiner 784076) in a final reaction volume of 21 µl. UCHL1 was diluted in reaction buffer (20 mM Tris, pH 7.5, 100 mM NaCl, 0.05% Tween 20, 0.5 mg/ml BSA, 5 mM-beta mercaptoethanol) to the equivalent of 0, 0.01, 0.05, 0.1, 0.5, and 1 µl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

UCHL1 Biochemical IC50 Assay

Dilution plates were prepared at 21 times the final concentration (2100 µM for a final concentration of 100 µM) in 50% DMSO in a 96-well polypropylene V-bottom plate (Greiner #651201). A typical 8-point dilution series to be 100, 30, 10, 3, 1, 0.3, 0.1, 0.03 μM final. Reactions were performed in duplicate in black 384 well plates (small volume, Greiner 784076) in a final reaction volume of 21 μl. Either 1 μl of 50% DMSO or diluted compound was added to the plate. UCHL1 was diluted in reaction buffer (20 mM Tris, pH 7.5, 100 mM NaCl, 0.05% Tween 20, 0.5 mg/ml BSA, 5 mM-beta mercaptoethanol) to the equivalent of 0.05 μl/well and 10 μl of diluted UCHL1 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in UCHL1 Biochemical IC50 Assay

Ranges
A<1 μM;
1<B<10 μM;
10<C<30 μM

| Example Number | Activity range |
|---|---|
| 1 | A |
| 2 | A |
| 3 | B |
| 4 | A |
| 5 | B |
| 6 | B |
| 7 | B |
| 8 | B |
| 9 | C |
| 10 | C |
| 11 | B |
| 12 | B |
| 13 | B |
| 14 | B |
| 15 | B |
| 16 | C |
| 17 | B |
| 18 | B |
| 19 | B |
| 20 | B |
| 21 | B |
| 22 | B |
| 23 | C |
| 24 | C |
| 25 | C |
| 26 | C |
| 27 | C |
| 28 | B |
| 29 | B |
| 30 | C |
| 31 | B |
| 32 | B |
| 33 | B |
| 34 | B |
| 35 | B |
| 36 | C |
| 37 | C |
| 38 | B |
| 39 | C |
| 40 | B |
| 41 | A |
| 42 | A |
| 43 | A |
| 44 | B |
| 45 | C |
| 46 | C |
| 47 | A |
| 48 | B |
| 49 | B |
| 50 | B |
| 51 | A |
| 52 | B |
| 53 | B |
| 54 | B |
| 55 | B |
| 56 | C |
| 57 | A |
| 58 | B |
| 59 | A |
| 60 | A |
| 61 | B |
| 62 | A |
| 63 | B |
| 64 | A |
| 65 | A |
| 66 | A |
| 67 | A |
| 68 | A |
| 69 | A |
| 70 | B |
| 71 | C |
| 72 | A |
| 73 | A |
| 74 | A |
| 75 | A |
| 76 | A |
| 77 | B |
| 78 | B |
| 79 | C |
| 80 | C |
| 81 | B |
| 82 | A |
| 83 | B |
| 84 | B |
| 85 | B |
| 86 | A |
| 87 | B |
| 88 | B |
| 89 | C |
| 90 | C |
| 91 | A |
| 92 | A |
| 93 | A |
| 94 | A |
| 95 | A |
| 96 | A |
| 97 | A |
| 98 | B |
| 99 | A |
| 100 | A |
| 101 | A |
| 102 | B |
| 103 | B |
| 104 | A |
| 105 | B |
| 106 | C |
| 107 | B |
| 108 | B |
| 109 | B |
| 110 | B |
| 111 | A |
| 112 | A |
| 113 | A |
| 114 | A |
| 115 | B |
| 116 | A |
| 117 | A |
| 118 | A |
| 119 | B |
| 120 | A |
| 121 | B |
| 122 | B |
| 123 | A |
| 124 | A |

| Example Number | Activity range |
|---|---|
| 125 | A |
| 126 | A |
| 127 | A |
| 128 | A |
| 129 | A |
| 130 | A |
| 131 | A |
| 132 | A |
| 133 | A |
| 134 | B |
| 135 | B |
| 136 | B |
| 137 | A |
| 138 | A |
| 139 | A |
| 140 | A |
| 141 | B |
| 142 | B |
| 143 | B |
| 144 | B |
| 145 | B |
| 146 | A |
| 147 | A |
| 148 | B |
| 149 | A |
| 150 | A |
| 151 | A |
| 152 | A |
| 153 | A |
| 154 | A |
| 155 | A |
| 156 | A |
| 157 | B |
| 158 | A |
| 159 | A |
| 160 | A |
| 161 | A |
| 162 | A |
| 163 | A |
| 164 | A |
| 165 | B |
| 166 | A |
| 167 | A |
| 168 | A |
| 169 | A |
| 170 | A |
| 171 | B |
| 172 | B |
| 173 | A |
| 174 | A |
| 175 | B |
| 176 | B |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | B |
| 189 | A |
| 190 | A |
| 191 | A |
| 192 | A |
| 193 | A |
| 194 | A |
| 195 | A |
| 196 | A |
| 197 | B |
| 198 | A |
| 199 | B |
| 200 | B |
| 201 | B |
| 202 | A |
| 203 | A |
| 204 | A |
| 205 | A |
| 206 | A |
| 207 | B |
| 208 | A |
| 209 | A |
| 210 | A |
| 211 | B |
| 212 | A |
| 213 | A |
| 214 | A |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | B |
| 249 | A |
| 250 | A |
| 251 | A |
| 252 | B |
| 253 | A |
| 254 | A |
| 255 | A |
| 256 | B |
| 257 | B |
| 258 | B |
| 259 | B |
| 260 | B |
| 261 | A |
| 262 | A |
| 263 | B |
| 264 | B |
| 265 | B |
| 266 | A |
| 267 | B |
| 268 | B |
| 269 | A |
| 269 | B |
| 270 | A |
| 271 | A |
| 272 | B |
| 273 | B |
| 274 | B |
| 275 | B |

-continued

| Example Number | Activity range |
|---|---|
| 276 | A |
| 277 | A |
| 278 | A |
| 279 | B |
| 280 | B |
| 281 | A |
| 282 | B |
| 283 | B |
| 284 | A |
| 285 | B |
| 286 | A |
| 287 | A |
| 288 | A |
| 289 | A |
| 290 | A |
| 291 | B |
| 292 | B |
| 294 | A |
| 295 | B |
| 296 | C |
| 297 | A |
| 298 | A |
| 299 | A |
| 300 | A |
| 301 | A |
| 302 | A |
| 303 | A |
| 304 | A |
| 305 | A |
| 306 | A |
| 307 | A |
| 308 | A |
| 309 | A |
| 310 | A |

The invention claimed is:

1. A compound having the formula (I)

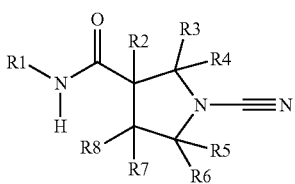

(I)

or a pharmaceutically acceptable salt thereof, wherein:

$R_1$ represents a 5 to 10 membered heteroaryl ring which may be optionally substituted;

$R_2$, $R_3$, $R_4$, $R_5$, $R_6$ and $R_8$ each independently represent a hydrogen atom, cyano, an optionally substituted $C_1$-$C_3$ alkyl, an optionally substituted $C_1$-$C_3$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, $R_6$ is linked to $R_7$ to form an optionally substituted $C_3$-$C_4$ cycloalkyl ring; and $R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group or is linked to $R_6$ to form an optionally substituted $C_3$-$C_4$ cycloalkyl ring.

2. The compound according to claim 1 wherein $R_1$ represents a 5 to 10 membered heteroaryl ring substituted with one or more of Q1-$(R_9)_n$, wherein:

n is 0 or 1;

Qi represents a hydrogen atom, a halogen atom, cyano, a covalent bond, —$NR_{10}$—$CONR_{10}$—, —$NR_{10}CO$—, an oxygen atom, oxo, nitro, —$S(O)_m$—, $C_1$-$C_6$ alkoxy, $C_1$-$C_6$ haloalkoxy, $C_1$-$C_6$ hydroxyalkyl, —CO—, —$SO_2R_{11}$, —$NR_{11}R_{12}$, —$NR_{11}COR_{12}$, —$NR_{10}CONR_{11}R_{12}$, —$CONR_{11}R_{12}$, —$CO_2R_{11}$, —$NR_{11}CO_2R_{12}$, —$SO_2NR_{11}R_{12}$, —$NR_{11}SO_2R_{12}$, $NR_{11}SO_2NR_{13}R_{14}$ and $SO_2NR_{11}$ or an optionally substituted $C_1$-$C_6$ alkylene, —$C_2$-$C_6$ alkenylene or —$C_1$-$C_6$ alkyl group;

m is 0, 1 or 2;

$R_9$ represents an optionally substituted 3 to 10 membered heterocyclyl, heteroaryl, aryl or cycloalkyl ring; and $R_{10}$, $R_{11}$ and $R_{12}$ each independently represent a hydrogen atom or an optionally substituted $C_1$-$C_6$ alkyl or optionally substituted $C_1$-$C_6$ alkylene group.

3. The compound according to claim 2 wherein $R_9$ represents a 3 to 10 membered heterocyclyl, heteroaryl, aryl or cycloalkyl ring substituted with one or more substituents selected from halogen, optionally substituted $C_1$-$C_6$ haloalkyl, optionally substituted $C_1$-$C_6$ alkoxy, $C_1$-$C_6$ haloalkoxy, optionally substituted $C_1$-$C_6$ alkyl, optionally substituted $C_2$-$C_6$ alkenyl, optionally substituted $C_2$-$C_6$ alkynyl, $C_1$-$C_6$ hydroxyalkyl, oxo, cyano, nitro, optionally substituted heterocyclyl, optionally substituted cycloalkyl, optionally substituted heteroaryl, optionally substituted aryl, -$Q_2$-$NR_{13}CONR_{14}R_{15}$, -$Q_2$-$NR_{13}R_{14}$, -$Q_2$-$NR_{13}COR_{14}$, -$Q_2$-$COR_{13}$, -$Q_2$-$SO_2R_{13}$, -$Q_2$-$CONR_{13}$, $Q_2$-$CONR_{13}R_{14}$, -$Q_2$-$CO_2R_{13}$, -$Q_2$-$SO_2NR_{13}R_{14}$, -$Q_2$-$NR_{13}SO_2R_{14}$ and -$Q_2$-$NR_{13}SO_2NR_{14}R_{15}$; wherein $Q_2$ represents a covalent bond or a $C_1$-$C_6$ alkylene or $C_2$-$C_6$ alkenylene group; and $R_{13}$, $R_{14}$ and $R_{15}$ each independently represent hydrogen or an optionally substituted $C_1$-$C_6$ alkyl, or an optionally substituted heterocyclyl, or an optionally substituted heteroaryl, or an optionally substituted aryl, or an optionally substituted cycloalkyl.

4. The compound according to claim 1 wherein $R_1$ is selected from thiazolyl, pyridinyl, isoxazolyl, thiadiazolyl, indazolyl, imidazolyl, benzothiazolyl, benzoimidazolyl, pyrazolyl, pyridazinyl, pyrimidinyl, napthyridinyl, pyrazinyl, isoquinolinyl, tetrahydrothiazolopyridinyl, imidazopyridinyl, triazolyl, pyrazolopyridinyl, tetrahydropyrazolopyrazinyl, tetrahydrothiazoloazepinyl and thiazolopyridinyl.

5. The compound according to claim 1 wherein $R_2$, $R_3$, $R_4$, $R_5$, $R_6$, $R_7$ and $R_8$ each independently represent hydrogen.

6. The compound according to claim 1 wherein $R_7$ represents cyano, an optionally substituted $C_1$-$C_3$ alkyl, an optionally substituted $C_1$-$C_3$ alkoxy group, an optionally substituted aryl or heteroaryl ring, or links with $R_6$ to form an optionally substituted $C_3$-$C_4$ cycloalkyl ring.

7. The compound according to claim 1 wherein $R_3$ represents methyl.

8. The compound according to claim 1 wherein $R_2$ represents cyano, methyl, substituted methyl or methoxy.

9. The compound according to claim 3 wherein $R_9$ is selected from morpholinyl, piperidinyl, pyrrolidinyl, diazepanyl, piperazinyl, pyridazinyl, pyrazinyl, pyrazolyl, cyclopropyl, cyclohexyl, cyclopentyl, pyridinyl, imidazolyl, indolinyl, isoindolinyl, pyrimidinyl, isoxazolyl, dihydroindenyl, dihydroisoquinolinyl, tetrahydropyranyl, phenyl, oxadiazolyl, triazolyl, isoquinolinyl, indazolyl, pyrazolopyridinyl, pyrazolopyrimidinyl, imidazolpyridinyl, imidazopyrimidinyl, imidazopyrazinyl, oxazolyl and quinolinyl.

10. A compound according to formula (II)

(II)

or a pharmaceutically acceptable salt thereof, wherein:
$R_1$ represents a 5 to 10 membered heteroaryl ring which may be optionally substituted;
$R_2$, $R_3$, $R_4$, $R_5$, $R_6$ and $R_8$ each independently represent a hydrogen atom, cyano, an optionally substituted $C_1$-$C_3$ alkyl, an optionally substituted $C_1$-$C_3$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, or $R_6$ is linked to $R_7$ to form an optionally substituted $C_3$-$C_4$ cycloalkyl ring; and
$R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group or is linked to $R_6$ to form an optionally substituted $C_3$-$C_4$ cycloalkyl ring.

11. The compound according to claim 1 having the formula (III)

(III)

or a pharmaceutically acceptable salt thereof, wherein:
Y represents the remaining atoms of a 5 or 6 membered heteroaryl ring which may optionally substituted or fused with further ring which may be further optionally substituted;
$R_2$, $R_3$, $R_4$, $R_5$, $R_6$ and $R_8$ each independently represent a hydrogen atom, cyano, an optionally substituted $C_1$-$C_3$ alkyl, an optionally substituted $C_1$-$C_3$ alkoxy group, one or more spirocyclic groups where $R_3$ is linked to $R_4$, $R_5$ is linked to $R_6$ or $R_8$ is linked to $R_7$, or $R_2$ is linked to $R_8$ to form an optionally substituted $C_3$-$C_4$ cycloalkyl ring, or $R_6$ is linked to $R_7$ to form an optionally substituted $C_3$-$C_4$ cycloalkyl; and
$R_7$ represents a hydrogen atom, a fluorine atom, cyano, an optionally substituted $C_1$-$C_3$ alkyl, an optionally substituted $C_1$-$C_3$ alkoxy group or an optionally substituted aryl or heteroaryl ring or is linked to $R_8$ to form a spirocyclic group, or is linked to $R_6$ to form an optionally substituted $C_3$-$C_4$ cycloalkyl.

12. A compound of formula (I) as defined in claim 1 selected from the group consisting of:

(S)-1-cyano-N-(5-phenylthiazol-2-yl)pyrrolidine-3-carboxamide,
1-cyano-N-(5-(3-fluorophenyl)thiazol-2-yl)pyrrolidine-3-carboxamide,
1-cyano-N-(5-(2-fluorophenyl)thiazol-2-yl)pyrrolidine-3-carboxamide,
N-(5-(4-chlorophenyl)thiazol-2-yl)-1-cyanopyrrolidine-3-carboxamide,
N-(5-(3-chlorophenyl)thiazol-2-yl)-1-cyanopyrrolidine-3-carboxamide,
N-(5-(2-chlorophenyl)thiazol-2-yl)-1-cyanopyrrolidine-3-carboxamide,
1-cyano-N-(5-methylthiazol-2-yl)pyrrolidine-3-carboxamide,
N-(5-(tert-butyl)thiazol-2-yl)-1-cyanopyrrolidine-3-carboxamide,
1-cyano-N-(4-phenylthiazol-2-yl)pyrrolidine-3-carboxamide,
1-cyano-N-(2-phenylthiazol-5-yl)pyrrolidine-3-carboxamide,
1-cyano-N-(5-phenyl-1,3,4-thiadiazol-2-yl)pyrrolidine-3-carboxamide,
1-cyano-N-(5-ethyl-1,3,4-thiadiazol-2-yl)pyrrolidine-3-carboxamide,
1-cyano-N-(3-phenylisoxazol-5-yl)pyrrolidine-3-carboxamide,
1-cyano-N-(3-(4-methoxyphenyl)isoxazol-5-yl)pyrrolidine-3-carboxamide,
1-cyano-N-(5-phenylisoxazol-3-yl)pyrrolidine-3-carboxamide,
N-(5-(tert-butyl)isoxazol-3-yl)-1-cyanopyrrolidine-3-carboxamide,
N-(3-(tert-butyl)-1H-pyrazol-5-yl)-1-cyanopyrrolidine-3-carboxamide,
N-(benzo[d]thiazol-2-yl)-1-cyanopyrrolidine-3-carboxamide,
1-cyano-N-(6-methylbenzo[d]thiazol-2-yepyrolidine-3-carboxamide,
1-cyano-N-(6-(trifluoromethyl)benzo[d]thiazol-2-yl)pyrrolidine-3-carboxamide,
1-cyano-N-(6-methoxybenzo[d]thiazol-2-yl)pyrrolidine-3-carboxamide,
N-(6-bromobenzo[d]thiazol-2-yl)-1-cyanopyrrolidine-3-carboxamide,
N-(1H-benzo[d]imidazol-2-yl)-1-cyanopyrrolidine-3-carboxamide,
1-cyano-N-(pyridin-2-yl)pyrrolidine-3-carboxamide,
N-(5-chloropyridin-2-yl)-1-cyanopyrrolidine-3-carboxamide,
1-cyano-N-(5-methylpyridin-2-yl)pyrrolidine-3-carboxamide,
1-cyano-N-(5-methoxypyridin-2-yl)pyrrolidine-3-carboxamide,
1-cyano-N-(5-morpholinopyridin-2-yl)pyrrolidine-3-carboxamide,
1-cyano-N-(5-(piperidin-1-yl)pyridin-2-yl)pyrrolidine-3-carboxamide,
N-(5-(1H-imidazol-1-yl)pyridin-2-yl)-1-cyanopyrrolidine-3-carboxamide,
1-cyano-N-(4-phenylpyridin-2-yl)pyrrolidine-3-carboxamide,
N-([2,3'-bipyridin]-6'-yl)-1-cyanopyrrolidine-3-carboxamide,
N-([3,3'-bipyridin]-6-yl)-1-cyanopyrrolidine-3-carboxamide,
N-([3,4'-bipyridin]-6-yl)-1-cyanopyrrolidine-3-carboxamide, 1-cyano-N-(6-phenylpyridin-3-yl)pyrrolidine-3-carboxamide,
1-cyano-N-(6-phenylpyridazin-3-yl)pyrrolidine-3-carboxamide,
1-cyano-N-(2-phenylpyrimidin-5-yl)pyrrolidine-3-carboxamide,
1-cyano-N-(5-cyclohexylpyridin-2-yl)pyrrolidine-3-carboxamide,
N-(1-benzyl-1H-indazol-5-yl)-1-cyanopyrrolidine-3-carboxamide,
1-cyano-N-(1-propyl-1H-benzo[d]imidazol-5-yl)pyrrolidine-3-carboxamide,
(S)-1-cyano-N-(1-phenyl-1H-imidazol-4-yl)pyrrolidine-3-carboxamide,
(S)-1-cyano-N-(5-phenyl-1H-pyrazol-3-yl) pyrrolidine-3-carboxamide,
(S)-1-cyano-N-(5-(tetrahydro-2H-pyran-4-yl)-1H-pyrazol-3-yl)pyrrolidine-3-carboxamide,
(S)-1-cyano-N-(1-phenyl-1H-1,2,3-triazol-4-yl)pyrrolidine-3-carboxamide,
(S)-1-cyano-N-(1-phenyl-1H-pyrazol-3-yl)pyrrolidine-3-carboxamide,
(S) 1-cyano-N-(4-methylbenzo[d]thiazol-2-yl)pyrrolidine-3-carboxamide,
(S)-1-cyano-N-(7-methylbenzo[d]thiazol-2-yl)pyrrolidine-3-carboxamide,
(S)—N-(4-bromobenzo[d]thiazol-2-yl)-1-cyanopyrrolidine-3-carboxamide,
(S)-1-cyano-N-(imidazo[1,2-a]pyridin-2-yl)pyrrolidine-3-carboxamide,
(S)—N-(7-bromoimidazo[1,2-a]pyridin-2-yl)-1-cyanopyrrolidine-3-carboxamide,
(S)—N-(6-bromoimidazo[1,2-a]pyridin-2-yl)-1-cyanopyrrolidine-3-carboxamide,
(S)-1-cyano-N-(pyrazolo[1,5-a]pyridin-2-yl)pyrrolidine-3-carboxamide,
(S)-1-cyano-N-(4-methoxypyridin-2-yl)pyrrolidine-3-carboxamide,
(S)-1-cyano-N-(5-phenylpyridin-2-yl)pyrrolidine-3-carboxamide,
(S)-1-cyano-N-(6-phenylpyridin-2-yl)pyrrolidine-3-carboxamide,
(S)-1-cyano-N-(1,8-naphthyridin-2-yl)pyrrolidine-3-carboxamide,
(S)—N-(5-benzylthiazol-2-yl)-1-cyanopyrrolidine-3-carboxamide,
(S)-1-cyano-N-(isoquinolin-3-yl)pyrrolidine-3-carboxamide,
(S)-1-cyano-N-(5-(tetrahydro-2H-pyran-4-yl)thiazol-2-yl)pyrrolidine-3-carboxamide,
(S)-1-cyano-N-(1-methyl-5-phenyl-1H-pyrazol-3-yl)pyrrolidine-3-carboxamide,
1-cyano-N-(5-(4-methoxypiperidin-1-yl)pyridin-2-yl)pyrrolidine-3-carboxamide,
(S)—N-(6-(1H-1,2,3-thiazol-1-yl)benzo[d]thiazol-2-yl)-1-cyanopyrrolidine-3-carboxamide,
(S)—N-(6-(2H-1,2,3-triazol-2-yl)benzo[d]thiazol-2-yl)-1-cyanopyrrolidine-3-carboxamide,
(S)-1-cyano-N-(5-(4-(methylcarbamoyl)phenyl)thiazol-2-yl)pyrrolidine-3-carboxamide,
(S)-1-cyano-N-(4-methyl-5-(morpholinomethyl)thiazol-2-yl)pyrrolidine-3-carboxamide,
(S)-1-cyano-N-(5-(4-fluorophenyl)thiazol-2-yl)pyrrolidine-3-carboxamide,
(S)-1-cyano-N-(5-(3,4-difluorophenyl)thiazol-2-yl)pyrrolidine-3-carboxamide,
(S)-1-cyano-N-(5-(4-(trifluoromethyl)phenyl)thiazol-2-yl)pyrrolidine-3-carboxamide,
(S)-1-cyano-N-(5-(pyridin-4-yl)thiazol-2-yl)pyrrolidine-3-carboxamide,
(S)-1-cyano-N-(5-(pyridin-2-yl)thiazol-2-yl)pyrrolidine-3-carboxamide,
(R)-1-cyano-N-(5-phenylpyridin-2-yl)pyrrolidine-3-carboxamide,
(2S,3S)-1-cyano-2-methyl-N-(5-phenylthiazol-2-yl)pyrrolidine-3-carboxamide,
(2S,3S)-1-cyano-N-(5-(4-fluorophenyl)thiazol-2-yl)-2-methylpyrrolidine-3-carboxamide,
(2S,3 S)-1-cyano-2-methyl-N-(1-phenyl-1H-imidazol-4-yl)pyrrolidine-3-carboxamide,
(2S,3 S)-1-cyano-2-methyl-N-(5-phenyl-1H-pyrazol-3-yl)pyrrolidine-3-carboxamide,
(2S,3S)-1-cyano-2-methyl-N-(5-(tetrahydro-2H-pyran-4-yl)thiazol-2-yepyrrolidine-3-carboxamide,
(2S,3S)—N-(5-(2-chlorophenyl)thiazol-2-yl)-1-cyano-2-methylpyrrolidine-3-carboxamide,
1-cyano-3-methyl-N-(5-phenylthiazol-2-yl)pyrrolidine-3-carboxamide,
1-cyano-3-methyl-N-(1-phenyl-1H-imidazol-4-yl)pyrrolidine-3-carboxamide,
1-cyano-3-(methoxymethyl)-N-(5-phenylthiazol-2-yl) pyrrolidine-3-carboxamide,
1,3-dicyano-N-(5-phenylthiazol-2-yepyrrolidine-3-carboxamide,
(3S,4S)-1-cyano-4-methyl-N-(5-phenylthiazol-2-yl)pyrrolidine-3-carboxamide,
(3S,4S)-1-cyano-4-methyl-N-(5-methylthiazol-2-yl)pyrrolidine-3-carboxamide,
(3S,4S)—N-(5-(2-chlorophenyl)thiazol-2-yl)-1-cyano-4-methylpyrrolidine-3-carboxamide,
(3S,4S)-1-cyano-4-methyl-N-(1-phenyl-1H-imidazol-4-yl)pyrrolidine-3-carboxamide,
(3S,4S)-1-cyano-4-ethyl-N-(5-phenylthiazol-2-yl)pyrrolidine-3-carboxamide,
(3S,4S)-1-cyano-4-ethyl-N-(1-phenyl-1H-imidazol-4-yl) pyrrolidine-3-carboxamide,
1-cyano-5-methyl-N-(5-phenylthiazol-2-yl)pyrrolidine-3-carboxamide,
1-cyano-5-methyl-N-(1-phenyl-1H-imidazol-4-yl)pyrrolidine-3-carboxamide,
1-cyano-5-methyl-N-(5-phenyl-1H-pyrazol-3-yl)pyrrolidine-3-carboxamide,
(S)-1-cyano-N-(5-morpholinothiazol-2-yl)pyrrolidine-3-carboxamide,
1-cyano-N-(5-(4-methylpiperazin-1-yl)thiazol-2-yl)pyrrolidine-3-carboxamide,
N-(5-(2-(acetamidomethyl)piperidin-1-yl)thiazol-2-yl)-1-cyanopyrrolidine-3-carboxamide,
1-cyano-N-(5-(methyl(phenyl)amino)thiazol-2-yl)pyrrolidine-3-carboxamide,
1-cyano-N-(5-(indolin-1-yethiazol-2-yl)pyrrolidine-3-carboxamide,
(S)-1-cyano-N-(5-(piperidin-1-yl)thiazol-2-yl)pyrrolidine-3-carboxamide,
(S)-1-cyano-N-(5-(isoindolin-2-yl)thiazol-2-yl)pyrrolidine-3-carboxamide,
(S)-1-cyano-N-(5-(3,4-dihydroisoquinolin-2(1H)-yl)thiazol-2-yl)pyrrolidine-3-carboxamide,
(S)-1-cyano-N-(5-((R)-2-(methoxymethyl)pyrrolidin-1-yl)thiazol-2-yl)pyrrolidine-3-carboxamide,
(S)-1-cyano-N-(5-((S)-2-(methoxymethyl)pyrrolidin-1-yl)thiazol-2-yl)pyrrolidine-3-carboxamide, (S)-1-cyano-N-(5-(5-oxo-1,4-diazepan-1-yl)thiazol-2-yl)pyrrolidine-3-carboxamide,
(R)-1-cyano-N-(5-morpholinothiazol-2-yl)pyrrolidine-3-carboxamide,
(R)-1-cyano-N-(5-(piperidin-1-yl)thiazol-2-yl)pyrrolidine-3-carboxamide,
(3S,4S)-1-cyano-4-methyl-N-(5-(piperidin-1-yl)thiazol-2-yl)pyrrolidine-3-carboxamide,
1-cyano-5-methyl-N-(5-(piperidin-1-yl)thiazol-2-yl)pyrrolidine-3-carboxamide,
(S)-1-cyano-N-(6-(pyrrolidin-1-yl)pyridin-2-yl)pyrrolidine-3-carboxamide,
(S)-1-cyano-N-(4-(pyrrolidin-1-yl)pyridin-2-yl)pyrrolidine-3-carboxamide,
(S)-1-cyano-N-(5-(pyrrolidin-1-yl)pyrazin-2-yl)pyrrolidine-3-carboxamide,
N-(5-(2-aminophenyl)thiazol-2-yl)-1-cyanopyrrolidine-3-carboxamide,
N-(5-(3-aminophenyl)thiazol-2-yl)-1-cyanopyrrolidine-3-carboxamide,
N-(5-(4-aminophenyl)thiazol-2-yl)-1-cyanopyrrolidine-3-carboxamide,
1-cyano-N-(5-(pyridin-3-yl)thiazol-2-yl)pyrrolidine-3-carboxamide,
(E)-1-cyano-N-(5-(2-cyclopropylvinyl)thiazol-2-yl)pyrrolidine-3-carboxamide,
N-(5-(4-acetamidophenyl)thiazol-2-yl)-1-cyanopyrrolidine-3-carboxamide,
N-(5-(2-acetamidophenyl)thiazol-2-yl)-1-cyanopyrrolidine-3-carboxamide,
1-cyano-N-(5-(3-(methylsulfonamido)phenylthiazol-2-yl)pyrrolidine-3-carboxamide,
(S)-1-cyano-N-(5-(3-cyanophenyl)thiazol-2-yl)pyrrolidine-3-carboxamide,
(S)-1-cyano-N-(5-(4-cyanophenyl)thiazol-2-yl)pyrrolidine-3-carboxamide,
1-cyano-N-(5-(3,5-dimethylisoxazol-4-yl)benzo[d]thiazol-2-yl)pyrrolidine-3-carboxamide,
(S)-1-cyano-N-(6-(3,5-dimethylisoxazol-4-yl)benzo[d]thiazol-2-yl)pyrrolidine-3-carboxamide,
(S)-1-cyano-N-(6-(4-methoxyphenyl)benzo[d]thiazol-2-yl)pyrrolidine-3-carboxamide,
(S)-1-cyano-N-(6-phenylbenzo[d]thiazol-2-yl)pyrrolidine-3-carboxamide,
(S)-1-cyano-N-(6-(1-methyl-1H-pyrazol-5-yl)benzo[d]thiazol-2-yl)pyrrolidine-3-carboxamide,
(S)-1-cyano-N-(6-(1-methyl-1H-pyrazol-4-yl)benzo[d]thiazol-2-yl)pyrrolidine-3-carboxamide,
(S)-1-cyano-N-(6-(3,5-dimethyl-1H-pyrazol-4-yl)benzo[d]thiazol-2-yl)pyrrolidine-3-carboxamide,
(S)-1-cyano-N-(6-(5-methylisoxazol-4-yl)benzo[d]thiazol-2-yl)pyrrolidine-3-carboxamide,
(S)-1-cyano-N-(7-(3,5-dimethylisoxazol-4-yl)imidazo[1,2-a]pyridin-2-yl)pyrrolidine-3-carboxamide,
(S)-1-cyano-N-(6-(3,5-dimethylisoxazol-4-yl)imidazo[1,2-a]pyridin-2-yl)pyrrolidine-3-carboxamide,
(S)-1-cyano-N-(6-cyclopropylimidazo[1,2-a]pyridin-2-yl)pyrrolidine-3-carboxamide,
1-cyano-N-(6-cyclopropylbenzo[d]thiazol-2-yl)pyrrolidine-3-carboxamide,
(S)-1-cyano-N-(6-(3,6-dimethoxypyridazin-4-yl)imidazo[1,2-a]pyridin-2-yl)pyrrolidine-3-carboxamide,
(S)-1-cyano-N-(6-(3,6-dimethoxypyridazin-4-yl)benzo[d]thiazol-2-yl)pyrrolidine-3-carboxamide,
(2S,3S)-1-cyano-N-(6-(3,5-dimethylisoxazol-4-yl)benzo[d]thiazol-2-yl)-2-methylpyrrolidine-3-carboxamide,
1-cyano-N-(5-(p-tolyl)pyridin-2-yl)pyrrolidine-3-carboxamide,
1-cyano-N-(5-(m-tolyppyrindin-2-yl)pyrrolidine-3-carboxamide,
1-cyano-N-(5-(o-tolyl)pyridin-2-yl)pyrrolidine-3-carboxamide,
(S)-1-cyano-N-(6-(3,5-dimethylisoxazol-4-yl)-5-methylimidazo[1,2-a]pyridin-2-yl)pyrrolidine-carboxamide,
(S)-1-cyano-N-(6-(3,5-dimethylisoxazol-4-yl)-7-methylbenzo[d]thiazol-2-yl)pyrrolidine-3-carboxamide,
(S)-1-cyano-N-(7-methyl-6-(1-methyl-1H-pyrazol-4-yl)benzo[d]thiazol-2-yl)pyrrolidine-3-carboxamide,
1-cyano-N-(5-(morpholinomethyl)thiazol-2-yl)pyrrolidine-3-carboxamide,
1-cyano-N-(5-(pyrrolidin-1-ylmethyl)thiazol-2-yl)pyrrolidine-3-carboxamide,
(3S)-1-cyano-N-(54(2,6-dimethylmorpholino)methyl)thiazol-2-yl)pyrrolidine-3-carboxamide,
(S)-1-cyano-N-(5-(((R)-2-(methoxymethyl)pyrrolidin-1-yl)methyl)thiazol-2-yl)pyrrolidine-3-carboxamide,
(S)-1-cyano-N-(5-(((S)-2-(methoxymethyl)pyrrolidin-1-yl)methypthiazol-2-yl)pyrrolidine-3-carboxamide,
(2S,3S)-1-cyano-N-(5-(((R)-2-(methoxymethyl)pyrrolidin-1-yl)methyl)thiazol-2-yl)-2-methylpyrrolidine-3-carboxamide,
(S)—N-(1-benzyl-1H-imidazol-4-yl)-1-cyanopyrrolidine-3-carboxamide,
(S)-1-cyano-N-(1-phenethyl-1H-imidazol-4-yl)pyrrolidine-3-carboxamide,
(S)-1-cyano-N-(1-isobutyl-1H-imidazol-4-yl)pyrrolidine-3-carboxamide,
(2S,3 S)—N-(1-benzyl-1H-imidazol-4-yl)-1-cyano-2-methylpyrrolidine-3-carboxamide,
(S)-1-cyano-N-(1-(4-fluorophenyl)-1H-imidazol-4-yl)pyrrolidine-3-carboxamide,
(S)-1-cyano-N-(1-(3-fluorophenyl)-1H-imidazol-4-yl)pyrrolidine-3-carboxamide,
(S)-1-cyano-N-(1-(2-fluorophenyl)-1H-imidazol-4-yl)pyrrolidine-3-carboxamide,
(S)-1-cyano-N-(1-(4-(trifluoromethyl)phenyl)-1H-imidazol-4-yl)pyrrolidine-3-carboxamide,
(S)-1-cyano-N-(1-(3-(trifluoromethyl)phenyl)-1H-imidazol-4-yl)pyrrolidine-3-carboxamide,
(S)-1-cyano-N-(1-(4-(methylcarbamoyl)phenyl)-1H-imidazol-4-yl)pyrrolidine-3-carboxamide,
(S)-1-cyano-N-(1-(3-(methylcarbamoyl)phenyl)-1H-imidazol-4-yl)pyrrolidine-3-carboxamide,
(S)-1-cyano-N-(1-(2-(methylcarbamoyl)phenyl)-1H-imidazol-4-yl)pyrrolidine-3-carboxamide,
(S)-1-cyano-N-(1-(4-((2-methoxyethyl)carbamoyl)phenyl)-1H-imidazol-4-yl)pyrrolidine-3-carboxamide,
(S)-1-cyano-N-(1-(4-methoxyphenyl)-1H-imidazol-4-yl)pyrrolidine-3-carboxamide,
(S)-1-cyano-N-(1-(2-methoxyphenyl)-1H-imidazol-4-yl)pyrrolidine-3-carboxamide,
(S)-1-cyano-N-(1-(tetrahydro-2H-pyran-4-yl)-1H-imidazol-4-yl)pyrrolidine-3-carboxamide,
(S)-1-cyano-N-(1-cyclohexyl-1H-imidazol-4-yl)pyrrolidine-3-carboxamide,
(3S)-1-cyano-N-(1-(2,3-dihydro-1H-inden-1-yl)-1H-imidazol-4-yl)pyrrolidin-3-carboxamide,
(S)-1-cyano-N-(1-(2,3-dihydro-1H-inden-2-yl)-1H-imidazol-4-yl)pyrrolidine-3-carboxamide,
(S)-1-cyano-N-(1-((tetrahydro-2H-pyran-4-yl)methyl)-1H-imidazol-4-yl)pyrrolidine-3-carboxamide,
(S)-1-cyano-N-(1-((S)-1-phenylethyl)-1H-imidazol-4-yl)pyrrolidine-3-carboxamide, (S)-1-cyano-N-(1-((R)-1-phenylethyl)-1H-imidazol-4-yl)pyrrolidine-3-carboxamide,
(S)-1-cyano-N-(1-(pyridin-2-ylmethyl)-1H-imidazol-4-yl)pyrrolidine-3-carboxamide,
(S)-1-cyano-N-(1-(pyridin-3-ylmethyl)-1H-imidazol-4-yl)pyrrolidine-3-carboxamide,
(S)-1-cyano-N-(1-(pyridin-4-ylmethyl)-1H-imidazol-4-yl)pyrrolidine-3-carboxamide,
(S)-1-cyano-N-(1 ((3,5-dimethylisoxazol-4-yl)methyl)-1H-imidazol-4-yl)pyrrolidine-3-carboxamide,
(2S,3S)-1-cyano-2-methyl-N-(1-((S)-1-phenylethyl)-1H-imidazol-4-yl)pyrrolidine-3-carboxamide,
(3S,4S)-1-cyano-4-methyl-N-(1-((S)-1-phenylethyl)-1H-imidazol-4-yl)pyrrolidine-3-carboxamide,
(S)-1-cyano-N-(1-(4-methylpyridin-2-yl)-1H-imidazol-4-yl)pyrrolidine-3-carboxamide,
(S)-1-cyano-N-(1-(6-methylpyridin-2-yl)-1H-imidazol-4-yepyrrolidine-3-carboxamide,
(R)-1-cyano-N-(1-(2-methylpyrimidin-4-yl)-1H-imidazol-4-yl)pyrrolidine-3-carboxamide,
(S)-1-cyano-N-(1-(4-cyanophenyl)-1H-imidazol-4-yl)pyrrolidine-3-carboxamide,
(S)—N-(1-benzyl-2-methyl-1H-imidazol-4-yl)-1-cyanopyrrolidine-3-carboxamide,
(S)-1-cyano-N-(1-(2-(3,5-dimethylisoxazol-4-yl)ethyl)-1H-imidazol-4-yl)pyrrolidine-3-carboxamide,
(S)-1-cyano-N-(1-(3-cyanophenyl)-1H-imidazol-4-yl)pyrrolidine-3-carboxamide,
(S)-1-cyano-N-(1-(pyridin-3-yl)-1H-imidazol-4-yl)pyrrolidine-3-carboxamide,
(S)-1 I-cyano-N-(1-(pyridin-4-yl)-1H-imidazol-4-yl)pyrrolidine-3-carboxamide,
(S)-1-cyano-N-(1I-(3-methoxyphenyl)-1H-imidazol-4-yl)pyrrolidine-3-carboxamide,
(3S)—N-(1-(1-benzoylpiperidin-3-yl)-1H-imidazol-4-yl)-1-cyanopyrrolidine-3-carboxamide,
(3 S)—N-(1-(1-benzoylpyrrolidin-3-yl)-1H-imidazol-4-yl)-1-cyanopyrrolidine-3-carboxamide,
(3S)—N-(1-(1-benzylpiperidin-3-yl)-1H-imidazol-4-yl)-1-cyanopyrrolidine-3-carboxamide,
(3S)-1-cyano-N-(1-(1-methylpiperidin-3-yl)-1H-imidazol-4-yl)pyrrolidine-3-carboxamide,
(3S)-1-cyano-N-(1-(1-methylpyrrolidin-3-yl)-1H-imidazol-4-yl)pyrrolidine-3-carboxamide,
(S)—N-(5-acetyl-4,5,6,7-tetrahydrothiazolo[5,4-c]pyridin-2-yl)-1-cyanopyrrolidine-3-carboxamide,
(S)-1-cyano-N-(5-isobutyryl-4,5,6,7-tetrahydrothiazolo[5,4-c]pyridin-2-yl)pyrrolidine-3-carboxamide,
(S)—N-(5-benzoyl-4,5,6,7-tetrahydrothiazolo[5,4-c]pyridin-2-yl)-1-cyanopyrrolidine-3-carboxamide,
(S)-1-cyano-N-(5-(2-methoxybenzoyl)-4,5,6,7-tetrahydrothiazolo[5,4-c]pyridin-2-yl)pyrrolidine-3-carboxamide,
(S)-1-cyano-N-(5-picolinoyl-4,5,6,7-tetrahydrothiazolo[5,4-c]pyridin-2-yl)pyrrolidine-3-carboxamide,
(S)-1-cyano-N-(5-(1-methyl-1H-pyrazole-3-carbonyl)-4,5,6,7-tetrahydrothiazolo[5,4-c]pyridin-2-yl)pyrrolidine-3-carboxamide,
(S)-1-cyano-N-(5-(1-methyl-2-oxo-1,2-dihydropyridine-3-carbonyl)-4,5,6,7-tetrahydrothiazolo[5,4-c]pyridin-2-yl)pyrrolidine-3-carboxamide,
(S)-1-cyano-N-(5-nicotinoyl-4,5,6,7-tetrahydrothiazolo[5,4-c]pyridin-2-yl)pyrrolidine-3-carboxamide,
(S)-1-cyano-N-(5-(dimethylglycyl)-4,5,6,7-tetrahydrothiazolo[5,4-c]pyridin-2-yl)pyrrolidine-3-carboxamide,
Methyl (S)-2-(1-cyanopyrrolidine-3-carboxamido)-6,7-dihydrothiazolo[5,4-c]pyridine-5(4H)-carboxylate,
2-methoxyethyl(S)-2-(1-cyanopyrrolidine-3-carboxamido)-6,7-dihydrothiazolo[5,4-c]pyridine-5(4H)-carboxylate,
(S)-1-cyano-N-(5-methyl-4,5,6,7-tetrahydrothiazolo[5,4-c]pyridin-2-yl)pyrrolidine-3-carboxamide,
(S)—N-(5-benzyl-4,5,6,7-tetrahydrothiazolo[5,4-c]pyridin-2-yl)-1-cyanopyrrolidine-3-carboxamide,
(S)-1-cyano-N-(5-(methylsulfonyl)-4,5,6,7-tetrahydrothiazolo[5,4-c]pyridin-2-yl)pyrrolidine-3-carboxamide,
(S)-1-cyano-N-(5-(isopropylsulfonyl)-4,5,6,7-tetrahydrothiazolo[5,4-c]pyridin-2-yl)pyrrolidine-3-carboxamide,
(S)-1-cyano-N-(5-(phenylsulfonyl)-4,5,6,7-tetrahydrothiazolo[5,4-c]pyridin-2-yl)pyrrolidine-3-carboxamide,
(S)-1-cyano-N-(5-(4-ethynylphenyl)thiazol-2-yl)pyrrolidine-3-carboxamide,
(S)-1-cyano-N-(5-(3-ethynylphenyl)thiazol-2-yl)pyrrolidine-3-carboxamide,
(3S)-1-cyano-N-(5-(N-(1-phenylethyl)sulfamoyl)pyridin-2-yl)pyrrolidine-3-carboxamide,
(3 S)-1-cyano-N-(5-(N-methyl-N-(1-phenylethyl)sulfamoyl)pyridin-2-yl)pyrrolidine-3-carboxamide,
(S)-1-cyano-N-(6-(5-methyl-1,2,4-oxadiazol-3-yl)imidazo[1,2-a]pyridin-2-yl)pyrrolidine-3-carboxamide,
(3S,4S)-1-cyano-N-(6-(3,5-dimethylisoxazol-4-yl)imidazo[1,2-a]pyridin-2-yl)-4-(trifluoromethyl)pyrrolidine-3-carboxamide,
(S)-1-cyano-N-(4-(1-methyl-1H-pyrazol-4-yl)pyridin-2-yl)pyrrolidine-3-carboxamide,
(S)-1-cyano-N-(5-(N,N-dimethylsulfamoyl)-4,5,6,7-tetrahydrothiazolo[5,4-c]pyridin-2-yl)pyrrolidine-3-carboxamide,
(S)-1-cyano-N-(5-(pyridazin-4-yl)thiazol-2-yl)pyrrolidine-3-carboxamide,
(S)-1-cyano-N-(5-(4-cyano-3-fluorophenyl)thiazol-2-yl)pyrrolidine-3-carboxamide,
(S)—N-(5-(1H-indazol-7-yethiazol-2-yl)-1-cyanopyrrolidine-3-carboxamide,
(S)—N-(5-(3-(1H-imidazol-1-yl)phenyl)thiazol-2-yl)-1-cyanopyrrolidine-3-carboxamide,
(S)-1-cyano-N-(5-(4-(methylsulfonamido)phenyl)thiazol-2-yl)pyrrolidine-3-carboxamide,
(S)—N-(5-(3-(1H-pyrazol-1-yl)phenyl)thiazol-2-yl)-1-cyanopyrrolidine-3-carboxamide,
(S)-1-cyano-N-(5-(4-cyano-3-(trifluoromethoxy)phenyl)thiazol-2-yl)pyrrolidine-3-carboxamide,
(S)-1-cyano-N-(5-(4-cyano-3-methoxyphenyl)thiazol-2-yl)pyrrolidine-3-carboxamide,
(S)-1-cyano-N-(5-(4-sulfamoylphenypthiazol-2-yepyrrolidine-3-carboxamide,
(S)—N-(5-(1H-indazol-6-yl)thiazol-2-yl)-1-cyanopyrrolidine-3-carboxamide,
(S)—N-(5-(1H-indazol-5-yl)thiazol-2-yl)-1-cyanopyrrolidine-3-carboxamide,
(S)-6-(2-(1-cyanopyrrolidine-3-carboxamido)thiazol-5-yl)-N-methylpicolinamide,
(S)-6-(2-(1-cyanopyrrolidine-3-carboxamido)thiazol-5-yl)-N-ethylpicolinamide,
(S)-1-cyano-N-(5-(1-methyl-1H-indazol-5-yl)thiazol-2-yl)pyrrolidine-3-carboxamide,
(S)-1-cyano-N-(5-(1-(2-methoxyethyl)-1H-indazol-5-yl)thiazol-2-yl)pyrrolidine-3-carboxamide,
(S)-1-cyano-N-(5-(2-oxoindolin-7-yl)thiazol-2-yl)pyrrolidine-3-carboxamide,
(S)-1-cyano-N-(5-(3-methyl-1H-indazol-5-yl)thiazol-2-yepyrrolidine-3-carboxamide, (S)—N-(5-(1H-indazol-4-yl)thiazol-2-yl)-1-cyanopyrrolidine-3-carboxamide,
(S)-1-cyano-N-(5-(4-fluoro-3-(methylcarbamoyl)phenyl) thiazol-2-yl)pyrrolidine-3-carboxamide,
(S)—N-(5-(3-carbamoylphenyethiazol-2-yl)-1-cyanopyrrolidine-3-carboxamide,
(S)-1-cyano-N-(5-(3-(methylcarbamoyl)phenyl)thiazol-2-yl)pyrrolidine-3-carboxamide,
(S)-1-cyano-N-(5-(3-(ethylcarbamoyl)phenyl)thiazol-2-yl)pyrrolidine-3-carboxamide,
(S)-1-cyano-N-(5-(3-(dimethylcarbamoyl)phenyl)thiazol-2-yl)pyrrolidine-3-carboxamide,
(S)—N-(5-(3-carbamoyl-4-fluorophenyl)thiazol-2-yl)-1-cyanopyrrolidine-3-carboxamide,
(S)—N-(5-(3-carbamoyl-4-chlorophenyl)thiazol-2-yl)-1-cyanopyrrolidine-3-carboxamide,
(S)—N-(5-(4-chloro-3-(methylcarbamoyflphenyl)thiazol-2-yl)-1-cyanopyrrolidine-3-carboxamide,
(S)—N-(5-(4-chloro-3-(prop-2-yn-1-ylcarbanioyflphenypthiazol-2-yl)-1-cyanopyrrolidine-3-carboxamide,
(S)-1-cyano-N-(5-(isopropylsulfonyl)-4,5,6,7-tetrahydropyrazolo[1,5-a]pyrazin-2-yl)pyrrolidine-3-carboxamide,
(S)-1-cyano-N-(5-phenyl-4,5,6,7-tetrahydropyrazolo[1,5-a]pyrazin-2-yl)pyrrolidine-3-carboxamide,
(S)—N-(5-benzyl-4,5,6,7-tetrahydropyrazolo[1,5-a]pyrazin-2-yl)-1-cyanopyrrolidine-3-carboxamide,
(S)-1-cyano-N-(1-(4-cyano-3-(2-methoxyethoxy)phenyl)-1H-imidazol-4-yl)pyrrolidine-3-carboxamide,
(S)-1-cyano-N-(1-(2-cyano-5-(2-methoxyethoxy)phenyl)-1H-imidazol-4-yl)pyrrolidine-3-carboxamide,
(S)-1-cyano-N-(1-(4-cyano-3-(3-morpholinopropoxy) phenyl)-1H-imidazol-4-yl)pyrrolidine-3-carboxamide,
(S)-1-cyano-N-(1-(2-cyano-5-(3-morpholinopropoxy) phenyl)-1H-imidazol-4-yl)pyrrolidine-3-carboxamide,
(S)-1-cyano-N-(1-(4-cyano-3-(((S)-tetrahydrofuran-3-yl) oxy)phenyl)-1H-imidazol-4-yl)pyrrolidine-3-carboxamide,
(S)-1-cyano-N-(1-(2-cyano-5-(((S)-tetrahydrofuran-3-yl) oxy)phenyl)-1H-imidazol-4-yl)pyrrolidine-3-carboxamide,
(S)-1-cyano-N-(1-(4-cyano-3-(oxetan-3-yloxy)phenyl)-1H-imidazol-4-yl)pyrrolidine-3-carboxamide,
(S)-1-cyano-N-(1-(2-cyano-5-(oxetan-3-yloxy)phenyl)-1H-imidazol-4-yl)pyrrolidine-3-carboxamide,
(S)-1-cyano-N-(4-(pyrazolo[1,5-a]pyrimidin-7-yl)pyridin-2-yl)pyrrolidine-3-carboxamide,
(S)-1-cyano-N-(4-(imidazo[1,2-a]pyrimidin-5-yl)pyridin-2-yl)pyrrolidine-3-carboxamide,
(S)-1-cyano-N-(4-(imidazo[1,2-a]pyridin-5-yl)pyridin-2-yl)pyrrolidine-3-carboxamide,
(S)-1-cyano-N-(4-(imidazo[1,2-a]pyrazin-6-yl)pyridin-2-yl)pyrrolidine-3-carboxamide,
(S)-1-cyano-N-(4-(imidazo[1,2-a]pyrimidin-6-yl)pyridin-2-yl)pyrrolidine-3-carboxamide,
(S)-1-cyano-N-(1,7-naphthyridin-6-yl)pyrrolidine-3-carboxamide,
(S)—N-(6-(3-chlorophenyl)pyrimidin-4-yl)-1-cyanopyrrolidine-3-carboxamide,
(S)—N-(2'-amino-[4,4'-hipyridin]-2-yl)-1-cyanopyrrolidine-3-carboxamide,
(S)-1-cyano-N-(2'-(methylamino)-[4,4'-bipyridin]-2-yl) pyrrolidine-3-carboxamide,
(S)-3-(1-cyanopyrrolidine-3-carboxamido)-N-methylisoquinoline-6-carboxamide,
(S)-1-cyano-N-(6-(3,5-dimethylisoxazol-4-yl)isoquinolin-3-yl) pyrrolidine-3-carboxamide, (S)—N-(4-(1H-indazol-4-yl)pyridin-2-yl)-1-cyanopyrrolidine-3-carboxamide,
(S)-1-cyano-N-(6-ethynylisoquinolin-3-yl)pyrrolidine-3-carboxamide,
(2S,3S)-1-cyano-N-(6-ethynylisoquinolin-3-yl)-2-methylpyrrolidine-3-carboxamide,
(S)-3-(1-cyanopyrrolidine-3-carboxamido)isoquinoline-6-carboxamide,
(2S,3S)—N-(6-(1H-pyrazol-4-yflisoquinolin-3-yl)-1-cyano-2-methylpyrrolidine-3-carboxamide,
(S)-1-cyano-N-(pyrazolo[1,5-a]pyridin-2-yl)pyrrolidine-3-carboxamide,
(S)-1-cyano-N-(4-phenylpyridin-2-yl)pyrrolidine-3-carboxamide,
(S)-1-cyano-N-(5-(pyridin-3-yl)thiazol-2-yl)pyrrolidine-3-carboxamide,
(S)-1-cyano-N-(5-(pyridin-3-yl)thiazol-2-yl)pyrrolidine-3-carboxamide,
(S)-1-cyano-N-(6-(trifluoromethyl)imidazo[1,2-a]pyridin-2-yl)pyrrolidine-3-carboxamide,
(S)-1-cyano-N-(1-methyl-5-(m-tolyl)-1H-pyrazol-3-yl) pyrrolidine-3-carboxamide,
(S)-1-cyano-N-(quinolin-3-yl)pyrrolidine-3-carboxamide,
(S)—N-(4-(tert-butyl)pyridin-2-yl)-1-cyanopyrrolidine-3-carboxamide,
(S)-1-cyano-N-(6-(pyridin-4-yl)pyrimidin-4-yl)pyrrolidine-3-carboxamide,
(S)-1-cyano-N-(5-phenylpyridazin-3-yl)pyrrolidine-3-carboxamide,
(S)-1-cyano-N-(6-(oxazol-5-yl)imidazo[1,2-a]pyridin-2-yl)pyrrolidine-3-carboxamide,
(S)-1-cyano-N-(6-(isopropylsulfonyl)-5,6,7,8-tetrahydro-4H-thiazolo[4,5-d]azepin-2-yl)pyrrolidine-3-carboxamide,
(S)-1-cyano-N-(1-(4-(1-(2-methoxyethyl)-1H-pyrazol-4-yl)phenyl)-1H-imidazol-4-yl)pyrrolidine-3-carboxamide,
3-cyano-N-(5-phenylthiazol-2-yl)-3-azabicyclo[3.1.0] hexane-1-carboxamide,
2-cyano-N-(5-phenylthiazol-2-yl)-2-azabicyclo[3.1.0] hexane-4-carboxamide,
(3S,4S)-1-cyano-N-(5-phenylthiazol-2-yl)-4-(trifluoromethyl)pyrrolidine-3-carboxamide,
(3S,4R)-1-cyano-N-(5-phenylthiazol-2-yl)-4-(pyridin-3-yl)pyrrolidine-3-carboxamide,
(3 S,4R)-1-cyano-N-(5-phenylthiazol-2-yl)-4-(pyrimidin-5-yl)pyrrolidine-3-carboxamide,
1-cyano-3-methoxy-N-(5-phenylthiazol-2-yl)pyrrolidine-3-carboxamide,
(S)-1-cyano-N-(6-(3,5-dimethylisoxazol-4-yl)thiazolo[4,5-b]pyridin-2-yl)pyrrolidine-3-carboxamide,
(S)-1-cyano-N-(5-(3,5-dimethylisoxazol-4-yl)thiazolo[5,4-b]pyridin-2-yl)pyrrolidine-3-carboxamide,
(S)-1-cyano-N-(6-(2,6-dimethylphenyl)benzo[d]thiazol-2-yl)pyrrolidine-carboxamide,
(S)-1-cyano-N-(6-(1,3-dimethyl-1H-pyrazol-4-yl)benzo[d]thiazol-2-yl)pyrrolidine-3-carboxamide,
(S)-1-cyano-N-(6-(5-(trifluoromethyl)-1H-pyrazol-4-yl) isoquinolin-3-yl)pyrrolidine-3-carboxamide,
(S)-1-cyano-N-(4-(3-(5-methylisoxazol-4-yl)phenyl) pyridin-2-yl)pyrrolidine-3-carboxamide,
(S)—N-(4-(1H-pyrazol-4-yl)pyridin-2-yl)-1-cyanopyrrolidine-3-carboxamide,
(S)—N-(6-(1H-pyrazol-4-yl)benzo[d]thiazol-2-yl)-1-cyanopyrrolidine-3-carboxamide, (S)—N-(1-(4-(1 H-pyrazol-4-yl)phenyl)-1H-imidazol-4-yl)-1-cyanopyrrolidine-3-carboxamide,
(S)-1-cyano-N-(4-5-methyl-1H-pyrazol-4-yl)pyridin-2-yl)pyrrolidine-3-carboxamide,
(S)-1-cyano-N-(6-(3,5-dimethylisoxazol-4-yl)thiazolo[4,5-c]pyridin-2-yl)pyrrolidine-3-carboxamide,
(S)-1-cyano-N-(2'-(5-methylisoxazol-4-yl)-[4,4'-bipyridin]-2-yl)pyrrolidine-3-carboxamide,
(S)-1-cyano-N-(1-(1,3-dimenthyl-1H-indazol-5-yl)-1H-imidazol-4-yflpyrrolidine-3-carboxamide,
(S)-1-cyano-N-(1-(3-methyl-1H-indazol-6-yl)-1H-imidazol-4-yl)pyrrolidine-3-carboxamide,
(S)—N-(1-(1H-indazol-5-yl)-1H-imidazol-4-yl)-1-cyanopyrrolidine-3-carboxamide,
(S)—N-(1-(1H-indazol-6-yl)-1H-imidazol-4-yl)-1-cyanopyrrolidine-3-carboxamide,
(S)-1-cyano-N-(1-(4-fluoro-3-methoxyphenyl)-1H-imidazol-4-yl)pyrrolidine-3-carboxamide,
(S)—N-(1-(1H-indazol-4-yl)-1H-imidazol-4-yl)-1-cyanopyrrolidine-3-carboxamide,
(S)-1-cyano-N-(1-(4-cyano-3-cyclopropylphenyl)-1H-imidazol-4-yl)pyrrolidine-3-carboxamide,
(S)-1-cyano-N-(1-(quinolin-4-yl)-1H-imidazol-4-yl)pyrrolidine-3-carboxamide,
(S)-1-cyano-N-methyl-N-(4-(4-(methylcarbamoyl)phenyethiazol-2-yl)pyrrolidine-2-carboxamide,
(S)-1-cyano-N-(1-(4-cyano-3-methoxyphenyl)-1H-imidazol-4-yl)pyrrolidine-3-carboxamide,
(S)-1-cyano-N-(1-(4-cyano-3-methylphenyl)-1H-imidazol-4-yl)pyrrolidine-3-carboxamide,
(S)-1-cyano-N-(1-(4-cyano-3-(trifluoromethyl)phenyl)-1H-imidazol-4-yl)pyrrolidine-3-carboxamide, and
(S)-1-cyano-N-(1-(4-cyano-3-(trifluoromethoxy)phenyl)-1H-imidazol-4-yepyrrolidine-3-carboxamide.

13. A process for the preparation of a compound of formula (I) or a pharmaceutically acceptable salt thereof as defined according to claim 1 which comprises reacting an amine of formula (VI) with cyanogen bromide;

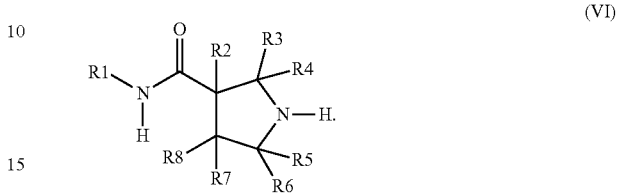

(VI)

14. A method of treating a cancer linked to UCHL1 activity, comprising administering an effective amount of the compound according to claim 1 to a patient having said cancer.

15. A method of treating a patient with a neurodegenerative disorder linked to UCHL1 activity, inflammation linked to UCHL1 activity, a viral or bacterial infection linked to UCHL1 activity, or a metabolic disorder linked to UCHL1 activity, comprising administering an effective amount of the compound according to claim 1 to the patient.

16. A pharmaceutical composition comprising a compound according to claim 1 and one or more pharmaceutically acceptable excipients.

* * * * *